United States Patent
Lin et al.

(10) Patent No.: US 10,227,579 B2
(45) Date of Patent: Mar. 12, 2019

(54) GH61 POLYPEPTIDE VARIANTS AND POLYNUCLEOTIDES ENCODING SAME

(71) Applicants: Novoyzmes A/S, Bagsvaerd (DK); Novozymes, Inc., Davis, CA (US)

(72) Inventors: Janine Lin, Davis, CA (US); Doreen Bohan, Fairfield, CA (US); Michelle Maranta, Davis, CA (US); Leslie Beresford, Woodland, CA (US); Michael Lamsa, Woodland, CA (US); Matt Sweeney, Sacramento, CA (US); Mark Wogulis, Davis, CA (US); Elizabeth Znameroski, Davis, CA (US); Frank Winther Rasmussen, Roskilde (DK)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 600 days.

(21) Appl. No.: 14/395,984

(22) PCT Filed: Apr. 26, 2013

(86) PCT No.: PCT/US2013/038477
§ 371 (c)(1),
(2) Date: Oct. 21, 2014

(87) PCT Pub. No.: WO2013/163590
PCT Pub. Date: Oct. 31, 2013

(65) Prior Publication Data
US 2015/0082493 A1    Mar. 19, 2015

Related U.S. Application Data

(60) Provisional application No. 61/639,648, filed on Apr. 27, 2012.

(51) Int. Cl.
| | |
|---|---|
| *C12N 9/02* | (2006.01) |
| *C12N 9/42* | (2006.01) |
| *D21C 5/00* | (2006.01) |
| *C11D 3/386* | (2006.01) |
| *C12P 19/02* | (2006.01) |
| *C12P 19/14* | (2006.01) |

(52) U.S. Cl.
CPC ........ *C12N 9/2437* (2013.01); *C11D 3/38645* (2013.01); *C12N 9/0071* (2013.01); *C12N 9/2434* (2013.01); *C12P 19/02* (2013.01); *C12P 19/14* (2013.01); *D21C 5/005* (2013.01); *C12Y 302/01004* (2013.01)

(58) Field of Classification Search
CPC .................................................. C12N 9/2402
See application file for complete search history.

(56) References Cited

U.S. PATENT DOCUMENTS

2011/0078831 A1    3/2011  Tang et al.

FOREIGN PATENT DOCUMENTS

| WO | 2011050038 A2 | 4/2011 |
|---|---|---|
| WO | 2012044835 A1 | 4/2012 |

OTHER PUBLICATIONS

Uniport Accession No. A1CXI7 (2007).*
Langston et al (Applied and Environmental Microbiology, Oct. 2011, p. 7007-7015).*
Horn et al. Biotechnology for Biofuels 2012, 5:45.*
Dimarogona et al (Bioresourse Technology 110 (2012) 480-487).*
Quinlan et al (PNAS, Sep. 13, 2011, 108(37) pp. 15079-15084).*
Uniprot Accession A1CXI7 (2007).*
GenBank Accession GAO83771.1 (2015).*
GenBank Accession KOS47081 (2015).*
Harris et al (Biochemistry 2010, 49, 3305-3316 3305) (Year: 2010).*
Uniprot Accession A1CXI7 (2007) (Year: 2007).*
WO 2012-021410—Geneseq Access No. AZT54345.
WO 2011-080267—Geneseq Access No. AZJ19469.
Machida et al, 2006—Uniprot Access No. Q2UGM5.
Harris et al, 2010, Biochem 49 (15), 3305-3316.
Fedorova et al, 2007—Uniprot Access No. A1CXI7.
Fedorova et al, 2007, EBI Accession No. A1CH98.

* cited by examiner

*Primary Examiner* — Lee A Visone
(74) *Attorney, Agent, or Firm* — Robert Starnes

(57) ABSTRACT

The present invention relates to GH61 polypeptide variants. The present invention also relates to polynucleotides encoding the variants; nucleic acid constructs, vectors, and host cells comprising the polynucleotides; and methods of using the variants.

32 Claims, 11 Drawing Sheets
Specification includes a Sequence Listing.

```
        M  T  L  S  K  I  T  S  I  A  G  L  L  A  S  A  S
  1  ATGACTTTGTCCAAGATCACTTCCATTGCTGGCCTTCTGGCCTCAGCGTCT
        L  V  A  G  H  G  F  V  S  G  I  V  A  D  G  K  Y
 52  CTCGTGGCTGGCCACGGCTTTGTTTCTGGCATTGTTGCTGATGGGAAATAG

103  TATGTGCTTGAACCACACAAATGACAGCTGCAACAGCTAACTTCTATTCCA
        Y  G  G  Y  L  V  N  Q  Y  P  Y  M  S  N  P  P
154  GTTACGGAGGGTACCTTGTTAACCAATACCCCTACATGAGCAACCCTCCCG
        D  T  I  A  W  S  T  T  A  T  D  L  G  F  V  D  G
205  ACACCATTGCCTGGTCCACCACCGCCACCGACCTCGGCTTTGTGGACGGCA
        T  G  Y  Q  S  P  D  I  I  C  H  R  D  A  K  N  G
256  CCGGCTACCAGTCTCCGGATATTATCTGCCACAGAGACGCAAAGAATGGCA
        K  L  T  A  T  V  A  A  G  S  Q  I  E  F  Q  W  T
307  AGTTGACCGCAACCGTTGCAGCCGGTTCACAGATCGAATTCCAGTGGACGA
        T  W  P  E  S  H  H  G  P
358  CGTGGCCAGAGTCTCACCATGGACCGGTACGACGCCGAAGAGAAGAGAACA
                                   L  I  T  Y  L  A  P
409  TATTGTGACCAGATAGGCTAACATAGCATAGTTGATTACTTACCTCGCTCC
        C  N  G  D  C  A  T  V  D  K  T  T  L  K  F  V  K
460  ATGCAACGGCGACTGTGCCACCGTGGACAAGACCACCCTGAAGTTTGTCAA
        I  A  A  Q  G  L  I  D  G  S  N  P  P  G  V  W  A
511  GATCGCCGCTCAAGGCTTGATCGACGGCTCCAACCCACCTGGTGTTTGGGC
        D  D  E  M  I  A  N  N  N  T  A  T  V  T  I  P  A
562  TGATGATGAAATGATCGCCAACAACAACACGGCCACAGTGACCATTCCTGC
        S  Y  A  P  G  N  Y  V  L  R  H  E  I  I  A  L  H
613  CTCCTATGCCCCCGGAAACTACGTCCTTCGCCACGAGATCATCGCCCTTCA
        S  A  G  N  L  N  G  A  Q  N  Y  P  Q  C  F  N  I
664  CTCTGCGGGTAACCTGAACGGCGCGCAGAACTACCCCCAGTGTTTCAACAT
        Q  I  T  G  G  G  S  A  Q  G  S  G  T  A  G  T  S
715  CCAAATCACCGGTGGCGGCAGTGCTCAGGGATCTGGCACCGCTGGCACGTC
        L  Y  K  N  T  D  P  G  I  K  F  D  I  Y  S  D  L
766  CCTGTACAAGAATACTGATCCTGGCATCAAGTTTGACATCTACTCGGATCT
        S  G  G  Y  P  I  P  G  P  A  L  F  N  A  *
817  GAGCGGTGGATACCCTATTCCTGGTCCTGCACTGTTCAACGCTTAA
```

Fig. 1

SEQUENCE LISTING

```
<160> NUMBER OF SEQ ID NOS: 411

<210> SEQ ID NO 1
<211> LENGTH: 1846
<212> TYPE: DNA
<213> ORGANISM: Thielavia terrestris

<400> SEQUENCE: 1
aattgaagga gggagtggcg gagtggccac caagtcaggc ggctgtcaac taaccaagga      60
tgggaacagt tcggctcgcc ttgcccgagg gcagcgttcc ctgatgggga cgaaccatgg     120
gactggggtc agctgctgta taaaagttca aatcgatgat ctctcagatg gcgctgctgg     180
ggtgttctgc gcttttccat cctcgcaacc tggtatccca ctagtccagc gttcggcacc     240
atgaagtcgt tcaccattgc cgccttggca gccctatggg cccaggaggc cgccgcccac     300
gcgaccttcc aggacctctg gattgatgga gtcgactacg gctcgcaatg tgtccgcctc     360
ccggcgtcca actcccccgt caccaatgtt gcgtccgacg atatccgatg caatgtcggc     420
acctcgaggc ccaccgtcaa gtgcccggtc aaggccggct ccacggtcac gatcgagatg     480
caccaggttc gcacgcctct ctgcgtaggc cccccagcta ctatatggca ctaacacgac     540
ctccagcaac ctggcgaccg gtcttgcgcc aacgaggcta tcggcggcga ccactacggc     600
cccgtaatgg tgtacatgtc caaggtcgat gacgcggtga cagccgacgg ttcatcgggc     660
tggttcaagg tgttccagga cagctgggcc aagaaccccgt cgggttcgac gggcgacgac     720
gactactggg gcaccaagga cctcaactcg tgctgcggca agatgaacgt caagatcccc     780
```

```
gaagacatcg agccgggcga ctacctgctc cgcgccgagg ttatcgcgct gcacgtggcc     840
gccagctcgg gcggcgcgca gttctacatg tcctgctacc agctgaccgt gacgggctcc     900
ggcagcgcca ccccctcgac cgtgaatttc ccgggcgcct actcggccag cgacccgggc     960
atcctgatca acatccacgc gcccatgtcg acctacgtcg tcccgggccc gaccgtgtac    1020
gcgggcggct cgaccaagtc ggctggcagc tcctgctccg gctgcgaggc gacctgcacg    1080
gttggttccg gccccagcgc gacactgacg cagcccacct ccaccgcgac cgcgacctcc    1140
gcccctggcg gcggcggctc cggctgcacg gcggccaagt accagcagtg cggcggcacc    1200
ggctacactg gtgcaccac ctgcgctgta agttccctcg tgatatgcag cggaacaccg    1260
tctggactgt tttgctaact cgcgtcgtag tccgggtcta cctgcagcgc cgtctcgcct    1320
ccgtactact cgcagtgcct ctaagccggg agcgcttgct cagcgggctg ctgtgaagga    1380
gctccatgtc cccatgccgc catggccgga gtaccgggct gagcgcccaa ttcttgtata    1440
tagttgagtt ttcccaatca tgaatacata tgcatctgca tggactgttg cgtcgtcagt    1500
ctacatcctt tgctccactg aactgtgaga ccccatgtca tccggaccat cgatcggtg     1560
ctcgctctac catctcggtt gatgggtctg gcttgagag tcactggcac gtcctcggcg    1620
gtaatgaaat gtggaggaaa gtgtgagctg tctgacgcac tcggcgctga tgagacgttg    1680
agcgcggccc acactggtgt tctgtaagcc agcacacaaa agaatactcc aggatggccc    1740
atagcggcaa atatacagta tcagggatgc aaaaagtgca aaagtaaggg gctcaatcgg    1800
ggatcgaacc cgagacctcg cacatgactt atttcaagtc agggt               1846
```

```
<210> SEQ ID NO 2
<211> LENGTH: 326
<212> TYPE: PRT
<213> ORGANISM: Thielavia terrestris

<400> SEQUENCE: 2
```

| | | | | | | | | | | | | | | | |
|---|---|---|---|---|---|---|---|---|---|---|---|---|---|---|---|
| Met | Lys | Ser | Phe | Thr | Ile | Ala | Ala | Leu | Ala | Ala | Leu | Trp | Ala | Gln | Glu |
| 1 | | | | 5 | | | | | 10 | | | | | 15 | |
| Ala | Ala | Ala | His | Ala | Thr | Phe | Gln | Asp | Leu | Trp | Ile | Asp | Gly | Val | Asp |
| | | | 20 | | | | | 25 | | | | | 30 | | |
| Tyr | Gly | Ser | Gln | Cys | Val | Arg | Leu | Pro | Ala | Ser | Asn | Ser | Pro | Val | Thr |
| | | 35 | | | | | 40 | | | | | 45 | | | |
| Asn | Val | Ala | Ser | Asp | Asp | Ile | Arg | Cys | Asn | Val | Gly | Thr | Ser | Arg | Pro |
| | 50 | | | | | 55 | | | | | 60 | | | | |
| Thr | Val | Lys | Cys | Pro | Val | Lys | Ala | Gly | Ser | Thr | Val | Thr | Ile | Glu | Met |
| 65 | | | | | 70 | | | | | 75 | | | | | 80 |
| His | Gln | Gln | Pro | Gly | Asp | Arg | Ser | Cys | Ala | Asn | Glu | Ala | Ile | Gly | Gly |
| | | | | 85 | | | | | 90 | | | | | 95 | |
| Asp | His | Tyr | Gly | Pro | Val | Met | Val | Tyr | Met | Ser | Lys | Val | Asp | Asp | Ala |
| | | | 100 | | | | | 105 | | | | | 110 | | |
| Val | Thr | Ala | Asp | Gly | Ser | Ser | Gly | Trp | Phe | Lys | Val | Phe | Gln | Asp | Ser |
| | | 115 | | | | | 120 | | | | | 125 | | | |
| Trp | Ala | Lys | Asn | Pro | Ser | Gly | Ser | Thr | Gly | Asp | Asp | Tyr | Trp | Gly |
| | 130 | | | | | 135 | | | | | 140 | | | | |
| Thr | Lys | Asp | Leu | Asn | Ser | Cys | Cys | Gly | Lys | Met | Asn | Val | Lys | Ile | Pro |
| 145 | | | | | 150 | | | | | 155 | | | | | 160 |
| Glu | Asp | Ile | Glu | Pro | Gly | Asp | Tyr | Leu | Leu | Arg | Ala | Glu | Val | Ile | Ala |
| | | | | 165 | | | | | 170 | | | | | 175 | |
| Leu | His | Val | Ala | Ala | Ser | Ser | Gly | Gly | Ala | Gln | Phe | Tyr | Met | Ser | Cys |

180                 185                 190
Tyr Gln Leu Thr Val Thr Gly Ser Gly Ser Ala Thr Pro Ser Thr Val
                195                 200                 205

Asn Phe Pro Gly Ala Tyr Ser Ala Ser Asp Pro Gly Ile Leu Ile Asn
            210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
                275                 280                 285

Cys Thr Ala Ala Lys Tyr Gln Gln Cys Gly Gly Thr Gly Tyr Thr Gly
            290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3
accccgggat cactgcccct aggaaccagc acacctcggt ccaatcatgc ggttcgacgc        60
cctctccgcc ctcgctcttg cgccgcttgt ggctggccac ggcgccgtga ccagctacat       120
catcggcggc aaaacctatc ccggctacga gggcttctcg cctgcctcga gcccgccgac       180
gatccagtac cagtggcccg actacaaccc gaccctgagc gtgaccgacc cgaagatgcg       240
ctgcaacggc ggcacctcgg cagagctcag cgcgcccgtc caggccggcg agaacgtgac       300
ggccgtctgg aagcagtgga cccaccagca aggccccgtc atggtctgga tgttcaagtg       360
ccccggcgac ttctcgtcgt gccacggcga cggcaagggc tggttcaaga tcgaccagct       420
gggcctgtgg ggcaacaacc tcaactcgaa caactgggc accgcgatcg tctacaagac       480
cctccagtgg agcaacccga tcccaagaa cctcgcgccg gcaactacc tcatccgcca       540 cgagctgctc gccctgcacc aggccaacac gccgcagttc tacgccgagt gcgcccagct       600
ggtcgtctcc ggcagcggct ccgccctgcc ccgtccgac tacctctaca gcatccccgt       660
ctacgcgccc cagaacgacc ccggcatcac cgtgagtggg cttccgttcc gcggcgagct       720
ctgtggaaat cttgctgacg atgggctagg ttgacatcta caacggcggg cttacctcct       780
acaccccgcc cggcggcccc gtctggtctg gcttcgagtt ttaggcgcat tgagtcgggg       840
gctacgaggg gaaggcatct gttcgcatga gcgtgggtac                             880

<210> SEQ ID NO 4
<211> LENGTH: 239
<212> TYPE: PRT
<213> ORGANISM: Thielavia terrestris

<400> SEQUENCE: 4

Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro

```
                      20                  25                  30
Gly Tyr Glu Gly Phe Ser Pro Ala Ser Ser Pro Thr Ile Gln Tyr
            35                  40                  45

Gln Trp Pro Asp Tyr Asn Pro Thr Leu Ser Val Thr Asp Pro Lys Met
 50                  55                  60

Arg Cys Asn Gly Gly Thr Ser Ala Glu Leu Ser Ala Pro Val Gln Ala
 65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
            115                 120                 125

Gly Asn Asn Leu Asn Ser Asn Asn Trp Gly Thr Ala Ile Val Tyr Lys
            130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
            195                 200                 205

Gln Asn Asp Pro Gly Ile Thr Val Asp Ile Tyr Asn Gly Gly Leu Thr
            210                 215                 220

Ser Tyr Thr Pro Pro Gly Gly Pro Val Trp Ser Gly Phe Glu Phe
225                 230                 235

<210> SEQ ID NO 5
<211> LENGTH: 1000
<212> TYPE: DNA
<213> ORGANISM: Thielavia terrestris

<400> SEQUENCE: 5
ctcctgttcc tgggccaccg cttgttgcct gcactattgg tagagttggt ctattgctag    60
agttggccat gcttctcaca tcagtcctcg gctcggctgc cctgcttgct agcggcgctg   120
cggcacacgg cgccgtgacc agctacatca tcgccggcaa gaattacccg ggtgggtag    180 ctgattattg agggcgcatt caaggttcat accggtgtgc atggctgaca accggctggc   240
agataccaag gcttttctcc tgcgaactcg ccgaacgtca tccaatggca atggcatgac   300
tacaaccccg tcttgtcgtg cagcgactcg aagcttcgct gcaacggcgg cacgtcggcc   360
accctgaacg ccacggccgc accgggcgac accatcaccg ccatctgggc gcagtggacg   420
cacagccagg gccccatcct ggtgtggatg tacaagtgcc cgggctcctt cagctcctgt   480
gacggctccg cgctggctg gttcaagatc gacgaggccg gcttccacgg cgacggcgtc   540
aaggtcttcc tcgacaccga gaacccgtcc ggctgggaca tcgccaagct cgtcggcggc   600
aacaagcagt ggagcagcaa ggtccccgag ggcctcgccc ccggcaacta cctcgtccgc   660
cacgagttga tcgccctgca ccaggccaac aacccgcagt tctacccgga gtgcgcccag   720
gtcgtcatca ccggctccgg caccgcgcag ccggatgcct catacaaggc ggctatcccc   780
ggctactgca accagaatga cccgaacatc aaggtgagat ccaggcgtaa tgcagtctac   840
tgctggaaag aaagtggtcc aagctaaacc gcgctccagg tgcccatcaa cgaccactcc   900
```

```
atccctcaga cctacaagat tcccggccct cccgtcttca agggcaccgc cagcaagaag    960
gcccgggact tcaccgcctg aagttgttga atcgatggag                         1000
```

<210> SEQ ID NO 6
<211> LENGTH: 258
<212> TYPE: PRT
<213> ORGANISM: Thielavia terrestris

<400> SEQUENCE: 6

```
Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala
```

<210> SEQ ID NO 7
<211> LENGTH: 681
<212> TYPE: DNA
<213> ORGANISM: Thielavia terrestris

<400> SEQUENCE: 7

```
atgctcgcaa acggtgccat cgtcttcctg gccgccgccc tcggcgtcag tggccactac    60
acctggccac gggttaacga cggcgccgac tggcaacagg tccgtaaggc ggacaactgg   120
caggacaacg gctacgtcgg ggatgtcacg tcgccacaga tccgctgttt ccaggcgacc   180
ccgtccccgg cccatccgt cctcaacacc acggccggct cgaccgtgac ctactgggcc   240
aaccccgacg tctaccaccc cgggcctgtg cagttttaca tggcccgcgt gcccgatggc   300
```

-continued

```
gaggacatca actcgtggaa cggcgacggc gccgtgtggt tcaaggtgta cgaggaccat      360
cctacctttg gcgctcagct cacatggccc agcacgggca agagctcgtt cgcggttccc      420 atcccccgt gcatcaagtc cggctactac ctcctccggg cggagcaaat cggcctgcac       480
gtcgcccaga gcgtaggcgg agcgcagttc tacatctcat gcgcccagct cagcgtcacc      540
ggcggcggca gcaccgagcc gccgaacaag gtggccttcc ccggcgctta cagtgcgacg      600
gacccgggca ttctgatcaa catctactac cctgttccca cgtcctacca gaaccccggc      660
ccggccgtct tcagctgctg a                                                681
```

<210> SEQ ID NO 8
<211> LENGTH: 226
<212> TYPE: PRT
<213> ORGANISM: Thielavia terrestris

<400> SEQUENCE: 8

```
Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225
```

<210> SEQ ID NO 9
<211> LENGTH: 960
<212> TYPE: DNA
<213> ORGANISM: Thielavia terrestris

<400> SEQUENCE: 9

```
atgaagggac ttttcagtgc cgccgccctc tccctggccg tcggccaggc ttcggcccat      60
tacatcttcc agcaactctc catcaacggg aaccagtttc cggtgtacca atatattcgc     120
```

```
aagaacacca attataacag tcccgttacc gatctcacgt ccgacgatct tcggtgcaat    180
gtcggcgccc agggtgctgg gacagacacc gtcacggtga aggccggcga ccagttcacc    240
ttcacccttg acacccctgt ttaccaccag gggcccatct ccatctacat gtccaaggcc    300
ccgggcgcgg cgtcagacta cgatggcagc ggcggctggt tcaagatcaa ggactggggc    360
ccgactttca acgccgacgg cacggccacc tgggacatgg ccggctcata cacctacaac    420
atcccgacct gcattcccga cggcgactat ctgctccgca tccagtcgct ggccatccac    480
aacccctggc cggcgggcat cccgcagttc tacatctcct gcgcccagat caccgtgacc    540
ggcggcggca acggcaaccc tggcccgacg gccctcatcc ccggcgcctt caaggacacc    600
gacccgggct acacggtgaa catctacacg aacttccaca actacacggt tccggcccg    660
gaggtcttca gctgcaacgg cggcggctcg aacccgcccc cgccggtgag tagcagcacg    720
cccgcgacca cgacgctggt cacgtcgacg cgcaccacgt cctccacgtc ctccgcctcg    780
acgccggcct cgaccggcgg ctgcaccgtc gccaagtggg gccagtgcgg cggcaacggg    840
tacaccggct gcacgacctg cgcggccggg tccacctgca gcaagcagaa cgactactac    900
tcgcagtgct gtaagggag gccgcaaagc atgaggtgtt tgaagaggag gagaggggtc    960
```

<210> SEQ ID NO 10
<211> LENGTH: 304
<212> TYPE: PRT
<213> ORGANISM: Thielavia terrestris
<400> SEQUENCE: 10

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Gly Ser Asn Pro Pro Pro Val Ser Ser Thr
225                 230                 235                 240

Pro Ala Thr Thr Thr Leu Val Thr Ser Thr Arg Thr Thr Ser Ser Thr
            245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
            275                 280                 285

Ala Gly Ser Thr Cys Ser Lys Gln Asn Asp Tyr Tyr Ser Gln Cys Leu
            290                 295                 300

<210> SEQ ID NO 11
<211> LENGTH: 954
<212> TYPE: DNA
<213> ORGANISM: Thielavia terrestris

<400> SEQUENCE: 11
atgaagggcc tcagcctcct cgccgctgcg tcggcagcga ctgctcatac catcttcgtg       60
cagctcgagt caggggggaac gacctatccg gtatcctacg gcatccggga ccctagctac     120
gacggtccca tcaccgacgt cacctccgac tcactggctt gcaatggtcc cccgaacccc      180
acgacgccgt ccccgtacat catcaacgtc accgccggca ccacggtcgc ggcgatctgg      240
aggcacaccc tcacatccgg ccccgacgat gtcatggacg ccagccacaa ggggccgacc     300
ctggcctacc tcaagaaggt cgatgatgcc ttgaccgaca cgggtatcgg cggcggctgg     360
ttcaagatcc aggaggccgg ttacgacaat ggcaattggg ctaccagcac ggtgatcacc     420
aacggtggct ccaatatat tgacatcccc gcctgcattc ccaacggcca gtatctgctc      480
cgcgccgaga tgatcgcgct ccacgccgcc agcacgcagg tggtgcccca gctctacatg     540
gagtgcgcgc agatcaacgt ggtgggcggc tccggcagcg ccagcccgca gacgtacagc     600
atcccgggca tctaccaggc aaccgacccg ggcctgctga tcaacatcta ctccatgacg     660
ccgtccagcc agtacaccat tccgggtccg cccctgttca cctgcagcgg cagcggcaac     720
aacggcggcg gcagcaaccc gtcgggcggg cagaccacga cggcgaagcc cacgacgacg     780
acggcggcga cgaccacctc ctccgccgct cctaccagca gccaggggg cagcagcggt      840 tgcaccgttc cccagtggca gcagtgcggt ggcatctcgt tcaccggctg caccacctgc     900
gcggcgggct acacctgcaa gtatctgaac gactattact cgcaatgcca gtaa          954

<210> SEQ ID NO 12
<211> LENGTH: 317
<212> TYPE: PRT
<213> ORGANISM: Thielavia terrestris

<400> SEQUENCE: 12

Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
            35                  40                  45

Ser Asp Ser Leu Ala Cys Asn Gly Pro Pro Asn Pro Thr Thr Pro Ser
        50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His

```
            85                  90                  95
Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Thr Cys Ala Ala Gly Tyr
    290                 295                 300

Thr Cys Lys Tyr Leu Asn Asp Tyr Tyr Ser Gln Cys Gln
305                 310                 315

<210> SEQ ID NO 13
<211> LENGTH: 799
<212> TYPE: DNA
<213> ORGANISM: Thermoascus aurantiacus

<400> SEQUENCE: 13
atgtcctttt tccaagataat tgctactgcc ggcgttcttg cctctgcttc tctagtggct      60
ggccatggct tcgttcagaa catcgtgatt gatggtaaaa agtatgtcat tgcaagacgc     120
acataagcgg caacagctga caatcgacag ttatggcggg tatctagtga accagtatcc     180
atacatgtcc aatcctccag aggtcatcgc ctggtctact acggcaactg atcttggatt     240
tgtggacggt actggatacc aaacccccaga tatcatctgc cataggggcg ccaagcctgg     300
agccctgact gctccagtct ctccaggagg aactgttgag cttcaatgga ctccatggcc     360
tgattctcac catggcccag ttatcaacta ccttgctccg tgcaatggtg attgttccac     420
tgtggataag acccaattag aattcttcaa aattgccgag agcggtctca tcaatgatga     480
caatcctcct gggatctggg cttcagacaa tctgatagca gccaacaaca gctggactgt     540
caccattcca accacaattg cacctggaaa ctatgttctg aggcatgaga ttattgctct     600
tcactcagct cagaaccagg atggtgccca gaactatccc cagtgcatca atctgcaggt     660
cactggaggt ggttctgata accctgctgg aactcttgga acggcactct accacgatac     720
cgatcctgga attctgatca acatctatca gaaactttcc agctatatca tccctggtcc     780
tcctctgtat actggttaa                                                  799
```

<210> SEQ ID NO 14
<211> LENGTH: 249
<212> TYPE: PRT
<213> ORGANISM: Thermoascus aurantiacus

<400> SEQUENCE: 14

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Tyr Tyr Gly Gly Tyr Leu Val Asn Gln Tyr Pro Tyr Met Ser Asn
            35                  40                  45

Pro Pro Glu Val Ile Ala Trp Ser Thr Thr Ala Thr Asp Leu Gly Phe
    50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His His Gly Pro Val Ile
                100                 105                 110

Asn Tyr Leu Ala Pro Cys Asn Gly Asp Cys Ser Thr Val Asp Lys Thr
            115                 120                 125

Gln Leu Glu Phe Phe Lys Ile Ala Glu Ser Gly Leu Ile Asn Asp Asp
    130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
    195                 200                 205

Ser Asp Asn Pro Ala Gly Thr Leu Gly Thr Ala Leu Tyr His Asp Thr
210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                245

<210> SEQ ID NO 15
<211> LENGTH: 1172
<212> TYPE: DNA
<213> ORGANISM: Trichoderma reesei

<400> SEQUENCE: 15
ggatctaagc cccatcgata tgaagtcctg cgccattctt gcagcccttg gctgtcttgc      60
cgggagcgtt ctcggccatg gacaagtcca aacttcacg atcaatggac aatacaatca     120
gggtttcatt ctcgattact actatcagaa gcagaatact ggtcacttcc ccaacgttgc     180
tggctggtac gccgaggacc tagacctggg cttcatctcc cctgaccaat acaccacgcc     240
cgacattgtc tgtcacaaga acgcggcccc aggtgccatt tctgccactg cagcggccgg     300
cagcaacatc gtcttccaat ggggccctgg cgtctggcct caccccctacg gtcccatcgt     360 tacctacgtg gctgagtgca gcggatcgtg cacgaccgtg aacaagaaca acctgcgctg     420

-continued

```
ggtcaagatt caggaggccg gcatcaacta taacacccaa gtctgggcgc agcaggatct    480
gatcaaccag ggcaacaagt ggactgtgaa gatcccgtcg agcctcaggc ccggaaacta    540
tgtcttccgc catgaacttc ttgctgccca tggtgcctct agtgcgaacg gcatgcagaa    600
ctatcctcag tgcgtgaaca tcgccgtcac aggctcgggc acgaaagcgc tccctgccgg    660
aactcctgca actcagctct acaagcccac tgaccctggc atcttgttca acccttacac    720
aacaatcacg agctacacca tccctggccc agccctgtgg caaggctaga tccagggggta   780 cggtgttggc gttcgtgaag tcggagctgt tgacaaggat atctgatgat gaacggagag    840
gactgatggg cgtgactgag tgtatatatt tttgatgacc aaattgtata cgaaatccga    900
acgcatggtg atcattgttt atccctgtag tatattgtct ccaggctgct aagagcccac    960
cgggtgtatt acggcaacaa agtcaggaat ttgggtggca atgaacgcag gtctccatga   1020
atgtatatgt gaagaggcat cggctggcat gggcattacc agatataggc cctgtgaaac   1080
atatagtact tgaacgtgct actggaacgg atcataagca agtcatcaac atgtgaaaaa   1140
acactacatg taaaaaaaaa aaaaaaaaaa aa                                  1172
```

<210> SEQ ID NO 16
<211> LENGTH: 249
<212> TYPE: PRT
<213> ORGANISM: Trichoderma reesei

<400> SEQUENCE: 16

```
Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Tyr Gln Lys Gln Asn Thr Gly
        35                  40                  45

His Phe Pro Asn Val Ala Gly Trp Tyr Ala Glu Asp Leu Asp Leu Gly
    50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
        115                 120                 125

Lys Asn Asn Leu Arg Trp Val Lys Ile Gln Glu Ala Gly Ile Asn Tyr
    130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
        195                 200                 205

Lys Ala Leu Pro Ala Gly Thr Pro Ala Thr Gln Leu Tyr Lys Pro Thr
    210                 215                 220

Asp Pro Gly Ile Leu Phe Asn Pro Tyr Thr Thr Ile Thr Ser Tyr Thr
225                 230                 235                 240
```

Ile Pro Gly Pro Ala Leu Trp Gln Gly
            245

<210> SEQ ID NO 17
<211> LENGTH: 924
<212> TYPE: DNA
<213> ORGANISM: Myceliophthora thermophila

<400> SEQUENCE: 17

```
atgaagttca cctcgtccct cgctgtcctg gccgctgccg gcgcccaggc tcactgttag      60
tcgaccctcg aacccaacac ccccctcccc ccttttctcc tccatctcct cggcctcact     120
tagtagccgc tgacaacgac tagatacctt ccctagggcc ggcactggtg gctcgctctc     180
tggcgagtgg gaggtggtcc gcatgaccga gaaccattac tcgcacggcc cggtcaccga     240
tgtcaccagc cccgagatga cctgctatca gtccggcgtg cagggtgcgc ccagaccgt      300
ccaggtcaag gcgggctccc aattcacctt cagcgtggat ccctcgatcg ccacccccgg     360
ccctctccag ttctacatgg ctaaggtgcc gtcgggccag acggccgcca cctttgacgg     420
cacgggagcc gtgtggttca agatctacca agacggcccg aacggcctcg caccgacag      480
cattacctgg cccagcgccg gttcgtgact tcctccccac tcgctttttt ttttttattt     540
tttattttt tttctttcgg aactcaagaa tctttctctc tctctcccgt ctttggcctt      600
gaacaacact aaaactcttc cttactgtat taattaggca aaaccgaggt ctcggtcacc     660
atccccagct gcatcgatga tggcgagtac ctgctccggg tcgagcacat cgcgctccac     720
agcgccagca gcgtgggcgg cgctcagttc tacattgcct gcgcccagct ctccgtcacc     780
ggcggctccg gcaccctcaa cacgggctcg ctcgtctccc tgcccggcgc ctacaaggcc     840
accgacccgg gcatcctctt ccagctctac tggcccatcc cgaccgagta catcaacccc     900
ggcccggccc ccgtctcttg ctaa                                            924
```

<210> SEQ ID NO 18
<211> LENGTH: 232
<212> TYPE: PRT
<213> ORGANISM: Myceliophthora thermophila

<400> SEQUENCE: 18

Met Lys Phe Thr Ser Ser Leu Ala Val Leu Ala Ala Gly Ala Gln
1               5                   10                  15

Ala His Tyr Thr Phe Pro Arg Ala Gly Thr Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
        50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Asp Asp Gly Glu Tyr Leu Leu Arg Val Glu

```
                145                 150                 155                 160
His Ile Ala Leu His Ser Ala Ser Ser Val Gly Gly Ala Gln Phe Tyr
                    165                 170                 175

Ile Ala Cys Ala Gln Leu Ser Val Thr Gly Gly Ser Gly Thr Leu Asn
                180                 185                 190

Thr Gly Ser Leu Val Ser Leu Pro Gly Ala Tyr Lys Ala Thr Asp Pro
            195                 200                 205

Gly Ile Leu Phe Gln Leu Tyr Trp Pro Ile Pro Thr Glu Tyr Ile Asn
        210                 215                 220

Pro Gly Pro Ala Pro Val Ser Cys
225                 230
```

<210> SEQ ID NO 19
<211> LENGTH: 854
<212> TYPE: DNA
<213> ORGANISM: Myceliophthora thermophila

<400> SEQUENCE: 19

```
atgaaggccc tctctctcct tgcggctgcc tcggcagtct ctgcgcatac catcttcgtc    60
cagctcgaag cagacggcac gaggtacccg gtctcgtacg ggatccggga cccaagctac   120
gacggcccca tcaccgacgt cacatccaac gacgttgctt gcaacggcgg gccgaacccg   180
acgaccccct ccagcgacgt catcaccgtc accgcgggca ccacggtcaa ggccatctgg   240
aggcacaccc tccaatccgg cccggacgat gtcatggacg ccagccacaa gggcccgacc   300
ctggcctacc tcaagaaggt cggcgatgcc accaaggact cgggcgtcgg cggtggctgg   360
ttcaagattc aggaggacgg ctacaacaac ggccagtggg gcaccagcac cgttatctcc   420
aacggcggcg agcactacat gtgagccatt cctccgagag aagaccaaga ctcttgacga   480
tctcgctgac ccgtgcaaca agtgacatcc cggcctgcat ccccgagggt cagtacctcc   540
tccgcgccga tgatcgcc ctccacgcgc ccgggtcccc cggcggtgcc cagctctacg   600
taagcctctg cccttccccc cttcctcttg atcgaatcgg actgcccacc cccttttcg    660
actccgacta acaccgttgc cagatggaat gtgcccagat caacatcgtc ggcggctccg   720
gctcggtgcc cagctcgacc gtcagcttcc ccggcgcgta cagccccaac gacccgggtc   780
tcctcatcaa catctattcc atgtcgccct cgagctcgta caccatcccg ggcccgcccg   840
tcttcaagtg ctag                                                    854
```

<210> SEQ ID NO 20
<211> LENGTH: 235
<212> TYPE: PRT
<213> ORGANISM: Myceliophthora thermophila

<400> SEQUENCE: 20

```
Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
                20                  25                  30

Tyr Gly Ile Arg Asp Pro Ser Tyr Asp Gly Pro Ile Thr Asp Val Thr
            35                  40                  45

Ser Asn Asp Val Ala Cys Asn Gly Gly Pro Asn Pro Thr Thr Pro Ser
        50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
```

|  |  |  | 85 |  |  |  | 90 |  |  |  | 95 |  |  |
|--|--|--|--|--|--|--|--|--|--|--|--|--|--|

Lys Gly Pro Thr Leu Ala Tyr Leu Lys Lys Val Gly Asp Ala Thr Lys
                                100                 105                 110

Asp Ser Gly Val Gly Gly Gly Trp Phe Lys Ile Gln Glu Asp Gly Tyr
         115                 120                 125

Asn Asn Gly Gln Trp Gly Thr Ser Thr Val Ile Ser Asn Gly Gly Glu
     130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                 165                 170                 175

Gln Leu Tyr Met Glu Cys Ala Gln Ile Asn Ile Val Gly Gly Ser Gly
             180                 185                 190

Ser Val Pro Ser Ser Thr Val Ser Phe Pro Gly Ala Tyr Ser Pro Asn
         195                 200                 205

Asp Pro Gly Leu Leu Ile Asn Ile Tyr Ser Met Ser Pro Ser Ser Ser
210                 215                 220

Tyr Thr Ile Pro Gly Pro Pro Val Phe Lys Cys
225                 230                 235

<210> SEQ ID NO 21
<211> LENGTH: 1242
<212> TYPE: DNA
<213> ORGANISM: Myceliophthora thermophila

<400> SEQUENCE: 21

```
atgaagtcct tcgccctcac cactctggcc gccctggccg gcaacgccgc cgctcacgcg      60
accttccagg ccctctgggt cgacggcgtc gactacggcg cgcagtgtgc ccgtctgccc     120
gcgtccaact ccccggtcac cgacgtgacc tccaacgcga tccgctgcaa cgccaacccg     180
tcgcccgctc ggggcaagtg cccggtcaag gccggctcga ccgttacggt cgagatgcat     240
caggtacgtt ggatgaatga aggggaaagg aagcagaggc agaaggggaa aggcgaaggg     300
aaagaaaaag aaaagaaaat ggaaaagaaa aagaaatgga aagaaaaaag aaaaatgaaa     360
aagaaagtgg aaaccgtcag actaactggg gctcctcccc cccaccccct ctttgatatc     420
agcaacccgg tgaccggtcg tgcagcagcg aggcgatcgg cggggcgcac tacggccccg     480
tcatggtgta catgtccaag gtgtcggacg cggcgtcggc ggacgggtcg tcgggctggt     540
tcaaggtgtt cgaggacggc tgggccaaga cccgtccgg cgggtcgggc gacgacgact     600
actggggcac caaggacctg aactcgtgct gcgggaagat gaacgtcaag atccccgccg     660
acctgccctc gggcgactac ctgctccggg ccgaggccct cgcgctgcac acggcgggca     720
gcgccggcgg cgcccagttc tacatgacgt gctaccagct caccgtgacg ggctccggca     780
gcgccagccc gcccaccgtc tccttcccgg gcgcctacaa ggccaccgac ccgggcatcc     840
tcgtcaacat ccacgccccg ctgtccggct acaccgtgcc cggcccggcc gtctactccg     900
gcggctccac caagaaggcc ggcagcgcct gcaccggctg cgagtccacc tgcgccgtcg     960
gctccggccc caccgccacc gtctcccagt cgcccggttc caccgccacc tccgccccg    1020
gcggcggcgg cggctgcacc gtccagaagt accagcagtg cggcggcgag ggctacaccg    1080
gctgcaccaa ctgcgcggta cgttttcaa cccgtttt ttttttcctt ccctaccta    1140
tttggttacc taattaatta ctttccggct gctgacttt tgctttagtc cggctctacc    1200
tgcagcgccg tctcgccgcc ctactactcg cagtgcgtct aa                      1242
```

<210> SEQ ID NO 22
<211> LENGTH: 323
<212> TYPE: PRT
<213> ORGANISM: Myceliophthora thermophila

<400> SEQUENCE: 22

```
Met Lys Ser Phe Ala Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Ala
                85                  90                  95

His Tyr Gly Pro Val Met Val Tyr Met Ser Lys Val Ser Asp Ala Ala
                100                 105                 110

Ser Ala Asp Gly Ser Ser Gly Trp Phe Lys Val Phe Glu Asp Gly Trp
            115                 120                 125

Ala Lys Asn Pro Ser Gly Gly Ser Gly Asp Asp Tyr Trp Gly Thr
        130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285

Gln Lys Tyr Gln Gln Cys Gly Gly Glu Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val
```

<210> SEQ ID NO 23
<211> LENGTH: 1253
<212> TYPE: DNA
<213> ORGANISM: Myceliophthora thermophila

<400> SEQUENCE: 23
atgaagcctt ttagcctcgt cgccctggcg accgccgtga gcggccatgc catcttccag    60

```
cgggtgtcgg tcaacgggca ggaccagggc cagctcaagg gggtgcgggc gccgtcgagc      120
aactccccga tccagaacgt caacgatgcc aacatggcct gcaacgccaa cattgtgtac      180
cacgacagca ccatcatcaa ggtgcccgcg ggagcccgcg tcggcgcgtg gtggcagcac      240
gtcatcggcg gccgcagggc gccaacgac ccggacaacc cgatcgcggc ctcccacaag       300
ggtatgatga tcgatgatgc ctctctcttc ccccgttctt gatggacagg cgatggctcc      360
caggaacacg cgtgactgac caccgaatcc aggccccatc caggtctacc tggccaaggt      420
ggacaacgcg gcgacggcgt cgccgtcggg cctcaggtgg ttcaaggtgg ccgagcgcgg      480
cctgaacaac ggcgtgtggg ccgtcgatga gctcatcgcc aacaacggct ggcactactt      540
cgacctgccg tcgtgcgtgg ccccggcca gtacctgatg cgcgtcgagc tgctcgccct       600
gcacagcgcg tcaagccccg gcggcgccca gttctacatg ggctgcgcac agatcgaagg      660
tgcgtcgatc tttgttctcc ttccgtgtcc tctctgatcc tttctctctt cttttctttt     720
cttttactcc ctttccttcc atcttcggag aagcaacgaa ggggggaaagg gatagaagag    780 aggaatgaga gacgacgaaa gagaggattg gggaaagaca agacagggaa aaaaagacaa      840
gaaaaaaaaa aaaaaaaaaa aacagagtga gctaacaaga acaatcagtc actggctccg     900
gcaccaactc gggctccgac tttgtctcgt tccccggcgc ctactcggcc aacgatccgg     960
gcatcttgct aagcatctac gacagctcgg caagcccac caacggcggg cgctcgtacc      1020
cgatccccgg cccgcgcccc atctcctgct ccggcagcgg cgacggcggc aacaacggcg     1080
gcggcggcga cgacaacaac aataacaacg gtggtggcaa caacgcggc ggcggcggcg       1140 gcagcgtccc cctgtacggg cagtgcggcg gcatcggcta cacgggcccg accacctgtg     1200
cccagggaac ttgcaaggtg tcgaacgaat actacagcca gtgcctcccc tag             1253
```

<210> SEQ ID NO 24
<211> LENGTH: 310
<212> TYPE: PRT
<213> ORGANISM: Myceliophthora thermophila

<400> SEQUENCE: 24

```
Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Ser Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Ser Gly Leu Arg Trp Phe Lys Val Ala Glu
        115                 120                 125

Arg Gly Leu Asn Asn Gly Val Trp Ala Val Asp Glu Leu Ile Ala Asn
    130                 135                 140

Asn Gly Trp His Tyr Phe Asp Leu Pro Ser Cys Val Ala Pro Gly Gln
145                 150                 155                 160
```

Tyr Leu Met Arg Val Glu Leu Leu Ala Leu His Ser Ala Ser Ser Pro
              165                 170                 175

Gly Gly Ala Gln Phe Tyr Met Gly Cys Ala Gln Ile Glu Val Thr Gly
          180                 185                 190

Ser Gly Thr Asn Ser Gly Ser Asp Phe Val Ser Phe Pro Gly Ala Tyr
      195                 200                 205

Ser Ala Asn Asp Pro Gly Ile Leu Leu Ser Ile Tyr Asp Ser Ser Gly
  210                 215                 220

Lys Pro Thr Asn Gly Gly Arg Ser Tyr Pro Ile Pro Gly Pro Arg Pro
225                 230                 235                 240

Ile Ser Cys Ser Gly Ser Gly Asp Gly Asn Asn Gly Gly Gly Gly Gly
              245                 250                 255

Asp Asp Asn Asn Asn Asn Asn Gly Gly Gly Asn Asn Gly Gly Gly Gly
          260                 265                 270

Gly Gly Ser Val Pro Leu Tyr Gly Gln Cys Gly Gly Ile Gly Tyr Thr
      275                 280                 285

Gly Pro Thr Thr Cys Ala Gln Gly Thr Cys Lys Val Ser Asn Glu Tyr
  290                 295                 300

Tyr Ser Gln Cys Leu Pro
305                 310

<210> SEQ ID NO 25
<211> LENGTH: 814
<212> TYPE: DNA
<213> ORGANISM: Myceliophthora thermophila

<400> SEQUENCE: 25
atgaagctct ccctcttctc cgtcctggcc actgccctca ccgtcgaggg gcatgccatc      60
ttccagaagg tctccgtcaa cggagcggac cagggctccc tcaccggcct ccgcgctccc     120
aacaacaaca accccgtgca ggatgtcaac agccaggaca tgatctgcgg ccagtcggga     180
tcgacgtcga acactatcat cgaggtcaag gccggcgata ggatcggtgc ctggtatcag     240
catgtcatcg gcggtgccca gttccccaac gacccagaca cccgattgc caagtcgcac      300
aagggccccg tcatggccta cctcgccaag gttgacaatg ccgcaaccgc cagcaagacg     360
ggcctgaagt ggtatgtatt cccgcggccc gagggacatc gggttgggca agtcgagact     420
gacggagctc gcttctccgt ataggttcaa gatttgggag gatacctta atcccagcac      480
caagacctgg ggtgtcgaca acctcatcaa taacaacggc tgggtgtact caacctccc      540
gcagtgcatc gccgacggca actacctcct ccgcgtcgag gtcctcgctc tgcactcggc     600
ctactctcag ggccaggctc agttctacca gtcctgcgcc cagatcaacg tatccggcgg     660
cggctccttc acaccgccgt cgactgtcag cttcccgggt gcctacagcg ccagcgaccc     720
cggtatcctg atcaacatct acggcgccac cggccagccc gacaacaacg ccagccgta      780
cactgcccct gggcccgcgc ccatctcctg ctga                                  814

<210> SEQ ID NO 26
<211> LENGTH: 246
<212> TYPE: PRT
<213> ORGANISM: Myceliophthora thermophila

<400> SEQUENCE: 26

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asp
        35                  40                  45

Val Asn Ser Gln Asp Met Ile Cys Gly Gln Ser Gly Ser Thr Ser Asn
 50                  55                  60

Thr Ile Ile Glu Val Lys Ala Gly Asp Arg Ile Gly Ala Trp Tyr Gln
 65                  70                  75                  80

His Val Ile Gly Gly Ala Gln Phe Pro Asn Asp Pro Asp Asn Pro Ile
                 85                  90                  95

Ala Lys Ser His Lys Gly Pro Val Met Ala Tyr Leu Ala Lys Val Asp
                100                 105                 110

Asn Ala Ala Thr Ala Ser Lys Thr Gly Leu Lys Trp Phe Lys Ile Trp
                115                 120                 125

Glu Asp Thr Phe Asn Pro Ser Thr Lys Thr Trp Gly Val Asp Asn Leu
130                 135                 140

Ile Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
                180                 185                 190

Val Ser Gly Gly Gly Ser Phe Thr Pro Pro Ser Thr Val Ser Phe Pro
                195                 200                 205

Gly Ala Tyr Ser Ala Ser Asp Pro Gly Ile Leu Ile Asn Ile Tyr Gly
                210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245

<210> SEQ ID NO 27
<211> LENGTH: 1115
<212> TYPE: DNA
<213> ORGANISM: Thermoascus aurantiacus

<400> SEQUENCE: 27

```
atgtcgttct cgaagattgc tgcgatcacc ggggccatta cctatgcgtc tctggccgcc      60
gctcacggtt atgttacagg aatcgtagcc gatggcacct agtatgtaac gctcatgcca     120
agatccgcat tgctgtacta acaattagca gctacggggg ctatatcgtg acccaatacc     180
cctacatgtc gacaccgccg gatgtcatcg cctggtctac caaagcaact gatcttggtt     240
tcgtggatcc cagtagctat gcttcgtctg atattatctg ccacaagggt gctgagcctg     300
gtgccctgag cgccaaggtg gctgctggag ggaccgtcga gctgcagtgg acggattggc     360
ctgagagtca aagggcccg gtcattgact acctcgccgc tgtaacggg gactgctcga     420
ctgtcgacaa gaccaaacta gagttcttca agattgatga gagtggccta attgacggca     480
gcagcgcccc aggcacatgg gcctctgaca acttgattgc caataacaac agctggaccg     540
tcaccatccc gagcacgatt gctcccggca actatgtcct gagacatgaa atcattgccc     600
tccactccgc cggaaataca aatggtgctc agaactaccc ccagtgtatc aaccttgagg     660
tcacaggcag tggcaccgac acccctgccg gcaccctcgg aacggagctt tataaggcaa     720
cggaccctgg cattctggtc aacatctacc agacccctga cagctacgat attcccggcc     780
ctgctctgta caccggtggt agctctggta gctctggttc ctccaacacc gccaaggcca     840
```

```
ccacttcgac ggcttctagc tctatcgtga ccccgacgcc tgttaacaac ccaaccgtta    900
ctcagactgc cgttgttgat gtcacccaga ctgtttccca gaatgctgcc gtcgccacca    960
cgactccggc tccactgca gttgctacag ctgtcccaac gggaaccacc tttagctttg   1020
attcgatgac ctcggatgaa ttcgtcagcc tgatgcgtgc gaccgtgaat tggctgcttt   1080
ctaacaagaa gcatgcccgg gatctttctt actaa                              1115
```

<210> SEQ ID NO 28
<211> LENGTH: 354
<212> TYPE: PRT
<213> ORGANISM: Thermoascus aurantiacus

<400> SEQUENCE: 28

```
Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
            20                  25                  30

Thr Tyr Tyr Gly Gly Tyr Ile Val Thr Gln Tyr Pro Tyr Met Ser Thr
        35                  40                  45

Pro Pro Asp Val Ile Ala Trp Ser Thr Lys Ala Thr Asp Leu Gly Phe
50                  55                  60

Val Asp Pro Ser Ser Tyr Ala Ser Ser Asp Ile Ile Cys His Lys Gly
65                  70                  75                  80

Ala Glu Pro Gly Ala Leu Ser Ala Lys Val Ala Ala Gly Gly Thr Val
                85                  90                  95

Glu Leu Gln Trp Thr Asp Trp Pro Glu Ser His Lys Gly Pro Val Ile
            100                 105                 110

Asp Tyr Leu Ala Ala Cys Asn Gly Asp Cys Ser Thr Val Asp Lys Thr
        115                 120                 125

Lys Leu Glu Phe Phe Lys Ile Asp Glu Ser Gly Leu Ile Asp Gly Ser
130                 135                 140

Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
            180                 185                 190

Ala Gln Asn Tyr Pro Gln Cys Ile Asn Leu Glu Val Thr Gly Ser Gly
        195                 200                 205

Thr Asp Thr Pro Ala Gly Thr Leu Gly Thr Glu Leu Tyr Lys Ala Thr
210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Ser Gly Ser Ser Gly
                245                 250                 255

Ser Ser Asn Thr Ala Lys Ala Thr Ser Thr Ala Ser Ser Ser Ile
            260                 265                 270

Val Thr Pro Thr Pro Val Asn Asn Pro Thr Val Thr Gln Thr Ala Val
        275                 280                 285

Val Asp Val Thr Gln Thr Val Ser Gln Asn Ala Ala Val Ala Thr Thr
290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
```

```
                    325                 330                 335
Ala Thr Val Asn Trp Leu Leu Ser Asn Lys Lys His Ala Arg Asp Leu
                340                 345                 350

Ser Tyr

<210> SEQ ID NO 29
<211> LENGTH: 862
<212> TYPE: DNA
<213> ORGANISM: Aspergillus fumigatus

<400> SEQUENCE: 29
atgactttgt ccaagatcac ttccattgct ggccttctgg cctcagcgtc tctcgtggct    60
ggccacggct ttgtttctgg cattgttgct gatgggaaat agtatgtgct tgaaccacac   120
aaatgacagc tgcaacagct aacttctatt ccagttacgg agggtacctt gttaaccaat   180 accctacat gagcaaccct cccgacacca ttgcctggtc caccaccgcc accgacctcg    240
gctttgtgga cggcaccggc taccagtctc cggatattat ctgccacaga gacgcaaaga   300
atggcaagtt gaccgcaacc gttgcagccg gttcacagat cgaattccag tggacgacgt   360
ggccagagtc tcaccatgga ccggtacgac gccgaagaga agagaacata ttgtgaccag   420
ataggctaac atagcatagt tgattactta cctcgctcca tgcaacggcg actgtgccac   480
cgtggacaag accaccctga gtttgtcaa gatcgccgct caaggcttga tcgacggctc    540
caacccacct ggtgtttggg ctgatgatga atgatcgcc aacaacaaca cggccacagt    600
gaccattcct gcctcctatg cccccggaaa ctacgtcctt cgccacgaga tcatcgccct   660
tcactctgcg ggtaacctga acggcgcgca gaactacccc cagtgtttca acatccaaat   720
caccggtggc ggcagtgctc agggatctgg caccgctggc acgtccctgt acaagaatac   780
tgatcctggc atcaagtttg acatctactc ggatctgagc ggtggatacc ctattcctgg   840
tcctgcactg ttcaacgctt aa                                            862

<210> SEQ ID NO 30
<211> LENGTH: 250
<212> TYPE: PRT
<213> ORGANISM: Aspergillus fumigatus

<400> SEQUENCE: 30

Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
                20                  25                  30

Lys Tyr Tyr Gly Gly Tyr Leu Val Asn Gln Tyr Pro Tyr Met Ser Asn
            35                  40                  45

Pro Pro Asp Thr Ile Ala Trp Ser Thr Thr Ala Thr Asp Leu Gly Phe
        50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140
```

Asn Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250

<210> SEQ ID NO 31
<211> LENGTH: 1021
<212> TYPE: DNA
<213> ORGANISM: Penicillium pinophilum

<400> SEQUENCE: 31
atgccttcta ctaaagtcgc tgcccttcct gctgttctag ctttggcctc cacggttgct        60
ggccatggtt ttgtgcaaaa catcgttatc gacggtaaat cgtaagcagt gatgcatcca       120
ttattaaact agacatgctt acaaaaaaat cagttactct ggataccttg tgaatcagtt       180 ccctacgag tccaacccac cagctgttat gggtgggca acaactgcaa ccgacctggg         240
attcgtcgct cccagtgagt acaccaatgc agacattatc tgccacaaga acgccacacc      300
tggcgcgctt tctgctccag ttgctgcagg gggcactgtc gagctccagt ggactacatg       360
gcccgatagt catcacggtc ctgtcatcag ctacctcgcc aactgcaatg caattgttc        420 taccgtggat aagactaagc tagactttgt caagattgac caaggtggtt tgatcgacga       480
tactaccccc ccgggtacat gggcttccga caaacttatc gctgccaaca cagctggac       540 tgtaactatc ccctccacca tcgcgcctgg aaactacgtt ttgcgccacg aaatcattgc      600
tcttcactcc gctggaaacg cagacggtgc ccaaaactac cctcaatgca tcaacttgga       660
gatcaccggc agcggaaccg ccgctccctc tggtaccgct ggcgaaaagc tctacacctc       720
tactgacccc ggtatcttgg tcaatatcta ccaatccttg tcgacctacg ttattcccgg       780
accaactctg tggagcggtg ctgccaatgg cgctgttgcc actggttctg ctactgcggt      840
tgctacgact gccactgctt ctgcgaccgc tactcctacc acacttgtta cctctgtcgc       900
tccagcttca tctacctttg ccactgctgt tgtgaccact gtcgctcctg cagtaactga       960
tgtcgtgact gtcaccgatg tagttaccgt gaccaccgtc atcaccacta ctgtcctttg      1020
a                                                                     1021

<210> SEQ ID NO 32
<211> LENGTH: 322
<212> TYPE: PRT
<213> ORGANISM: Penicillium pinophilum

<400> SEQUENCE: 32

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

```
Lys Ser Tyr Ser Gly Tyr Leu Val Asn Gln Phe Pro Tyr Glu Ser Asn
             35                  40                  45

Pro Pro Ala Val Ile Gly Trp Ala Thr Thr Ala Thr Asp Leu Gly Phe
 50                  55                  60

Val Ala Pro Ser Glu Tyr Thr Asn Ala Asp Ile Ile Cys His Lys Asn
 65                  70                  75                  80

Ala Thr Pro Gly Ala Leu Ser Ala Pro Val Ala Gly Gly Thr Val
                 85                  90                  95

Glu Leu Gln Trp Thr Thr Trp Pro Asp Ser His His Gly Pro Val Ile
             100                 105                 110

Ser Tyr Leu Ala Asn Cys Asn Gly Asn Cys Ser Thr Val Asp Lys Thr
             115                 120                 125

Lys Leu Asp Phe Val Lys Ile Asp Gln Gly Gly Leu Ile Asp Asp Thr
         130                 135                 140

Thr Pro Pro Gly Thr Trp Ala Ser Asp Lys Leu Ile Ala Ala Asn Asn
145                 150                 155                 160

Ser Trp Thr Val Thr Ile Pro Ser Thr Ile Ala Pro Gly Asn Tyr Val
                     165                 170                 175

Leu Arg His Glu Ile Ile Ala Leu His Ser Ala Gly Asn Ala Asp Gly
             180                 185                 190

Ala Gln Asn Tyr Pro Gln Cys Ile Asn Leu Glu Ile Thr Gly Ser Gly
             195                 200                 205

Thr Ala Ala Pro Ser Gly Thr Ala Gly Glu Lys Leu Tyr Thr Ser Thr
         210                 215                 220

Asp Pro Gly Ile Leu Val Asn Ile Tyr Gln Ser Leu Ser Thr Tyr Val
225                 230                 235                 240

Ile Pro Gly Pro Thr Leu Trp Ser Gly Ala Ala Asn Gly Ala Val Ala
                     245                 250                 255

Thr Gly Ser Ala Thr Ala Val Ala Thr Thr Ala Thr Ala Ser Ala Thr
             260                 265                 270

Ala Thr Pro Thr Thr Leu Val Thr Ser Val Ala Pro Ala Ser Ser Thr
         275                 280                 285

Phe Ala Thr Ala Val Val Thr Val Ala Pro Ala Val Thr Asp Val
290                 295                 300

Val Thr Val Thr Asp Val Val Thr Val Thr Val Ile Thr Thr Thr
305                 310                 315                 320

Val Leu

<210> SEQ ID NO 33
<211> LENGTH: 1486
<212> TYPE: DNA
<213> ORGANISM: Thermoascus sp.

<400> SEQUENCE: 33
atgttgtcgt tcgcttctgc caagtcagct gtgctgacga cccttctact tcttggatcc    60
gctcaggctc acactttgat gaccaccctg tttgtggatg gcgtcaatca gggagatggt   120
gtctgtattc gcatgaacaa caacggtagt actgccaaca cctatatcca gcctgtcacg   180
agcaaggata ttgcctgcgg taagtacagt accggtccag atatcatact ctatttcaat   240
ccgacaacag tcagagctgg agagcaatgc taaacatccc caggcattca aggcgaaatt   300
ggcgccgctc gagtctgtcc agccaaggct tcatccaccc tcacgttcca attccgagag   360
cagccatcca acccgaattc cgctcctctc gatccctcgc acaaaggccc cgctgcggtg   420
```

```
tacctgaaaa aggtagactc cgccatcgcg agcaacaacg ccgctggaga cggctggttc    480
aagatctggg agtccgtcta cgacgagtcc acgggcaaat ggggtacgac caagatgatc    540
gagaacaacg ggcacatctc tgtcaaggtc cccgacgata tcgagggtgg gtattatctc    600
gcgcgtacgg agcttctggc gctgcacgcg gcgaacgaag gggatccgca gttctacgtt    660
ggctgcgcgc agctgttcat cgattcagcg gggacagcga aaccgcctac tgtctctatt    720
ggagagggga cctacgatct gagcatgcct gccatgacgt acaatatcta ccagactccg    780
ttggctctac catacccgat gtatgggcct cctgtctaca cacctggctc tggctcgggt    840
tctggctctg gttccgggtc agcttctgca acgagatctt ctgctattcc tactgccacc    900
gctgttacgg actgttcttc cgaagaggac agggaagact cagtcatggc aaccggtgtt    960
cccgttgcaa gaagcacact cagaacctgg gttgacagac tgtcatggca tggtaaggcc   1020
cgtgagaacg tgaaaccagc cgccaggaga agcgcccttg tccagaccga gggtctgaag   1080
ccggaaggct gcatcttcgt caacggcaac tggtgcggtt tcgaggtccc cgattacaac   1140
gatgcggaaa gctgctgggc tgtacgttcc cgtctaatta cttaaaacga aataaaagct   1200
aacagtactt ttctttttct aatcccaggc ctccgacaac tgctggaaac agtccgactc   1260
gtgctggaac cagacccagc ccaccggcta caacaactgc cagatctggc aagaccagaa   1320
atgcaagccc atccaggact cgtgtagcca atccaacccg actggaccgc gaacaaggg    1380 caaggatata actccaacgt ggccgccccct ggagggctcg atgaagacct tcaccaagcg   1440
cactgtcagt taccgtgatt ggattatgaa aaggaaagga gcataa                  1486
```

<210> SEQ ID NO 34
<211> LENGTH: 444
<212> TYPE: PRT
<213> ORGANISM: Thermoascus sp.

<400> SEQUENCE: 34

```
Met Leu Ser Phe Ala Ser Ala Lys Ser Ala Val Leu Thr Thr Leu Leu
1               5                  10                  15

Leu Leu Gly Ser Ala Gln Ala His Thr Leu Met Thr Thr Leu Phe Val
                20                  25                  30

Asp Gly Val Asn Gln Gly Asp Gly Val Cys Ile Arg Met Asn Asn Asn
            35                  40                  45

Gly Ser Thr Ala Asn Thr Tyr Ile Gln Pro Val Thr Ser Lys Asp Ile
        50                  55                  60

Ala Cys Gly Ile Gln Gly Glu Ile Gly Ala Ala Arg Val Cys Pro Ala
65                  70                  75                  80

Lys Ala Ser Ser Thr Leu Thr Phe Gln Phe Arg Glu Gln Pro Ser Asn
                85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Gly Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190
```

Gly Cys Ala Gln Leu Phe Ile Asp Ser Ala Gly Thr Ala Lys Pro Pro
            195                 200                 205

Thr Val Ser Ile Gly Glu Gly Thr Tyr Asp Leu Ser Met Pro Ala Met
        210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
            275                 280                 285

Ala Thr Gly Val Pro Val Ala Arg Ser Thr Leu Arg Thr Trp Val Asp
        290                 295                 300

Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
                325                 330                 335

Ile Phe Val Asn Gly Asn Trp Cys Gly Phe Glu Val Pro Asp Tyr Asn
            340                 345                 350

Asp Ala Glu Ser Cys Trp Ala Ala Ser Asp Asn Cys Trp Lys Gln Ser
            355                 360                 365

Asp Ser Cys Trp Asn Gln Thr Gln Pro Thr Gly Tyr Asn Asn Cys Gln
        370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
            420                 425                 430

Ser Tyr Arg Asp Trp Ile Met Lys Arg Lys Gly Ala
        435                 440

<210> SEQ ID NO 35
<211> LENGTH: 835
<212> TYPE: DNA
<213> ORGANISM: Penicillium sp.

<400> SEQUENCE: 35
atgctgtctt cgacgactcg caccctcgcc tttacaggcc ttgcgggcct tctgtccgct      60
cccctggtca aggcccatgg ctttgtccag ggcattgtca tcggtgacca attgtaagtc     120
cctctcttgc agttctgtcg attaactgct ggactgcttg cttgactccc tgctgactcc     180
caacagctac agcgggtaca tcgtcaactc gttcccctac gaatccaacc cacccccgt      240 catcggctgg ccacgaccg ccaccgacct gggcttcgtc gacggcacag gataccaagg      300
cccggacatc atctgccacc ggaatgcgac gcccgcgccg ctgacagccc ccgtggccgc     360
cggcggcacc gtcgagctgc agtggacgcc gtggccggac agccaccacg gacccgtcat     420
cacctacctg gcgccgtgca acggcaactg ctcgaccgtc gacaagacga cgctggagtt     480
cttcaagatc gaccagcagg gcctgatcga cgacacgagc ccgccgggca cctgggcgtc     540
ggacaacctc atcgccaaca caatagctg accgtcacc attcccaaca gcgtcgcccc      600
cggcaactac gtcctgcgcc acgagatcat cgccctgcac tcggccaaca acaaggacgg     660

```
cgcccagaac tacccccagt gcatcaacat cgaggtcacg ggcggcggct ccgacgcgcc      720
tgagggtact ctgggcgagg atctctacca tgacaccgac ccgggcattc tggtcgacat      780
ttacgagccc attgcgacgt ataccattcc ggggccgcct gagccgacgt tctag           835
```

<210> SEQ ID NO 36
<211> LENGTH: 253
<212> TYPE: PRT
<213> ORGANISM: Penicillium sp.

<400> SEQUENCE: 36

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 37
<211> LENGTH: 878
<212> TYPE: DNA
<213> ORGANISM: Thielavia terrestris

<400> SEQUENCE: 37

```
atgaagttct cactggtgtc tctgctggct tacggcctct cggtcgaggc gcactccatc       60
ttccaggttc gtctcgcaca tcacgctcaa ctcggctcgt ggcgtaaggg caaggattaa      120
cacggccggc agagagtctc ggtcaacggc caagaccaag gcctgctcac cggcctccgc      180
gctccaagca acaacaaccc agtgcaagat gtcaacagcc agaacatgat ttgcggccag      240
tcgggctcca gtcgcagacc gttatcaacg tcaaggccg gcgacaggat cggctcgctc      300
```

```
tggcagcatg tcatcggcgg cgcccagttt tcgggtgacc cggacaaccc gatcgcccac    360
tcgcacaagg gccccgtgat ggcgtacctt gctaaggtcg acaatgccgc gtccgcgagc    420
caaacgggtc tgaagtggta agtagcgggc gacgctcagg ggacggggat cgggggcctg    480
ctccatccga gactaacacc gtggacaggt caagatctg gcaggacggg ttcgatacca     540
gcagcaagac atggggcgtc gacaacctga tcaagaacaa cggctgggtg tacttccacc    600
tgccgcagtg cctcgctccg ggccagtatc tcctgcgcgt cgaggttctg gcgctgcact    660
cggcgtacca gcagggccag gcccagttct accagtcctg cgcccagatc aacgtctccg    720
gctccgggtc cttcagcccg tcccagacgg tcagcatccc gggcgtctac agcgccaccg    780
acccgagcat cctcatcaac atctacggca gcacggggca gcccgacaac ggcggcaagg    840
cttacaaccc ccctggaccc gccccgatct cctgctga                            878
```

<210> SEQ ID NO 38
<211> LENGTH: 246
<212> TYPE: PRT
<213> ORGANISM: Thielavia terrestris

<400> SEQUENCE: 38

```
Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
            20                  25                  30

Leu Leu Thr Gly Leu Arg Ala Pro Ser Asn Asn Pro Val Gln Asp
        35                  40                  45

Val Asn Ser Gln Asn Met Ile Cys Gly Gln Ser Gly Ser Lys Ser Gln
50                  55                  60

Thr Val Ile Asn Val Lys Ala Gly Asp Arg Ile Gly Ser Leu Trp Gln
65                  70                  75                  80

His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
            100                 105                 110

Asn Ala Ala Ser Ala Ser Gln Thr Gly Leu Lys Trp Phe Lys Ile Trp
        115                 120                 125

Gln Asp Gly Phe Asp Thr Ser Ser Lys Thr Trp Gly Val Asp Asn Leu
130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
            180                 185                 190

Val Ser Gly Ser Gly Ser Phe Ser Pro Ser Gln Thr Val Ser Ile Pro
        195                 200                 205

Gly Val Tyr Ser Ala Thr Asp Pro Ser Ile Leu Ile Asn Ile Tyr Gly
210                 215                 220

Ser Thr Gly Gln Pro Asp Asn Gly Gly Lys Ala Tyr Asn Pro Pro Gly
225                 230                 235                 240

Pro Ala Pro Ile Ser Cys
            245
```

<210> SEQ ID NO 39

<211> LENGTH: 1253
<212> TYPE: DNA
<213> ORGANISM: Thielavia terrestris

<400> SEQUENCE: 39

```
atgaggacga cattcgccgc cgcgttggca gccttcgctg cgcaggaagt ggcaggccat      60
gccatcttcc aacagctctg ggtggacggc accgactata tacgtgctcc ccttttcctt     120
ttgtgtttgc ccatcctcga ttgataaccc gaggccatcc aatgctgact cttacagcac     180
ggctcctcct gcgtccgcat gccgctgtcg aactcgcccg tcacgaacgt cggcagcagg     240
gacatgatct gcaacgccgg cacgcgcccc gtcagcggga agtgcccgt caaggccggc      300
ggcaccgtga cggttgagat gcaccaggtg ggctgatttc ctgagcgtcc tattcctccc     360
ggaagcccct ttcccatcct ttgccctggc taaccccctc c gccctccca gcaacccggg    420
gatcggtcgt gtaacaacga agccatcggc ggcgcccact ggggaccggt gcaggtgtac     480
ctcagcaagg tggaggacgc gagcacggcg gacgggtcga cgggctggtt caagatcttc     540
gcggacacgt ggtccaagaa ggcgggcagc tcggtggggg acgacgacaa ctggggcacg     600
cgcgacctca cgcgtgctg cggcaagatg caggtcaaga tcccggcgga catcccgtcg      660
ggcgactacc tgctgcgggc ggaggcgctg gcgctgcaca cggcgggcca ggtgggcggc     720
gcgcagttct acatgagctg ctaccagatc accgtgtcgg gcggcggcag cgccagcccg     780
gccaccgtca agttccccgg cgcctacagc gccaacgacc cgggcatcca catcaacatc     840
cacgcggccg tgtccaacta cgtcgcgccc ggcccggccg tctattccgg cggcacgacc     900
aaggtggccg gtccgggtg ccaaggctgc gagaacacgt gcaaggtcgg ctcgtcgccc      960
acggcgacgg cgccgtcggg caagagcggc gcgggttccg acggcggcgc tgggaccgac    1020
ggcgggtctt cgtcttcgag ccccgacacg ggcagcgcgt gcagcgtgca ggcctacggg    1080
cagtgcggcg ggaacgggta ctcgggttgc acccagtgcg cggtaagttc ggggtcgtct    1140
gtcttttgta ggaacatccg agaggcttgg ctgacgaggc gttgttgtag cccggctata    1200
cttgcaaggc ggtctctccg ccgtactatt cgcagtgcgc ccttcttct tag            1253
```

<210> SEQ ID NO 40
<211> LENGTH: 334
<212> TYPE: PRT
<213> ORGANISM: Thielavia terrestris

<400> SEQUENCE: 40

```
Met Arg Thr Thr Phe Ala Ala Ala Leu Ala Ala Phe Ala Ala Gln Glu
  1               5                  10                  15

Val Ala Gly His Ala Ile Phe Gln Gln Leu Trp His Gly Ser Ser Cys
             20                  25                  30

Val Arg Met Pro Leu Ser Asn Ser Pro Val Thr Asn Val Gly Ser Arg
         35                  40                  45

Asp Met Ile Cys Asn Ala Gly Thr Arg Pro Val Ser Gly Lys Cys Pro
     50                  55                  60

Val Lys Ala Gly Gly Thr Val Thr Val Glu Met His Gln Gln Pro Gly
 65                  70                  75                  80

Asp Arg Ser Cys Asn Asn Glu Ala Ile Gly Gly Ala His Trp Gly Pro
             85                  90                  95

Val Gln Val Tyr Leu Ser Lys Val Glu Asp Ala Ser Thr Ala Asp Gly
        100                 105                 110

Ser Thr Gly Trp Phe Lys Ile Phe Ala Asp Thr Trp Ser Lys Lys Ala
        115                 120                 125
```

Gly Ser Ser Val Gly Asp Asp Asn Trp Gly Thr Arg Asp Leu Asn
    130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
        195                 200                 205

Tyr Ser Ala Asn Asp Pro Gly Ile His Ile Asn Ile His Ala Ala Val
    210                 215                 220

Ser Asn Tyr Val Ala Pro Gly Pro Ala Val Tyr Ser Gly Gly Thr Thr
225                 230                 235                 240

Lys Val Ala Gly Ser Gly Cys Gln Gly Cys Glu Asn Thr Cys Lys Val
                245                 250                 255

Gly Ser Ser Pro Thr Ala Thr Ala Pro Ser Gly Lys Ser Gly Ala Gly
                260                 265                 270

Ser Asp Gly Gly Ala Gly Thr Asp Gly Gly Ser Ser Ser Ser Pro
            275                 280                 285

Asp Thr Gly Ser Ala Cys Ser Val Gln Ala Tyr Gly Gln Cys Gly Gly
    290                 295                 300

Asn Gly Tyr Ser Gly Cys Thr Gln Cys Ala Pro Gly Tyr Thr Cys Lys
305                 310                 315                 320

Ala Val Ser Pro Pro Tyr Tyr Ser Gln Cys Ala Pro Ser Ser
                325                 330

<210> SEQ ID NO 41
<211> LENGTH: 798
<212> TYPE: DNA
<213> ORGANISM: Thielavia terrestris

<400> SEQUENCE: 41

| | | | | | |
|---|---|---|---|---|---|
| atgaagctga | gcgttgccat | cgccgtgctg | gcgtcggctc | ttgccgaggc | tcactgtgag | 60 |
| tgcatcgtct | cactccagct | actgcgaagc | ttgctgacga | tggtccctag | acaccttccc | 120 |
| cagcatcgga | aacaccgctg | actggcagta | tgtgcggatt | acaacgaact | accagagcaa | 180 |
| cgggccggtg | acggacgtca | cctcggatca | aattcggtgc | tacgaacgga | acccaggcac | 240 |
| gggagcgcag | ggcatataca | acgtcaccgc | cggccagacc | atcaactaca | cgcgaaggc | 300 |
| gtccatctcc | cacccggggc | ccatgtcctt | ctacattgct | aaggttcccg | ccggccaaac | 360 |
| cgctgcgacc | tgggacggta | aggggctgt | gtggaccaag | atctaccagg | acatgcccaa | 420 |
| gttcggcagc | agcctgacct | ggcccaccat | gggtaagaat | tctcaccctg | gaaatgaacg | 480 |
| cacatttgca | cagatctaac | atggcctaca | ggcgccaagt | ctgtcccgt | caccatccct | 540 |
| cgttgcctcc | agaacggcga | ttaccttctg | cgagccgagc | acatcgctct | acacagcgcg | 600 |
| agcagcgtcg | gtggcgccca | gttctacctc | tcgtgcgccc | agcttactgt | cagcggcggc | 660 |
| agtggcacct | ggaaccccaa | gaaccgggtc | tccttccccg | cgcgttacaa | ggcaacagac | 720 |
| ccgggcatct | tgatcaacat | ctactacccc | gtgccgacca | gctactcgcc | gcccggcccg | 780 |
| ccggctgaga | cgtgctaa | | | | | 798 |

<210> SEQ ID NO 42
<211> LENGTH: 227

<212> TYPE: PRT
<213> ORGANISM: Thielavia terrestris

<400> SEQUENCE: 42

Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
            20                  25                  30

Val Arg Ile Thr Thr Asn Tyr Gln Ser Asn Gly Pro Val Thr Asp Val
        35                  40                  45

Thr Ser Asp Gln Ile Arg Cys Tyr Glu Arg Asn Pro Gly Thr Gly Ala
    50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
        115                 120                 125

Trp Pro Thr Met Gly Ala Lys Ser Val Pro Val Thr Ile Pro Arg Cys
    130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
                165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
        195                 200                 205

Ile Tyr Tyr Pro Val Pro Thr Ser Tyr Ser Pro Pro Gly Pro Pro Ala
    210                 215                 220

Glu Thr Cys
225

<210> SEQ ID NO 43
<211> LENGTH: 977
<212> TYPE: DNA
<213> ORGANISM: Thielavia terrestris

<400> SEQUENCE: 43
atgaagctgt catcccagct cgccgccctc acgctggccg cggcctccgt gtcaggccac      60
tacatcttcg agcagattgc ccatggcggc accaagttcc cacccttacga gtacatccga     120 agaaacacga actataacag ccctgtcacc agtctctcgt cgaacgacct gcgatgcaac     180
gtaggcggcg agacggctgg caacacgacc gtcctgacg tgaaggcggg cgactccttc      240
accttctact cggacgtggc cgtgtaccac caggggccca tctcactgtg cgtgccccgg      300
gccaactttg atcagtccca agcggactgt ccgctcgcct ggataaccac aattgactga     360
cagcccgcac agctacatgt ccaaggcctc cggctccgtc gtggactacg acggctccgg     420
cgactggttc aagatccacg actggggccc gaccttcagc aacggccagg cctcgtggcc      480
gctgcggggt gcgtccctc cctttccctc cccttcctc ccccttcctc ccccccttc        540 ccccctttc tgtctggtcg cacgccctgc tgacgtcccc gtagacaact accagtacaa      600
catcccgacg tgcatcccga acggcgagta cctgctgcgc atccagtcgc tggcgatcca    660

```
caacccgggc gccacgccgc agttctacat cagctgcgcg caggtccggg tctcggcgg    720 cggcagcgcc tcccctccc caacggccaa gatccccggc gcgttcaagg cgaccgatcc    780
cgggtatacc gcgaatgtga gtgccctatg ttccttgcgc tccttgttcc ttgctccttg    840
ctcggcgtgc ttgaacgcta cgggctgtgg agggagggat ggatggatga ataggatgct    900
gactgatggt gggacaccag atttacaata acttccactc gtatacggtg ccgggtccgg    960
cggtctttca gtgctag                                                   977
```

<210> SEQ ID NO 44
<211> LENGTH: 223
<212> TYPE: PRT
<213> ORGANISM: Thielavia terrestris

<400> SEQUENCE: 44

```
Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
        35                  40                  45

Val Thr Ser Leu Ser Ser Asn Asp Leu Arg Cys Asn Val Gly Gly Glu
    50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125

Ala Ser Trp Pro Leu Arg Asp Asn Tyr Gln Tyr Asn Ile Pro Thr Cys
    130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
                165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
        195                 200                 205

Asn Phe His Ser Tyr Thr Val Pro Gly Pro Ala Val Phe Gln Cys
    210                 215                 220
```

<210> SEQ ID NO 45
<211> LENGTH: 1107
<212> TYPE: DNA
<213> ORGANISM: Thielavia terrestris

<400> SEQUENCE: 45

```
atgccttctt tcgcctccaa gactctcctt tccaccctgg cgggtgccgc atccgtggcc    60
gcccacgggc acgtgtcgaa catcgtcatc aacggggtct cgtaccaggg ttacgatccg    120
acctccttcc cttacatgca gaacccgccc atcgtggtcg gctggactgc cgccgacacg    180
gacaacggct tgttgccccc ggatgccttc gccagtggcg atatcatctg ccacaagaac    240
```

-continued

```
gccaccaacg ccaagggcca cgccgtggtc gccgcgggag acaagatctt catccagtgg    300
aacacatggc ccgagtccca ccacggcccc gtcatcgact acctcgcgag ctgcggcagc    360
gcgtcctgcg agaccgtcga caagaccaag ctcgagttct tcaagatcga cgaggtcggc    420
ctggtcgacg gcagctcggc gcccggtgtg tggggctccg accagctcat cgccaacaac    480
aactcgtggc tcgtcgagat cccgcccacc atcgcgccgg gcaactacgt cctgcgccac    540
gagatcatcg cgctgcacag cgccgaaaac gccgacggcg cccagaacta cccgcagtgc    600
ttcaacctgc agatcaccgg caccggcacc gccacccct ccggcgtccc cggcacctcg    660
ctctacaccc cgaccgaccc gggcatcctc gtcaacatct acagcgcccc gatcacctac    720
accgtcccgg ggccggccct catctccggc gccgtcagca tcgcccagtc ctcctccgcc    780
atcaccgcct ccggcaccgc cctgaccggc tctgccaccg cacccgccgc cgccgctgct    840
accacaactt ccaccaccaa cgccgcggct gctgctacct ctgctgctgc tgctgctggt    900
acttccacaa ccaccaccag cgccgcggcc gtggtccaga cctcctcctc ctcctcctcc    960
gccccgtcct ctgccgccgc cgccgccacc accaccgcgg ctgccagcgc ccgcccgacc    1020
ggctgctcct ctggccgctc caggaagcag ccgcgccgcc acgcgcggga tatggtggtt    1080
gcgcgagggg ctgaggaggc aaactga    1107
```

<210> SEQ ID NO 46
<211> LENGTH: 368
<212> TYPE: PRT
<213> ORGANISM: Thielavia terrestris

<400> SEQUENCE: 46

```
Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30

Val Ser Tyr Gln Gly Tyr Asp Pro Thr Ser Phe Pro Tyr Met Gln Asn
        35                  40                  45

Pro Pro Ile Val Val Gly Trp Thr Ala Ala Asp Thr Asp Asn Gly Phe
    50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Gly Asp Lys Ile
            85                  90                  95

Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
        115                 120                 125

Thr Lys Leu Glu Phe Phe Lys Ile Asp Glu Val Gly Leu Val Asp Gly
    130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
        195                 200                 205

Gly Thr Ala Thr Pro Ser Gly Val Pro Gly Thr Ser Leu Tyr Thr Pro
    210                 215                 220
```

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
            245                 250                 255

Ser Ser Ser Ala Ile Thr Ala Ser Gly Thr Ala Leu Thr Gly Ser Ala
        260                 265                 270

Thr Ala Pro Ala Ala Ala Ala Thr Thr Ser Thr Thr Asn Ala
    275                 280                 285

Ala Ala Ala Ala Thr Ser Ala Ala Ala Ala Gly Thr Ser Thr Thr
    290                 295                 300

Thr Thr Ser Ala Ala Ala Val Val Gln Thr Ser Ser Ser Ser Ser Ser
305                 310                 315                 320

Ala Pro Ser Ser Ala Ala Ala Ala Thr Thr Thr Ala Ala Ala Ser
            325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
            355                 360                 365

<210> SEQ ID NO 47
<211> LENGTH: 993
<212> TYPE: DNA
<213> ORGANISM: Thielavia terrestris

<400> SEQUENCE: 47
atgccgcccg cactccctca actcctaacc acggtcctga ccgccctcac cctcggttcc    60
accgccctcg cccactcaca cctcgcgtac attatcgtta acggcaagct ctaccagggc   120
ttcgacccgc gcccgcacca ggccaactac ccttcccggg tcgggtggtc caccggcgcc   180
gtcgacgacg gcttcgtcac gccggccaac tactccaccc cggacatcat tgccacatc    240 gccggcacca gccggccgg ccacgcgccc gtgcgcccgg gcgaccgcat ccacgtccag    300
tggaacggct ggccggtcgg ccacatcggt cccgtgctgt cgtacctcgc ccgctgcgag   360
tcggacacgg gctgcacggg ccagaacaag accgcgctgc ggtggaccaa gatcgacgac   420
tccagcccga ccatgcagaa cgtcgccggc gcgggcaccc agggcgaggg caccccggc    480 aagcgctggg ccaccgacgt gctgatcgcc gccaacaaca gctggcaggt cgccgtgccg   540
gcggggctgc cgaccggcgc gtacgtgctg cgcaacgaga tcatcgcgct gcactacgcg   600
gcgaggaaga acggggcgca gaactatccg ctctgcatga acctgtgggt ggacgccagt   660
ggtgataata gtagtgtggc tgcaacgacg gcggcggtga cggcgggggg tctgcagatg   720
gatgcgtatg acgcgcgcgg gttctacaag gagaacgatc cgggcgtgct ggtcaatgtc   780
acggccgcgc tgtcgtcgta tgtcgtgccc gggccgacgg tggcggcggg cgccacgccg   840
gtgccgtacg cgcagcagag cccgagcgtg tcgacggcgg cgggcacgcc cgtcgtcgtt   900
acaaggacta gcgagacggc gccgtacacg ggcgccatga cgccgacggt tgcggcgagg   960
atgaagggga gggggtatga tcggcggggt tag                              993

<210> SEQ ID NO 48
<211> LENGTH: 330
<212> TYPE: PRT
<213> ORGANISM: Thielavia terrestris

<400> SEQUENCE: 48

Met Pro Pro Ala Leu Pro Gln Leu Leu Thr Thr Val Leu Thr Ala Leu

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   | 10 |   |   |   |   | 15 |   |
| Thr | Leu | Gly | Ser | Thr | Ala | Leu | Ala | His | Ser | His | Leu | Ala | Tyr | Ile | Ile |
|   |   |   | 20 |   |   |   |   | 25 |   |   |   |   | 30 |   |   |
| Val | Asn | Gly | Lys | Leu | Tyr | Gln | Gly | Phe | Asp | Pro | Arg | Pro | His | Gln | Ala |
|   |   | 35 |   |   |   |   | 40 |   |   |   |   | 45 |   |   |   |
| Asn | Tyr | Pro | Ser | Arg | Val | Gly | Trp | Ser | Thr | Gly | Ala | Val | Asp | Asp | Gly |
|   | 50 |   |   |   |   | 55 |   |   |   |   | 60 |   |   |   |   |
| Phe | Val | Thr | Pro | Ala | Asn | Tyr | Ser | Thr | Pro | Asp | Ile | Ile | Cys | His | Ile |
| 65 |   |   |   |   | 70 |   |   |   |   | 75 |   |   |   |   | 80 |
| Ala | Gly | Thr | Ser | Pro | Ala | Gly | His | Ala | Pro | Val | Arg | Pro | Gly | Asp | Arg |
|   |   |   |   | 85 |   |   |   |   | 90 |   |   |   |   | 95 |   |
| Ile | His | Val | Gln | Trp | Asn | Gly | Trp | Pro | Val | Gly | His | Ile | Gly | Pro | Val |
|   |   |   | 100 |   |   |   |   | 105 |   |   |   |   | 110 |   |   |
| Leu | Ser | Tyr | Leu | Ala | Arg | Cys | Glu | Ser | Asp | Thr | Gly | Cys | Thr | Gly | Gln |
|   |   | 115 |   |   |   |   | 120 |   |   |   |   | 125 |   |   |   |
| Asn | Lys | Thr | Ala | Leu | Arg | Trp | Thr | Lys | Ile | Asp | Asp | Ser | Ser | Pro | Thr |
|   | 130 |   |   |   |   | 135 |   |   |   |   | 140 |   |   |   |   |
| Met | Gln | Asn | Val | Ala | Gly | Ala | Gly | Thr | Gln | Gly | Glu | Gly | Thr | Pro | Gly |
| 145 |   |   |   |   | 150 |   |   |   |   | 155 |   |   |   |   | 160 |
| Lys | Arg | Trp | Ala | Thr | Asp | Val | Leu | Ile | Ala | Ala | Asn | Asn | Ser | Trp | Gln |
|   |   |   |   | 165 |   |   |   |   | 170 |   |   |   |   | 175 |   |
| Val | Ala | Val | Pro | Ala | Gly | Leu | Pro | Thr | Gly | Ala | Tyr | Val | Leu | Arg | Asn |
|   |   |   | 180 |   |   |   |   | 185 |   |   |   |   | 190 |   |   |
| Glu | Ile | Ile | Ala | Leu | His | Tyr | Ala | Ala | Arg | Lys | Asn | Gly | Ala | Gln | Asn |
|   |   |   | 195 |   |   |   |   | 200 |   |   |   |   | 205 |   |   |
| Tyr | Pro | Leu | Cys | Met | Asn | Leu | Trp | Val | Asp | Ala | Ser | Gly | Asp | Asn | Ser |
|   | 210 |   |   |   |   | 215 |   |   |   |   | 220 |   |   |   |   |
| Ser | Val | Ala | Ala | Thr | Thr | Ala | Val | Thr | Ala | Gly | Gly | Leu | Gln | Met | |
| 225 |   |   |   |   | 230 |   |   |   |   | 235 |   |   |   |   | 240 |
| Asp | Ala | Tyr | Asp | Ala | Arg | Gly | Phe | Tyr | Lys | Glu | Asn | Asp | Pro | Gly | Val |
|   |   |   |   | 245 |   |   |   |   | 250 |   |   |   |   | 255 |   |
| Leu | Val | Asn | Val | Thr | Ala | Ala | Leu | Ser | Ser | Tyr | Val | Val | Pro | Gly | Pro |
|   |   |   | 260 |   |   |   |   | 265 |   |   |   |   | 270 |   |   |
| Thr | Val | Ala | Ala | Gly | Ala | Thr | Pro | Val | Pro | Tyr | Ala | Gln | Gln | Ser | Pro |
|   |   | 275 |   |   |   |   | 280 |   |   |   |   | 285 |   |   |   |
| Ser | Val | Ser | Thr | Ala | Ala | Gly | Thr | Pro | Val | Val | Thr | Arg | Thr | Ser | |
|   | 290 |   |   |   |   | 295 |   |   |   |   | 300 |   |   |   |   |
| Glu | Thr | Ala | Pro | Tyr | Thr | Gly | Ala | Met | Thr | Pro | Thr | Val | Ala | Ala | Arg |
| 305 |   |   |   |   | 310 |   |   |   |   | 315 |   |   |   |   | 320 |
| Met | Lys | Gly | Arg | Gly | Tyr | Asp | Arg | Arg | Gly | | | | | | |
|   |   |   |   | 325 |   |   |   |   | 330 |   |   |   |   |   |   |

<210> SEQ ID NO 49
<211> LENGTH: 1221
<212> TYPE: DNA
<213> ORGANISM: Thielavia terrestris

<400> SEQUENCE: 49

```
atgaagacat tcaccgccct cctggccgca gccggcctcg tcgccggcca tggatatgtc      60
gacaacgcca ccattggcgg ccagtttat caggtactct accgcttcac ccaaggtccg      120
ctggccacaa ctctataggt gtcataaatt aacaagccac cgtcccgcag ttctatcagg      180
tgtgctcgct accgaccatg tggtcccgtc tcagcaagcc actcacacgc ccatgatccc      240
ctagccttac gtcgacccgt atttagcaac cttggcacgt agtatttatt gtcccaaata      300
```

```
ttgagctgaa ctgcacctcc ctagaatccc gcggtgctaa cattctttca gcccgacagg    360
gtctctcgat ccatcccggg caacggcccg gtcacggacg tcactctcat cgacctgcag    420
tgcaacgcca attccacccc ggccaagctc cacgccactg ccgctgccgg ctcggacgtg    480
attctccgct ggacgctctg gcctgagtcg cacgttggcc ccgtcatcac ctacatggcc    540
cgctgccccg acacgggctg ccaggactgg atgccgggca cttcgtagga gcccatcttg    600
caccatatcc atttcaaccg ccacacgca ctgacccata tgtctgtcta cccctgcagt    660
gcggtctggt tcaagatcaa ggagggcggc cgcgacggca cttccaacac ctgggccgac    720
gtacgtgtac cccgtcccag agagccaaag ccccccttc aacaaagcaa acatctcaat     780
agcccgagcc tacgcactaa cccctctcct tcccctcga aaacacagac cccgctgatg      840
acggcgccca cctcgtacac gtacacgatc ccctcctgcc tgaagaaggg ctactacctg    900
gtccgccacg agatcatcgc gctgcacgcc gcctacacct accccggcgc gcagttctac    960
ccgggctgcc accagctcaa cgtcacgggc ggcgggtcca ccgtaccgtc gagcggcctg   1020
gtggcctttc ccggggcgta caagggcagt gaccccggga ttacgtacga tgcgtataaa   1080
ggtgggttgg ctggttggcc caggtcttgg tgatggggga atgtggtgat gaggtttatt   1140
atttgggatc ccgtggctaa cgtaaccctg ggtgtagcgc aaacgtacca gattcctggg   1200
ccggcggtct ttacttgctg a                                              1221
```

<210> SEQ ID NO 50
<211> LENGTH: 236
<212> TYPE: PRT
<213> ORGANISM: Thielavia terrestris

<400> SEQUENCE: 50

```
Met Lys Thr Phe Thr Ala Leu Leu Ala Ala Ala Gly Leu Val Ala Gly
1               5                   10                  15

His Gly Tyr Val Asp Asn Ala Thr Ile Gly Gly Gln Phe Tyr Gln Asn
            20                  25                  30

Pro Ala Val Leu Thr Phe Phe Gln Pro Asp Arg Val Ser Arg Ser Ile
        35                  40                  45

Pro Gly Asn Gly Pro Val Thr Asp Val Thr Leu Ile Asp Leu Gln Cys
    50                  55                  60

Asn Ala Asn Ser Thr Pro Ala Lys Leu His Ala Thr Ala Ala Gly
65                  70                  75                  80

Ser Asp Val Ile Leu Arg Trp Thr Leu Trp Pro Glu Ser His Val Gly
                85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
        195                 200                 205
```

Tyr Lys Gly Ser Asp Pro Gly Ile Thr Tyr Asp Ala Tyr Lys Ala Gln
    210                 215                 220

Thr Tyr Gln Ile Pro Gly Pro Ala Val Phe Thr Cys
225                 230                 235

<210> SEQ ID NO 51
<211> LENGTH: 933
<212> TYPE: DNA
<213> ORGANISM: Thielavia terrestris

<400> SEQUENCE: 51

```
atggccttgc tgctcttggc aggcttggcc attctggccg gccggctca tgcccacggc      60
ggcctcgcca actacacagt gggcaacacc tggtataggg ggtgcgtaag gggggcaccg     120
acaacgcctg cttagtaact ccaccatttc gagcgggcta acaccgggcg cagctacgac     180
cccttcacgc cggcggccga ccagatcggc cagccgtgga tgatccaacg cgcgtgggac     240
tcgatcgacc cgatcttcag cgtcaacgac aaggcgctcg cctgcaacac cccggccacg     300
gcgccgacct cttacattcc catccgcgcg ggcgagaaca tcacggccgt gtactggtac     360
tggctgcacc cggtgggccc catgacggcg tggctggcgc ggtgcgacgg cgactgccgc     420
gacgccgacg tcaacgaggc gcgctggttc aagatctggg aggccggcct gctcagcggg     480
ccgaacctgg ccgagggcat gtggtaccag aaggcgttcc agaactggga cggcagcccg     540
gacctgtggc ccgtcacgat cccggccggg ctgaagagcg cctgtacat gatccggcac      600
gagatcttgt cgatccacgt cgaggataaa ccgcagtttt atcccgagtg tgcgcatctg     660
aatgtgaccg ggggtgggga cctgctgccg cctgatgagt ttttggtgaa gttcccgggc     720
gcttacaaag aagatagtga gtgaaacgcg aagcttcggt agccattggg ttgcgctgat     780
ggaggttaga cccgtcgatc aagatcaata tctactcgga ccagtacgcc aatacaacgg     840
tgagtgtaac aggtcgagca aaccaaaca  gatgccgatg actgatgatc tcagaattac     900
acaattcccg gagggccgat atgggatggg tga                                  933
```

<210> SEQ ID NO 52
<211> LENGTH: 250
<212> TYPE: PRT
<213> ORGANISM: Thielavia terrestris

<400> SEQUENCE: 52

Met Ala Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
            20                  25                  30

Arg Gly Tyr Asp Pro Phe Thr Pro Ala Ala Asp Gln Ile Gly Gln Pro
        35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

Tyr Ile Pro Ile Arg Ala Gly Glu Asn Ile Thr Ala Val Tyr Trp Tyr
                85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
        115                 120                 125

Trp Glu Ala Gly Leu Leu Ser Gly Pro Asn Leu Ala Glu Gly Met Trp
    130                 135                 140

Tyr Gln Lys Ala Phe Gln Asn Trp Asp Gly Ser Pro Asp Leu Trp Pro
145                 150                 155                 160

Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
                180                 185                 190

Cys Ala His Leu Asn Val Thr Gly Gly Gly Asp Leu Leu Pro Pro Asp
                195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250

<210> SEQ ID NO 53
<211> LENGTH: 1584
<212> TYPE: DNA
<213> ORGANISM: Thielavia terrestris

<400> SEQUENCE: 53

```
atgatgccgt cccttgttcg cttctcaatg ggtctggcga ccgccttcgc ctcgctgtcc    60
acagcacata ccgtcttcac cacgcttttc atcaacggcg tcgaccaagg ggacgggacc   120
tgcatccgca tggccaagaa gggcagcgtt gcacccatc ccattgctgg tggcctcgac   180
agcccagaca tggcttgtgg tatgccctct gcgtttcccc tgcgagagct tcctcgagc   240 taacccaatg ccgcgttgcc caggccgaga cggacaacaa gccgtggcat tcacctgccc   300
agccccggcg ggctccaagt tgagcttcga gttccgcatg tgggccgacg cctctcagcc   360
cggctctatc gacccatccc acctcggctc gacggcaatc tacctcaaac aagtctccaa   420
catcagctcc gactcggctg ccggccctgg ctggttcaag atctacgccg agggctacga   480
cacagccgcc aagaagtggg ccacagagaa gctcatcgac aacggcgcc tgctgagcat   540 cgagcttccg cccactctgc cggcgggata ctacctcgcc cgcagcgaga tcgtcaccat   600
ccagaacgtc accaacgacc acgtcgaccc gcagttctac gttggctgcg cacagctctt   660
cgtccagggg cctccgacca cccccaccgt cccgccagac agactcgtct ccatcccggg   720
ccacgtccat gcctccgacc cggggctgac cttcaacatc tggcgcgacg accctccaa   780 gacggcctac accgtcgtcg gcccggcccc cttctccccc accgccgccc ccaccccac   840 ctccaccaac accaacgggc agcaacaaca caacagcaa caggcgataa agcagacgga   900
cggcgtgatc cccgccgact gccagctcaa gaacgccaac tggtgcggcg ccgaggtgcc   960
cgcgtacgcc gacgaggccg gctgctgggc gtcgtcggcc gactgcttcg cccagctgga  1020
cgcctgctac acgtcggcgc cgcccacggg cagccgcggc tgccggctgt gggaggactg  1080
gtgcaccggc attcagcagg gctgccgcgc ggggcggtgg cgggggccgc cgcccttca  1140 tggggagggg gcagcagcgg aagtgtgaac ggttcgggga cgggtggcgg tggtggtggt  1200
ggtggtggtg gcactggctc ttcttcggct tctgccccga cggagacggc ctctgctggc  1260
cgggggggcg caagaatagc tgccgtggcc ggctgcggag cgggacagg agacatggtt  1320 gaagaggttt tcctctttta ttgggacgct tgcagcggct ggcgacggag ccgtggtggt  1380
ggttcgattc ttgcgaggct tatccttcat gtccttcttc cactttgag accgaggcga  1440
```

```
gcccctcgag tccatttact tctcttccac ctgtacctca acttctgtta tccaggaacc    1500
agtggtttct ataatcgcct gagcattaaa ctaggcatat ggccaagcaa aatgtcgcct    1560
gatgtagcgc attacgtgaa ataa                                          1584
```

<210> SEQ ID NO 54
<211> LENGTH: 478
<212> TYPE: PRT
<213> ORGANISM: Thielavia terrestris

<400> SEQUENCE: 54

```
Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Asp Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160

Leu Pro Pro Thr Leu Pro Ala Gly Tyr Tyr Leu Ala Arg Ser Glu Ile
                165                 170                 175

Val Thr Ile Gln Asn Val Thr Asn Asp His Val Asp Pro Gln Phe Tyr
            180                 185                 190

Val Gly Cys Ala Gln Leu Phe Val Gln Gly Pro Thr Thr Pro Thr
        195                 200                 205

Val Pro Pro Asp Arg Leu Val Ser Ile Pro Gly His Val His Ala Ser
    210                 215                 220

Asp Pro Gly Leu Thr Phe Asn Ile Trp Arg Asp Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln Gln
            260                 265                 270

Gln Ala Ile Lys Gln Thr Asp Gly Val Ile Pro Ala Asp Cys Gln Leu
        275                 280                 285

Lys Asn Ala Asn Trp Cys Gly Ala Glu Val Pro Ala Tyr Ala Asp Glu
    290                 295                 300

Ala Gly Cys Trp Ala Ser Ser Ala Asp Cys Phe Ala Gln Leu Asp Ala
305                 310                 315                 320

Cys Tyr Thr Ser Ala Pro Pro Thr Gly Ser Arg Gly Cys Arg Leu Trp
                325                 330                 335

Glu Asp Trp Cys Thr Gly Ile Gln Gln Gly Cys Arg Ala Gly Arg Trp
```

```
            340                 345                 350
Arg Gly Pro Pro Phe His Gly Glu Gly Ala Ala Glu Thr Ala
        355                 360                 365

Ser Ala Gly Arg Gly Gly Ala Arg Ile Ala Val Ala Gly Cys Gly
        370                 375                 380

Gly Gly Thr Gly Asp Met Val Glu Glu Val Phe Leu Phe Tyr Trp Asp
385                 390                 395                 400

Ala Cys Ser Gly Trp Arg Arg Ser Arg Gly Gly Gly Ser Ile Leu Ala
                405                 410                 415

Arg Leu Ile Leu His Val Leu Leu Pro Leu Leu Arg Pro Arg Arg Ala
                420                 425                 430

Pro Arg Val His Leu Leu Leu Phe His Leu Tyr Leu Asn Phe Cys Tyr
                435                 440                 445

Pro Gly Thr Ser Gly Phe Tyr Asn Arg Leu Ser Ile Lys Leu Gly Ile
                450                 455                 460

Trp Pro Ser Lys Met Ser Pro Asp Val Ala His Tyr Val Lys
465                 470                 475

<210> SEQ ID NO 55
<211> LENGTH: 868
<212> TYPE: DNA
<213> ORGANISM: Thielavia terrestris

<400> SEQUENCE: 55
atgcagctcc tcgtgggctt gctgcttgca gccgtggctg ctcgagcaca ttgtatttct      60 accccttttcc gcgtgcctcc cagcctcaag gcaagaagac gcacgcagca gctaacggac    120
cctatcagac acatttccca gactcgtggt aaatgggcag cccgaggaca aggactggtc    180
ggttacgcgc atgaccaaga acgcgcagag caagcaggga gtccaggacc cgaccagtcc    240
cgacattcgc tgctacacgt cgcagacggc gcctaacgtg gctacggtcc ctgccggagc    300
caccgtccat tacatatcga ctcagcagat caaccacccg ggcccgacgc agtactacct    360
cgccaaggta ccggcggggt cgtcggccaa gacgtgggac gggtcagggg ccgtctggtt    420
caagatctcg accaccatgc cttacttgga caacaacaag cagcttgtct ggccgaatca    480
gagtaggaac aattcccgct ccaatcttcg atttggcctt gagctacggc cgattgcatg    540
ggagagaccg ttgactgacg gggcaaccca accttcatca gacacgtaca cgacggtcaa    600
cacgaccatc cccgccgata cgcccagtgg ggaataccte ctccgggtcg agcagatcgc    660
gctgcacctg gcctcgcagc ccaacggggc tcagttctac ctggcctgct cgcagatcca    720
gattacgggc ggcggcaacg gcacgcccgg cccgctagtc gcgttgccgg ggcgtacaa     780 gagcaacgac ccgggcattt tggtcaacat ctactctatg cagcccggcg attacaagcc    840
gcccgggccg ccggtgtgga gtggctga                                       868

<210> SEQ ID NO 56
<211> LENGTH: 230
<212> TYPE: PRT
<213> ORGANISM: Thielavia terrestris

<400> SEQUENCE: 56

Met Gln Leu Leu Val Gly Leu Leu Leu Ala Ala Val Ala Ala Arg Ala
1               5                   10                  15

His Tyr Thr Phe Pro Arg Leu Val Val Asn Gly Gln Pro Glu Asp Lys
            20                  25                  30

Asp Trp Ser Val Thr Arg Met Thr Lys Asn Ala Gln Ser Lys Gln Gly
```

```
                35                  40                  45
Val Gln Asp Pro Thr Ser Pro Asp Ile Arg Cys Tyr Thr Ser Gln Thr
 50                  55                  60

Ala Pro Asn Val Ala Thr Val Pro Ala Gly Ala Thr Val His Tyr Ile
 65                  70                  75                  80

Ser Thr Gln Gln Ile Asn His Pro Gly Pro Thr Gln Tyr Tyr Leu Ala
                 85                  90                  95

Lys Val Pro Ala Gly Ser Ser Ala Lys Thr Trp Asp Gly Ser Gly Ala
                100                 105                 110

Val Trp Phe Lys Ile Ser Thr Thr Met Pro Tyr Leu Asp Asn Asn Lys
                115                 120                 125

Gln Leu Val Trp Pro Asn Gln Asn Thr Tyr Thr Thr Val Asn Thr Thr
130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
                180                 185                 190

Pro Leu Val Ala Leu Pro Gly Ala Tyr Lys Ser Asn Asp Pro Gly Ile
                195                 200                 205

Leu Val Asn Ile Tyr Ser Met Gln Pro Gly Asp Tyr Lys Pro Pro Gly
    210                 215                 220

Pro Pro Val Trp Ser Gly
225                 230
```

<210> SEQ ID NO 57
<211> LENGTH: 1068
<212> TYPE: DNA
<213> ORGANISM: Thielavia terrestris

<400> SEQUENCE: 57

```
atgaagctgt acctggcggc ctttctaggc gccgtcgcca ccccgggagc gttcgctcat    60
cgtaggttcc ccgtctatct ccctaggggt agcaccacga ctaatttctc gtcgtccccc   120
tgtagaaatc cacgggattc tacttgtcaa cggcaccgaa acgccggaat ggaaatacgt   180
ccggtaatat ctaccttgct ctccttcttc acaaccagc ctaacacatc atcagtgacg    240
tggcctggga gggcgcctac gaaccggaaa ataccccaa caccgagttc tttaagacgc    300
ccccgcagac ggacatcaac aacccgaaca tcacctgcgg caggaacgcg ttcgactcgg   360
ccagcaagac tgagacggcc gacatactgg ccggctcaga ggtcggcttc cgcgtctcgt   420
gggacggcaa cggcaagtac ggcgtgttct ggcatcccgg gccggggcag atctacctct   480
ctcgtgctcc gaacgacgac ctggaggact accgcggcga cggagactgg ttcaagatcg   540
caaccggcgc cgccgtctcc aataccgagt ggctgctgtg aacaagcat gacgtgagcc    600
ccaacattcc tcgcccaatc gatccccaac ctggtcacca tggcggcgtc cgggatgcaa   660
agagactaac tccagaggaa cctacctagt tcaacttcac catccccaag acgacgccgc   720
cgggcaagta cctgatgcgc atcgagcagt tcatgccctc cacggtcgaa tacagccagt   780
ggtacgtcaa ctgcgcccac gtcaacatca tcggcccgg cggaggcacg ccgacgggct    840
tgccaggtt tcccggcacc tacactgttg acgatcccgg taagccggac ctaccggaca   900
cagaggcctc gggatagctt gctaaccttg tttgctctct ctctttttct ctcccgacta   960
ggcatcaagg tgccgttgaa ccagatcgtc aacagcggag agttgccgca ggaccaactg  1020
```
aggctgctcg agtacaagcc cccgggccca gcgctgtgga ctggttga                1068

<210> SEQ ID NO 58
<211> LENGTH: 257
<212> TYPE: PRT
<213> ORGANISM: Thielavia terrestris

<400> SEQUENCE: 58

Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Thr Pro Thr
        195                 200                 205

Gly Phe Ala Arg Phe Pro Gly Thr Tyr Thr Val Asp Asp Pro Gly Ile
    210                 215                 220

Lys Val Pro Leu Asn Gln Ile Val Asn Ser Gly Glu Leu Pro Gln Asp
225                 230                 235                 240

Gln Leu Arg Leu Leu Glu Tyr Lys Pro Pro Gly Pro Ala Leu Trp Thr
                245                 250                 255

Gly

<210> SEQ ID NO 59
<211> LENGTH: 871
<212> TYPE: DNA
<213> ORGANISM: Thermoascus crustaceus

<400> SEQUENCE: 59
atggcctttt cccagataat ggctattacc ggcgtttttc ttgcctctgc ttccctggtg      60
gctggccatg gctttgttca gaatatcgtg attgatggta aaaggtacct aactacctac     120
cttactatct gatgtcattt acaagaaagg gcacagacac aagcggcaaa aaaaagaaag     180
aaagaaagaa agaagaaaag ctgacaaaaa ttcaacaagt tatggcgggt acatcgtgaa     240
ccaatatcca tacatgtcag atcctccgga ggtcgtcggc tggtctacca ccgcaaccga     300

-continued

```
cctcggattc gtggacggta ccggatacca aggacctgat atcatctgcc acagggcgc    360 caagcctgca gccctgactg cccaagtggc cgccggagga accgtcaagc tggaatggac    420
tccatggcct gattctcacc acggcccggt gatcaactac cttgctcctt gcaacggtga    480
ctgttccacc gtggacaaga cccaattgaa attcttcaag atcgcccagg ccggtctcat    540
cgatgacaac agtcctcctg gtatctgggc ctcagacaat ctgatagcgg ccaacaacag    600
ctggactgtc accatcccaa ccacaactgc acctggaaac tatgttctaa ggcatgagat    660
cattgctctc cactcagctg gaacaagga tggtgcgcag aactatcccc agtgcatcaa    720
cctgaaggtc actggaaatg gttctggcaa tcctcctgct ggtgctcttg gaacggcact    780
ctacaaggat acagatccgg gaattctgat caatatctac cagaaacttt ccagctatgt    840
tattcctggt cctgctttgt acactggtta g                                  871
```

<210> SEQ ID NO 60
<211> LENGTH: 251
<212> TYPE: PRT
<213> ORGANISM: Thermoascus crustaceus

<400> SEQUENCE: 60

```
Met Ala Phe Ser Gln Ile Met Ala Ile Thr Gly Val Phe Leu Ala Ser
1               5                   10                  15

Ala Ser Leu Val Ala Gly His Gly Phe Val Gln Asn Ile Val Ile Asp
            20                  25                  30

Gly Lys Ser Tyr Gly Gly Tyr Ile Val Asn Gln Tyr Pro Tyr Met Ser
        35                  40                  45

Asp Pro Pro Glu Val Val Gly Trp Ser Thr Thr Ala Thr Asp Leu Gly
    50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
                85                  90                  95

Val Lys Leu Glu Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Lys Phe Phe Lys Ile Ala Gln Ala Gly Leu Ile Asp Asp
    130                 135                 140

Asn Ser Pro Pro Gly Ile Trp Ala Ser Asp Asn Leu Ile Ala Ala Asn
145                 150                 155                 160

Asn Ser Trp Thr Val Thr Ile Pro Thr Thr Thr Ala Pro Gly Asn Tyr
                165                 170                 175

Val Leu Arg His Glu Ile Ile Ala Leu His Ser Ala Gly Thr Lys Asp
            180                 185                 190

Gly Ala Gln Asn Tyr Pro Gln Cys Ile Asn Leu Lys Val Thr Gly Asn
        195                 200                 205

Gly Ser Gly Asn Pro Pro Ala Gly Ala Leu Gly Thr Ala Leu Tyr Lys
    210                 215                 220

Asp Thr Asp Pro Gly Ile Leu Ile Asn Ile Tyr Gln Lys Leu Ser Ser
225                 230                 235                 240

Tyr Val Ile Pro Gly Pro Ala Leu Tyr Thr Gly
                245                 250
```

<210> SEQ ID NO 61
<211> LENGTH: 1102

<212> TYPE: DNA
<213> ORGANISM: Thermoascus crustaceus

<400> SEQUENCE: 61

```
atgtcattct cgaagatact tgctatcgct ggggccatta cctacgcatc ttcagctgcc      60
gctcatggtt atgtccaggg aattgttgtc gatggcagct agtatgtcac tctggatgga     120
accttcagca cgtactgtac taacaatcag cagctacggg ggatatatgg tgacccaata     180
tccctacacc gctcaacctc cggaactcat cgcctggtcc actaaagcaa ccgatcttgg     240
gtttgtggac ggcagtggct atacttctcc tgatatcatc tgccataagg gtgctgagcc     300
tggtgcccag agcgccaaag tggcagctgg agggaccgtt gagctgcagt ggacggcatg     360
gcccgagtct cacaagggcc cagttattga ctacctcgcc gcctgcgacg gggactgctc     420
atctgttgat aagactgcac taaagttctt taagattgac gagagtggtc tgattgacgg     480
caacggtgct ggaacatggg cctctgatac gttgatcaaa ataacaaca gctggactgt      540
caccatccca agcacaattg cttccggaaa ctacgtacta agacacgaaa taattgcgct     600
ccattctgcc ggaaacaaag atggtgctca gaactatccc cagtgtatca acctcgaggt     660
cactggtagt ggcaccgaaa accctgctgg cactctcgga acagcgcttt acacagacac     720
tgatcctggc cttctggtca acatctacca gggtctgtcc aactattcaa tccctggtcc     780
tgctctgtat agcggcaaca gtgataacgc tggttccctc aaccctacca ccacgccgtc     840
aattcagaat gctgctgctg ctccctccac ttccacagca tctgttgtca ctgattcttc     900
gtcagccacc cagactgcta gtgtcgccgc cacgactcca gcctccactt cggctgttac     960
agcctcacca gctcccgata ctggaagcga cgtaaccaaa tatctggatt cgatgagctc    1020
ggatgaggtc ctcaccctgg tgcgcgggac cctgtcttgg ctggtttcta acaagaaaca    1080
tgcgcgggat ctttctcact ga                                             1102
```

<210> SEQ ID NO 62
<211> LENGTH: 349
<212> TYPE: PRT
<213> ORGANISM: Thermoascus crustaceus

<400> SEQUENCE: 62

```
Met Ser Phe Ser Lys Ile Leu Ala Ile Ala Gly Ala Ile Thr Tyr Ala
1               5                   10                  15

Ser Ser Ala Ala Ala His Gly Tyr Val Gln Gly Ile Val Val Asp Gly
                20                  25                  30

Ser Tyr Tyr Gly Gly Tyr Met Val Thr Gln Tyr Pro Tyr Thr Ala Gln
            35                  40                  45

Pro Pro Glu Leu Ile Ala Trp Ser Thr Lys Ala Thr Asp Leu Gly Phe
        50                  55                  60

Val Asp Gly Ser Gly Tyr Thr Ser Pro Asp Ile Ile Cys His Lys Gly
65                  70                  75                  80

Ala Glu Pro Gly Ala Gln Ser Ala Lys Val Ala Ala Gly Gly Thr Val
                85                  90                  95

Glu Leu Gln Trp Thr Ala Trp Pro Glu Ser His Lys Gly Pro Val Ile
            100                 105                 110

Asp Tyr Leu Ala Ala Cys Asp Gly Asp Cys Ser Ser Val Asp Lys Thr
        115                 120                 125

Ala Leu Lys Phe Phe Lys Ile Asp Glu Ser Gly Leu Ile Asp Gly Asn
    130                 135                 140

Gly Ala Gly Thr Trp Ala Ser Asp Thr Leu Ile Lys Asn Asn Asn Ser
```

```
                145                 150                 155                 160
Trp Thr Val Thr Ile Pro Ser Thr Ile Ala Ser Gly Asn Tyr Val Leu
                    165                 170                 175
Arg His Glu Ile Ile Ala Leu His Ser Ala Gly Asn Lys Asp Gly Ala
                    180                 185                 190
Gln Asn Tyr Pro Gln Cys Ile Asn Leu Glu Val Thr Gly Ser Gly Thr
                    195                 200                 205
Glu Asn Pro Ala Gly Thr Leu Gly Thr Ala Leu Tyr Thr Asp Thr Asp
        210                 215                 220
Pro Gly Leu Leu Val Asn Ile Tyr Gln Gly Leu Ser Asn Tyr Ser Ile
225                 230                 235                 240
Pro Gly Pro Ala Leu Tyr Ser Gly Asn Ser Asp Asn Ala Gly Ser Leu
                    245                 250                 255
Asn Pro Thr Thr Thr Pro Ser Ile Gln Asn Ala Ala Ala Pro Ser
                    260                 265                 270
Thr Ser Thr Ala Ser Val Val Thr Asp Ser Ser Ser Ala Thr Gln Thr
        275                 280                 285
Ala Ser Val Ala Ala Thr Thr Pro Ala Ser Thr Ser Ala Val Thr Ala
        290                 295                 300
Ser Pro Ala Pro Asp Thr Gly Ser Asp Val Thr Lys Tyr Leu Asp Ser
305                 310                 315                 320
Met Ser Ser Asp Glu Val Leu Thr Leu Val Arg Gly Thr Leu Ser Trp
                    325                 330                 335
Leu Val Ser Asn Lys Lys His Ala Arg Asp Leu Ser His
                    340                 345

<210> SEQ ID NO 63
<211> LENGTH: 1493
<212> TYPE: DNA
<213> ORGANISM: Thermoascus crustaceus

<400> SEQUENCE: 63
atgttgtcat tcattcccac caagtcagct gcgctgacga ctcttctact tcttggaaca      60
gctcatgctc acactttgat gaccaccatg tttgtggacg gcgtcaacca gggagatggt     120
gtctgcattc gcatgaacaa tgacggcgga actgccaata cctatatcca gcctatcacg     180
agcaaggata tcgcctgcgg taagtaccca gatgtcatca tactctgcca taacatccgt     240
catatctact agaatcggag caatgttaag tatttccagg catccaaggc gaaatcggcg     300
cctcccgagt ctgcccagtc aaggcatctt ccaccctaac cttccaattc gcgagcaac      360
ccaacaaccc aaactcctcc cctctcgatc catcgcacaa aggccccgcc gcggtgtacc     420
tgaaaaaggt cgactccgcc atcgcgagca acaacgccgc cggagacagc tggttcaaga     480
tctgggagtc cgtctacgac gagtccacgg gcaaatgggg cacgaccaag atgatcgaga     540
acaacgggca catctccgtc aaggtgcccg atgatatcga gggtggttac tatcttgccc     600
ggacggagct gctggcgcta cattctgcgg atcaggggga tccgcagttc tatgttggct     660
gtgcgcagct gtttatcgat tcggatggga cggcgaaacc gcccactgtt tctattggag     720
agggacgta cgatctgagc atgcctgcca tgacgtataa tatctgggag acaccgttgg     780
ctctgccgta tccgatgtat gggcctcctg tctatacgcc tggctctggt tctggatcag     840
tccgtgcgac gagctcttct gctgtcccta ctgcaaccga atcctctttt gtagaggaaa     900
gagcaaaccc cgtcacggca aacagtgttt attctgcaag gggcaaattc aaaacctgga     960
ttgataaaact gtcatggcgc gggaaggtcc gtgagaacgt cagacaagcc gcgggaagaa    1020
```

```
gaagcactct cgtccagact gtgggtctaa agccaaaagg ctgcatcttc gtcaatggaa   1080
actggtgcgg cttcgaggtt cccgactaca acgatgcgga gagctgctgg gctgtatgtt   1140
cccctcctta gcctcttaca tccctaagta ctacatttga aaacaacaaa aagaaatgta   1200
tatactaact acgtacgctc tactctaggc ctccgacaac tgctggaaac agtccgacgc   1260
ctgctggaac aagacccaac ccacgggcta caataactgc cagatctggc aggacaagaa   1320
atgcaaggtc atccaggatt cctgtagcgg acccaacccg catggaccac cgaataaggg   1380
caaggatttg actccggagt ggccgccact gaagggctcg atggatacgt tctccaagcg   1440
tactatcggt taccgcgatt ggattgttag aaggagaggt gcatgagggt gta          1493

<210> SEQ ID NO 64
<211> LENGTH: 436
<212> TYPE: PRT
<213> ORGANISM: Thermoascus crustaceus

<400> SEQUENCE: 64

Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
            20                  25                  30

Asp Gly Val Asn Gln Gly Asp Gly Val Cys Ile Arg Met Asn Asn Asp
        35                  40                  45

Gly Gly Thr Ala Asn Thr Tyr Ile Gln Pro Ile Thr Ser Lys Asp Ile
    50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Ser Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Trp Glu Thr Pro Leu Ala Leu Pro Tyr Pro Met Tyr
225                 230                 235                 240

Gly Pro Pro Val Tyr Thr Pro Gly Ser Gly Ser Val Arg Ala
                245                 250                 255

Thr Ser Ser Ser Ala Val Pro Thr Ala Thr Glu Ser Ser Phe Val Glu
            260                 265                 270

Glu Arg Ala Asn Pro Val Thr Ala Asn Ser Val Tyr Ser Ala Arg Gly
        275                 280                 285
```

Lys Phe Lys Thr Trp Ile Asp Lys Leu Ser Trp Arg Gly Lys Val Arg
            290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
                325                 330                 335

Gly Phe Glu Val Pro Asp Tyr Asn Asp Ala Glu Ser Cys Trp Ala Ala
                340                 345                 350

Ser Asp Asn Cys Trp Lys Gln Ser Asp Ala Cys Trp Asn Lys Thr Gln
                355                 360                 365

Pro Thr Gly Tyr Asn Asn Cys Gln Ile Trp Gln Asp Lys Lys Cys Lys
            370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
                405                 410                 415

Asp Thr Phe Ser Lys Arg Thr Ile Gly Tyr Arg Asp Trp Ile Val Arg
                420                 425                 430

Arg Arg Gly Ala
        435

<210> SEQ ID NO 65
<211> LENGTH: 1035
<212> TYPE: DNA
<213> ORGANISM: Aspergillus aculeatus

<400> SEQUENCE: 65
atgaagtata ttcctctcgt tattgcagtt gctgccggcc tggcacgtcc ggctactgcc      60
cactacatct tcagcaagct cgtgctgaac ggagaggcat ctgcggactg caatacatc     120 cgcgagacta ctcgcagcat agtctatgag ccgaccaagt acacctctac cttcgataac     180
ctaacaccca gcgatagcga cttccgctgt aatctcggtt ccttcagcaa tgctgcgaag     240
accgaggtcg ctgaggttgc ggcaggcgat accatcgcaa tgaagctatt ctacgacacc     300
agtattgcgc atcctggccc gggacaagtt tatatgtcca aggcaccgac cggcaatgtt     360
caggaatacc aaggagacgg ggattggttc aaaatctggg aaaagaccct ttgcaacacg     420
gatggtgatc tgactacaga ggcctggtgc acctggggca tgtcacagtt tgaatttcaa     480
atcccagctg cgaccccggc aggagagtac ctagtgcgcg ccgagcatat aggcctgcat     540
ggcgctcaag cgaacgaggc cgaattcttc tacagctgtg cgcagatcaa ggttacaggc     600
tcgggaactg gatctcccag tctcacgtat caaattcctg gtctctataa cgacactatg     660
accctgttca atggcctcaa tctttggact gattcagccg agaaggtgca gctggatttc     720
ctggagacgc caattgggga cgacgtgtgg agcggagcag gctcggggag cccatctgct     780
gccacctctt cgaccagcgg tgcaactctt gcagctcagg gtacaactac ctctgccgcg     840
catgctcagg cccagaccac cattaccacc agcaccagca ccatcacgtc tctcgaatca     900
gccagctcaa ccgatctcgt tgcgcagtat ggtcagtgcg gaggccttaa ctggtccggt     960
ccaaccgagt gtgagacacc ttatacctgt gtgcagcaga cccttactac ccatcaatgc    1020
gtgaattcgt gctga                                                   1035

<210> SEQ ID NO 66
<211> LENGTH: 344
<212> TYPE: PRT
<213> ORGANISM: Aspergillus aculeatus

<400> SEQUENCE: 66

```
Met Lys Tyr Ile Pro Leu Val Ile Ala Val Ala Ala Gly Leu Ala Arg
1               5                   10                  15
Pro Ala Thr Ala His Tyr Ile Phe Ser Lys Leu Val Leu Asn Gly Glu
            20                  25                  30
Ala Ser Ala Asp Trp Gln Tyr Ile Arg Glu Thr Thr Arg Ser Ile Val
        35                  40                  45
Tyr Glu Pro Thr Lys Tyr Thr Ser Phe Asp Asn Leu Thr Pro Ser
50                  55                  60
Asp Ser Asp Phe Arg Cys Asn Leu Gly Ser Phe Ser Asn Ala Ala Lys
65                  70                  75                  80
Thr Glu Val Ala Glu Val Ala Ala Gly Asp Thr Ile Ala Met Lys Leu
                85                  90                  95
Phe Tyr Asp Thr Ser Ile Ala His Pro Gly Pro Gly Gln Val Tyr Met
            100                 105                 110
Ser Lys Ala Pro Thr Gly Asn Val Gln Glu Tyr Gln Gly Asp Gly Asp
        115                 120                 125
Trp Phe Lys Ile Trp Glu Lys Thr Leu Cys Asn Thr Asp Gly Asp Leu
130                 135                 140
Thr Thr Glu Ala Trp Cys Thr Trp Gly Met Ser Gln Phe Glu Phe Gln
145                 150                 155                 160
Ile Pro Ala Ala Thr Pro Ala Gly Glu Tyr Leu Val Arg Ala Glu His
                165                 170                 175
Ile Gly Leu His Gly Ala Gln Ala Asn Glu Ala Glu Phe Phe Tyr Ser
            180                 185                 190
Cys Ala Gln Ile Lys Val Thr Gly Ser Gly Thr Gly Ser Pro Ser Leu
        195                 200                 205
Thr Tyr Gln Ile Pro Gly Leu Tyr Asn Asp Thr Met Thr Leu Phe Asn
210                 215                 220
Gly Leu Asn Leu Trp Thr Asp Ser Ala Glu Lys Val Gln Leu Asp Phe
225                 230                 235                 240
Leu Glu Thr Pro Ile Gly Asp Asp Val Trp Ser Gly Ala Gly Ser Gly
                245                 250                 255
Ser Pro Ser Ala Ala Thr Ser Ser Thr Ser Gly Ala Thr Leu Ala Ala
            260                 265                 270
Gln Gly Thr Thr Thr Ser Ala Ala His Ala Gln Ala Gln Thr Thr Ile
        275                 280                 285
Thr Thr Ser Thr Ser Thr Ile Thr Ser Leu Glu Ser Ala Ser Ser Thr
290                 295                 300
Asp Leu Val Ala Gln Tyr Gly Gln Cys Gly Gly Leu Asn Trp Ser Gly
305                 310                 315                 320
Pro Thr Glu Cys Glu Thr Pro Tyr Thr Cys Val Gln Asn Pro Tyr
                325                 330                 335
Tyr His Gln Cys Val Asn Ser Cys
            340
```

<210> SEQ ID NO 67
<211> LENGTH: 1203
<212> TYPE: DNA
<213> ORGANISM: Aspergillus aculeatus

<400> SEQUENCE: 67
atgtctgttg ctaagtttgc tggtgttatc ctcggttcgg ccgctctcgt cgctggccac    60

-continued

```
ggttacgtgt cgggtgctgt tgtcgacgga acctactatg gcggctacat tgtcacttcc    120
taccctatt ccagcgatcc cccggagacc attggatggt ctaccgaggc gaccgacttg    180
ggtttcgtcg atggtagcga gtatgctgat gccgacatca tttgccacaa gagtgccaag    240
cccggtgcca tctctgctga ggtcaaggcc ggtggtactg ttgagctcca gtggactacc    300
tggcccgaca gccaccacgg ccctgtcctg acctaccttg ccaactgcaa tggtgactgc    360
agcagcgtca ccaagaccga cctcgagttt tcaagattg acgagagcgg tctcatcaac    420
gacgacgacg tccccggtac ctgggccagt gataacttga tcgccaacaa caacagctgg    480
actgtgacca tccctctga cattgcggct ggcaactacg tcctccgtca cgaaatcatt    540
gcccttcact ctgctggtaa caaggatggt gctcagaact accctcagtg cctcaacttg    600
aaggtcactg gcggcggtga tctcgctcct tctggcactg ctggtgagag cctgtacaag    660
gacaccgatg ctggtatcct cgtcaacatc taccagtctc tttcctccta cgatattccc    720
ggacctgcta tgtacaacgc tacctccagc tcctccagct cctccagctc cagtccagc    780
tccagctcca gctccagctc cggctcttcc agctccgccg ccgcctccag cagctccagc    840
agctccagca ctactgccgc cgccgccgcc gctaccagcg ctgcttcttc cgtcacctct    900
gctgctggct ccgtcgttac tcagactgct accgctgttg agactgatac tgccactgcc    960
taccagacct ccactgaggt tgcgcaagtc accgtcaccg tagcgctcc ccagcagacc   1020
tacgttgcca ctcccagcag ctccagctct gcctccagca gctccagtgc ttccgtatcc   1080
accagcacca gcctcaccag ctacttcgag tccctgagcg ctgatcagtt cctcagcgtt   1140
ctcaagcaga ctttcacctg gttggtcagc gagaagaagc acgcccgtga cctctccgcc   1200
taa                                                                1203
```

<210> SEQ ID NO 68
<211> LENGTH: 400
<212> TYPE: PRT
<213> ORGANISM: Aspergillus aculeatus

<400> SEQUENCE: 68

```
Met Ser Val Ala Lys Phe Ala Gly Val Ile Leu Gly Ser Ala Ala Leu
1               5                   10                  15

Val Ala Gly His Gly Tyr Val Ser Gly Ala Val Asp Gly Thr Tyr
            20                  25                  30

Tyr Gly Gly Tyr Ile Val Thr Ser Tyr Pro Tyr Ser Ser Asp Pro Pro
        35                  40                  45

Glu Thr Ile Gly Trp Ser Thr Glu Ala Thr Asp Leu Gly Phe Val Asp
    50                  55                  60

Gly Ser Glu Tyr Ala Asp Ala Asp Ile Ile Cys His Lys Ser Ala Lys
65                  70                  75                  80

Pro Gly Ala Ile Ser Ala Glu Val Lys Ala Gly Gly Thr Val Glu Leu
                85                  90                  95

Gln Trp Thr Thr Trp Pro Asp Ser His His Gly Pro Val Leu Thr Tyr
            100                 105                 110

Leu Ala Asn Cys Asn Gly Asp Cys Ser Ser Val Thr Lys Thr Asp Leu
        115                 120                 125

Glu Phe Phe Lys Ile Asp Glu Ser Gly Leu Ile Asn Asp Asp Val
    130                 135                 140

Pro Gly Thr Trp Ala Ser Asp Asn Leu Ile Ala Asn Asn Ser Trp
145                 150                 155                 160

Thr Val Thr Ile Pro Ser Asp Ile Ala Ala Gly Asn Tyr Val Leu Arg
```

```
                      165                 170                 175
His Glu Ile Ile Ala Leu His Ser Ala Gly Asn Lys Asp Gly Ala Gln
                180                 185                 190

Asn Tyr Pro Gln Cys Leu Asn Leu Lys Val Thr Gly Gly Asp Leu
        195                 200                 205

Ala Pro Ser Gly Thr Ala Gly Glu Ser Leu Tyr Lys Asp Thr Asp Ala
    210                 215                 220

Gly Ile Leu Val Asn Ile Tyr Gln Ser Leu Ser Ser Tyr Asp Ile Pro
225                 230                 235                 240

Gly Pro Ala Met Tyr Asn Ala Thr Ser Ser Ser Ser Ser Ser Ser
                245                 250                 255

Ser Ser Ser Ser Ser Ser Ser Ser Ser Gly Ser Ser Ser
            260                 265                 270

Ala Ala Ala Ser Ser Ser Ser Ser Ser Ser Thr Thr Ala Ala Ala
            275                 280                 285

Ala Ala Ala Thr Ser Ala Ala Ser Ser Val Thr Ser Ala Ala Gly Ser
    290                 295                 300

Val Val Thr Gln Thr Ala Thr Ala Val Glu Thr Asp Thr Ala Thr Ala
305                 310                 315                 320

Tyr Gln Thr Ser Thr Glu Val Ala Gln Val Thr Val Thr Gly Ser Ala
                325                 330                 335

Pro Gln Gln Thr Tyr Val Ala Thr Pro Ser Ser Ser Ser Ala Ser
            340                 345                 350

Ser Ser Ser Ser Ala Ser Val Ser Thr Ser Thr Ser Leu Thr Ser Tyr
            355                 360                 365

Phe Glu Ser Leu Ser Ala Asp Gln Phe Leu Ser Val Leu Lys Gln Thr
    370                 375                 380

Phe Thr Trp Leu Val Ser Glu Lys Lys His Ala Arg Asp Leu Ser Ala
385                 390                 395                 400

<210> SEQ ID NO 69
<211> LENGTH: 1170
<212> TYPE: DNA
<213> ORGANISM: Aspergillus aculeatus

<400> SEQUENCE: 69
atgaagtcct ctactttcgg tatgctcgct ctggcagcag cagccaagat ggtcgatgcc      60
cacaccaccg tcttcgccgt ctggatcaac ggcgaggacc agggtctggg caacagtgcc     120
agtggctaca tccggtctcc ccccagcaac agccccgtca aggacgtgac ctcgaccgac     180
atcacctgca acgtcaacgg cgaccaggcg gcggctaaga ccctctccgt caagggcggc     240
gacgtcgtca ccttcgagtg gcaccacgac agccgggacg cctccgacga catcatcgcc     300
tcctcccaca agggccccgt catggtctac atggccccga ccaccgccgg cagcagcggc     360
aagaactggg tcaagatcgc cgaggacgga tactccgacg gcacctgggc cgtcgacacc     420
ctgatcgcca acagcggcaa gcacaacatc accgtccccg acgtccccgc cggcgactac     480
ctcttccgcc cggagatcat cgccctccac gaggccgaga cgagggcgg cgcccagttc     540 tacatggagt gtgtccagtt caaggtcacc tccgacggtg ccaacactct gcccgacggt     600
gtcagcctgc ccggcgccta ctccgccact gaccccggta tcctcttcaa catgtacggc     660
tccttcgaca gctatcccat ccccggtccc tccgtctggg atggcactag ctctggctct     720
tcctcttctt cctcttcttc ctcttccagc tcttccgccg ccgctgccgt tgttgccacc     780
tcctcttcct cttcctctgc ttccatcgag gccgtgacca ccaagggtgc cgtcgccgcc     840
```

-continued

```
gtctccaccg ccgccgccgt ggctcctacc accaccaccg ctgcccccac caccttcgcc      900
acggccgtcg cctccaccaa gaaggccact gcctgccgca acaagaccaa gtcctcctcc      960
gctgccacca ccgccgccgc cgtcgccgag accacctctt ccaccgctgc cgccaccgct     1020
gctgcttcct ctgcctcttc cgcctccggc accgccggca agtacgagcg ctgcggtggc     1080
cagggctgga ccggtgccac cacctgcgtt gatggctgga cctgcaagca gtggaaccct     1140
tactactacc agtgcgttga gtctgcctag                                      1170
```

<210> SEQ ID NO 70
<211> LENGTH: 389
<212> TYPE: PRT
<213> ORGANISM: Aspergillus aculeatus

<400> SEQUENCE: 70

| Met | Lys | Ser | Ser | Thr | Phe | Gly | Met | Leu | Ala | Leu | Ala | Ala | Ala | Ala | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Met Val Asp Ala His Thr Thr Val Phe Ala Val Trp Ile Asn Gly Glu
            20                  25                  30

Asp Gln Gly Leu Gly Asn Ser Ala Ser Gly Tyr Ile Arg Ser Pro Pro
        35                  40                  45

Ser Asn Ser Pro Val Lys Asp Val Thr Ser Thr Asp Ile Thr Cys Asn
50                  55                  60

Val Asn Gly Asp Gln Ala Ala Lys Thr Leu Ser Val Lys Gly Gly
65                  70                  75                  80

Asp Val Val Thr Phe Glu Trp His His Asp Ser Arg Asp Ala Ser Asp
                85                  90                  95

Asp Ile Ile Ala Ser His Lys Gly Pro Val Met Val Tyr Met Ala
            100                 105                 110

Pro Thr Thr Ala Gly Ser Ser Gly Lys Asn Trp Val Lys Ile Ala Glu
        115                 120                 125

Asp Gly Tyr Ser Asp Gly Thr Trp Ala Val Asp Thr Leu Ile Ala Asn
    130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
            180                 185                 190

Gly Ala Asn Thr Leu Pro Asp Gly Val Ser Leu Pro Gly Ala Tyr Ser
        195                 200                 205

Ala Thr Asp Pro Gly Ile Leu Phe Asn Met Tyr Gly Ser Phe Asp Ser
    210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ala Ala Ala
                245                 250                 255

Val Val Ala Thr Ser Ser Ser Ser Ser Ala Ser Ile Glu Ala Val
            260                 265                 270

Thr Thr Lys Gly Ala Val Ala Val Ser Thr Ala Ala Val Ala
        275                 280                 285

Pro Thr Thr Thr Ala Ala Pro Thr Thr Phe Ala Thr Ala Val Ala
    290                 295                 300

Ser Thr Lys Lys Ala Thr Ala Cys Arg Asn Lys Thr Lys Ser Ser Ser

```
                  305                 310                 315                 320
Ala Ala Thr Thr Ala Ala Val Ala Glu Thr Thr Ser Ser Thr Ala
                325                 330                 335

Ala Ala Thr Ala Ala Ala Ser Ser Ala Ser Ser Ala Ser Gly Thr Ala
            340                 345                 350

Gly Lys Tyr Glu Arg Cys Gly Gly Gln Gly Trp Thr Gly Ala Thr Thr
            355                 360                 365

Cys Val Asp Gly Trp Thr Cys Lys Gln Trp Asn Pro Tyr Tyr Tyr Gln
        370                 375                 380

Cys Val Glu Ser Ala
385

<210> SEQ ID NO 71
<211> LENGTH: 1221
<212> TYPE: DNA
<213> ORGANISM: Aspergillus aculeatus

<400> SEQUENCE: 71
atgcgtcagg ctcagtcttt gtccctcttg acagctcttc tgtctgccac gcgtgtggct      60
ggacacggtc acgtcactaa cgttgtcgtc aacggtgttt actacgaggg cttcgatatc     120
aacagcttcc cctacgagtc cgatccccct aaggtggcgg cttggaccac tcctaacact     180
ggcaacggtt tcatttcccc cagcgactac ggtaccgatg acattatttg ccaccagaat     240
gccaccaacg cccaggccca cattgttgtt gcggctggtg acaagatcaa catccagtgg     300
accgcgtggc ccgattccca ccacggtcct gtccttgact acctcgctcg ctgcgacggt     360
gagtgtgaga cggttgataa gaccactctt gagttttttca agatcgacgg cgtcggtctc     420
atcagtgaca ccgaagtgcc cggtacctgg ggagatgacc agctgatcgc caacaacaac     480
agctggttgg tcgagatccc cccgaccatt gctcctggca actatgttct tcgccacgag     540
cttatcgctc tccacagcgc cggcactgaa gatggtgctc agaactaccc ccagtgtttc     600
aacctccagg tcactggctc cggtactgac gagcccgctg gtaccctcgg caccaagctc     660
tacactgagg atgaggctgg tatcgttgtg aacatctaca cctctctgtc ttcctatgcc     720
gtccccggcc ccacccagta cagcggcgcc gtctctgtca gccaatccac ttcggccatt     780
acctccaccg gaactgctgt tgtcggtagc ggcagcgctg ttgccacctc tgccgccgcg     840
gctaccacca gcgctgctgc cttcttctgcc gctgctgcta ccaccgctgc tgccgttacc     900
agcgccaatg ccaacactca gattgcccag cccagcagca gctcttctta ctcccagatc     960
gccgtgcagg tgcccctcctc ctggaccacc cttgtgaccg tcactcctcc cgccgccgcc    1020
gccaccaccc ctgctgccgt ccctgagcct cagacccccct ctgccagctc tggagccacc    1080
actaccagca gcagcagcgg cgccgcccag tctctctacg ccagtgcgg tggtatcaac    1140 tggaccggag ctacctcttg cgttgagggc gctacttgct accagtacaa cccttactac    1200
taccagtgca tctctgccta a                                              1221

<210> SEQ ID NO 72
<211> LENGTH: 406
<212> TYPE: PRT
<213> ORGANISM: Aspergillus aculeatus

<400> SEQUENCE: 72

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Val Asn Gly
```

```
                 20                  25                  30
Val Tyr Tyr Glu Gly Phe Asp Ile Asn Ser Phe Pro Tyr Glu Ser Asp
                35                  40                  45

Pro Pro Lys Val Ala Ala Trp Thr Thr Pro Asn Thr Gly Asn Gly Phe
        50                  55                  60

Ile Ser Pro Ser Asp Tyr Gly Thr Asp Asp Ile Cys His Gln Asn
65                  70                  75                  80

Ala Thr Asn Ala Gln Ala His Ile Val Val Ala Gly Asp Lys Ile
                    85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
            115                 120                 125

Thr Leu Glu Phe Phe Lys Ile Asp Gly Val Gly Leu Ile Ser Asp Thr
            130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
                180                 185                 190

Ala Gln Asn Tyr Pro Gln Cys Phe Asn Leu Gln Val Thr Gly Ser Gly
                195                 200                 205

Thr Asp Glu Pro Ala Gly Thr Leu Gly Thr Lys Leu Tyr Thr Glu Asp
            210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255

Thr Ser Ala Ile Thr Ser Thr Gly Thr Ala Val Val Gly Ser Gly Ser
                260                 265                 270

Ala Val Ala Thr Ser Ala Ala Ala Thr Thr Ser Ala Ala Ala Ser
            275                 280                 285

Ser Ala Ala Ala Thr Thr Ala Ala Val Thr Ser Ala Asn Ala
            290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
            325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Ser Ser Ser Gly Ala
            355                 360                 365

Ala Gln Ser Leu Tyr Gly Gln Cys Gly Gly Ile Asn Trp Thr Gly Ala
            370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
            405

<210> SEQ ID NO 73
<211> LENGTH: 1284
<212> TYPE: DNA
<213> ORGANISM: Aspergillus aculeatus
```

<400> SEQUENCE: 73

```
atgtctcttt ccaagattgc cactcttctg ctgggctcgg tctcgctggt cgctggtcat      60
gggtatgtct cgagcatcga ggtggacggt accacctatg agggtactt ggtcgacact      120
tattactacg aatccgaccc gcccgagtta atcgcctggt ccacaaatgc cacggatgat      180
ggctatgtat cgccctccga ctacgagagc gtgaacatca tctgccacaa ggggtctgcg      240
cccggcgcgt tgtcggcccc tgtcgcgccc ggaggctggg tgcagatgac ctggaacacc      300
tggcccaccg accatcacgg ccctgtcatc acgtatatgg ccaattgcca cggttcttgc      360
gcagatgtgg acaagaccac cctcgagttc ttcaagatcg atgctggcgg cttgatcgat      420
gacacggacg tgcctggaac ttgggcgacc gatgagctca ttgaagatag ctatagtcgc      480
aacatcacta tccccagcga tattgccccc gggtactatg ttttgcgaca cgagatcatt      540
gctctgcaca gcgccgagaa cctggacgga gcccagaact accccagtg catcaatctg      600
gaagtcaccg gcagcgagac agcaaccccg agtggcacct gggcactgc tctgtacaag      660
gagaccgacc ccggcatcta tgttgacatc tggaacacgt tgagcacgta ctattccc      720
ggccccgcgc tgtacactgc tggtagcact gcgaccgcag ccgctgctgc cgataccacc      780
actacttctg ctggcaccac cgctgaggcc accaccgctg ccgccgccgt gagtaccacc      840
gcggacgctg ttccgaccga gtcttcagct ccttccgaga ccagcgcgac taccgcgaac      900
cctgctcggc ccactgccgg cagcgacatc cgcttccagc ccggtcaggt caaggctggt      960
gcttcagtca caactcggc tactgagact tcctctggtg agtctgccac gacgaccaca     1020
acatcagtgg ccactgcggc ttcgagcgcg gattcgtcga cgacttctgg ggttttgagt     1080
ggcgcctgca gccaggaggg ctactggtac tgcaacgggg gcactgcgtt ccagcgctgt     1140
gtcaacgggg aatgggatgc gtcccagagt gtggctgcgg gcacggtctg caccgccggt     1200
atctcggaga ccatcaccat ttcagccgcc gccacgcgcc gggatgccat gcgtcgtcat     1260
ctggcgcgtc ccaagcgtca ctga                                            1284
```

<210> SEQ ID NO 74
<211> LENGTH: 427
<212> TYPE: PRT
<213> ORGANISM: Aspergillus aculeatus

<400> SEQUENCE: 74

```
Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
                20                  25                  30

Tyr Gly Gly Tyr Leu Val Asp Thr Tyr Tyr Glu Ser Asp Pro Pro
        35                  40                  45

Glu Leu Ile Ala Trp Ser Thr Asn Ala Thr Asp Asp Gly Tyr Val Ser
    50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
                85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
        115                 120                 125
```

```
Glu Phe Phe Lys Ile Asp Ala Gly Gly Leu Ile Asp Thr Asp Val
130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
            180                 185                 190

Asn Tyr Pro Gln Cys Ile Asn Leu Glu Val Thr Gly Ser Glu Thr Ala
                195                 200                 205

Thr Pro Ser Gly Thr Leu Gly Thr Ala Leu Tyr Lys Glu Thr Asp Pro
210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala Ala
                245                 250                 255

Ala Asp Thr Thr Thr Thr Ser Ala Gly Thr Thr Ala Glu Ala Thr Thr
                260                 265                 270

Ala Ala Ala Ala Val Ser Thr Thr Ala Asp Ala Val Pro Thr Glu Ser
                275                 280                 285

Ser Ala Pro Ser Glu Thr Ser Ala Thr Thr Ala Asn Pro Ala Arg Pro
                290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ala Ser Ser Ala Asp Ser
                340                 345                 350

Ser Thr Thr Ser Gly Val Leu Ser Gly Ala Cys Ser Gln Glu Gly Tyr
                355                 360                 365

Trp Tyr Cys Asn Gly Gly Thr Ala Phe Gln Arg Cys Val Asn Gly Glu
370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Ala Thr Arg Arg Asp Ala
                405                 410                 415

Met Arg Arg His Leu Ala Arg Pro Lys Arg His
                420                 425
```

<210> SEQ ID NO 75
<211> LENGTH: 804
<212> TYPE: DNA
<213> ORGANISM: Aspergillus aculeatus

<400> SEQUENCE: 75

```
atgcttgtca aactcatctc ttttctttca gctgctacca gcgtagctgc tcatggtcat    60
gtgtcaaaca ttgtgatcaa cggggtgtcc taccgcggat gggacatcaa ttcggaccct   120
tacaattcca accctccggt ggtggttgca tggcaaacac ccaacacagc taatggcttc   180
atctcccctg atgcatacga cacagatgat gttatttgcc atctgagcgc tacgaatgcc   240
agaggccacg cagtcgtcgc tgctggcgac aagatcagcc tccagtggac gacctggcct   300
gacagtcacc atggccctgt catcagctac ctagccaact gcggctccag ctgcgagaca   360
gtcgataaga ccaccctcga gttcttcaag atcgatggtg ttggcttggt ggatgagagc   420
```

```
aatcccctg gtatctgggg agacgatgag ctcattgcca caacaactc ttggctggta    480 gagattccag ctagtatcgc gccaggatac tatgtgctgc gtcacgagtt gatcgctctg    540
catggagcag ggagtgagaa tggagcccag aattacatgc aatgtttcaa ccttcaggtt    600
actgggactg gcacggtcca gccttccggg gtcctgggca cggagctgta caaacccaca    660
gacgctggaa ttcttgtcaa tatctaccag tcgctctcca cctatgttgt tcctggcccg    720 acctgatcc cccaggccgt ttccctcgtt cagtcgagct ccaccattac cgcctcgggc    780
acggcagtga caaccacggc ttga                                          804
```

<210> SEQ ID NO 76
<211> LENGTH: 267
<212> TYPE: PRT
<213> ORGANISM: Aspergillus aculeatus

<400> SEQUENCE: 76

```
Met Leu Val Lys Leu Ile Ser Phe Leu Ser Ala Thr Ser Val Ala
1               5                   10                  15

Ala His Gly His Val Ser Asn Ile Val Ile Asn Gly Val Ser Tyr Arg
                20                  25                  30

Gly Trp Asp Ile Asn Ser Asp Pro Tyr Asn Ser Asn Pro Val Val
            35                  40                  45

Val Ala Trp Gln Thr Pro Asn Thr Ala Asn Gly Phe Ile Ser Pro Asp
50                  55                  60

Ala Tyr Asp Thr Asp Asp Val Ile Cys His Leu Ser Ala Thr Asn Ala
65                  70                  75                  80

Arg Gly His Ala Val Val Ala Ala Gly Asp Lys Ile Ser Leu Gln Trp
                85                  90                  95

Thr Thr Trp Pro Asp Ser His His Gly Pro Val Ile Ser Tyr Leu Ala
            100                 105                 110

Asn Cys Gly Ser Ser Cys Glu Thr Val Asp Lys Thr Thr Leu Glu Phe
        115                 120                 125

Phe Lys Ile Asp Gly Val Gly Leu Val Asp Glu Ser Asn Pro Pro Gly
    130                 135                 140

Ile Trp Gly Asp Asp Glu Leu Ile Ala Asn Asn Asn Ser Trp Leu Val
145                 150                 155                 160

Glu Ile Pro Ala Ser Ile Ala Pro Gly Tyr Tyr Val Leu Arg His Glu
                165                 170                 175

Leu Ile Ala Leu His Gly Ala Gly Ser Glu Asn Gly Ala Gln Asn Tyr
            180                 185                 190

Met Gln Cys Phe Asn Leu Gln Val Thr Gly Thr Gly Thr Val Gln Pro
        195                 200                 205

Ser Gly Val Leu Gly Thr Glu Leu Tyr Lys Pro Thr Asp Ala Gly Ile
    210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                245                 250                 255

Thr Ala Ser Gly Thr Ala Val Thr Thr Thr Ala
            260                 265
```

<210> SEQ ID NO 77
<211> LENGTH: 822
<212> TYPE: DNA
<213> ORGANISM: Aspergillus aculeatus

<400> SEQUENCE: 77

```
atgaagtatc ttgcgatctt cgcggcagca gcagctggac tggcccgccc gacagcagcg      60
cactacatct tcagcaagct gattctggac ggcgaagtct ctgaggactg gcagtatatt     120
cgtaaaacca cccgggagac atgctatttg ccgaccaagt tcaccgacac cttcgacaac     180
ttgactccga acgaccagga tttccggtgc aatctcggct cgttcagcaa cgccgccaag     240
accgaagtgg ccgaggtgga agcgggctcc acgattggca tgcagctttt cgctggtagc     300
cacatgcgtc acccgggacc tgcgcaagtc ttcatgtcta aggccccgtc cggcaacgta     360
cagagctacg agggtgacgg ctcctggttc aagatctggg agcgtacact ctgcgacaaa     420
agtggcgatc tgactggaga tgcgtggtgt acatacggcc agaccgagat cgagtttcaa     480
atccccgagg cgaccccgac gggcgaatac ctggtccgag cggagcacat cggtcttcac     540
cgcgcacaga gtaatcaagc cgagttctac tacagctgcg cccaggtcaa ggtcacgggc     600
aatggtaccg gggtgccgag ccagacatat cagatccctg gcatgtacaa tgaccgctcg     660
gagcttttca acgggctgaa cttgtggtcc tactcggtgg agaacgtcga ggcagccatg     720
aagaattcta tcgtgggtga tgaaatttgg aatggaagtt ctgttccctc tgagtcccat     780
gtcccgaagt ataagaagag tcatgcttgt cgtgtttatt ga                        822
```

<210> SEQ ID NO 78
<211> LENGTH: 273
<212> TYPE: PRT
<213> ORGANISM: Aspergillus aculeatus

<400> SEQUENCE: 78

```
Met Lys Tyr Leu Ala Ile Phe Ala Ala Ala Ala Gly Leu Ala Arg
1               5                   10                  15

Pro Thr Ala Ala His Tyr Ile Phe Ser Lys Leu Ile Leu Asp Gly Glu
            20                  25                  30

Val Ser Glu Asp Trp Gln Tyr Ile Arg Lys Thr Thr Arg Glu Thr Cys
        35                  40                  45

Tyr Leu Pro Thr Lys Phe Thr Asp Thr Phe Asp Asn Leu Thr Pro Asn
    50                  55                  60

Asp Gln Asp Phe Arg Cys Asn Leu Gly Ser Phe Ser Asn Ala Ala Lys
65                  70                  75                  80

Thr Glu Val Ala Glu Val Glu Ala Gly Ser Thr Ile Gly Met Gln Leu
                85                  90                  95

Phe Ala Gly Ser His Met Arg His Pro Gly Pro Ala Gln Val Phe Met
            100                 105                 110

Ser Lys Ala Pro Ser Gly Asn Val Gln Ser Tyr Glu Gly Asp Gly Ser
        115                 120                 125

Trp Phe Lys Ile Trp Glu Arg Thr Leu Cys Asp Lys Ser Gly Asp Leu
    130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
            180                 185                 190

Cys Ala Gln Val Lys Val Thr Gly Asn Gly Thr Gly Val Pro Ser Gln
        195                 200                 205

Thr Tyr Gln Ile Pro Gly Met Tyr Asn Asp Arg Ser Glu Leu Phe Asn
    210                 215                 220
```

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255

Ser Glu Ser His Val Pro Lys Tyr Lys Lys Ser His Ala Cys Arg Val
            260                 265                 270

Tyr

<210> SEQ ID NO 79
<211> LENGTH: 969
<212> TYPE: DNA
<213> ORGANISM: Aurantiporus alborubescens

<400> SEQUENCE: 79
atgcgaacca tcgccacgtt tgttacgctt gtagcctcag ttctccctgc ggtcctcgca      60
cacggaggtg tcctctccta ttcsaacggg gggaattggt actggggatg gaagccttac     120
aattcacctg acgggcagac caccatccaa cgcccgtggg caacatacaa tccgatcact     180
gatgcgacgg atcctaccat tgcttgcaac aacgacggga catctggagc tctgcagttg     240
actgcgacag tcgcggcggg atctgccatc acggcgtatt ggaaccaggt gtggccgcat     300
gataaagggc cgatgacgac atacctcgca caatgccccg gcagtacctg cacaggagtc     360
aacgcgaaga ctctgaaatg gttcaagatc gatcacgccg ggttgctttc tggtactgtc     420
tacagtggct cgtgggcatc aggcaagatg attgcacaga actcgacctg acaactacc     480 attccagcga cggtgccttc agggaactat ctgatacgtt tcgagactat tgccctgcac     540
tctttgccag cgcaatttta ccctgagtgc gcacaaattc aaatcacggg cggaggttcc     600
cgtgctccaa ccgctgcaga gcttgttagc ttccctggcg cgtacagcaa caatgatcct     660
ggtgtcaaca ttgacatcta ctccaatgcc gcgcagagtg caaccacata cgtaatacca     720
ggacctccat tgtacggcgg tgcttccgga tctggtccat cttccgcgcc tccatcaagt     780
accccaggta gttcgtccac ttcccacggt cccacgtccg tcagcacgtc cagcagtgct     840
gcaccatcga cgacaggaac cgtgacgcag tacggtcagt gcggtggcat tggttgggct     900
ggagctaccg gctgtatctc accattcaag tgcacggtca tcaacgatta ttactaccag     960
tgcctctga                                                             969

<210> SEQ ID NO 80
<211> LENGTH: 322
<212> TYPE: PRT
<213> ORGANISM: Aurantiporus alborubescens

<400> SEQUENCE: 80

Met Arg Thr Ile Ala Thr Phe Val Thr Leu Val Ala Ser Val Leu Pro
1               5                   10                  15

Ala Val Leu Ala His Gly Gly Val Leu Ser Tyr Ser Asn Gly Gly Asn
                20                  25                  30

Trp Tyr Trp Gly Trp Lys Pro Tyr Asn Ser Pro Asp Gly Gln Thr Thr
            35                  40                  45

Ile Gln Arg Pro Trp Ala Thr Tyr Asn Pro Ile Thr Asp Ala Thr Asp
        50                  55                  60

Pro Thr Ile Ala Cys Asn Asn Asp Gly Thr Ser Gly Ala Leu Gln Leu
65                  70                  75                  80

Thr Ala Thr Val Ala Ala Gly Ser Ala Ile Thr Ala Tyr Trp Asn Gln
                85                  90                  95

Val Trp Pro His Asp Lys Gly Pro Met Thr Thr Tyr Leu Ala Gln Cys
            100                 105                 110

Pro Gly Ser Thr Cys Thr Gly Val Asn Ala Lys Thr Leu Lys Trp Phe
        115                 120                 125

Lys Ile Asp His Ala Gly Leu Leu Ser Gly Thr Val Tyr Ser Gly Ser
    130                 135                 140

Trp Ala Ser Gly Lys Met Ile Ala Gln Asn Ser Thr Trp Thr Thr Thr
145                 150                 155                 160

Ile Pro Ala Thr Val Pro Ser Gly Asn Tyr Leu Ile Arg Phe Glu Thr
                165                 170                 175

Ile Ala Leu His Ser Leu Pro Ala Gln Phe Tyr Pro Glu Cys Ala Gln
            180                 185                 190

Ile Gln Ile Thr Gly Gly Gly Ser Arg Ala Pro Thr Ala Ala Glu Leu
        195                 200                 205

Val Ser Phe Pro Gly Ala Tyr Ser Asn Asn Asp Pro Gly Val Asn Ile
    210                 215                 220

Asp Ile Tyr Ser Asn Ala Ala Gln Ser Ala Thr Thr Tyr Val Ile Pro
225                 230                 235                 240

Gly Pro Pro Leu Tyr Gly Gly Ala Ser Gly Ser Gly Pro Ser Ser Ala
                245                 250                 255

Pro Pro Ser Ser Thr Pro Gly Ser Ser Ser Thr Ser His Gly Pro Thr
            260                 265                 270

Ser Val Ser Thr Ser Ser Ser Ala Ala Pro Ser Thr Thr Gly Thr Val
        275                 280                 285

Thr Gln Tyr Gly Gln Cys Gly Gly Ile Gly Trp Ala Gly Ala Thr Gly
    290                 295                 300

Cys Ile Ser Pro Phe Lys Cys Thr Val Ile Asn Asp Tyr Tyr Tyr Gln
305                 310                 315                 320

Cys Leu

<210> SEQ ID NO 81
<211> LENGTH: 705
<212> TYPE: DNA
<213> ORGANISM: Aurantiporus alborubescens

<400> SEQUENCE: 81
atgaaggcta tcttggctat tttctcggcc cttgctccac ttgccgctgc gcattatacc      60
ttccctgatt ttattgtcaa cggaacaaca actgccgatt gggtctacat ccgagagacc     120
gcgaaccact actcgaatgg tcctgtaacc aacgtgaacg atccagaatt ccgatgctac     180
gagctggacc tgcaaaacac ggcagcgagt accctcaccg ccacggtctc tgcaggctcc     240
agcgtcggct ttaaagctaa cagcgcccct taccatcctg ttatctcga tgtgtatatg      300 tccaaagcga ccccagctgc taattcaccc agtgctggaa cggaccaaag ctggttcaag     360
gtctatgaat ccgctccggt cttcgcgaat ggggccctaa gcttccctcc ggagaacatc     420
caatctttca cgttcacaat cccgaagtcc cttcccagtg ccaatatctc atccgtgtg      480 gaacacatcg ctctccactc cgccagtagc tacggaggtg cacaattcta catcagctgc     540
gctcaagtca atgtcgtcaa cggcgggaac ggaaacccag accgttagt caagattccc      600 ggcgtttaca ctgggaacga gcctggcatc ctcatcaaca tctacagctt cccaccgggt     660
ttcagtggct accaatcccc gggacctgct gtgtggcgtg gttga                     705

<210> SEQ ID NO 82

<211> LENGTH: 234
<212> TYPE: PRT
<213> ORGANISM: Aurantiporus alborubescens

<400> SEQUENCE: 82

Met Lys Ala Ile Leu Ala Ile Phe Ser Ala Leu Ala Pro Leu Ala Ala
1               5                   10                  15

Ala His Tyr Thr Phe Pro Asp Phe Ile Val Asn Gly Thr Thr Thr Ala
            20                  25                  30

Asp Trp Val Tyr Ile Arg Glu Thr Ala Asn His Tyr Ser Asn Gly Pro
        35                  40                  45

Val Thr Asn Val Asn Asp Pro Glu Phe Arg Cys Tyr Glu Leu Asp Leu
    50                  55                  60

Gln Asn Thr Ala Ala Ser Thr Leu Thr Ala Thr Val Ser Ala Gly Ser
65                  70                  75                  80

Ser Val Gly Phe Lys Ala Asn Ser Ala Leu Tyr His Pro Gly Tyr Leu
                85                  90                  95

Asp Val Tyr Met Ser Lys Ala Thr Pro Ala Ala Asn Ser Pro Ser Ala
            100                 105                 110

Gly Thr Asp Gln Ser Trp Phe Lys Val Tyr Glu Ser Ala Pro Val Phe
        115                 120                 125

Ala Asn Gly Ala Leu Ser Phe Pro Ser Glu Asn Ile Gln Ser Phe Thr
    130                 135                 140

Phe Thr Ile Pro Lys Ser Leu Pro Ser Gly Gln Tyr Leu Ile Arg Val
145                 150                 155                 160

Glu His Ile Ala Leu His Ser Ala Ser Tyr Gly Gly Ala Gln Phe
                165                 170                 175

Tyr Ile Ser Cys Ala Gln Val Asn Val Val Asn Gly Gly Asn Gly Asn
            180                 185                 190

Pro Gly Pro Leu Val Lys Ile Pro Gly Val Tyr Thr Gly Asn Glu Pro
        195                 200                 205

Gly Ile Leu Ile Asn Ile Tyr Ser Phe Pro Pro Gly Phe Ser Gly Tyr
    210                 215                 220

Gln Ser Pro Gly Pro Ala Val Trp Arg Gly
225                 230

<210> SEQ ID NO 83
<211> LENGTH: 702
<212> TYPE: DNA
<213> ORGANISM: Trichophaea saccata

<400> SEQUENCE: 83
atgacgcccc tgaaactccg cccccttctc ctcctggtgc tttccacgac cctcagcctc          60
gtgcacgcgc actatcgctt ctacgaactg atcgccaacg ggccacccca cgcttccttc         120
gaatacatcc gccaatgggt gcccatctac agcaactctc ccgtaaccga cgtcaccagc         180
gtcaacctcc gctgcaacgt caacgccact cccgccgccg aggtgatcac cgttgctgcc         240
ggtagcaccg tcggcttcgt agcagacaca acagtaacgc accccggtgc gttcaccgcg         300
tacatggcga aagcgcccga agacatcacg gaatgggatg caacggggga ctggttcaag         360
atctgggaga agggtccaac gagtataacc agtagcggga taacctggga cgtcacggat         420
acccaatgga ccttcaccat cccttccgcg acaccaaacg gtcaatacct actccgcttc         480
gagcacatag cgctccacgc cgccagcacc gtgggggggtg ctcaattcta catgtcgtgc         540
gcgcagatac aagtaacgaa cggcggcaac gggagtcccg ggcccaccat caagttcccg         600

```
ggcggataca gcgccacaga ccccggtatc ctgatcaata tctattatcc catccccact    660
agttacacta ttcctggtcc accggtttgg accggtaagt aa                       702
```

<210> SEQ ID NO 84
<211> LENGTH: 233
<212> TYPE: PRT
<213> ORGANISM: Trichophaea saccata

<400> SEQUENCE: 84

```
Met Thr Pro Leu Lys Leu Arg Pro Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
    50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
            100                 105                 110

Asp Gly Asn Gly Asp Trp Phe Lys Ile Trp Glu Lys Gly Pro Thr Ser
        115                 120                 125

Ile Thr Ser Ser Gly Ile Thr Trp Asp Val Thr Asp Thr Gln Trp Thr
    130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
            180                 185                 190

Pro Gly Pro Thr Ile Lys Phe Pro Gly Gly Tyr Ser Ala Thr Asp Pro
        195                 200                 205

Gly Ile Leu Ile Asn Ile Tyr Tyr Pro Ile Pro Thr Ser Tyr Thr Ile
    210                 215                 220

Pro Gly Pro Pro Val Trp Thr Gly Lys
225                 230
```

<210> SEQ ID NO 85
<211> LENGTH: 714
<212> TYPE: DNA
<213> ORGANISM: Trichophaea saccata

<400> SEQUENCE: 85

```
atgaaatgcc ttctctccct ccttctcgcc gcgacagcgg tctccgctca cacgatcttc    60
caagaaatcg gcataaacgg ggtgatgcaa gctcgctacg actacatgcg gctgccgtcc   120
tacgacggtc ccattacgga cgtaacgagc acctacatgg cgtgcaacgg tggtcccaat   180
ccattggtcc aaatctcgaa cgacgtcgct ttcgtaaaag ccggcgacag catcacgctg   240
caatgggcgc aaacgttgac gacagatttc aacacggggc tgatcatcga tccatcgcac   300
ttgggtcctg tgatggtcta catggccaaa gtaccctccg ccaccggtcc gatccccaac   360
agcggctggt tcaaaatcta cgaagacggc tacgacccga caacaaagac atgggcggta   420
```

```
accaagctca tcaacaacaa gggaaaagtg accgtcacca tcccatcgtg tctaccggca    480
ggggactact tgctgcgcgg tgaaatcatt gccttgcacg cggctagtac ctatccaggc    540
gcacagtttt acatggagtg tgcgcagttg cggcttacca gtggcggcac taagatgcct    600
accacgtata acattccggg gatctattcg cccactgatc cgggtgttac gttcaatctt    660
tacaatggat tcacgagtta taccattcct ggcccaaggc cgtttacatg ctag          714
```

<210> SEQ ID NO 86
<211> LENGTH: 237
<212> TYPE: PRT
<213> ORGANISM: Trichophaea saccata

<400> SEQUENCE: 86

```
Met Lys Cys Leu Leu Ser Leu Leu Ala Ala Thr Ala Val Ser Ala
1               5                   10                  15

His Thr Ile Phe Gln Glu Ile Gly Ile Asn Gly Val Met Gln Ala Arg
                20                  25                  30

Tyr Asp Tyr Met Arg Leu Pro Ser Tyr Asp Gly Pro Ile Thr Asp Val
            35                  40                  45

Thr Ser Thr Tyr Met Ala Cys Asn Gly Gly Pro Asn Pro Leu Val Gln
50                  55                  60

Ile Ser Asn Asp Val Ala Phe Val Lys Ala Gly Asp Ser Ile Thr Leu
65                  70                  75                  80

Gln Trp Ala Gln Thr Leu Thr Thr Asp Phe Asn Thr Gly Leu Ile Ile
                85                  90                  95

Asp Pro Ser His Leu Gly Pro Val Met Val Tyr Met Ala Lys Val Pro
            100                 105                 110

Ser Ala Thr Gly Pro Ile Pro Asn Ser Gly Trp Phe Lys Ile Tyr Glu
        115                 120                 125

Asp Gly Tyr Asp Pro Thr Thr Lys Thr Trp Ala Val Thr Lys Leu Ile
130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
                165                 170                 175

Thr Tyr Pro Gly Ala Gln Phe Tyr Met Glu Cys Ala Gln Leu Arg Leu
            180                 185                 190

Thr Ser Gly Gly Thr Lys Met Pro Thr Thr Tyr Asn Ile Pro Gly Ile
        195                 200                 205

Tyr Ser Pro Thr Asp Pro Gly Val Thr Phe Asn Leu Tyr Asn Gly Phe
210                 215                 220

Thr Ser Tyr Thr Ile Pro Gly Pro Arg Pro Phe Thr Cys
225                 230                 235
```

<210> SEQ ID NO 87
<211> LENGTH: 1455
<212> TYPE: DNA
<213> ORGANISM: Penicillium thomii

<400> SEQUENCE: 87

```
atgtctctgt ctaagatttc tggattgatc ctcggatctg ctgccttggt ggctggccac    60
ggttacgtga gcggaatcgt cgttgacgat acctactatg tggataccct tgtcacccag    120 taccccttatg agagtgacgc cccagagctc attgcctggt cggagcaaga gaccgatctg    180
ggttacatcg atggctctga gtatgccaac tccaacatca tctgtcacaa ggaggccaaa    240
```

```
cctggtgctt tggaagcacc cgttaaggct ggtggctccg tcgagctcca gtggaccact    300
tggcctacca gccaccacgg tcctgtcatt acctacatgg ccaactgtaa cggcgactgt    360
gacgacgttg acaagactac tttgcagttc ttcaagattg accagggtgg tttgatcagc    420
gataccaccg agcccggtac ctgggcaact gacaacctca tcgccaacaa caatagccgt    480
actgtcaccg tccccagcga cattgccgat ggaaactacg tcctccgtca cgagatcatt    540
gccctccact ccgccgggga gaccaacggt gcccagaact accccaatg  tatcaacttg    600 aaggtcactg gcggcggtag cgctactcct tctggtaccc tgggtaccgc cctgtacaag    660
aacaccgacc ccggtatcct gatcaacatc tacacttccc tcagcaccta cgatatcccc    720
ggcccaaccc tgtacactgc cggcgccgcc gctgctaccg ctgcctccac ggctgcctct    780
tccaccgccg ctgccgttac tactgccgac gccgtcacta ccgccgctgc cgtcaccagc    840
agctctgcat ccgtggaagt tgtgcccaca actactccca gctcatcaat cgtcagtgcc    900
ttcccaacct ggagcccctc ttctacccca cccttctcca actcttccaa cggatggcgt    960
ccgtcattca gccgcggacc tggtggcccc cgcttcacat ctgctcctgc tcctcagttc   1020
tccgctccta gcggcgctca gcagaagcag tctgccactg ctaccccat  cgtggctacc   1080 cctgtcgtga tcaccatgac cgagaccagc acctcctggg tcaccgaaat ggttactctt   1140
actgacaagt ctgttgtgca gaccaccagc gctgtcccag tcgtcgtcgc cgccaccact   1200
acccttaccg agggaagcga gcctgctcag acagcctccc ccagcgttgt ctccggctcc   1260
tctagctccg gctctagctc ctcatctacc accaccacct caaagacctc aactggatcc   1320
gactacgtct ccagcgactg gatgtcttac ctcagctcct tgagcgctgc tgaggtcctc   1380
cagatgctgc gccagacctt ccgttggatg gtcagcaacg acaaggtgca cgctcgtgat   1440
attaccatca actag                                                   1455
```

<210> SEQ ID NO 88
<211> LENGTH: 484
<212> TYPE: PRT
<213> ORGANISM: Penicillium thomii

<400> SEQUENCE: 88

Met Ser Leu Ser Lys Ile Ser Gly Leu Ile Leu Gly Ser Ala Ala Leu
1               5                   10                  15

Val Ala Gly His Gly Tyr Val Ser Gly Ile Val Asp Asp Thr Tyr
            20                  25                  30

Tyr Gly Gly Tyr Leu Val Thr Gln Tyr Pro Tyr Glu Ser Asp Ala Pro
        35                  40                  45

Glu Leu Ile Ala Trp Ser Glu Gln Glu Thr Asp Leu Gly Tyr Ile Asp
    50                  55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Gly Ser Val Glu Leu
                85                  90                  95

Gln Trp Thr Thr Trp Pro Thr Ser His His Gly Pro Val Ile Thr Tyr
            100                 105                 110

Met Ala Asn Cys Asn Gly Asp Cys Asp Val Asp Lys Thr Thr Leu
        115                 120                 125

Gln Phe Phe Lys Ile Asp Gln Gly Gly Leu Ile Ser Asp Thr Thr Glu
    130                 135                 140

Pro Gly Thr Trp Ala Thr Asp Asn Leu Ile Ala Asn Asn Asn Ser Arg
145                 150                 155                 160

Thr Val Thr Val Pro Ser Asp Ile Ala Asp Gly Asn Tyr Val Leu Arg
            165                 170                 175

His Glu Ile Ile Ala Leu His Ser Ala Gly Glu Thr Asn Gly Ala Gln
            180                 185                 190

Asn Tyr Pro Gln Cys Ile Asn Leu Lys Val Thr Gly Gly Ser Ala
        195                 200                 205

Thr Pro Ser Gly Thr Leu Gly Thr Ala Leu Tyr Lys Asn Thr Asp Pro
        210                 215                 220

Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Thr Ala Ala Ser
            245                 250                 255

Thr Ala Ala Ser Ser Thr Ala Ala Ala Val Thr Thr Ala Asp Ala Val
            260                 265                 270

Thr Thr Ala Ala Ala Val Thr Ser Ser Ala Ser Val Glu Val Val
        275                 280                 285

Pro Thr Thr Thr Pro Ser Ser Ser Ile Val Ser Ala Phe Pro Thr Trp
        290                 295                 300

Ser Pro Ser Ser Thr Pro Pro Phe Ser Asn Ser Ser Asn Gly Trp Arg
305                 310                 315                 320

Pro Ser Phe Ser Arg Gly Pro Gly Pro Arg Phe Thr Ser Ala Pro
            325                 330                 335

Ala Pro Gln Phe Ser Ala Pro Ser Gly Ala Gln Gln Lys Gln Ser Ala
            340                 345                 350

Thr Ala Thr Pro Ile Val Ala Thr Pro Val Val Ile Thr Met Thr Glu
            355                 360                 365

Thr Ser Thr Ser Trp Val Thr Glu Met Val Thr Leu Thr Asp Lys Ser
            370                 375                 380

Val Val Gln Thr Thr Ser Ala Val Pro Val Val Ala Ala Thr Thr
385                 390                 395                 400

Thr Leu Thr Glu Gly Ser Glu Pro Ala Gln Thr Ala Ser Pro Ser Val
            405                 410                 415

Val Ser Gly Ser Ser Ser Ser Gly Ser Ser Ser Ser Thr Thr Thr
        420                 425                 430

Thr Ser Lys Thr Ser Thr Gly Ser Asp Tyr Val Ser Ser Asp Trp Met
        435                 440                 445

Ser Tyr Leu Ser Ser Leu Ser Ala Ala Glu Val Leu Gln Met Leu Arg
            450                 455                 460

Gln Thr Phe Arg Trp Met Val Ser Asn Asp Lys Val His Ala Arg Asp
465                 470                 475                 480

Ile Thr Ile Asn

<210> SEQ ID NO 89
<211> LENGTH: 1021
<212> TYPE: DNA
<213> ORGANISM: Talaromyces stipitatus

<400> SEQUENCE: 89
atgccttcca ctaaagttgc tgctctatct gccgtcctgg ctttggcctc cacggttgct      60
ggccatggct ttgtgcaaaa tattgtcatt gacggtaaat cgtaagtgac ttgcttttgt     120
actatagagc tagataaata cttatactaa ataattcagc tacactggct acctcgtgaa     180
ccagtatcct taccagtcca acccaccagc tgttattggg tggtcaacca ctgcaaccga     240

-continued

```
cttgggattt gtcgatggat ctggatacac caacccggat atcatctgcc acaaaaacgc    300
caaacccggt cagctttctg ctccggttgc cgcaggaggc aaggttgagc tcgaatggac    360
aacatggccc gagagccatc acggccctgt catcagctat ctcgccaatt gcaatggcga    420
ttgtactacc gtggataaga cgaagctcga atttgtcaaa atcgatcagc ggggtctgat    480
cgacgacagc aatcctcccg gtacatgggc cgccgaccag ctcatcgccg ccaacaacag    540
ctggactgta actattcccg agagcatcgc gcctggaaac tacgtccttc gccacgaaat    600
catcgctctt cactccgcca acaacgcaac cggagctcaa aactaccctc aatgcatcaa    660
cttgcaaatc actggcagcg ggacggccaa cccatctggt acccctggcg agaaactcta    720
taccccaact gacccaggta tcttggtcaa catctaccag tcattgtcgt cttatgttat    780
tcccggtccg actttgtgga gtggtgctgc agcgcacgtt gttgccactg cagccggttc    840
tgctactggg gttgcttctg ccaccgctac tccgaccact cttgtgactg ccgtttcatc    900
gcctaccggt gctccttcag tggtgactcc tgaggctcct tcagtaacct cgttcgcccc    960
agtggtgact gttactgatg tcgttactgt gactaccgtc atcactacta ctatctctta   1020
g                                                                   1021
```

<210> SEQ ID NO 90
<211> LENGTH: 320
<212> TYPE: PRT
<213> ORGANISM: Talaromyces stipitatus

<400> SEQUENCE: 90

```
Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
                20                  25                  30

Lys Ser Tyr Thr Gly Tyr Leu Val Asn Gln Tyr Pro Tyr Gln Ser Asn
            35                  40                  45

Pro Pro Ala Val Ile Gly Trp Ser Thr Thr Ala Thr Asp Leu Gly Phe
        50                  55                  60

Val Asp Gly Ser Gly Tyr Thr Asn Pro Asp Ile Ile Cys His Lys Asn
65                  70                  75                  80

Ala Lys Pro Gly Gln Leu Ser Ala Pro Val Ala Ala Gly Gly Lys Val
                85                  90                  95

Glu Leu Glu Trp Thr Thr Trp Pro Glu Ser His His Gly Pro Val Ile
            100                 105                 110

Ser Tyr Leu Ala Asn Cys Asn Gly Asp Cys Thr Thr Val Asp Lys Thr
        115                 120                 125

Lys Leu Glu Phe Val Lys Ile Asp Gln Arg Gly Leu Ile Asp Asp Ser
    130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
            180                 185                 190

Ala Gln Asn Tyr Pro Gln Cys Ile Asn Leu Gln Ile Thr Gly Ser Gly
        195                 200                 205

Thr Ala Asn Pro Ser Gly Thr Pro Gly Glu Lys Leu Tyr Thr Pro Thr
    210                 215                 220

Asp Pro Gly Ile Leu Val Asn Ile Tyr Gln Ser Leu Ser Ser Tyr Val
```

```
                    225                 230                 235                 240

Ile Pro Gly Pro Thr Leu Trp Ser Gly Ala Ala His Val Val Ala
                245                 250                 255

Thr Ala Ala Gly Ser Ala Thr Gly Val Ala Ser Ala Thr Ala Thr Pro
            260                 265                 270

Thr Thr Leu Val Thr Ala Val Ser Ser Pro Thr Gly Ala Pro Ser Val
                275                 280                 285

Val Thr Pro Glu Ala Pro Ser Val Thr Ser Phe Ala Pro Val Val Thr
            290                 295                 300

Val Thr Asp Val Val Thr Val Thr Thr Val Ile Thr Thr Thr Ile Ser
305                 310                 315                 320

<210> SEQ ID NO 91
<211> LENGTH: 872
<212> TYPE: DNA
<213> ORGANISM: Thermomyces lanuginosus

<400> SEQUENCE: 91
atgaagggct ccagcgctgc gtcggtgctt cttaccttcc tcgcgggcat ctcccgtacc     60
tctgcgcacg ggtatgtctc caacctcgtt atcaacggcg tctactatcg gggctggctc    120
cccggcgaag accccctacaa ccctgacccc ccgattggcg ttggctggga gacgcccaac    180
ctgggcaacg gcttcgtgac gccgtcggaa gcgtcgaccg acgccgtcat ctgccacaag    240
gaagccacac cagcccgcgg tcatgtctcc gtgaaggccg gtgacaagat ctacatccaa    300
tggcagccga atccatggcc ggattccacc acggtgcgt caaacttctg cccgaaagct    360
gttcacactc actaacaaca cttttaggcc ccgtcctgga ctatctggcc ccttgcaacg    420
ggccctgtga gtccgtcgac aagaccagcc tgcgcttctt caagatcgac ggagtgggtc    480
ttatcgacgg ctcttctcct ccgggctact gggccgacga cgaactcatt gcgaacggca    540
acgggtggct ggttcagatc cccgaggaca tcaagcccgg gtaactacgtc ctgcgacacg    600 agatcatcgc cttgcacagc gccgggaacc cggacggcgc ccagctgtac ccgcagtgct    660
tcaaccttga gattacggga tccggcaccc tcgagccgga gggcgtgcca gccaccgagt    720
tctactcgcc cgatgacccg ggcatcctgg tcaacatcta cgagccctg tccacgtatg    780 aggtgccggg tccctcgctc atcccgcagg cggttcagat cgagcagtct tcgtctgcga    840
ttacggcgac gggcacgccg acgccggcat ga                                  872

<210> SEQ ID NO 92
<211> LENGTH: 272
<212> TYPE: PRT
<213> ORGANISM: Thermomyces lanuginosus

<400> SEQUENCE: 92

Met Lys Gly Ser Ser Ala Ala Ser Val Leu Leu Thr Phe Leu Ala Gly
1               5                   10                  15

Ile Ser Arg Thr Ser Ala His Gly Tyr Val Ser Asn Leu Val Ile Asn
                20                  25                  30

Gly Val Tyr Tyr Arg Gly Trp Leu Pro Gly Glu Asp Pro Tyr Asn Pro
            35                  40                  45

Asp Pro Pro Ile Gly Val Gly Trp Glu Thr Pro Asn Leu Gly Asn Gly
        50                  55                  60

Phe Val Thr Pro Ser Glu Ala Ser Thr Asp Ala Val Ile Cys His Lys
65                  70                  75                  80

Glu Ala Thr Pro Ala Arg Gly His Val Ser Val Lys Ala Gly Asp Lys
```

```
              85                  90                  95
Ile Tyr Ile Gln Trp Gln Pro Asn Pro Trp Pro Asp Ser His His Gly
            100                 105                 110
Pro Val Leu Asp Tyr Leu Ala Pro Cys Asn Gly Pro Cys Glu Ser Val
            115                 120                 125
Asp Lys Thr Ser Leu Arg Phe Phe Lys Ile Asp Gly Val Gly Leu Ile
        130                 135                 140
Asp Gly Ser Ser Pro Pro Gly Tyr Trp Ala Asp Asp Glu Leu Ile Ala
145                 150                 155                 160
Asn Gly Asn Gly Trp Leu Val Gln Ile Pro Glu Asp Ile Lys Pro Gly
                165                 170                 175
Asn Tyr Val Leu Arg His Glu Ile Ile Ala Leu His Ser Ala Gly Asn
            180                 185                 190
Pro Asp Gly Ala Gln Leu Tyr Pro Gln Cys Phe Asn Leu Glu Ile Thr
        195                 200                 205
Gly Ser Gly Thr Val Glu Pro Glu Gly Val Pro Ala Thr Glu Phe Tyr
    210                 215                 220
Ser Pro Asp Asp Pro Gly Ile Leu Val Asn Ile Tyr Glu Pro Leu Ser
225                 230                 235                 240
Thr Tyr Glu Val Pro Gly Pro Ser Leu Ile Pro Gln Ala Val Gln Ile
                245                 250                 255
Glu Gln Ser Ser Ser Ala Ile Thr Ala Thr Gly Thr Pro Thr Pro Ala
            260                 265                 270

<210> SEQ ID NO 93
<211> LENGTH: 1039
<212> TYPE: DNA
<213> ORGANISM: Thermomyces lanuginosus

<400> SEQUENCE: 93
atggcattct ctacggttac agtttttgtt acgttcctgg ccttcatctc catagcttct      60
gctcatggct tcgtgacaaa aatcaccgta ctcggagata taataagga gtacgtctca     120
gtctcgctag gttgctaaca caggagagat cgctgaccat gcagctacc ccggctttga     180
cccgagcact cccaaggagg ttcctccggg tctcgatgtc gcttggtcta ctagtgccag     240
tgatcaggga tacatgagca gttcaaatgc ctcgtatcac agtaaggact ttatctgcca     300
cagaaacgcc aaacctgctc cagacgcagc tcaagttcat gcgggcgaca aggtgcagct     360
tcactggact caatggcctg gacctgagga tcaccagggt cctatccttg attacctcgc     420
gagctgcaac ggaccctgct caaacgtgga gaaggcgagc cttaagtgga cgaagattga     480
cgaggcaggg cgcttttccca acggaacgtg ggcaacggac ctgctcagga atggggaaa     540
cacgtggaat gtgacgattc catcggatct tgctcctgga gaatatgtcc tccgcaacga     600
gatcattgca cttcactcgg cgagaaatat gggtggagct cagcactaca tgcaatgtgt     660
caatctgaac gtcactggca ccggccatag agagctacag ggcgtctccg ccgcagaatt     720
ttacaatcct acggatcctg gaattttgat taacgtctgg caaactcaaa gcctttcctc     780
ctaccatatt cccggaccta cactgttagc cgccgatacc ggcaacgacg gtgccattc     840
tgcatcatct accttggcga ctgtgacaag cagacgtctt ccactccga gcgacgccat     900
gcccgggaat ggttcatacg gtgcaatttc gccgccctc aaacctgcta aggattcca     960
tcctgttttgt aacgcccgat tcagacatgg cagcactttc actttgacta ccctggtcgc    1020
accaccagcc aggacctaa                                                  1039
```

<210> SEQ ID NO 94
<211> LENGTH: 327
<212> TYPE: PRT
<213> ORGANISM: Thermomyces lanuginosus

<400> SEQUENCE: 94

Met Ala Phe Ser Thr Val Thr Val Phe Val Thr Phe Leu Ala Phe Ile
1               5                   10                  15

Ser Ile Ala Ser Ala His Gly Phe Val Thr Lys Ile Thr Val Leu Gly
            20                  25                  30

Asp Asn Asn Lys Asp Tyr Pro Gly Phe Asp Pro Ser Thr Pro Lys Glu
        35                  40                  45

Val Pro Pro Gly Leu Asp Val Ala Trp Ser Thr Ser Ala Ser Asp Gln
50                  55                  60

Gly Tyr Met Ser Ser Asn Ala Ser Tyr His Ser Lys Asp Phe Ile
65                  70                  75                  80

Cys His Arg Asn Ala Lys Pro Ala Pro Asp Ala Ala Gln Val His Ala
                85                  90                  95

Gly Asp Lys Val Gln Leu His Trp Thr Gln Trp Pro Gly Pro Glu Asp
            100                 105                 110

His Gln Gly Pro Ile Leu Asp Tyr Leu Ala Ser Cys Asn Gly Pro Cys
        115                 120                 125

Ser Asn Val Glu Lys Ala Ser Leu Lys Trp Thr Lys Ile Asp Glu Ala
130                 135                 140

Gly Arg Phe Pro Asn Gly Thr Trp Ala Thr Asp Leu Leu Arg Asn Gly
145                 150                 155                 160

Gly Asn Thr Trp Asn Val Thr Ile Pro Ser Asp Leu Ala Pro Gly Glu
                165                 170                 175

Tyr Val Leu Arg Asn Glu Ile Ile Ala Leu His Ser Ala Arg Asn Met
            180                 185                 190

Gly Gly Ala Gln His Tyr Met Gln Cys Val Asn Leu Asn Val Thr Gly
        195                 200                 205

Thr Gly His Arg Glu Leu Gln Gly Val Ser Ala Ala Glu Phe Tyr Asn
210                 215                 220

Pro Thr Asp Pro Gly Ile Leu Ile Asn Val Trp Gln Thr Gln Ser Leu
225                 230                 235                 240

Ser Ser Tyr His Ile Pro Gly Pro Thr Leu Leu Ala Ala Asp Thr Gly
                245                 250                 255

Asn Asp Gly Gly His Ser Ala Ser Ser Thr Leu Ala Thr Val Thr Ser
            260                 265                 270

Arg Arg Leu Ser Thr Pro Ser Asp Ala Met Pro Gly Asn Gly Ser Tyr
        275                 280                 285

Gly Ala Ile Ser Pro Pro Leu Lys Pro Ala Lys Gly Phe His Pro Val
290                 295                 300

Cys Asn Ala Arg Phe Arg His Gly Ser Thr Phe Thr Leu Thr Thr Leu
305                 310                 315                 320

Val Ala Pro Pro Ala Arg Thr
                325

<210> SEQ ID NO 95
<211> LENGTH: 881
<212> TYPE: DNA
<213> ORGANISM: Thermomyces lanuginosus

<400> SEQUENCE: 95

-continued

```
atgaaaggct ccaccactgc gtctttgctt cttccgctcc tggcgagcgt tactcgcacc    60
tctgcgcacg ggtttgtctc caacctcgtc atcaatggcg tcttctatcg gggctggctc   120
ccgaccgagg acccctacaa ggctgacccc ccgattggcg tcggctggga gacgcctaac   180
ctgggcaacg gcttcgtgct gcccgaagaa gcgtcgaccg atgccatcgt ctgccacaaa   240
gaggccgagc cggcccgcgg ctatgccagc gtcgctgccg gtgacaagat ctacattcag   300
tggcagccga accatggcc ggagtctcat cacggtacgt caaactgccc attgttgcaa   360
ttcagaatca tctactaaca actcttcaag gccccgtcat tgactacctg ccccttgca    420
acggtgactg ctcgactgtc aacaagacca gtttggagtt cttcaagatc gacggcgtgg   480
gcctcatcga cggctcctcc ccgccgggta agtgggctga cgacgagctc attgccaacg   540
gcaacggctg gctggtccag atccccgagg acatcaagcc gggcaactac gtcctgcgcc   600
atgagatcat cgccttgcac gaggcgttca accagaacgg cgctcagatc tacccgcagt   660
gcttcaacct ccagattacc ggctccggca ctgtcgagcc cgagggcacg ccggctaccg   720
agctgtattc gcccaccgat ccgggcattc tggttgacat ctacaacccc ttgagcacgt   780
acgtcgtgcc cggcccgacg ctcatcccgc aggcggttga gattgagcag tcttcgtcgg   840
ctgtcacggc gactggtacg ccgacgccgg cggcggcgta a                       881
```

<210> SEQ ID NO 96
<211> LENGTH: 274
<212> TYPE: PRT
<213> ORGANISM: Thermomyces lanuginosus

<400> SEQUENCE: 96

```
Met Lys Gly Ser Thr Thr Ala Ser Leu Leu Pro Leu Leu Ala Ser
1               5                   10                  15

Val Thr Arg Thr Ser Ala His Gly Phe Val Ser Asn Leu Val Ile Asn
            20                  25                  30

Gly Val Phe Tyr Arg Gly Trp Leu Pro Thr Glu Asp Pro Tyr Lys Ala
        35                  40                  45

Asp Pro Pro Ile Gly Val Gly Trp Glu Thr Pro Asn Leu Gly Asn Gly
    50                  55                  60

Phe Val Leu Pro Glu Glu Ala Ser Thr Asp Ala Ile Val Cys His Lys
65                  70                  75                  80

Glu Ala Glu Pro Ala Arg Gly Tyr Ala Ser Val Ala Ala Gly Asp Lys
                85                  90                  95

Ile Tyr Ile Gln Trp Gln Pro Asn Pro Trp Pro Glu Ser His His Gly
            100                 105                 110

Pro Val Ile Asp Tyr Leu Ala Pro Cys Asn Gly Asp Cys Ser Thr Val
        115                 120                 125

Asn Lys Thr Ser Leu Glu Phe Phe Lys Ile Asp Gly Val Gly Leu Ile
    130                 135                 140

Asp Gly Ser Ser Pro Pro Gly Lys Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Ala Phe Asn
            180                 185                 190

Gln Asn Gly Ala Gln Ile Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220
```

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
            245                 250                 255

Glu Gln Ser Ser Ser Ala Val Thr Ala Thr Gly Thr Pro Thr Pro Ala
        260                 265                 270

Ala Ala

<210> SEQ ID NO 97
<211> LENGTH: 821
<212> TYPE: DNA
<213> ORGANISM: Humicola insolens

<400> SEQUENCE: 97
atgaagctca gcgttgtcct cacaggcctg gcggcagccc tcgccgaggc tcattgtcag      60
tccatacgac agcgaaaccc ctggatgatc acgagactaa ccagtcctac cagacacctt     120
ccccagcgtc ggcaacaccg ccgactggca ggtcgtgcgc cagacgacca acttccagag     180
caacggcccc gtgacggacg tcaactcgga ccagatccgg tgctacgagc gcttccccgg     240 ccaggggggcg cccggcatct acaacgtcac cgccggccag accatctcgt acaacgccaa     300
ggcctctatc tcccacccgg gccccatggc cttctacatc gccaaggtcc ctgccggcta     360
caccgccgcc aactgggatg gcaggggcgc cgtgtggtcc aagatctacc aggacatgcc     420
gcgcattgcg gggagtctga cctggcctac caatggtacg aaatcctctt ctatccttca     480
tacttgctat tcctccaact gcctggcagc tcacactaac ttccacacac caggcgcccc     540
gttccgtctc ggtaaccatc ccccgctgcc tgcaagacgg ccactacctg ttgcgcgccg     600
agcacatcgg cctgcacagc gcgagcggcg tgggcggcgc gcagttctac atctcgtgtg     660
cccagctcta cgtcagcggc ggcaccggca cttggaaccc gcgcaacaag gtcgcgttcc     720
ccggcgccta cagcccgacg cacccgggca tcatgatcaa catctactgg ccggtgccga     780
cgagctacac gccgccgggg ccgccggttg agacgtgctg a                        821

<210> SEQ ID NO 98
<211> LENGTH: 227
<212> TYPE: PRT
<213> ORGANISM: Humicola insolens

<400> SEQUENCE: 98

Met Lys Leu Ser Val Val Leu Thr Gly Leu Ala Ala Ala Leu Ala Glu
1               5                   10                  15

Ala His Tyr Thr Phe Pro Ser Val Gly Asn Thr Ala Asp Trp Gln Val
            20                  25                  30

Val Arg Gln Thr Thr Asn Phe Gln Ser Asn Gly Pro Val Thr Asp Val
        35                  40                  45

Asn Ser Asp Gln Ile Arg Cys Tyr Glu Arg Phe Pro Gly Gln Gly Ala
    50                  55                  60

Pro Gly Ile Tyr Asn Val Thr Ala Gly Gln Thr Ile Ser Tyr Asn Ala
65                  70                  75                  80

Lys Ala Ser Ile Ser His Pro Gly Pro Met Ala Phe Tyr Ile Ala Lys
                85                  90                  95

Val Pro Ala Gly Tyr Thr Ala Ala Asn Trp Asp Gly Arg Gly Ala Val
            100                 105                 110

Trp Ser Lys Ile Tyr Gln Asp Met Pro Arg Ile Ala Gly Ser Leu Thr
        115                 120                 125

Trp Pro Thr Asn Gly Ala Arg Ser Val Ser Val Thr Ile Pro Arg Cys
            130                 135                 140

Leu Gln Asp Gly His Tyr Leu Leu Arg Ala Glu His Ile Gly Leu His
145                 150                 155                 160

Ser Ala Ser Gly Val Gly Gly Ala Gln Phe Tyr Ile Ser Cys Ala Gln
                165                 170                 175

Leu Tyr Val Ser Gly Gly Thr Gly Thr Trp Asn Pro Arg Asn Lys Val
                180                 185                 190

Ala Phe Pro Gly Ala Tyr Ser Pro Thr His Pro Gly Ile Met Ile Asn
        195                 200                 205

Ile Tyr Trp Pro Val Pro Thr Ser Tyr Thr Pro Pro Gly Pro Pro Val
        210                 215                 220

Glu Thr Cys
225

<210> SEQ ID NO 99
<211> LENGTH: 1120
<212> TYPE: DNA
<213> ORGANISM: Humicola insolens

<400> SEQUENCE: 99

```
atgcgcccct tcctcgccgc cctcgccgcg gccaccacgg tccacgccca cggctgggtc      60
gacaacgcca ccatcgacgg cgtcttctac cagctctacc acccgtacat ggacccgtac     120
atgggcgagt cgccccgcc tcgcatctcg cgcaagctgg tgtggaacgg ctacgtgaac     180
gacgtgacgt ccatcgacct gcaatgcggc ggacacacgg ccgaagggca atcggcacg     240
gaacccgcgc cgctgcacgc ccccgccacg gccgggtcga cggtcaacct ccgctggacg     300
ctgtggccgg actcgcacat ggggcccatc atgacgtaca tggcgcggtg tccggacgag     360
ggttgtgata agtggttgcc gggggaggag taagtgtttc ctggcgggaa tggctgtgta     420
tttgagaagg agatattatg agtgaaactg gagaggcga gaagaagaga tgctgacgcg     480
ggttttgctc tcctcagacc agtctggttc aaaatccacg aagccggccg gtacaccacc     540
gacaagtctt accccgacga catctgggaa gttgtaagtg ccctgcctac ctatccatcc     600
ctaattccct ccctcccctc tccacctcct ccttccgcgc ccccctcccc ccccttattt     660
gctaaccaac cccctccctt acagacccgc tcatgtacc cgccaacga aggctacaac     720
tacaccatcc ccgcctgcct cgcatccggc cactacctgg tccggcacga gatcatcgcc     780
ttacactcgg cctgggccaa aggcgaagcg cagttctatc cctcgtgcca ccagctgacc     840
gtcacctcca tcggcggtaa cgtgcgcgaa gcgccggccg agtaccgcgt cagtttcccc     900
ggcgcgtaca aggacgatga tccgggtatt ttcatcaacg tttggaaccg taagttcttt     960
ttttgttccc cttcctccca acctacctag gtgtcgtaat gtggtccgta agggtttgtt    1020
tgttgttgag ggatatagct gacaatggat gtgtgataac acagctggcc cctacaccat    1080
tcccggaccg ccggtctgga cgtgccccga gtctgagtaa                         1120
```

<210> SEQ ID NO 100
<211> LENGTH: 257
<212> TYPE: PRT
<213> ORGANISM: Humicola insolens

<400> SEQUENCE: 100

Met Arg Pro Phe Leu Ala Ala Leu Ala Ala Ala Thr Thr Val His Ala
1               5                   10                  15

```
His Gly Trp Val Asp Asn Ala Thr Ile Asp Gly Val Phe Tyr Gln Leu
            20                  25                  30
Tyr His Pro Tyr Met Asp Pro Tyr Met Gly Glu Phe Ala Pro Pro Arg
        35                  40                  45
Ile Ser Arg Lys Leu Val Trp Asn Gly Tyr Val Asn Asp Val Thr Ser
 50                  55                  60
Ile Asp Leu Gln Cys Gly His Thr Ala Glu Gly Gln Ile Gly Thr
65                  70                  75                  80
Glu Pro Ala Pro Leu His Ala Pro Ala Thr Ala Gly Ser Thr Val Asn
                85                  90                  95
Leu Arg Trp Thr Leu Trp Pro Asp Ser His Met Gly Pro Ile Met Thr
                100                 105                 110
Tyr Met Ala Arg Cys Pro Asp Glu Gly Cys Asp Lys Trp Leu Pro Val
            115                 120                 125
Trp Phe Lys Ile His Glu Ala Gly Arg Tyr Thr Thr Asp Lys Ser Tyr
        130                 135                 140
Pro Asp Asp Ile Trp Glu Val Thr Arg Leu Met Tyr Pro Ala Asn Glu
145                 150                 155                 160
Gly Tyr Asn Tyr Thr Ile Pro Ala Cys Leu Ala Ser Gly His Tyr Leu
                165                 170                 175
Val Arg His Glu Ile Ile Ala Leu His Ser Trp Ala Lys Gly Glu
                180                 185                 190
Ala Gln Phe Tyr Pro Ser Cys His Gln Leu Thr Val Thr Ser Ile Gly
            195                 200                 205
Gly Asn Val Arg Glu Ala Pro Ala Glu Tyr Arg Val Ser Phe Pro Gly
        210                 215                 220
Ala Tyr Lys Asp Asp Asp Pro Gly Ile Phe Ile Asn Val Trp Asn Pro
225                 230                 235                 240
Gly Pro Tyr Thr Ile Pro Gly Pro Pro Val Trp Thr Cys Pro Glu Ser
                245                 250                 255
Glu

<210> SEQ ID NO 101
<211> LENGTH: 878
<212> TYPE: DNA
<213> ORGANISM: Humicola insolens

<400> SEQUENCE: 101
atgagactct ccctgacaac cctcctggcc tctgccctgt ccgtccaggg tcacgccatc      60
ttccaggtgc gttcctttca ccacccacat catcatgatg aacctcaaag ttgctaaccc     120
ccgctgggca gagagttacc gtcaacggcc aggaccaagg ctcgttgact ggtctccggg     180
ccccgaataa caacaacccc gtgcagaacg tcaacagcca ggacatcatc tgtggcgctc     240
ccgggtcgcg gtcacagtcc gtcatcaacg tcaatgccgg cgaccgcatc ggtgcctggt     300
accagcatgt catcggcggc gcccagttcc ccggcgaccc ggacaacccg atcgccaggt     360
cccacaaggg ccccatctcc gtctatctgg ccaaggtgga caacgctgcc acggcgaacc     420
accagggtct gcaatggtaa acatacctcg ggtcaagtca gaacctctgt gatcgccgag     480
acgactaacc cctctttccc ataaacaggt tcagatctg gcacgacggc ttcaacccct     540
ccacccggca atgggccgtc gacaccatga tcaacaacaa cggctgggtc tatttcaacc     600
tcccgcagtg catcgctccc ggccactatc tcatgcgcgt cgagctgctc gctctccact     660
cggccaccta ccaaggccag gcgcagttct acatctcgtg cgcccagatc aacgtccagt     720
```

```
cgggcggcaa ctttactccc tgcagacgg ttagcttccc cggcgcctac caggccaacc      780 acccccggcat tcaggtcaac atttacggcg ccatgggcca gccggataac ggcggcaggc    840
cctaccagat tccgggcccg gagccgattc agtgctga                             878
```

<210> SEQ ID NO 102
<211> LENGTH: 246
<212> TYPE: PRT
<213> ORGANISM: Humicola insolens

<400> SEQUENCE: 102

```
Met Arg Leu Ser Leu Thr Thr Leu Leu Ala Ser Ala Leu Ser Val Gln
 1               5                  10                  15

Gly His Ala Ile Phe Gln Arg Val Thr Val Asn Gly Gln Asp Gln Gly
             20                  25                  30

Ser Leu Thr Gly Leu Arg Ala Pro Asn Asn Asn Pro Val Gln Asn
         35                  40                  45

Val Asn Ser Gln Asp Ile Ile Cys Gly Ala Pro Gly Ser Arg Ser Gln
 50                  55                  60

Ser Val Ile Asn Val Asn Ala Gly Asp Arg Ile Gly Ala Trp Tyr Gln
 65                  70                  75                  80

His Val Ile Gly Gly Ala Gln Phe Pro Gly Asp Pro Asp Asn Pro Ile
                 85                  90                  95

Ala Arg Ser His Lys Gly Pro Ile Ser Val Tyr Leu Ala Lys Val Asp
            100                 105                 110

Asn Ala Ala Thr Ala Asn His Gln Gly Leu Gln Trp Phe Lys Ile Trp
        115                 120                 125

His Asp Gly Phe Asn Pro Ser Thr Arg Gln Trp Ala Val Asp Thr Met
130                 135                 140

Ile Asn Asn Asn Gly Trp Val Tyr Phe Asn Leu Pro Gln Cys Ile Ala
145                 150                 155                 160

Pro Gly His Tyr Leu Met Arg Val Glu Leu Leu Ala Leu His Ser Ala
                165                 170                 175

Thr Tyr Gln Gly Gln Ala Gln Phe Tyr Ile Ser Cys Ala Gln Ile Asn
            180                 185                 190

Val Gln Ser Gly Gly Asn Phe Thr Pro Trp Gln Thr Val Ser Phe Pro
        195                 200                 205

Gly Ala Tyr Gln Ala Asn His Pro Gly Ile Gln Val Asn Ile Tyr Gly
    210                 215                 220

Ala Met Gly Gln Pro Asp Asn Gly Gly Arg Pro Tyr Gln Ile Pro Gly
225                 230                 235                 240

Pro Glu Pro Ile Gln Cys
                245
```

<210> SEQ ID NO 103
<211> LENGTH: 1067
<212> TYPE: DNA
<213> ORGANISM: Humicola insolens

<400> SEQUENCE: 103

```
atgggaccga cctgggcagt gattctgggg ctgattgctc cttctgtgct cagtcacagt     60
tgcgtctccc aacagaccct tcgactttta tcaagctggt actgactcat aacccaactc    120
acctagatat ccatgggatc ctcctggtca atggcacaga gacaccagag tggaaatacg    180
tcctgtatgt ttcctcatat cctagcccca ttgtacgagt tgttgacgtg atacagcgat    240
gttgcgccgg cggttccaat ttcaaaccca gactctctcc ccctggata ccaaggctat    300
```

```
aaggttgatc ccatcatcgg atccgggaac cccaacatca cttgtggccg gctagcattt    360
gactcggcac ccaagacgca aatcgccgat gtgctagccg gctccgaggt aggattccga    420
gtctcggctg atggcttggg aaatcgggat ctggagaagg gctacatccc gacgttctgg    480
cacccaggtc cggcccaggc atacttgtca cgtgccccga acgacgacct gtacagctac    540
aaaggcgacg gggactggtt caagattgcc tacgctggcc cggtggacga cctgacgtgg    600 tcccttggc cgggagtttc agatgtatgt tcatcctcca tagtcctgtt tttgccctct    660
ccaggaccaa attattaata tcgagtcgca gttcaacttc accattccgt tgtcgacacc    720
ccctggcaag tatttgctcc gaatcgagaa cttcatgcca acggcctcga caggatatct    780
tcagttctac gtcaattgtg catttgtcaa catcattgga ccaggaggtg ggaccccgac    840
cgagttcatt cgaattcccg gggattacac cgacgaggat ccaggtgagt ttgtgttatg    900
agacatgttc aactcgcacc gacgaatgct tgtttcctga cagagatttg taaaaactag    960
gctttctcgt tcccccggag caaagctcct tggatggcag agtcccaagg gaccagttga   1020
aactgatgag ctacacgcca ccaggtcctg cggtgtggac ggggtga                 1067
```

<210> SEQ ID NO 104
<211> LENGTH: 265
<212> TYPE: PRT
<213> ORGANISM: Humicola insolens

<400> SEQUENCE: 104

```
Met Gly Pro Thr Trp Ala Val Ile Leu Gly Leu Ile Ala Pro Ser Val
1               5                   10                  15

Leu Asn Ile His Gly Ile Leu Val Asn Gly Thr Glu Thr Pro Glu
            20                  25                  30

Trp Lys Tyr Val Leu Asp Val Ala Pro Ala Val Pro Ile Ser Asn Pro
        35                  40                  45

Asp Ser Leu Pro Pro Gly Tyr Gln Gly Tyr Lys Val Asp Pro Ile Ile
    50                  55                  60

Gly Ser Gly Asn Pro Asn Ile Thr Cys Gly Arg Leu Ala Phe Asp Ser
65                  70                  75                  80

Ala Pro Lys Thr Gln Ile Ala Asp Val Leu Ala Gly Ser Glu Val Gly
                85                  90                  95

Phe Arg Val Ser Ala Asp Gly Leu Gly Asn Arg Asp Leu Glu Lys Gly
            100                 105                 110

Tyr Ile Pro Thr Phe Trp His Pro Gly Pro Ala Gln Ala Tyr Leu Ser
        115                 120                 125

Arg Ala Pro Asn Asp Asp Leu Tyr Ser Tyr Lys Gly Asp Gly Asp Trp
    130                 135                 140

Phe Lys Ile Ala Tyr Ala Gly Pro Val Asp Asp Leu Thr Trp Ser Leu
145                 150                 155                 160

Trp Pro Gly Val Ser Asp Phe Asn Phe Thr Ile Pro Leu Ser Thr Pro
                165                 170                 175

Pro Gly Lys Tyr Leu Leu Arg Ile Glu Asn Phe Met Pro Thr Ala Ser
            180                 185                 190

Thr Gly Tyr Leu Gln Phe Tyr Val Asn Cys Ala Phe Val Asn Ile Ile
        195                 200                 205

Gly Pro Gly Gly Gly Thr Pro Thr Glu Phe Ile Arg Ile Pro Gly Asp
    210                 215                 220

Tyr Thr Asp Glu Asp Pro Gly Phe Leu Val Pro Pro Glu Gln Ser Ser
225                 230                 235                 240
```

Leu Asp Gly Arg Val Pro Arg Asp Gln Leu Lys Leu Met Ser Tyr Thr
            245                 250                 255

Pro Pro Gly Pro Ala Val Trp Thr Gly
        260                 265

<210> SEQ ID NO 105
<211> LENGTH: 1035
<212> TYPE: DNA
<213> ORGANISM: Humicola insolens

<400> SEQUENCE: 105

```
atgaaggccc tcaccctcct cgccgccgcg accgcggcct cggcgcacac catcttcgtg      60
cagctcgagg ccgacggcac gcgctacccc gtctcgcacg gcgtgcgcac cccgcagtac     120
gacggcccca tcaccgacgt ctcgtccaac gacctggcct gcaacggcgg gcccaacccg     180
accatgaaga cggacaagat catcaccgtg acggcgggca gcaccgtcaa ggccatctgg     240
cggcacacgc tgcagtcggg ccccaacgac gtcatggacc cagccacaa gggcccgacg      300
ctggcgtacc tgaagaaggt ggacaacgcg ctgacggatt cgggcgtggg cggcggctgg     360
ttcaagatcc aggaggacgg gcacagcaat gggaattggg gcacgctcaa ggtaatcaac     420
aaccagggca ttcactatat cgatatcccc gactgcatcg acagcgggca gtatttgttg     480
cgggccgaga tgatcgctct gcacgctgcc gggtcgccgg gcgtgcgca gctttatgtg      540
agtttcttcc ttcttttctt cttctctccc tttgtgataa gaataaagat ccacaccaca     600
gtcaaaccaa agcatcctaa cctcggcatc tactcacaga tggaatgcgc ccaaatcgaa     660
atcgtcggcg gcaagggcac cgtcaagccc cagacctact ccatcccggg catctacaag     720
tccaacgacc cgggcatcct catcaacatc tactccatgt cgccctcgag ccagtacatc     780
atccccggcc cgcccctctt cacctgcaac ggcggcggcg gcagcaacaa cggcggcggc     840
aacaacggcg gcagcaaccc cccgtccag cagcccccg ccaccaccct caccaccgcc      900
atcgcccagc ccacgcccat ctgctccgtc agcagtgggg gtcagtgcgg cggccagggc     960
tatagcggct gcaccacctg cgcgtcgccg tataggtgta acgagatcaa cgcgtggtat    1020
tcgcagtgct tgtaa                                                    1035
```

<210> SEQ ID NO 106
<211> LENGTH: 310
<212> TYPE: PRT
<213> ORGANISM: Humicola insolens

<400> SEQUENCE: 106

Met Lys Ala Leu Thr Leu Leu Ala Ala Ala Thr Ala Ala Ser Ala His
1               5                   10                  15

Thr Ile Phe Val Gln Leu Glu Ala Asp Gly Thr Arg Tyr Pro Val Ser
            20                  25                  30

His Gly Val Arg Thr Pro Gln Tyr Asp Gly Pro Ile Thr Asp Val Ser
        35                  40                  45

Ser Asn Asp Leu Ala Cys Asn Gly Gly Pro Asn Pro Thr Met Lys Thr
    50                  55                  60

Asp Lys Ile Ile Thr Val Thr Ala Gly Ser Thr Val Lys Ala Ile Trp
65                  70                  75                  80

Arg His Thr Leu Gln Ser Gly Pro Asn Asp Val Met Asp Pro Ser His
                85                  90                  95

Lys Gly Pro Thr Leu Ala Tyr Leu Lys Lys Val Asp Asn Ala Leu Thr
            100                 105                 110

Asp Ser Gly Val Gly Gly Gly Trp Phe Lys Ile Gln Glu Asp Gly His
    115                 120                 125

Ser Asn Gly Asn Trp Gly Thr Leu Lys Val Ile Asn Asn Gln Gly Ile
    130                 135                 140

His Tyr Ile Asp Ile Pro Asp Cys Ile Asp Ser Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Glu Ile Val Gly Gly Lys Gly
                180                 185                 190

Thr Val Lys Pro Gln Thr Tyr Ser Ile Pro Gly Ile Tyr Lys Ser Asn
                195                 200                 205

Asp Pro Gly Ile Leu Ile Asn Ile Tyr Ser Met Ser Pro Ser Ser Gln
    210                 215                 220

Tyr Ile Ile Pro Gly Pro Pro Leu Phe Thr Cys Asn Gly Gly Gly Gly
225                 230                 235                 240

Ser Asn Asn Gly Gly Gly Asn Asn Gly Gly Ser Asn Pro Pro Val Gln
                245                 250                 255

Gln Pro Pro Ala Thr Thr Leu Thr Thr Ala Ile Ala Gly Pro Thr Pro
                260                 265                 270

Ile Cys Ser Val Gln Gln Trp Gly Gln Cys Gly Gly Gln Gly Tyr Ser
                275                 280                 285

Gly Cys Thr Thr Cys Ala Ser Pro Tyr Arg Cys Asn Glu Ile Asn Ala
                290                 295                 300

Trp Tyr Ser Gln Cys Leu
305                 310

<210> SEQ ID NO 107
<211> LENGTH: 1065
<212> TYPE: DNA
<213> ORGANISM: Humicola insolens

<400> SEQUENCE: 107

```
atggctccca agacctcgac gttccttgcc tccctcacgg gcgccgccct cgtggctgcc      60
cacggccatg tcagccacat cattgtcaat ggcgtccagt accggaacta cgaccccacc     120
accgacttct acagcggcaa ccctccgacc gtgatcggct ggtcggccct caaccaggac     180
aacggcttca tcgagcccaa caacttcggc accccgacat catctgcca taagtcggcc      240
aagcccggcg gcggccacgt cacggtgagg ccggtgacaa agatcagcat cgtctggacc     300
cccgagtggc ccgagtcgca cgtcggcccc gtcatcgact accttgccgc gtgcaacggc     360
gactgcgaga cggtcgacaa gacctccctc cgcttcttca agatcgacgg cgccggctac     420
gacgccgcgg ccggccgctg ggccgccgac gctctgcgcg ccaacggcaa ctcgtggctt     480
gtgcagatcc ccgccgacct caaggccggc aactacgtgc ttcggcacga gatcatcgcc     540
ctgcacggcg ccgccaaccc caacggcgcc caggcctacc gcagtgcat caacatccgc      600
gtcaccggcg gcggcaacaa ccagccctcg ggcgtccccg caccagct ctacaaggcc       660
tcggaccagg gcatcctctt caaccctcgg gtcgccaacc ctcagtaccc cgtcccgggc     720
ccggccctca tcccggcgc cgtgagctcc atccctcaga gccgctcgac cgccaccgcc     780
acgggcaccg ccacccgccc cggcgccgac acggacccga cgggcgtccc tcccgtcgtc     840
accaccactt ctgcccggc tcaggtgacc accaccacca gcagccgcac cacctccctc     900
cctcagatca ccaccacctt cgcgaccagc accaccccgc cgccccggc cgctacccag     960
```

```
agcaagtggg gccagtgcgg cggcaacggc tggaccggcc cgaccgtctg cgcgccggc    1020 tcgagctgca acaagctcaa cgactggtac tcgcagtgca tctaa                   1065
```

<210> SEQ ID NO 108
<211> LENGTH: 354
<212> TYPE: PRT
<213> ORGANISM: Humicola insolens

<400> SEQUENCE: 108

```
Met Ala Pro Lys Thr Ser Thr Phe Leu Ala Ser Leu Thr Gly Ala Ala
1               5                   10                  15

Leu Val Ala Ala His Gly His Val Ser His Ile Ile Val Asn Gly Val
            20                  25                  30

Gln Tyr Arg Asn Tyr Asp Pro Thr Thr Asp Phe Tyr Ser Gly Asn Pro
        35                  40                  45

Pro Thr Val Ile Gly Trp Ser Ala Leu Asn Gln Asp Asn Gly Phe Ile
    50                  55                  60

Glu Pro Asn Asn Phe Gly Thr Pro Asp Ile Ile Cys His Lys Ser Ala
65                  70                  75                  80

Lys Pro Gly Gly Gly His Val Thr Val Arg Ala Gly Asp Lys Ile Ser
                85                  90                  95

Ile Val Trp Thr Pro Glu Trp Pro Glu Ser His Val Gly Pro Val Ile
            100                 105                 110

Asp Tyr Leu Ala Ala Cys Asn Gly Asp Cys Glu Thr Val Asp Lys Thr
        115                 120                 125

Ser Leu Arg Phe Phe Lys Ile Asp Gly Ala Gly Tyr Asp Ala Ala Ala
    130                 135                 140

Gly Arg Trp Ala Ala Asp Ala Leu Arg Ala Asn Gly Asn Ser Trp Leu
145                 150                 155                 160

Val Gln Ile Pro Ala Asp Leu Lys Ala Gly Asn Tyr Val Leu Arg His
                165                 170                 175

Glu Ile Ile Ala Leu His Gly Ala Ala Asn Pro Asn Gly Ala Gln Ala
            180                 185                 190

Tyr Pro Gln Cys Ile Asn Ile Arg Val Thr Gly Gly Gly Asn Asn Gln
        195                 200                 205

Pro Ser Gly Val Pro Gly Thr Gln Leu Tyr Lys Ala Ser Asp Pro Gly
    210                 215                 220

Ile Leu Phe Asn Pro Trp Val Ala Asn Pro Gln Tyr Pro Val Pro Gly
225                 230                 235                 240

Pro Ala Leu Ile Pro Gly Ala Val Ser Ser Ile Pro Gln Ser Arg Ser
                245                 250                 255

Thr Ala Thr Ala Thr Gly Thr Ala Thr Arg Pro Gly Ala Asp Thr Asp
            260                 265                 270

Pro Thr Gly Val Pro Pro Val Val Thr Thr Ser Ala Pro Ala Gln
        275                 280                 285

Val Thr Thr Thr Thr Ser Ser Arg Thr Thr Ser Leu Pro Gln Ile Thr
    290                 295                 300

Thr Thr Phe Ala Thr Ser Thr Thr Pro Pro Pro Ala Ala Thr Gln
305                 310                 315                 320

Ser Lys Trp Gly Gln Cys Gly Gly Asn Gly Trp Thr Gly Pro Thr Val
                325                 330                 335

Cys Ala Pro Gly Ser Ser Cys Asn Lys Leu Asn Asp Trp Tyr Ser Gln
            340                 345                 350
```

Cys Ile

<210> SEQ ID NO 109
<211> LENGTH: 804
<212> TYPE: DNA
<213> ORGANISM: Humicola insolens

<400> SEQUENCE: 109

```
atgtatcttt tacctatcgc cgcggccgcc ctagcgttca ccaccaccgc atacgcccac      60
gcccaagtct acggcttgcg tgtcaacgac caacaccaag gcgatgggcg caacaaatac     120
atccgctcgc ccagcagcaa ttcccccatc cggtgggacc acgtaaccca cccattcctc     180
atctgcaaca tccgcgacga caaccaaccc ccgggtcccg cgcctgactt tgtccgcgcc     240
ttcgccggcg accgcgtggc gttccaatgg taccacgccc gccccaacga cccgacggat     300
tacgtcctcg acagctccca cctcggcgtc ctcgttacct ggatcgcgcc gtacacggac     360
gggcccggga ccggcccat ttggaccaag atccaccagg acgggtggaa cggcacgcac     420
tgggccacga gccggctcat cagcaacggc gggttcgtcg agttccggct gcccggctcg     480
ctaaagcccg ggaagtacct ggtgcggcag gagattatcg ctctgcacca ggccgacatg     540
cccggtccga accgcgggcc tgagttctac cccagctgcg cgcaattgga ggttttgggg    600
tctggtgagg cggcgccgcc gcaggggtat gatatcaaca aggggtatgc ggagagcggg     660
gataagttgt ggttcaacat ttacatcaac aagaatgatg agttcaaaat gcctggaccg     720
gaggtttggg atggtgggtg tcggtttgga gagcgatggg caaccgagga accaggcaag     780
cccaaggtga accaacacgg ataa                                             804
```

<210> SEQ ID NO 110
<211> LENGTH: 267
<212> TYPE: PRT
<213> ORGANISM: Humicola insolens

<400> SEQUENCE: 110

Met Tyr Leu Leu Pro Ile Ala Ala Ala Leu Ala Phe Thr Thr Thr
1               5                  10                  15

Ala Tyr Ala His Ala Gln Val Tyr Gly Leu Arg Val Asn Asp Gln His
            20                  25                  30

Gln Gly Asp Gly Arg Asn Lys Tyr Ile Arg Ser Pro Ser Ser Asn Ser
        35                  40                  45

Pro Ile Arg Trp Asp His Val Thr His Pro Phe Leu Ile Cys Asn Ile
    50                  55                  60

Arg Asp Asp Asn Gln Pro Pro Gly Pro Ala Pro Asp Phe Val Arg Ala
65                  70                  75                  80

Phe Ala Gly Asp Arg Val Ala Phe Gln Trp Tyr His Ala Arg Pro Asn
                85                  90                  95

Asp Pro Thr Asp Tyr Val Leu Asp Ser Ser His Leu Gly Val Leu Val
            100                 105                 110

Thr Trp Ile Ala Pro Tyr Thr Asp Gly Pro Gly Thr Gly Pro Ile Trp
        115                 120                 125

Thr Lys Ile His Gln Asp Gly Trp Asn Gly Thr His Trp Ala Thr Ser
    130                 135                 140

Arg Leu Ile Ser Asn Gly Gly Phe Val Glu Phe Arg Leu Pro Gly Ser
145                 150                 155                 160

Leu Lys Pro Gly Lys Tyr Leu Val Arg Gln Glu Ile Ile Ala Leu His
                165                 170                 175

Gln Ala Asp Met Pro Gly Pro Asn Arg Gly Pro Glu Phe Tyr Pro Ser
            180                 185                 190

Cys Ala Gln Leu Glu Val Phe Gly Ser Gly Glu Ala Ala Pro Pro Gln
        195                 200                 205

Gly Tyr Asp Ile Asn Lys Gly Tyr Ala Glu Ser Gly Asp Lys Leu Trp
    210                 215                 220

Phe Asn Ile Tyr Ile Asn Lys Asn Asp Glu Phe Lys Met Pro Gly Pro
225                 230                 235                 240

Glu Val Trp Asp Gly Gly Cys Arg Phe Gly Glu Arg Trp Ala Thr Glu
                245                 250                 255

Glu Pro Gly Lys Pro Lys Val Asn Gln His Gly
            260                 265

<210> SEQ ID NO 111
<211> LENGTH: 843
<212> TYPE: DNA
<213> ORGANISM: Humicola insolens

<400> SEQUENCE: 111
atgaagctcc tcgctcctct gatgctggct ggcgccgcca gcgcccgtga gtaacccctg      60
gctggatctc atgctggtgc cagtgttcca tgactgacaa ccaccctcag acaccatctt     120
cacctccctc gaggttgatg gccgcaacta cggcacgggc aacggcgtcc gcgtcccctc     180
ctacaacggc cccgtcgagg atgtcacgtc caactcgatc gcctgcaacg gcccgccgaa     240
cccgaccagc ccgaccgaca cggtcatcac cgtccaggct ggccagaacg tgactgccat     300
ctggcggtac atgctcaaca cccagggcac ctcgcccaac gacatcatgg acagcagcca     360
caagggtcct actctcgcct acctcaagaa ggtcaacgat gcccggactg actcgggcgt     420
cggcgatggc tggttcaaga tccagcacga cggcttcgac ggcaccacct ggggcaccga     480
gcgcgtcatc ttcggccagg ccgtcacac catcaagatc cccgagtgca tcgagcccgg     540
ccagtacctg ctgcgtgctg agatgatcgc cctccacggc gcccagaact acccgggtgc     600
tcagttctac atggagtgcg cccagctcaa cattgtcggt ggcaccggca ccaagaaacc     660
cagcaccgtc agcttccctg gcgcttacaa ggtatgtccg agtttggtac cgagataact     720
ggagatgaga aagtgatgc taacaaacca tgacagggca ccgaccccgg cgtcaagctc     780
agcatctggt ggccgcccgt caccaactac gtcattcccg ccccgatgt cttcaagtgc     840
taa                                                                    843

<210> SEQ ID NO 112
<211> LENGTH: 237
<212> TYPE: PRT
<213> ORGANISM: Humicola insolens

<400> SEQUENCE: 112

Met Lys Leu Leu Ala Pro Leu Met Leu Ala Gly Ala Ala Ser Ala His
1               5                   10                  15

Thr Ile Phe Thr Ser Leu Glu Val Asp Gly Arg Asn Tyr Gly Thr Gly
            20                  25                  30

Asn Gly Val Arg Val Pro Ser Tyr Asn Gly Pro Val Glu Asp Val Thr
        35                  40                  45

Ser Asn Ser Ile Ala Cys Asn Gly Pro Pro Asn Pro Thr Ser Pro Thr
    50                  55                  60

Asp Thr Val Ile Thr Val Gln Ala Gly Gln Asn Val Thr Ala Ile Trp
65                  70                  75                  80

Arg Tyr Met Leu Asn Thr Gln Gly Thr Ser Pro Asn Asp Ile Met Asp
              85                  90                  95

Ser Ser His Lys Gly Pro Thr Leu Ala Tyr Leu Lys Lys Val Asn Asp
          100                 105                 110

Ala Arg Thr Asp Ser Gly Val Gly Asp Gly Trp Phe Lys Ile Gln His
          115                 120                 125

Asp Gly Phe Asp Gly Thr Thr Trp Gly Thr Glu Arg Val Ile Phe Gly
      130                 135                 140

Gln Gly Arg His Thr Ile Lys Ile Pro Glu Cys Ile Glu Pro Gly Gln
145                 150                 155                 160

Tyr Leu Leu Arg Ala Glu Met Ile Ala Leu His Gly Ala Gln Asn Tyr
                  165                 170                 175

Pro Gly Ala Gln Phe Tyr Met Glu Cys Ala Gln Leu Asn Ile Val Gly
              180                 185                 190

Gly Thr Gly Thr Lys Lys Pro Ser Thr Val Ser Phe Pro Gly Ala Tyr
          195                 200                 205

Lys Gly Thr Asp Pro Gly Val Lys Leu Ser Ile Trp Trp Pro Val
          210                 215                 220

Thr Asn Tyr Val Ile Pro Gly Pro Asp Val Phe Lys Cys
225                 230                 235

<210> SEQ ID NO 113
<211> LENGTH: 705
<212> TYPE: DNA
<213> ORGANISM: Humicola insolens

<400> SEQUENCE: 113
atgaagctcc tctcaaccct cgccgccatt gcggccacct tggccacggc ggatgcgcac      60
tacatcttca acatcctgta cgtcaacggc cagcgcatgg gcggcgagta cacctacgtg     120
cggcgcaact ccaactcgta cttccccgtg ttccccgaca tcctcaactc aacgacatg     180 cgttgcaacg tgggtgccag accgggcaac acccaaaccg ccaccgtcag ggccggcgac     240
aggatcggct tcaaggtctt caacaacgag gtcatcgagc ccctggtcc cggcttcatc     300 tacatgtcca agccccgggg cagcgtcaac aactatgacg cagcggggga ctggttcaag     360
gtttacgaga ccggtctctg ccgcggtggt ggcaacgtcg acaccaactg gtgctcgtac     420
tacaaggacc ggctcgagtt taccatcccg cccaagactc ctcccggcga gtatctggtg     480
cgtatcgagc atatcggtct gcacgagggc cacgtcaaca gggcgcagtt ctacatcacc     540
tgcgcgcagc tcaagattga gggccccggc ggcggcaacc cgaacccact cgtgaagatc     600
ccgggcatct acagggccaa cgaccccggc atcgcctaca caagtggac caacaacccg     660 gcgccgtaca tcatgccggg tcccaaggtg tgggatggca actaa                     705

<210> SEQ ID NO 114
<211> LENGTH: 234
<212> TYPE: PRT
<213> ORGANISM: Humicola insolens

<400> SEQUENCE: 114

Met Lys Leu Leu Ser Thr Leu Ala Ala Ile Ala Ala Thr Leu Ala Thr
1               5                  10                  15

Ala Asp Ala His Tyr Ile Phe Asn Ile Leu Tyr Val Asn Gly Gln Arg
              20                  25                  30

Met Gly Gly Glu Tyr Thr Tyr Val Arg Arg Asn Ser Asn Ser Tyr Phe
          35                  40                  45

```
Pro Val Phe Pro Asp Ile Leu Asn Ser Asn Asp Met Arg Cys Asn Val
 50                  55                  60

Gly Ala Arg Pro Gly Asn Thr Gln Thr Ala Thr Val Arg Ala Gly Asp
 65                  70                  75                  80

Arg Ile Gly Phe Lys Val Phe Asn Asn Glu Val Ile Glu His Pro Gly
                 85                  90                  95

Pro Gly Phe Ile Tyr Met Ser Lys Ala Pro Gly Ser Val Asn Asn Tyr
                100                 105                 110

Asp Gly Ser Gly Asp Trp Phe Lys Val Tyr Glu Thr Gly Leu Cys Arg
                115                 120                 125

Gly Gly Gly Asn Val Asp Thr Asn Trp Cys Ser Tyr Tyr Lys Asp Arg
130                 135                 140

Leu Glu Phe Thr Ile Pro Pro Lys Thr Pro Pro Gly Glu Tyr Leu Val
145                 150                 155                 160

Arg Ile Glu His Ile Gly Leu His Glu Gly His Val Asn Arg Ala Gln
                165                 170                 175

Phe Tyr Ile Thr Cys Ala Gln Leu Lys Ile Glu Gly Pro Gly Gly Gly
                180                 185                 190

Asn Pro Asn Pro Leu Val Lys Ile Pro Gly Ile Tyr Arg Ala Asn Asp
                195                 200                 205

Pro Gly Ile Ala Tyr Asn Lys Trp Thr Asn Asn Pro Ala Pro Tyr Ile
                210                 215                 220

Met Pro Gly Pro Lys Val Trp Asp Gly Asn
225                 230
```

<210> SEQ ID NO 115
<211> LENGTH: 753
<212> TYPE: DNA
<213> ORGANISM: Humicola insolens

<400> SEQUENCE: 115

```
atgctgggaa gcgctcttct gctcctgggc actgccctgg cgccaccgc ccactacacg      60
ttccctagga tcaacagcgg cggcgactgg cagtatgtcc gccgggccga caactggcag     120
gacaacggct tcgttggcaa cgtcaactcg cctcagatcc ggtgcttcca gagcaggcac     180
caggccgccc cggccaccct caacgtcacc gccggctcca cggtgaccta ctacgccaat     240
cccaacgtct atcaccccgg cccgatggcc ttctacatgg cccgcgtccc cgatggccag     300
gatatcaact cgtggaccgg cgagggtgcc gtgtggttca agatctacca cgagcagcct     360
accggcctgg gccagcagct gaggtggtct agcgatggta cgtgaatggt gatcctgtgg     420
catctcaacc tcttccagac ttctgacccg agccccgcg gccctacagg caagaactcg     480
ttccaggttc agatccccg ctgcatccgc tctggctact acctgctccg tgctgagcac     540
atcggcttgc acagcgccgg cagccctggt ggcgctcagt tctacatctc ttgcgcccag     600
ctcgccgtca acggcggtgg cagcaccgag ccccccaaca aggtgtcctt ccctggtgcc     660
tacagcccgt ccgaccccgg cattcagatc aacatctact ggcctgttcc gacctcgtac     720
aagaaccccg ccccccggt cttccagtgc taa                                   753
```

<210> SEQ ID NO 116
<211> LENGTH: 226
<212> TYPE: PRT
<213> ORGANISM: Humicola insolens

<400> SEQUENCE: 116

Met Leu Gly Ser Ala Leu Leu Leu Leu Gly Thr Ala Leu Gly Ala Thr

```
              1               5              10              15
            Ala His Tyr Thr Phe Pro Arg Ile Asn Ser Gly Gly Asp Trp Gln Tyr
                           20                  25                  30
            Val Arg Arg Ala Asp Asn Trp Gln Asp Asn Gly Phe Val Gly Asn Val
                           35                  40                  45
            Asn Ser Pro Gln Ile Arg Cys Phe Gln Ser Arg His Gln Ala Ala Pro
             50                  55                  60
            Ala Thr Leu Asn Val Thr Ala Gly Ser Thr Val Thr Tyr Tyr Ala Asn
             65                  70                  75                  80
            Pro Asn Val Tyr His Pro Gly Pro Met Ala Phe Tyr Met Ala Arg Val
                           85                  90                  95
            Pro Asp Gly Gln Asp Ile Asn Ser Trp Thr Gly Glu Gly Ala Val Trp
                          100                 105                 110
            Phe Lys Ile Tyr His Glu Gln Pro Thr Gly Leu Gly Gln Gln Leu Arg
                          115                 120                 125
            Trp Ser Ser Asp Gly Lys Asn Ser Phe Gln Val Gln Ile Pro Arg Cys
                130                 135                 140
            Ile Arg Ser Gly Tyr Tyr Leu Leu Arg Ala Glu His Ile Gly Leu His
            145                 150                 155                 160
            Ser Ala Gly Ser Pro Gly Gly Ala Gln Phe Tyr Ile Ser Cys Ala Gln
                          165                 170                 175
            Leu Ala Val Asn Gly Gly Ser Thr Glu Pro Pro Asn Lys Val Ser
                          180                 185                 190
            Phe Pro Gly Ala Tyr Ser Pro Ser Asp Pro Gly Ile Gln Ile Asn Ile
                          195                 200                 205
            Tyr Trp Pro Val Pro Thr Ser Tyr Lys Asn Pro Gly Pro Pro Val Phe
                          210                 215                 220
            Gln Cys
            225

<210> SEQ ID NO 117
<211> LENGTH: 854
<212> TYPE: DNA
<213> ORGANISM: Humicola insolens

<400> SEQUENCE: 117
atgaagctgc ttcctgggtt gcttctggca gccacggctg cccaagccca ttgtacgttt      60
ccgatcccca agaccatctt cgagaatttt cgagccagat ctttctgaga gagttgctga    120
caattcctgc tagacacatt ccccaggctc gttgtcaacg ggcagcctga ggagagggac    180
tggtcggtca ctcggatgac aaagaaccac cagagcaagt cgggaattga aacccaact     240 agccccgaca tccgttgcta cagctcgcag actgccccta cgtggcgat gtgccggcc      300 gggtctacca tccactacat ctcgacccaa caaatcaacc atcctggccc gactcagtac    360
tatctcgcca aggtcccagc tggtcagtca gccaagacct gggatggctc tggcaacgtg    420
tggttcaaga tcgccacgag catgccggag tacgatcaaa acaggcagct ggtttggccc    480
ggtcatagta aggactcact ctcgtccgat catctctttt gagtgagtct tgggcatacc    540
cactgactac gtctgctatg acagatacct atcagaccat caacgccacc atcccggcca    600
acacgccgag cggagagtac ctcctgcgtg tcgagcaaat tgccctccac atggccagcc    660
agccgaacaa ggcccagttc tacatctcgt gctctcagat tcagattacc aatggcggaa    720
acggcactcc gggccctcta gttgcattcc cggggcata caggagcaac gaccctggca    780
tcctggtcaa tctctacagc ggcatgcagc cttcgcagta ccagcccct ggaccggccg    840
```

```
tgtggcgtgg ctga                                                      854
```

<210> SEQ ID NO 118
<211> LENGTH: 231
<212> TYPE: PRT
<213> ORGANISM: Humicola insolens

<400> SEQUENCE: 118

```
Met Lys Leu Leu Pro Gly Leu Leu Ala Ala Thr Ala Ala Gln Ala
1               5                   10                  15

His Tyr Thr Phe Pro Arg Leu Val Val Asn Gly Gln Pro Glu Glu Arg
            20                  25                  30

Asp Trp Ser Val Thr Arg Met Thr Lys Asn His Gln Ser Lys Ser Gly
        35                  40                  45

Ile Glu Asn Pro Thr Ser Pro Asp Ile Arg Cys Tyr Ser Ser Gln Thr
50                  55                  60

Ala Pro Asn Val Ala Ile Val Pro Ala Gly Ser Thr Ile His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Gln Ser Ala Lys Thr Trp Asp Gly Ser Gly Asn
            100                 105                 110

Val Trp Phe Lys Ile Ala Thr Ser Met Pro Glu Tyr Asp Gln Asn Arg
        115                 120                 125

Gln Leu Val Trp Pro Gly His Asn Thr Tyr Gln Thr Ile Asn Ala Thr
    130                 135                 140

Ile Pro Ala Asn Thr Pro Ser Gly Glu Tyr Leu Leu Arg Val Glu Gln
145                 150                 155                 160

Ile Ala Leu His Met Ala Ser Gln Pro Asn Lys Ala Gln Phe Tyr Ile
                165                 170                 175

Ser Cys Ser Gln Ile Gln Ile Thr Asn Gly Gly Asn Gly Thr Pro Gly
            180                 185                 190

Pro Leu Val Ala Phe Pro Gly Ala Tyr Arg Ser Asn Asp Pro Gly Ile
        195                 200                 205

Leu Val Asn Leu Tyr Ser Gly Met Gln Pro Ser Gln Tyr Gln Pro Pro
    210                 215                 220

Gly Pro Ala Val Trp Arg Gly
225                 230
```

<210> SEQ ID NO 119
<211> LENGTH: 863
<212> TYPE: DNA
<213> ORGANISM: Humicola insolens

<400> SEQUENCE: 119

```
atgctcctga actcggtcat cggctcggcc gtcctcctgg ccaccggcgc cgccgcccac     60
ggtgccgtga ccagctacgt cattgccggg aagaactacc tgggtaggt aacctcgtgg    120 aagcgaatgc aggcagttca ttcactaaca catacctccg ttagctacaa cggctacgcc    180
ccgtccacca cccccaacac gatccagtgg caatggtcga cctacgaccc catctactcc    240
gccaccgacc ccaagctccg ctgcaacggc ggccgctcgg ccacgcagtc cgccccggct    300
gctccgggcg acaacatcac cgccatctgt cagcagtgga cgcatagcca gggccccatc    360
ctcgtctgga tgtacaagtg tcccggcgcc ttcagctcgt cgacggctc gggccaggga    420 tggttcaaga ttgacgaggc cggcttcaat ggcgacggca agaccgtgtt cctcgacacc    480
```

```
gagcgcccct ccggctggga gatcgccaag ctggttggcg gcaacaaggg ctggaccagc    540
accatcccca agaacctggc cccgggcaac tacctggtcc gccacgagtt gattgccctt    600
caccaggcca acgccccgca gtggtaccct gagtgcgcgc aggtcgtgat caccggctcg    660
ggcactaagg agccgcctgc gtcgtacaag gctgccattc ccggctactg caaccagaac    720
gatcccaaca ttcgggtatg tgaggcctat ttggagttcg gctaaggcat gatactaact    780
ctacccccca ggttcctatc aacgaccact ccatccccca gacctacaag atccctggcc    840
ctccggtctg gcgcggcgag taa                                            863
```

<210> SEQ ID NO 120
<211> LENGTH: 248
<212> TYPE: PRT
<213> ORGANISM: Humicola insolens

<400> SEQUENCE: 120

```
Met Leu Leu Asn Ser Val Ile Gly Ser Ala Val Leu Ala Thr Gly
1               5                   10                  15

Ala Ala Ala His Gly Ala Val Thr Ser Tyr Val Ile Ala Gly Lys Asn
            20                  25                  30

Tyr Pro Gly Tyr Asn Gly Tyr Ala Pro Ser Thr Pro Asn Thr Ile
        35                  40                  45

Gln Trp Gln Trp Ser Thr Tyr Asp Pro Ile Tyr Ser Ala Thr Asp Pro
    50                  55                  60

Lys Leu Arg Cys Asn Gly Gly Arg Ser Ala Thr Gln Ser Ala Pro Ala
65                  70                  75                  80

Ala Pro Gly Asp Asn Ile Thr Ala Ile Trp Gln Gln Trp Thr His Ser
                85                  90                  95

Gln Gly Pro Ile Leu Val Trp Met Tyr Lys Cys Pro Gly Ala Phe Ser
            100                 105                 110

Ser Cys Asp Gly Ser Gly Gln Gly Trp Phe Lys Ile Asp Glu Ala Gly
        115                 120                 125

Phe Asn Gly Asp Gly Lys Thr Val Phe Leu Asp Thr Glu Arg Pro Ser
    130                 135                 140

Gly Trp Glu Ile Ala Lys Leu Val Gly Gly Asn Lys Gly Trp Thr Ser
145                 150                 155                 160

Thr Ile Pro Lys Asn Leu Ala Pro Gly Asn Tyr Leu Val Arg His Glu
                165                 170                 175

Leu Ile Ala Leu His Gln Ala Asn Ala Pro Gln Trp Tyr Pro Glu Cys
            180                 185                 190

Ala Gln Val Val Ile Thr Gly Ser Gly Thr Lys Glu Pro Pro Ala Ser
        195                 200                 205

Tyr Lys Ala Ala Ile Pro Gly Tyr Cys Asn Gln Asn Asp Pro Asn Ile
    210                 215                 220

Arg Val Pro Ile Asn Asp His Ser Ile Pro Gln Thr Tyr Lys Ile Pro
225                 230                 235                 240

Gly Pro Pro Val Trp Arg Gly Glu
                245
```

<210> SEQ ID NO 121
<211> LENGTH: 883
<212> TYPE: DNA
<213> ORGANISM: Humicola insolens

<400> SEQUENCE: 121

```
atgaagctca ccacctccat cgccctgctg gctgcggccg gcgcgcaggc tcactgtacg    60
tgctccctca tctcatccat ctcctcagac catgttttac ctattggtta ctaacaagct   120
ctcacgcaga caccttcccc cgcaccaagg tcgacggcgt cacctcgggc gagtgggaga   180
cgatccgcat caccgagaac cactggtcgc acgcccccgt gacggacgtg acctcgcagg   240
ccatgacgtg ctacgagaag acgcccggcc agggcgcgcc caagacggtt aacgtgaagg   300
ccggcggcac cgtcaccttc accgtcgaca cggacgtggg ccacccgggc cgctgcact    360
tctacttggc caaggtgccc gcgggcaaga cggccgcgac gtttgacggc aagggcgccg   420
tgtggttcaa gatttaccag gacggccccg gcgggttggg gaccagctcg ttgacttggc   480
ctagctttgg tgagctttct tttctttatt ttcttcaatc ctcccataat tacctcccga   540
cgaggaaata aatataccttt acctgatatt aacccatccc cccccacctc ctccaggcaa   600
gaaggaagtc tctgtccaaa tccccccctg cgtgcaggac ggcgagtacc tgctgcgcgt   660
cgagcacatt gcgctgcaca gcgccgcgag cgtcggcggc gcgcagctct acatttcgtg   720
cgcgcaaatc aacgtcaccg gcggcaccgg cacgctcaac ccgggccagc tcgtctcgtt   780
cccgggcgcc tacaagccca ccgacccggg catcctgttc cagctctact ggccgccgcc   840
gacccagtac atcaaccccg gtccggcgcc ggtgaagtgc tga                     883
```

<210> SEQ ID NO 122
<211> LENGTH: 233
<212> TYPE: PRT
<213> ORGANISM: Humicola insolens

<400> SEQUENCE: 122

```
Met Lys Leu Thr Thr Ser Ile Ala Leu Leu Ala Ala Gly Ala Gln
1               5                   10                  15

Ala His Tyr Thr Phe Pro Arg Thr Lys Val Asp Gly Val Thr Ser Gly
                20                  25                  30

Glu Trp Glu Thr Ile Arg Ile Thr Glu Asn His Trp Ser His Gly Pro
            35                  40                  45

Val Thr Asp Val Thr Ser Gln Ala Met Thr Cys Tyr Glu Lys Thr Pro
        50                  55                  60

Gly Gln Gly Ala Pro Lys Thr Val Asn Val Lys Ala Gly Gly Thr Val
65                  70                  75                  80

Thr Phe Thr Val Asp Thr Asp Val Gly His Pro Gly Pro Leu His Phe
                85                  90                  95

Tyr Leu Ala Lys Val Pro Ala Gly Lys Thr Ala Ala Thr Phe Asp Gly
            100                 105                 110

Lys Gly Ala Val Trp Phe Lys Ile Tyr Gln Asp Gly Pro Gly Gly Leu
        115                 120                 125

Gly Thr Ser Ser Leu Thr Trp Pro Ser Phe Gly Lys Lys Glu Val Ser
    130                 135                 140

Val Gln Ile Pro Pro Cys Val Gln Asp Gly Glu Tyr Leu Leu Arg Val
145                 150                 155                 160

Glu His Ile Ala Leu His Ser Ala Ala Ser Val Gly Gly Ala Gln Leu
                165                 170                 175

Tyr Ile Ser Cys Ala Gln Ile Asn Val Thr Gly Thr Gly Thr Leu
            180                 185                 190

Asn Pro Gly Gln Leu Val Ser Phe Pro Gly Ala Tyr Lys Pro Thr Asp
        195                 200                 205

Pro Gly Ile Leu Phe Gln Leu Tyr Trp Pro Pro Thr Gln Tyr Ile
    210                 215                 220
```

```
Asn Pro Gly Pro Ala Pro Val Lys Cys
225                 230
```

<210> SEQ ID NO 123
<211> LENGTH: 928
<212> TYPE: DNA
<213> ORGANISM: Humicola insolens

<400> SEQUENCE: 123

```
atgaagactc tcgcatccgc cctcattgcc gcgggccttc tggcccagta cgccgctgcc    60
catgccattt tccagtttgc cagcagcggt ggcactgact tgggacgtc ctgtgttagg    120
atgccggtga gtaacgggt gccctgaac atgtgttgct cacgaaacaa ggttatgttg     180
actctataca gcccaacaac tctcccgtca cgagcgtcac cagcagtgac atggcttgca    240
atgttggcgg atctcgcggt gtatctgca tttgcgaggt gaacggtaag agttctcctc    300
agccttttct ctgtcaagca ctaaacagca ctcgctaacc atttcaatct cagccggctc    360
cgacttcacc gtcgagatgc acgcgcagcc caacgaccgg tcgtgcgcca gcgaagccat    420
tggcggcaac cacttcgggc ccgtcatggt gtacatggcc aaggtggacg acgcgacgcg    480
ggcggacggt gcgtcggcgt cttggttcaa ggtggacgag ttcggctacg acgccggctc    540
caagacatgg ggaaccgaca tgctcaacaa gaactgcggc aagcggacgt ccgcatccc    600
gagcaaaatc ccgtctgggg actatctggt gcgtgcggag ctattgctt tgcacaccgc    660
gggccagccg tcgggtgcgc agttttatat gagctgctat gtgagttctt ccatgcttcc    720
ccttgtggtg tcactgtata gaagatgcta atatctccca cagcaagttc gcatcaaggg    780
cagcaacaac ggtcagcttc cggctggtgt tcggattcct ggcgcctaca gcgcgacgga    840
cccgggcatc tcgtcgata tctggggcaa tggtttcagc cagtacacta ttcctggccc    900
tcgtgtcatt gatgggagct ttttctga                                      928
```

<210> SEQ ID NO 124
<211> LENGTH: 243
<212> TYPE: PRT
<213> ORGANISM: Humicola insolens

<400> SEQUENCE: 124

```
Met Lys Thr Leu Ala Ser Ala Leu Ile Ala Ala Gly Leu Leu Ala Gln
1               5                   10                  15

Tyr Ala Ala Ala His Ala Ile Phe Gln Phe Ala Ser Ser Gly Gly Thr
            20                  25                  30

Asp Phe Gly Thr Ser Cys Val Arg Met Pro Pro Asn Asn Ser Pro Val
        35                  40                  45

Thr Ser Val Thr Ser Ser Asp Met Ala Cys Asn Val Gly Gly Ser Arg
    50                  55                  60

Gly Val Ser Gly Ile Cys Glu Val Asn Ala Gly Ser Asp Phe Thr Val
65                  70                  75                  80

Glu Met His Ala Gln Pro Asn Asp Arg Ser Cys Ala Ser Glu Ala Ile
                85                  90                  95

Gly Gly Asn His Phe Gly Pro Val Met Val Tyr Met Ala Lys Val Asp
            100                 105                 110

Asp Ala Thr Arg Ala Asp Gly Ala Ser Ala Ser Trp Phe Lys Val Asp
        115                 120                 125

Glu Phe Gly Tyr Asp Ala Gly Ser Lys Thr Trp Gly Thr Asp Met Leu
    130                 135                 140
```

Asn Lys Asn Cys Gly Lys Arg Thr Phe Arg Ile Pro Ser Lys Ile Pro
145                 150                 155                 160

Ser Gly Asp Tyr Leu Val Arg Ala Glu Ala Ile Ala Leu His Thr Ala
            165                 170                 175

Gly Gln Pro Ser Gly Ala Gln Phe Tyr Met Ser Cys Tyr Gln Val Arg
        180                 185                 190

Ile Lys Gly Ser Asn Asn Gly Gln Leu Pro Ala Gly Val Arg Ile Pro
    195                 200                 205

Gly Ala Tyr Ser Ala Thr Asp Pro Gly Ile Leu Val Asp Ile Trp Gly
    210                 215                 220

Asn Gly Phe Ser Gln Tyr Thr Ile Pro Gly Pro Arg Val Ile Asp Gly
225                 230                 235                 240

Ser Phe Phe

<210> SEQ ID NO 125
<211> LENGTH: 1092
<212> TYPE: DNA
<213> ORGANISM: Humicola insolens

<400> SEQUENCE: 125
atgcctcgct tcaccaagtc cattgtctcg gccctggccg gcgcttccct ggtcgcagcc      60
cacggccatg tcacccacat cgtcatcaac ggcgtgctgt acccgaactt cgaccctaca     120
tcccacccct tacctgcagaa cccgccgacc gttgtgggct ggaccgccgc caacaccgac    180
aacggcttcg ttgctcccga ccagttcgcc tcgggcgata tcatctgcca caaccaggcc    240
accaacgcgg cgccacacgc cgtggtcgcg ccggcgaca agatttggat ccagtgggac    300
cagtggcctg agagccacca cggccccgtc ctcgactacc tcgcctcctg cggcagctcg    360
ggctgcgagt cggtcaacaa gctcgacctc gagttcttca agatcggcga aaagggcctg    420
atcgacggct cctccgcgcc gggccggtgg gcgtcggacg agctgatcgc caacaacgcc    480
ggctggctgg tccagatccc cgccgacatt gcgcccggcc actacgtcct gcgccacgaa    540
atcatcgccc tccacgccgc cggccagccc aacggcgccc agaactaccc gcagtgcttc    600
aacctcctcg tcacgggctc cggcaccgcg cggccgcagg gcgtcaaggg aacagcgctg    660 tacacccca cgacaagggg catcttggcg ggcatctaca atgccccgt ctcgtacgag      720 attcccggcc ccgcgctcta ctccggcgcc gccaggaact tgcagcagag ctcgtcccag    780
gccacgtcga ctgccacggc tttgactggg gacgcggtgc ctgttccgac ccaagccccc    840
gtcactacca cttcctcttc ttcggccgat gccgccaccg ccacctccac caccgtccag    900
ccgccccagc aaaccaccct cacgaccgcc atcgccacgt cgaccgctgc tgctgccccg    960
acgaccaccg ccggcagcgg aaacggtggc aacggcccct cccaacccg ctgccctggc    1020 ctggctgggc tcgggtttga caagcgccgt cgccagctcc gcgctgagga gggtgtgcag    1080
gtggttgctt ga                                                        1092

<210> SEQ ID NO 126
<211> LENGTH: 363
<212> TYPE: PRT
<213> ORGANISM: Humicola insolens

<400> SEQUENCE: 126

Met Pro Arg Phe Thr Lys Ser Ile Val Ser Ala Leu Ala Gly Ala Ser
1               5                   10                  15

Leu Val Ala Ala His Gly His Val Thr His Ile Val Ile Asn Gly Val
            20                  25                  30

```
Leu Tyr Pro Asn Phe Asp Pro Thr Ser His Pro Tyr Leu Gln Asn Pro
        35                  40                  45

Pro Thr Val Val Gly Trp Thr Ala Ala Asn Thr Asp Asn Gly Phe Val
    50                  55                  60

Ala Pro Asp Gln Phe Ala Ser Gly Asp Ile Ile Cys His Asn Gln Ala
65                  70                  75                  80

Thr Asn Ala Gly Gly His Ala Val Val Ala Gly Asp Lys Ile Trp
                85                  90                  95

Ile Gln Trp Asp Gln Trp Pro Glu Ser His His Gly Pro Val Leu Asp
                100                 105                 110

Tyr Leu Ala Ser Cys Gly Ser Ser Gly Cys Glu Ser Val Asn Lys Leu
            115                 120                 125

Asp Leu Glu Phe Phe Lys Ile Gly Glu Lys Gly Leu Ile Asp Gly Ser
        130                 135                 140

Ser Ala Pro Gly Arg Trp Ala Ser Asp Glu Leu Ile Ala Asn Asn Ala
145                 150                 155                 160

Gly Trp Leu Val Gln Ile Pro Ala Asp Ile Ala Pro Gly His Tyr Val
                165                 170                 175

Leu Arg His Glu Ile Ile Ala Leu His Ala Ala Gly Gln Pro Asn Gly
            180                 185                 190

Ala Gln Asn Tyr Pro Gln Cys Phe Asn Leu Leu Val Thr Gly Ser Gly
        195                 200                 205

Thr Ala Arg Pro Gln Gly Val Lys Gly Thr Ala Leu Tyr Thr Pro Asn
    210                 215                 220

Asp Lys Gly Ile Leu Ala Gly Ile Tyr Asn Ala Pro Val Ser Tyr Glu
225                 230                 235                 240

Ile Pro Gly Pro Ala Leu Tyr Ser Gly Ala Ala Arg Asn Leu Gln Gln
                245                 250                 255

Ser Ser Ser Gln Ala Thr Ser Thr Ala Thr Leu Thr Gly Asp Ala
            260                 265                 270

Val Pro Val Pro Thr Gln Ala Pro Val Thr Thr Ser Ser Ser Ser
    275                 280                 285

Ala Asp Ala Ala Thr Ala Thr Ser Thr Val Gln Pro Pro Gln Gln
        290                 295                 300

Thr Thr Leu Thr Thr Ala Ile Ala Thr Ser Thr Ala Ala Ala Pro
305                 310                 315                 320

Thr Thr Thr Ala Gly Ser Gly Asn Gly Asn Arg Pro Phe Pro Thr
                325                 330                 335

Arg Cys Pro Gly Leu Ala Gly Leu Gly Phe Asp Lys Arg Arg Gln
            340                 345                 350

Leu Arg Ala Glu Glu Gly Val Gln Val Val Ala
        355                 360

<210> SEQ ID NO 127
<211> LENGTH: 1086
<212> TYPE: DNA
<213> ORGANISM: Humicola insolens

<400> SEQUENCE: 127 atgaaggac ttctcagcat cgccgccctt ccctggcgg ttggtgaggc ttcggcccac    60
tacatcttcc agcagctctc gacgggtggc accaagcacc ccatgtggaa gtacatccgc   120
cagcacacca actacaactc tcccgtcatc gacctcgact ccaacgacct ccgctgcaat   180
gtcggtgccc ggggtgctgg aactgagacc gttacggtcg ctgctggctc gagcctgacc   240
```

```
ttccacctcg acaccccgt ctaccaccag ggccctgtgt cggtgtaagt agaagttctc    300
agacgaacca ccaatgtcgg cagataattt ctaactccga tgtccagcta tatgtccaag    360
gctcccggct ccgtgtcgga ctatgacggc agcggcggct ggttcaagat tcaagactgg    420
ggcccgacct tcaccggcag cggcgccacc tggaagctgg atgactccta caccttcaac    480
atcccctcgt gcattcccga cggcgagtac ctcgtccgca tccagtccct gggtatccac    540
aaccctggc cggcgggtat tccgcagttc tatatctcgt gcgctcaggt gcgcgtcacc    600
ggcggtggca acgcgaaccc gagcccgcag gtgtcgatcc caggtgcctt caaggagacc    660
gacccgggct acactgccaa cgtgagtttc catccatgct acatatccct tttacgctct    720
cgatcccatg actaaccccc ccctgaaaag atctacaaca acttccgcag ctacaccgtc    780
cccggcccgt ccgtcttcac ctgcagcggc aacagcggcg gcggctccaa ccccagcaac    840
cctaaccccc cgaccccgac gaccttcacc acccaggtga ccaccccgac cccggcgtct    900
ccgccctctt gcaccgtcgc gaagtggtac gtctgaaaaa aaatctcctc caggccggac    960
atgagaaaac taacatgaac gaaaaacagg ggccagtgcg gtggccaggg ctacagcggc   1020
tgcaccaact gcgaggccgg ctcgacctgc aggcagcaga acgcttacta ttctcagtgc   1080
atctaa                                                             1086
```

<210> SEQ ID NO 128
<211> LENGTH: 296
<212> TYPE: PRT
<213> ORGANISM: Humicola insolens

<400> SEQUENCE: 128

Met Lys Gly Leu Leu Ser Ile Ala Ala Leu Ser Leu Ala Val Gly Glu
1               5                   10                  15

Ala Ser Ala His Tyr Ile Phe Gln Gln Leu Ser Thr Gly Gly Thr Lys
            20                  25                  30

His Pro Met Trp Lys Tyr Ile Arg Gln His Thr Asn Tyr Asn Ser Pro
        35                  40                  45

Val Ile Asp Leu Asp Ser Asn Asp Leu Arg Cys Asn Val Gly Ala Arg
    50                  55                  60

Gly Ala Gly Thr Glu Thr Val Thr Val Ala Ala Gly Ser Ser Leu Thr
65                  70                  75                  80

Phe His Leu Asp Thr Pro Val Tyr His Gln Gly Pro Val Ser Val Tyr
                85                  90                  95

Met Ser Lys Ala Pro Gly Ser Val Ser Asp Tyr Asp Gly Ser Gly Gly
            100                 105                 110

Trp Phe Lys Ile Gln Asp Trp Gly Pro Thr Phe Thr Gly Ser Gly Ala
        115                 120                 125

Thr Trp Lys Leu Asp Asp Ser Tyr Thr Phe Asn Ile Pro Ser Cys Ile
    130                 135                 140

Pro Asp Gly Glu Tyr Leu Val Arg Ile Gln Ser Leu Gly Ile His Asn
145                 150                 155                 160

Pro Trp Pro Ala Gly Ile Pro Gln Phe Tyr Ile Ser Cys Ala Gln Val
                165                 170                 175

Arg Val Thr Gly Gly Asn Ala Asn Pro Ser Pro Gln Val Ser Ile
            180                 185                 190

Pro Gly Ala Phe Lys Glu Thr Asp Pro Gly Tyr Thr Ala Asn Ile Tyr
        195                 200                 205

Asn Asn Phe Arg Ser Tyr Thr Val Pro Gly Pro Ser Val Phe Thr Cys

Ser Gly Asn Ser Gly Gly Gly Ser Asn Pro Ser Asn Pro Asn Pro Pro
225                 230                 235                 240

Thr Pro Thr Thr Phe Thr Thr Gln Val Thr Thr Pro Thr Pro Ala Ser
            245                 250                 255

Pro Pro Ser Cys Thr Val Ala Lys Trp Gly Gln Cys Gly Gly Gln Gly
        260                 265                 270

Tyr Ser Gly Cys Thr Asn Cys Glu Ala Gly Ser Thr Cys Arg Gln Gln
    275                 280                 285

Asn Ala Tyr Tyr Ser Gln Cys Ile
    290                 295

<210> SEQ ID NO 129
<211> LENGTH: 1032
<212> TYPE: DNA
<213> ORGANISM: Humicola insolens

<400> SEQUENCE: 129
atgaggccct ctcactcgt cgctctggcg acggccgtca gcggccacgc catcttccag    60
cgcgtgtcgg ttaacggcgt cgaccaaggc cagctcaagg gcgtccgcgc tccctcgagc    120
aactacccca tcgagaacgt caaccacccc gactttgcct gcaacaccaa catccagcac    180
cgcgacggca ccgtcatcaa gatccccgcc ggcgccaccg tcggcgcctg gtggcagcac    240
gagatcggcg ggccctcgtt cccgggtgac ccggataacc cgatcgctgc ttcgcacaag    300
ggtgagttcc catagataga tctcttctct cccgacccct tgtatcctct cataactaac    360
cacctcaacc ccccaggccc tatccaagtc tacctcgcca aggtcgacaa cgccgcgacc    420
gcctccccca acggcctgcg gtggttcaag attgccgaga agggcctgtc gggcggcgtc    480
tgggccgtcg acgagatgat ccgcaacaac ggctggcact acttcaccat gccgcagtgc    540
atcgcgcccg ccactacct gatgcgcgtc gagctgttgg cgctgcactc ggccagcttc    600
cccggcggcg cccagttcta catggagtgc gcccagatcg aggtcaccgg ctcgggcaac    660
ttctcgccct ccgagacggt cagcttcccc ggcgcctacc cggccaacca cccgggtatc    720
gtcgtcagca tctacgacgc ccagggtaac gccaacaacg cgggcgcga gtaccagatc    780 cccgggccgc ggccgatcac ctgctccggc ggtggaagca acaatggtgg cgggaacaac    840
aatggtggtg aaacaacaa cggcggcggc aacaacaacg cggtgggaa caacaacggt    900 ggtggtaaca ccggtggcgg ctcggcgccg ctctggggcc agtgcggcgg caatgggtat    960
accggcccga cgacttgtgc cgagggtact tgcaagaagc agaatgactg gtactcgcag    1020
tgtacgcctt ag    1032

<210> SEQ ID NO 130
<211> LENGTH: 318
<212> TYPE: PRT
<213> ORGANISM: Humicola insolens

<400> SEQUENCE: 130

Met Arg Pro Phe Ser Leu Val Ala Leu Ala Thr Ala Val Ser Gly His
1               5                   10                  15

Ala Ile Phe Gln Arg Val Ser Val Asn Gly Val Asp Gln Gly Gln Leu
            20                  25                  30

Lys Gly Val Arg Ala Pro Ser Ser Asn Tyr Pro Ile Glu Asn Val Asn
        35                  40                  45

His Pro Asp Phe Ala Cys Asn Thr Asn Ile Gln His Arg Asp Gly Thr

Val Ile Lys Ile Pro Ala Gly Ala Thr Val Gly Ala Trp Trp Gln His
65                  70                  75                  80

Glu Ile Gly Gly Pro Ser Phe Pro Gly Asp Pro Asn Pro Ile Ala
            85                  90                  95

Ala Ser His Lys Gly Pro Ile Gln Val Tyr Leu Ala Lys Val Asp Asn
            100                 105                 110

Ala Ala Thr Ala Ser Pro Asn Gly Leu Arg Trp Phe Lys Ile Ala Glu
        115                 120                 125

Lys Gly Leu Ser Gly Gly Val Trp Ala Val Asp Glu Met Ile Arg Asn
        130                 135                 140

Asn Gly Trp His Tyr Phe Thr Met Pro Gln Cys Ile Ala Pro Gly His
145                 150                 155                 160

Tyr Leu Met Arg Val Glu Leu Leu Ala Leu His Ser Ala Ser Phe Pro
                165                 170                 175

Gly Gly Ala Gln Phe Tyr Met Glu Cys Ala Gln Ile Glu Val Thr Gly
                180                 185                 190

Ser Gly Asn Phe Ser Pro Ser Glu Thr Val Ser Phe Pro Gly Ala Tyr
            195                 200                 205

Pro Ala Asn His Pro Gly Ile Val Val Ser Ile Tyr Asp Ala Gln Gly
        210                 215                 220

Asn Ala Asn Asn Gly Gly Arg Glu Tyr Gln Ile Pro Gly Pro Arg Pro
225                 230                 235                 240

Ile Thr Cys Ser Gly Gly Gly Ser Asn Asn Gly Gly Asn Asn Asn
                245                 250                 255

Gly Gly Gly Asn Asn Asn Gly Gly Asn Asn Gly Gly Gly Asn
            260                 265                 270

Asn Asn Gly Gly Gly Asn Thr Gly Gly Ser Ala Pro Leu Trp Gly
        275                 280                 285

Gln Cys Gly Gly Asn Gly Tyr Thr Gly Pro Thr Thr Cys Ala Glu Gly
        290                 295                 300

Thr Cys Lys Lys Gln Asn Asp Trp Tyr Ser Gln Cys Thr Pro
305                 310                 315

<210> SEQ ID NO 131
<211> LENGTH: 1113
<212> TYPE: DNA
<213> ORGANISM: Humicola insolens

<400> SEQUENCE: 131
atggtgttgc ggtctctctc tatcctggcc ttcgtagcca gaggcgtctt cgcccacggt      60
ggcctctcca actacacggt cggcgacacg tggtatagcg ggtgcgtcca tgaacaactc     120
ctatatcttc ccccctcca cattgcgacc gctgcacatc tcactcgtcc ataaacaaca     180
acatcaatcg gtagacactg tccaaaagct aaccaccgta cctcctgaac acagctacga     240 cccttcacc cccgccgccg cccaactctc caaccctgg ctgatccaac gccaatggac      300
cagcatcgac ccgctcttct ccccgacctc tccctacctc gcctgcaact tccccggcac     360
cgcgccacca tcttacatcc ctctccgcgc cggcgacatc tcaccgcgg tttactggtt      420 ctggctgcac cccgtggggc cgatgagcgt ttggctggcg cggtgcgcag gggactgccg     480
cgacgaggac gtgacgcggg cgcgctggtt caagatctgg catgcgggt ttctggaggg      540 gccgaatttg gagctcggga tgtggtatca gaagaagttc cagcgtggg atggcgggcc      600 ggcgctctgg cgggtgagga taccgagggg gttgaagaag gggttgtaca tggtcaggca     660

```
tgagattttg tcgattcatg tgggtggacg gccccagttt tatcccgagt gtgcgcactt      720
gaatgtgacg gagggtggtg aggtggtagt gccgggggag tggacgagaa ggttccctgg      780
ggcgtatgac gatgatggtg agtgccttgc tagacgggaa ggctctatgg atggggcgga      840
tgagacgaaa ggctggtgtg agactgtcag cactgacggc ctgcagacaa gtcagtcttc      900
atcgatatct accggccgga acatgaaaac aggacggtac gtgggacaag caagcctcgg      960 attttcaga ttttcgactc tgacaacgaa caggactatg agatccctgg aggcccgatt     1020
tgggaaaggt acgtacaatc gcatcatctt gactctgtat tcaggggcta acataaacac     1080
agcttggggg agatggagtt atggcctgaa tga                                   1113
```

<210> SEQ ID NO 132
<211> LENGTH: 259
<212> TYPE: PRT
<213> ORGANISM: Humicola insolens

<400> SEQUENCE: 132

```
Met Val Leu Arg Ser Leu Ser Ile Leu Ala Phe Val Ala Arg Gly Val
1               5                   10                  15

Phe Ala His Gly Gly Leu Ser Asn Tyr Thr Val Gly Asp Thr Trp Tyr
            20                  25                  30

Ser Gly Tyr Asp Pro Phe Thr Pro Ala Ala Gln Leu Ser Gln Pro
        35                  40                  45

Trp Leu Ile Gln Arg Gln Trp Thr Ser Ile Asp Pro Leu Phe Ser Pro
    50                  55                  60

Thr Ser Pro Tyr Leu Ala Cys Asn Phe Pro Gly Thr Ala Pro Pro Ser
65                  70                  75                  80

Tyr Ile Pro Leu Arg Ala Gly Asp Ile Leu Thr Ala Val Tyr Trp Phe
                85                  90                  95

Trp Leu His Pro Val Gly Pro Met Ser Val Trp Leu Ala Arg Cys Ala
            100                 105                 110

Gly Asp Cys Arg Asp Glu Asp Val Thr Arg Ala Arg Trp Phe Lys Ile
        115                 120                 125

Trp His Ala Gly Phe Leu Glu Gly Pro Asn Leu Glu Leu Gly Met Trp
    130                 135                 140

Tyr Gln Lys Lys Phe Gln Arg Trp Asp Gly Gly Pro Ala Leu Trp Arg
145                 150                 155                 160

Val Arg Ile Pro Arg Gly Leu Lys Lys Gly Leu Tyr Met Val Arg His
                165                 170                 175

Glu Ile Leu Ser Ile His Val Gly Gly Arg Pro Gln Phe Tyr Pro Glu
            180                 185                 190

Cys Ala His Leu Asn Val Thr Glu Gly Gly Glu Val Val Val Pro Gly
        195                 200                 205

Glu Trp Thr Arg Arg Phe Pro Gly Ala Tyr Asp Asp Asp Lys Ser
    210                 215                 220

Val Phe Ile Asp Ile Tyr Arg Pro Glu His Glu Asn Arg Thr Asp Tyr
225                 230                 235                 240

Glu Ile Pro Gly Gly Pro Ile Trp Glu Ser Leu Gly Glu Met Glu Leu
                245                 250                 255

Trp Pro Glu
```

<210> SEQ ID NO 133
<211> LENGTH: 1103
<212> TYPE: DNA

<213> ORGANISM: Humicola insolens

<400> SEQUENCE: 133

```
atgaggaccg tcttcgccgc cgcactggca gcactcgctg cccgggaagt cgccggccat 60
gccacgttcc agcaactctg ggttgacgga accgattata taagtgcccc cctttctcg 120
gttccatttg atatcatgat gctgacaccc ccagcacggc agcacctgcg tccgcctccc 180
cgccagcaac agccccctga ccgacgtcac cagcagcgac ttcgcctgca acatcggcgg 240
ccggcgcggc gtgggcggca aatgccccgt caaagccggc ggcgtggtca cgatcgagat 300
gcatcagcag cccaacgacc ggaactgccg cagcgaggcc atcggcggca tgcactgggg 360
tccggtgcag gtctacctca gcaaggtccc cgacgcgtcg accgccgagc cgacgcaggt 420
gggctggttc aagatcttct ccaacgcgtg ggccaagaag cccggcggca actcgggcga 480
cgacgactac tggggcacgc gcgagctcaa cggctgctgc gggcgcatgg acgtgccgat 540
ccccaccgac ctggaagacg gcgactacct gctgcgcgcc gaggcgctgg cgctgcacgc 600
```

```
catgccgggc cagttctaca tgtcgtgcta ccagatcacc atcacgggcg gcacgggcac 660
cgcgaagccg gcgactgtcc gcttccccgg agcgtacacc aacaacgacg ccggcatccg 720
cgccaacatc cacgccccgc tgagcaccta catcgcgccc ggcccggagg tgtactccgg 780
cggtaccacc cgggcgcccg gtgagggctg cccgggatgt gctacgacct gccaggttgg 840
ctcgtcgccc agcgcgcagg ctccaggcca tggcacggcc gtgggcggcg gagctggtgg 900
cccgtctgct tgcaccgtcc aggcgtatgg ccagtgcggt ggccagggat acacgggttg 960
caccgagtgc gcggtaagtt gggacttcct tgtcattaaa atcgcaaatg gaacggatgg 1020
gctaacattt gcgggtgcag gatggtttcg tttgccgcga cgtctcggct ccgtggtact 1080
ctcagtgcca gcctgctttc taa 1103
```

<210> SEQ ID NO 134
<211> LENGTH: 325
<212> TYPE: PRT
<213> ORGANISM: Humicola insolens

<400> SEQUENCE: 134

```
Met Arg Thr Val Phe Ala Ala Ala Leu Ala Ala Leu Ala Ala Arg Glu
1 5 10 15

Val Ala Gly His Ala Thr Phe Gln Gln Leu Trp Val Asp Gly Thr Asp
20 25 30

Tyr Gly Ser Thr Cys Val Arg Leu Pro Ala Ser Asn Ser Pro Leu Thr
35 40 45

Asp Val Thr Ser Ser Asp Phe Ala Cys Asn Ile Gly Gly Arg Arg Gly
50 55 60

Val Gly Gly Lys Cys Pro Val Lys Ala Gly Gly Val Val Thr Ile Glu
65 70 75 80

Met His Gln Gln Pro Asn Asp Arg Asn Cys Arg Ser Glu Ala Ile Gly
85 90 95

Gly Met His Trp Gly Pro Val Gln Val Tyr Leu Ser Lys Val Pro Asp
100 105 110

Ala Ser Thr Ala Glu Pro Thr Gln Val Gly Trp Phe Lys Ile Phe Ser
115 120 125

Asn Ala Trp Ala Lys Lys Pro Gly Gly Asn Ser Gly Asp Asp Asp Tyr
130 135 140

Trp Gly Thr Arg Glu Leu Asn Gly Cys Cys Gly Arg Met Asp Val Pro
145 150 155 160
```

```
Ile Pro Thr Asp Leu Glu Asp Gly Asp Tyr Leu Leu Arg Ala Glu Ala
                165                 170                 175

Leu Ala Leu His Ala Met Pro Gly Gln Phe Tyr Met Ser Cys Tyr Gln
            180                 185                 190

Ile Thr Ile Thr Gly Gly Thr Gly Thr Ala Lys Pro Ala Thr Val Arg
        195                 200                 205

Phe Pro Gly Ala Tyr Thr Asn Asn Asp Ala Gly Ile Arg Ala Asn Ile
    210                 215                 220

His Ala Pro Leu Ser Thr Tyr Ile Ala Pro Gly Pro Glu Val Tyr Ser
225                 230                 235                 240

Gly Gly Thr Thr Arg Ala Pro Gly Glu Gly Cys Pro Gly Cys Ala Thr
                245                 250                 255

Thr Cys Gln Val Gly Ser Ser Pro Ser Ala Gln Ala Pro Gly His Gly
            260                 265                 270

Thr Ala Val Gly Gly Gly Ala Gly Gly Pro Ser Ala Cys Thr Val Gln
        275                 280                 285

Ala Tyr Gly Gln Cys Gly Gly Gln Gly Tyr Thr Gly Cys Thr Glu Cys
    290                 295                 300

Ala Asp Gly Phe Val Cys Arg Asp Val Ser Ala Pro Trp Tyr Ser Gln
305                 310                 315                 320

Cys Gln Pro Ala Phe
                325

<210> SEQ ID NO 135
<211> LENGTH: 1039
<212> TYPE: DNA
<213> ORGANISM: Humicola insolens

<400> SEQUENCE: 135
atgaggctcc ccaagtggc ttccgttctg ccctcgcgg cccaggtcca cggtcacggc      60
tacatctacc gtgtcaccgc cgacaacatt gtgtaagcgc cctcagattc cggacctctt     120
cctacctggt ggctaacctt ctctcaactc ttcagctacc cgggatacga catctatgtc     180
gatcccctcc tccaaccgcc cccgtaccgc attgcctacg gtggtggcca gacgggtccc     240
gtctatgata tcaacagcaa ggatatcgcc tgccagcgcg tccacagccc cgctccgggt     300
ctgattgccc aggctcgcgc gggcagcaac atcaccttct ggtggtcgcg gtggctgtac     360
agccacaagg gtcccatctc ggcatggatg gctccgtatg agggcgacat tgccaatgtg     420
gacgtcaacc agctcgagtt cttcaagatt ggcgaggagt ccacgatgga accggcaag     480 tgggcgacgg agaagctggt ggacgacccc gagggcaagt ggaccgtcaa gatccccgcc     540
gatatcaagc ccggtctcta tgtcgtgcgg aacgaggtaa gtttcatccg tcccaaaaaa     600
ggggtcccat cccatgcatg gtgcatgccc agtctaatca tcatctcccg gatagatcat     660
cgccctccac ttcgccgtcc gcatgcctcc cttctttgcc gccttcaccc ccctcggacc     720
gcagttctac atgacctgct tcgccttcaa catcaccggc gacggcacgg ccactcccca     780
gggctacaag ttccctggcg cctacagcaa ggacgatccg gccctgtggt gggatctgga     840
ggagaacaag aacccgtacc ccggcgccgg ccccaagccc acgtctcgg cctacgatgt      900 cgacctcgtc cccaacgagt tgtacatcgt cagcccgacg aacaacgcga cggctgatga     960
gctctactgg gaggcccaga ggcaggcgct tgctgcccag gcggcgacga cggagtactt    1020
tgactcgatt ggtggctaa                                                1039
```

<210> SEQ ID NO 136
<211> LENGTH: 298
<212> TYPE: PRT
<213> ORGANISM: Humicola insolens

<400> SEQUENCE: 136

Met Arg Leu Pro Gln Val Ala Ser Val Leu Ala Leu Ala Ala Gln Val
1               5                   10                  15

His Gly His Gly Tyr Ile Tyr Arg Val Thr Ala Asp Asn Ile Val Tyr
            20                  25                  30

Pro Gly Tyr Asp Ile Tyr Val Asp Pro Leu Leu Gln Pro Pro Pro Tyr
        35                  40                  45

Arg Ile Ala Tyr Gly Gly Gly Gln Thr Gly Pro Val Tyr Asp Ile Asn
50                  55                  60

Ser Lys Asp Ile Ala Cys Gln Arg Val His Ser Pro Ala Pro Gly Leu
65                  70                  75                  80

Ile Ala Gln Ala Arg Ala Gly Ser Asn Ile Thr Phe Trp Trp Ser Arg
                85                  90                  95

Trp Leu Tyr Ser His Lys Gly Pro Ile Ser Ala Trp Met Ala Pro Tyr
            100                 105                 110

Glu Gly Asp Ile Ala Asn Val Asp Val Asn Gln Leu Glu Phe Phe Lys
        115                 120                 125

Ile Gly Glu Glu Phe His Asp Glu Thr Gly Lys Trp Ala Thr Glu Lys
130                 135                 140

Leu Val Asp Asp Pro Glu Gly Lys Trp Thr Val Lys Ile Pro Ala Asp
145                 150                 155                 160

Ile Lys Pro Gly Leu Tyr Val Val Arg Asn Glu Ile Ile Ala Leu His
                165                 170                 175

Phe Ala Val Arg Met Pro Pro Phe Phe Ala Ala Phe Thr Pro Leu Gly
            180                 185                 190

Pro Gln Phe Tyr Met Thr Cys Phe Ala Phe Asn Ile Thr Gly Asp Gly
        195                 200                 205

Thr Ala Thr Pro Gln Gly Tyr Lys Phe Pro Gly Ala Tyr Ser Lys Asp
210                 215                 220

Asp Pro Ala Leu Trp Trp Asp Leu Glu Glu Asn Lys Asn Pro Tyr Pro
225                 230                 235                 240

Gly Ala Gly Pro Lys Pro His Val Ser Ala Tyr Asp Val Asp Leu Val
                245                 250                 255

Pro Asn Glu Leu Tyr Ile Val Ser Pro Thr Asn Asn Ala Thr Ala Asp
            260                 265                 270

Glu Leu Tyr Trp Glu Ala Gln Arg Gln Ala Leu Ala Ala Gln Ala Ala
        275                 280                 285

Thr Thr Glu Tyr Phe Asp Ser Ile Gly Gly
290                 295

<210> SEQ ID NO 137
<211> LENGTH: 1025
<212> TYPE: DNA
<213> ORGANISM: Humicola insolens

<400> SEQUENCE: 137
atgcacgtcc agtctctcct tgccggagcg ctcgctctgg ctccgtcggc gtctgctcac    60
ttcctcttcc cgcacctgat gctgaacggt gtccgcacgg agcctacga gtatgtccgg    120 gagcacgact tcggcttcat gccgcacaac aacgactgga tcaactcgcc cgatttccgt    180
tgcaacgagg ggtcctggcg tcatcgccgc gagcccaaga ccgccgtagt cactgccggc    240

```
gttgacgtcg tgggcttcaa cctgcacctg gactttgacc tgtaccatcc gggccccgtg        300
acggtaagca catctgagtc agaacatacc tccctgtgac gtagactaat gagtctctta        360
ccgcagatct atctctcccg cgccccggc gacgtgcgtg actacgacgg atctggtgac         420
tggttcaagg tgtaccagct gggcacccgc caacccttca acggcactga cgagggctgg        480
gccacttgga agatgaagaa ctggcagttc cgcctgcccg ctgagatccc ggcgggcgag        540
tacctgatgc gcatcgagca gatgagcgtg caccctcctt accgccagaa ggagtggtac        600
gtgcagtgcg cccacctaaa gatcaacagc aactacaacg gccccgcgcc cggcccgacc        660
atcaagattc ccggagggta caagatcagc gatcctgcga ttcaatatga ccagtgggcg        720
cagccgccgc cgacgtacgc gcccatgccg ggaccgccgc tgtggcccaa caacaatcct        780
cagcagggca acccgaatca gggcggaaat aacggcggtg caaccaggg cggcggcaat         840
ggtggctgca ccgttccgaa gtggtatgta gagttcttca ctattatcat gagatgcagc        900
gttggacttg tgcttacacc tagaacaggg gccaatgcgg tggtcagggt tacagcgggt        960
gcaggaactg cgagtctggc tcgacatgcc gtgcccagaa cgactggtac tcgcagtgcc       1020
tgtaa                                                                   1025
```

<210> SEQ ID NO 138
<211> LENGTH: 298
<212> TYPE: PRT
<213> ORGANISM: Humicola insolens

<400> SEQUENCE: 138

```
Met His Val Gln Ser Leu Leu Ala Gly Ala Leu Ala Leu Ala Pro Ser
1               5                   10                  15

Ala Ser Ala His Phe Leu Phe Pro His Leu Met Leu Asn Gly Val Arg
            20                  25                  30

Thr Gly Ala Tyr Glu Tyr Val Arg Glu His Asp Phe Gly Phe Met Pro
        35                  40                  45

His Asn Asn Asp Trp Ile Asn Ser Pro Asp Phe Arg Cys Asn Glu Gly
    50                  55                  60

Ser Trp Arg His Arg Arg Glu Pro Lys Thr Ala Val Val Thr Ala Gly
65                  70                  75                  80

Val Asp Val Val Gly Phe Asn Leu His Leu Asp Phe Asp Leu Tyr His
                85                  90                  95

Pro Gly Pro Val Thr Ile Tyr Leu Ser Arg Ala Pro Gly Asp Val Arg
            100                 105                 110

Asp Tyr Asp Gly Ser Gly Asp Trp Phe Lys Val Tyr Gln Leu Gly Thr
        115                 120                 125

Arg Gln Pro Phe Asn Gly Thr Asp Glu Gly Trp Ala Thr Trp Lys Met
    130                 135                 140

Lys Asn Trp Gln Phe Arg Leu Pro Ala Glu Ile Pro Ala Gly Glu Tyr
145                 150                 155                 160

Leu Met Arg Ile Glu Gln Met Ser Val His Pro Tyr Arg Gln Lys
                165                 170                 175

Glu Trp Tyr Val Gln Cys Ala His Leu Lys Ile Asn Ser Asn Tyr Asn
            180                 185                 190

Gly Pro Ala Pro Gly Pro Thr Ile Lys Ile Pro Gly Gly Tyr Lys Ile
        195                 200                 205

Ser Asp Pro Ala Ile Gln Tyr Asp Gln Trp Ala Gln Pro Pro Thr
    210                 215                 220
```

```
Tyr Ala Pro Met Pro Gly Pro Pro Leu Trp Pro Asn Asn Asn Pro Gln
225                 230                 235                 240

Gln Gly Asn Pro Asn Gln Gly Gly Asn Gly Gly Gly Asn Gln Gly
            245                 250                 255

Gly Gly Asn Gly Gly Cys Thr Val Pro Lys Trp Gly Gln Cys Gly Gly
            260                 265                 270

Gln Gly Tyr Ser Gly Cys Arg Asn Cys Glu Ser Gly Ser Thr Cys Arg
        275                 280                 285

Ala Gln Asn Asp Trp Tyr Ser Gln Cys Leu
    290                 295
```

<210> SEQ ID NO 139
<211> LENGTH: 1035
<212> TYPE: DNA
<213> ORGANISM: Humicola insolens

<400> SEQUENCE: 139

```
atgccaccac cactactggc caccgtcctc tccttgctag ccctcacccg cggcgccctt     60
tcccattccc acctagccca cgtcatcatc aacggccagc tctaccacgg cttcgaccca    120
cgtccaaacc aaaacaacca tccagcccgt gtcggctggt ccacgaccgc cacagatgac    180
ggcttcgtca ccccgggcaa ttactcccat cccgacatca tctgccaccg cggcggcgtc    240
agcccgcgcg cccacgctcc cgtcaccgcc ggcggcaagg tccaggtcca atggaacggc    300
tggccgatcg acacgtcggg ccgatcctg acctacatcg cgccgtgcgg cggactgccg    360
ggcgccgaag aagggtgtac gggcgtggac aaaaccgacc tgcggtggac caagatcgac    420
gactcgatgc cgccgttccg gtttaccgac gccaccaagc cagtctctgg cagagcgcag    480
ttcccgatag ccaggtctg gcgacggat gcgctggtcg aggcgaataa tagctggtcg    540
gtggtcattc ccaggaatat cccgccgggg ccgtacgttt tgaggcagga gattgtggcc    600
ctgcattacg cggcgaagtt gaacggggcg cagaactatc cgttgtgtct gaacctctgg    660
gtggaaaagg ggcagcagga tcagggagag cccttcaaat tcgatgctta cgacgcgagg    720
gagttttaca gcgaggacca tccgggtgtg ttgattgatg ttatgacgat ggttgggccg    780
agagccgtgt accggatacc tggaccgacc gtggccagtg tgccacgag aattccgcac    840
tcattgcaga cgagcgccga gacgtgggtg gaagggacgc cggtggccgt gacgagggcg    900
acggaaacgg ttcagatgga gataactacg acacctgcag gtcagggagc tggtgtgagg    960
acagctaccc ctgccatgcc aacaccaaca gtgacgaaga ggtggaaggg aagattttgag   1020
atgggtaggc catga                                                    1035
```

<210> SEQ ID NO 140
<211> LENGTH: 344
<212> TYPE: PRT
<213> ORGANISM: Humicola insolens

<400> SEQUENCE: 140

```
Met Pro Pro Pro Leu Leu Ala Thr Val Leu Ser Leu Leu Ala Leu Thr
1               5                   10                  15

Arg Gly Ala Leu Ser His Ser His Leu Ala His Val Ile Ile Asn Gly
            20                  25                  30

Gln Leu Tyr His Gly Phe Asp Pro Arg Pro Asn Gln Asn Asn His Pro
        35                  40                  45

Ala Arg Val Gly Trp Ser Thr Thr Ala Thr Asp Asp Gly Phe Val Thr
    50                  55                  60
```

```
Pro Gly Asn Tyr Ser His Pro Asp Ile Ile Cys His Arg Gly Gly Val
 65                  70                  75                  80

Ser Pro Arg Ala His Ala Pro Val Thr Ala Gly Gly Lys Val Gln Val
                 85                  90                  95

Gln Trp Asn Gly Trp Pro Ile Gly His Val Gly Pro Ile Leu Thr Tyr
            100                 105                 110

Ile Ala Pro Cys Gly Gly Leu Pro Gly Ala Glu Glu Gly Cys Thr Gly
        115                 120                 125

Val Asp Lys Thr Asp Leu Arg Trp Thr Lys Ile Asp Asp Ser Met Pro
    130                 135                 140

Pro Phe Arg Phe Thr Asp Ala Thr Lys Pro Val Ser Gly Arg Ala Gln
145                 150                 155                 160

Phe Pro Ile Gly Gln Val Trp Ala Thr Asp Ala Leu Val Glu Ala Asn
                165                 170                 175

Asn Ser Trp Ser Val Val Ile Pro Arg Asn Ile Pro Gly Pro Tyr
            180                 185                 190

Val Leu Arg Gln Glu Ile Val Ala Leu His Tyr Ala Ala Lys Leu Asn
        195                 200                 205

Gly Ala Gln Asn Tyr Pro Leu Cys Leu Asn Leu Trp Val Glu Lys Gly
    210                 215                 220

Gln Gln Asp Gln Gly Glu Pro Phe Lys Phe Asp Ala Tyr Asp Ala Arg
225                 230                 235                 240

Glu Phe Tyr Ser Glu Asp His Pro Gly Val Leu Ile Asp Val Met Thr
                245                 250                 255

Met Val Gly Pro Arg Ala Val Tyr Arg Ile Pro Gly Pro Thr Val Ala
            260                 265                 270

Ser Gly Ala Thr Arg Ile Pro His Ser Leu Gln Thr Ser Ala Glu Thr
        275                 280                 285

Trp Val Glu Gly Thr Pro Val Ala Val Thr Arg Ala Thr Glu Thr Val
    290                 295                 300

Gln Met Glu Ile Thr Thr Thr Pro Ala Gly Gln Gly Ala Gly Val Arg
305                 310                 315                 320

Thr Ala Thr Pro Ala Met Pro Thr Pro Thr Val Thr Lys Arg Trp Lys
                325                 330                 335

Gly Arg Phe Glu Met Gly Arg Pro
            340

<210> SEQ ID NO 141
<211> LENGTH: 1057
<212> TYPE: DNA
<213> ORGANISM: Humicola insolens

<400> SEQUENCE: 141
atgaagtccc tgacctacgc cgcgctggcc gccctctggg cccagcagac cgctgctcat     60
gccaccttcc agcaactctg ggtcgacggc gtcgactacg cagtcagtg cgcccgcctg    120 ccgccgtcca actcccccat cgccagcgtc acctcgaccg ccatgcgctg caacaacggt    180
ccccgcgctg ccgccaagtg ccccgtcaag gctggcggca ccgtcaccat cgagatgcac    240
caggttggtt ccttgaagt gttccctac cacatataca gaccgtagct aacacaccca    300
tccttagcaa cccggtgacc ggtcctgcaa ccaggacgcc attggcggtg cccaccacgg    360
ccccgtgatg gtgtacatgt ccaaggtctc tgatgccttc accgccgacg gctcgtcagg    420
ctggttcaag atcttccagg acggctgggc caagaacccc aacggccgcg ttggcgacga    480
cgacttctgg ggcaccaagg acctcaacac ctgctgcggc aagatgaacg tcaagatccc    540
```

```
cgccgacatc gcccccggcg actacctgct ccgcgccgag gccatcgcgc tgcacgccgc    600 cggcccagc ggtggcgccc agccctacgt cacctgctac cagctcaccg tcacgggcgg     660
cggcaacgcc aacccgccca ccgtcaactt ccccggcgcc tacagcgagc gtgaccctgg    720
catcgccgtc agcatccacg gcgctctgtc caactacgtc gtccccggtc ctccggtcta    780
ctcgggcggc agcgagaagc gcgctggcag ccctgcgag gctgcgagg ccacctgcaa      840 ggtcggctcg agcccagcc agactcttgc tccttccaac ccggccccga cctctcccgc     900
caacggcggc ggcaacaacg gtggtggcaa cactggcggc ggctgcaccg tgcccaagtg    960
gcagcagtgc ggcggccagg gctactcggg ctgcaccgtc tgcgagtctg gctcgacttg    1020
ccgcgctcag aaccagtggt actctcagtg cgtgtaa                             1057
```

<210> SEQ ID NO 142
<211> LENGTH: 330
<212> TYPE: PRT
<213> ORGANISM: Humicola insolens

<400> SEQUENCE: 142

```
Met Lys Ser Leu Thr Tyr Ala Ala Leu Ala Ala Leu Trp Ala Gln Gln
1               5                   10                  15

Thr Ala Ala His Ala Thr Phe Gln Gln Leu Trp Val Asp Gly Val Asp
            20                  25                  30

Tyr Gly Ser Gln Cys Ala Arg Leu Pro Pro Ser Asn Ser Pro Ile Ala
        35                  40                  45

Ser Val Thr Ser Thr Ala Met Arg Cys Asn Asn Gly Pro Arg Ala Ala
    50                  55                  60

Ala Lys Cys Pro Val Lys Ala Gly Gly Thr Val Thr Ile Glu Met His
65                  70                  75                  80

Gln Gln Pro Gly Asp Arg Ser Cys Asn Gln Asp Ala Ile Gly Gly Ala
                85                  90                  95

His His Gly Pro Val Met Val Tyr Met Ser Lys Val Ser Asp Ala Phe
            100                 105                 110

Thr Ala Asp Gly Ser Ser Gly Trp Phe Lys Ile Phe Gln Asp Gly Trp
        115                 120                 125

Ala Lys Asn Pro Asn Gly Arg Val Gly Asp Asp Phe Trp Gly Thr
    130                 135                 140

Lys Asp Leu Asn Thr Cys Cys Gly Lys Met Asn Val Lys Ile Pro Ala
145                 150                 155                 160

Asp Ile Ala Pro Gly Asp Tyr Leu Leu Arg Ala Glu Ala Ile Ala Leu
                165                 170                 175

His Ala Ala Gly Pro Ser Gly Gly Ala Gln Pro Tyr Val Thr Cys Tyr
            180                 185                 190

Gln Leu Thr Val Thr Gly Gly Gly Asn Ala Asn Pro Thr Val Asn
        195                 200                 205

Phe Pro Gly Ala Tyr Ser Glu Arg Asp Pro Gly Ile Ala Val Ser Ile
    210                 215                 220

His Gly Ala Leu Ser Asn Tyr Val Val Pro Gly Pro Val Tyr Ser
225                 230                 235                 240

Gly Gly Ser Glu Lys Arg Ala Gly Ser Pro Cys Glu Gly Cys Glu Ala
                245                 250                 255

Thr Cys Lys Val Gly Ser Ser Pro Ser Gln Thr Leu Ala Pro Ser Asn
            260                 265                 270

Pro Ala Pro Thr Ser Pro Ala Asn Gly Gly Gly Asn Asn Gly Gly Gly
```

```
                275                 280                 285
Asn Thr Gly Gly Gly Cys Thr Val Pro Lys Trp Gln Gln Cys Gly Gly
        290                 295                 300

Gln Gly Tyr Ser Gly Cys Thr Val Cys Glu Ser Gly Ser Thr Cys Arg
305                 310                 315                 320

Ala Gln Asn Gln Trp Tyr Ser Gln Cys Val
                325                 330
```

<210> SEQ ID NO 143
<211> LENGTH: 772
<212> TYPE: DNA
<213> ORGANISM: Humicola insolens

<400> SEQUENCE: 143

```
atgaagctcc tcctcccgc cctcctggct ctggccgccg agtccgtctc ggcgcactac      60
atcttccaac aactcaccgt cgccggcacc aagtaccccg tgtggaagta catccggcgc     120
aacagcaatc cggcgtggct tcaaaacggc cctgtgaccg acctcgcctc gaccgacctg     180
cgctgcaacg tgggcgggca ggtcagcaac ggcaccgaga ctctcacggt ccgcgcgggc     240
gaccagttca cgttccacct cgacacggcg gtgtaccacc agggcccgac ctcgctgtac     300
atgtcgcgcg ctccgggcaa ggtggaggac tatgatggca gcgggccgtg gtttaagatt     360
tatgattggg ggccgacagg gaataattgg gtcatgaggg gtatggtttc cctattaat     420
tattattatt gtttacttgg ggcatcatct ggtggtggtg ctggtgacga tgataagagt     480
gatggagaag gacctggctg acgacctaaa aacccgatca gattcgtaca cgtacaacat     540
cccccgctgc atccccgacg gcgagtatct cctgcgcatc cagcagctgg gtctgcacaa     600
tccgggcgcc gcgccgcagt tctacatcag ctgcgcccag atcaaggtca ccggcggcgg     660
cactaccaac ccgacccca cggctctgat tccgggagcg ttcagggcta cggatccggg     720
atacactgtc aacgtaagtc aaactttgag caactccata tcaacctcgt ga             772
```

<210> SEQ ID NO 144
<211> LENGTH: 216
<212> TYPE: PRT
<213> ORGANISM: Humicola insolens

<400> SEQUENCE: 144

```
Met Lys Leu Leu Leu Pro Ala Leu Leu Ala Leu Ala Ala Glu Ser Val
1               5                   10                  15

Ser Ala His Tyr Ile Phe Gln Gln Leu Thr Val Ala Gly Thr Lys Tyr
            20                  25                  30

Pro Val Trp Lys Tyr Ile Arg Arg Asn Ser Asn Pro Ala Trp Leu Gln
        35                  40                  45

Asn Gly Pro Val Thr Asp Leu Ala Ser Thr Asp Leu Arg Cys Asn Val
    50                  55                  60

Gly Gly Gln Val Ser Asn Gly Thr Glu Thr Leu Thr Val Arg Ala Gly
65                  70                  75                  80

Asp Gln Phe Thr Phe His Leu Asp Thr Ala Val Tyr His Gln Gly Pro
                85                  90                  95

Thr Ser Leu Tyr Met Ser Arg Ala Pro Gly Lys Val Glu Asp Tyr Asp
            100                 105                 110

Gly Ser Gly Pro Trp Phe Lys Ile Tyr Asp Trp Gly Pro Thr Gly Asn
        115                 120                 125

Asn Trp Val Met Arg Asp Ser Tyr Thr Tyr Asn Ile Pro Arg Cys Ile
    130                 135                 140
```

```
Pro Asp Gly Glu Tyr Leu Leu Arg Ile Gln Gln Leu Gly Leu His Asn
145                 150                 155                 160

Pro Gly Ala Ala Pro Gln Phe Tyr Ile Ser Cys Ala Gln Ile Lys Val
                165                 170                 175

Thr Gly Gly Gly Thr Thr Asn Pro Thr Pro Thr Ala Leu Ile Pro Gly
            180                 185                 190

Ala Phe Arg Ala Thr Asp Pro Gly Tyr Thr Val Asn Val Ser Gln Thr
        195                 200                 205

Leu Ser Asn Ser Ile Ser Thr Ser
210                 215

<210> SEQ ID NO 145
<211> LENGTH: 1536
<212> TYPE: DNA
<213> ORGANISM: Humicola insolens

<400> SEQUENCE: 145
atgcgttctg tttcccttct tgcggccgct ttcgcgccgc tggctacggc acacacggtc     60
tttacagctc ttttcatcaa caatgtccac cagggcgacg gcacttgcgt ccgtatggct    120
aagcagggca acctcgccac ccatcccgtc agtctgaaca gcaatgagat ggcctgcggt    180
gggtaggccc cgttcctcga gcagctgatc tcgaactaac atgttgattc ttgaactcca    240
ggtcgcgatg ccaacaaacc agtggcattt acttgcccag cacctgcggg agccaagctg    300
accttattgt ttcgtatgtg gcagatggc tctcagccag gttccatcga caagtctcac    360
gttggtccca tgtccatcta cctcaagaaa gtctcagata tgaacaccga ctcggccgca    420
gggcccgggt ggttcaagat ctggagtgag gctacgacg ctgcgacgaa gaaatgggcc    480
acggagaaac tcatcgccaa caacggtttg ctcagcgtca acctacctcc cggcctccct    540
gcaggctact acctcgcccg ccacgaaatc gtcactctcc aaaacgtcac caacaacaag    600
gccgatccgc agttctacgt cggctgtgcg cagctgttcg tccaagggtt gggcaccgcc    660
gcctccgtgc ctgctgacaa aaccgtttcc atccccggcc atctgaaccc caacgacccg    720
gcgctggtat caaccccta tacccaaaac gctgcgacat acccaagctt cggcccaccg    780
ctcttcttcc caaatgctgc ttcggcggga tcaaacaagg cccagtcaac actcaagcaa    840
acctccggcg tcatccctc cgactgcctc atcaaaaacg ccaactggtg cggccgtgaa    900
gttccagact ataccaacga ggcgggatgc tggacggcgg cggggaactg ttgggagcag    960
gctgatcaat gctacaagac agccccgcca tcgggccata agggatgcaa gacctggag   1020 gagcagaagt gcaacgtcat ccagaactcc tgtgaagcga agaggttttc gggcccgcca   1080
aacagggggg tcaagtttgc tgatatggat gtgaatcagc ttgttccggg gcgatccct   1140 gaagcagtga acgccggtca gaatggggag gcggttgttg ttgacggcac aacgagctct   1200
gcagatgaga aggcgagtgt ggatttgaca acatcgtctc taccgacgcc gacgcctgcg   1260
gctgaagaaa acgggaagga ggatgaaaga ctggctcttg atccgaccct gacggaggac   1320
gagtcgtttt tctcagttga gccaacgtct gagcccactg gtgttcaggt tgaggtgcct   1380
ttgacaactg tggtcctcct tccaacgctc acctcatctt tgaatccatt gccaaccccg   1440
acctcaattt cccagccggc tcaccgggga agaccatgca caggtcgccg tcgtaggccg   1500
aggccagggt ttccgaaaca cccgcgcgat ttttaa                             1536

<210> SEQ ID NO 146
<211> LENGTH: 490
```

<212> TYPE: PRT
<213> ORGANISM: Humicola insolens

<400> SEQUENCE: 146

```
Met Arg Ser Val Ser Leu Leu Ala Ala Ala Phe Ala Pro Leu Ala Thr
 1               5                  10                  15

Ala His Thr Val Phe Thr Ala Leu Phe Ile Asn Asn Val His Gln Gly
             20                  25                  30

Asp Gly Thr Cys Val Arg Met Ala Lys Gln Gly Asn Leu Ala Thr His
         35                  40                  45

Pro Val Ser Leu Asn Ser Asn Glu Met Ala Cys Gly Arg Asp Gly Gln
 50                  55                  60

Gln Pro Val Ala Phe Thr Cys Pro Ala Pro Gly Ala Lys Leu Thr
 65                  70                  75                  80

Leu Leu Phe Arg Met Trp Ala Asp Gly Ser Gln Pro Gly Ser Ile Asp
                 85                  90                  95

Lys Ser His Val Gly Pro Met Ser Ile Tyr Leu Lys Lys Val Ser Asp
                100                 105                 110

Met Asn Thr Asp Ser Ala Ala Gly Pro Gly Trp Phe Lys Ile Trp Ser
                115                 120                 125

Glu Gly Tyr Asp Ala Ala Thr Lys Lys Trp Ala Thr Glu Lys Leu Ile
                130                 135                 140

Ala Asn Asn Gly Leu Leu Ser Val Asn Leu Pro Pro Gly Leu Pro Ala
145                 150                 155                 160

Gly Tyr Tyr Leu Ala Arg His Glu Ile Val Thr Leu Gln Asn Val Thr
                165                 170                 175

Asn Asn Lys Ala Asp Pro Gln Phe Tyr Val Gly Cys Ala Gln Leu Phe
                180                 185                 190

Val Gln Gly Leu Gly Thr Ala Ala Ser Val Pro Ala Asp Lys Thr Val
                195                 200                 205

Ser Ile Pro Gly His Leu Asn Pro Asn Asp Pro Ala Leu Val Phe Asn
                210                 215                 220

Pro Tyr Thr Gln Asn Ala Ala Thr Tyr Pro Ser Phe Gly Pro Pro Leu
225                 230                 235                 240

Phe Phe Pro Asn Ala Ala Ser Ala Gly Ser Asn Lys Ala Gln Ser Thr
                245                 250                 255

Leu Lys Gln Thr Ser Gly Val Ile Pro Ser Asp Cys Leu Ile Lys Asn
                260                 265                 270

Ala Asn Trp Cys Gly Arg Glu Val Pro Asp Tyr Thr Asn Glu Ala Gly
                275                 280                 285

Cys Trp Thr Ala Ala Gly Asn Cys Trp Glu Gln Ala Asp Gln Cys Tyr
                290                 295                 300

Lys Thr Ala Pro Pro Ser Gly His Lys Gly Cys Lys Thr Trp Glu Glu
305                 310                 315                 320

Gln Lys Cys Asn Val Ile Gln Asn Ser Cys Glu Ala Lys Arg Phe Ser
                325                 330                 335

Gly Pro Pro Asn Arg Gly Val Lys Phe Ala Asp Met Asp Val Asn Gln
                340                 345                 350

Leu Val Pro Gly Ala Ile Pro Glu Ala Val Asn Ala Gly Gln Asn Gly
                355                 360                 365

Glu Ala Val Val Val Asp Gly Thr Thr Ser Ser Ala Asp Glu Lys Ala
                370                 375                 380

Ser Val Asp Leu Thr Thr Ser Ser Leu Pro Thr Pro Thr Pro Ala Ala
385                 390                 395                 400
```

Glu Glu Asn Gly Lys Glu Asp Glu Arg Leu Ala Leu Asp Pro Thr Leu
            405                 410                 415

Thr Glu Asp Glu Ser Phe Phe Ser Val Glu Pro Thr Ser Glu Pro Thr
            420                 425                 430

Gly Val Gln Val Glu Val Pro Leu Thr Thr Val Val Leu Leu Pro Thr
            435                 440                 445

Leu Thr Ser Ser Leu Asn Pro Leu Pro Thr Pro Thr Ser Ile Ser Gln
        450                 455                 460

Pro Ala His Pro Gly Arg Pro Cys Thr Gly Arg Arg Arg Pro Arg
465                 470                 475                 480

Pro Gly Phe Pro Lys His Pro Arg Asp Phe
            485                 490

```
<210> SEQ ID NO 147
<211> LENGTH: 921
<212> TYPE: DNA
<213> ORGANISM: Humicola insolens

<400> SEQUENCE: 147
atgttcttcc gcaacgccgc cactcttgct ctggcctacg ccaccaccgg cgtctcggcc        60
cacgcgctca tgtacggcgt ctgggtcaac ggcgtcgacc aaggcgacgg ccgcaacgtc       120
tacatccgca cgcccccaa caacagcccg gtcaaagacc tcgccagccc ggacatcgtc       180
tgcaacgtca acggcgggcg cgccgttccg gacttcgtcc aggcctcggc gggggacacc       240
ctcaccttcg agtggctgca aacaccccgc ggcgacgaca tcatcgaccg ctcccacctc       300
ggccccatca tcacctacat cgccccttt accacgggca acccgacggg gcccgtctgg       360
accaaaatcg ccgaacaggg cttcaaccct tccacccgcc gctgggccgt cgacgatctg       420
atcgacaacg gcggcaagac cgacttcgtc ctgcccgcgt ccctcgcgcc gggcaggtac       480
atcatccggc aggagatcat cgcgcaccac gagtccgaaa ccacgttcga atccaacccg       540
gcgcggggtg cccagttcta cccgtcgtgc gtgcagatcc aagtctcttc tggctcgggc       600
accgccgtgc cggatcagaa ctttgacttc aacacgggct acacgtacgc cgaccccggc       660
atccacttca acatctacac ctcgttcaac agctactcca tccccggccc ggaggtttgg       720
acgggcgcta gcaccggcgg cggcaacggc aacggcaacg gcaacggcaa tgccacgcct       780
acgcagccta ctcccactcc cactgtcact cccactccca tcgagaccgc ccagccggtt       840
accacgacga ccacctcgac ccggccgttc cctacccgct gccctggccg ccgcctcaag       900
cgtgaggagc ccaaggcttg a                                                 921

<210> SEQ ID NO 148
<211> LENGTH: 306
<212> TYPE: PRT
<213> ORGANISM: Humicola insolens

<400> SEQUENCE: 148
```

Met Phe Phe Arg Asn Ala Ala Thr Leu Ala Leu Ala Tyr Ala Thr Thr
1               5                   10                  15

Gly Val Ser Ala His Ala Leu Met Tyr Gly Val Trp Val Asn Gly Val
            20                  25                  30

Asp Gln Gly Asp Gly Arg Asn Val Tyr Ile Arg Thr Pro Pro Asn Asn
        35                  40                  45

Ser Pro Val Lys Asp Leu Ala Ser Pro Asp Ile Val Cys Asn Val Asn
    50                  55                  60

Gly Gly Arg Ala Val Pro Asp Phe Val Gln Ala Ser Ala Gly Asp Thr
65                  70                  75                  80

Leu Thr Phe Glu Trp Leu His Asn Thr Arg Gly Asp Asp Ile Ile Asp
            85                  90                  95

Arg Ser His Leu Gly Pro Ile Ile Thr Tyr Ile Ala Pro Phe Thr Thr
        100                 105                 110

Gly Asn Pro Thr Gly Pro Val Trp Thr Lys Ile Ala Glu Gln Gly Phe
    115                 120                 125

Asn Pro Ser Thr Arg Arg Trp Ala Val Asp Asp Leu Ile Asp Asn Gly
130                 135                 140

Gly Lys Thr Asp Phe Val Leu Pro Ala Ser Leu Ala Pro Gly Arg Tyr
145                 150                 155                 160

Ile Ile Arg Gln Glu Ile Ile Ala His His Glu Ser Glu Thr Thr Phe
                165                 170                 175

Glu Ser Asn Pro Ala Arg Gly Ala Gln Phe Tyr Pro Ser Cys Val Gln
            180                 185                 190

Ile Gln Val Ser Ser Gly Ser Gly Thr Ala Val Pro Asp Gln Asn Phe
        195                 200                 205

Asp Phe Asn Thr Gly Tyr Thr Tyr Ala Asp Pro Gly Ile His Phe Asn
    210                 215                 220

Ile Tyr Thr Ser Phe Asn Ser Tyr Ser Ile Pro Gly Pro Glu Val Trp
225                 230                 235                 240

Thr Gly Ala Ser Thr Gly Gly Gly Asn Gly Asn Gly Asn Gly Asn Gly
                245                 250                 255

Asn Ala Thr Pro Thr Gln Pro Thr Pro Thr Pro Thr Val Thr Pro Thr
            260                 265                 270

Pro Ile Glu Thr Ala Gln Pro Val Thr Thr Thr Thr Ser Thr Arg
        275                 280                 285

Pro Phe Pro Thr Arg Cys Pro Gly Arg Arg Leu Lys Arg Glu Glu Pro
290                 295                 300

Lys Ala
305

<210> SEQ ID NO 149
<211> LENGTH: 1092
<212> TYPE: DNA
<213> ORGANISM: Humicola insolens

<400> SEQUENCE: 149
atggctcatc catgggcacg ttgcgtctat acagccatct ggctcgctgc ctccgcttct      60
ggacgtaggt acaagactcc ggcagtgcca tttatgaacc cacaacgtgg actggtcccg     120
tgctaacaca tcacagactc gcgcgtttgg agtgtctcgg tcaatggacg ctaccaggga     180
ccgggtgttg atgactacct gcgcgcaccg ccaagtgact ctccggtggt ggacctggac     240
tcaccaaccc tcaactgcaa tgtcaatgga acaagcctg ttccagggtt tgttgaggtg     300
tctgcgggag attctctgga atggaagtgg tactacatca cccgtacaa cccaagcgac     360
atgatcatcg cggcagaaca ccgcggaccg atcatcacct acatcacgaa ttacaccgat     420
ggccagcctc aaggagctgt ctggaccaag attgatcacg aaggctacga tcctgtgaca     480
gaccggttcg ccgtcgacaa cttgatcgcc aacaggggat ggaaagcaat caagcttccc     540
atgctcgccg acgggaagta catcctgcga caggagatca tcgcactcca cagcgcacac     600
aaccaaggcg gggcccagct gtatccgaac tgcattcaga tcaaggtcgt tggtggcaag     660
ggaagcgcgg tgcccaacca gaactttgat ctcaacaagg ggtacacatc cgatcacccg     720

```
ggacttcggt tcaacctgtg gcaaccattc aacaattaca ccattcccgg tcctgaggtc    780
tggaagggag ttgtggttgc gagcaatggt acaacgaaca gcaccacaaa tctcaccaac    840
aacaccggca ccggttttgc gaacagcact atggccactg gtgaaacaag gaccgagagg    900
agttttatga cacttaccgc atcacattca gacactggcg tccccgccaa atctcatact    960
gtggctgtaa gctggacaac atccgccgcc gttgttgggt ctccgattag cgttaccaca   1020
actttcagtt cctttaccac aacaccggtt ccgacgaact ctaccggtgc ttatctctac   1080
cggtacaagt ga                                                       1092
```

<210> SEQ ID NO 150
<211> LENGTH: 339
<212> TYPE: PRT
<213> ORGANISM: Humicola insolens

<400> SEQUENCE: 150

```
Met Ala His Pro Trp Ala Arg Cys Val Tyr Thr Ala Ile Trp Leu Ala
1               5                   10                  15

Ala Ser Ala Ser Gly His Ser Arg Val Trp Ser Val Ser Val Asn Gly
            20                  25                  30

Arg Tyr Gln Gly Pro Gly Val Asp Asp Tyr Leu Arg Ala Pro Pro Ser
        35                  40                  45

Asp Ser Pro Val Val Asp Leu Asp Ser Pro Thr Leu Asn Cys Asn Val
    50                  55                  60

Asn Gly Asn Lys Pro Val Pro Gly Phe Val Glu Val Ser Ala Gly Asp
65                  70                  75                  80

Ser Leu Glu Trp Lys Trp Tyr Tyr Ile Asn Pro Tyr Asn Pro Ser Asp
                85                  90                  95

Met Ile Ile Ala Ala Glu His Arg Gly Pro Ile Ile Thr Tyr Ile Thr
            100                 105                 110

Asn Tyr Thr Asp Gly Gln Pro Gln Gly Ala Val Trp Thr Lys Ile Asp
        115                 120                 125

His Glu Gly Tyr Asp Pro Val Thr Asp Arg Phe Ala Val Asp Asn Leu
    130                 135                 140

Ile Ala Asn Arg Gly Trp Lys Ala Ile Lys Leu Pro Met Leu Ala Asp
145                 150                 155                 160

Gly Lys Tyr Ile Leu Arg Gln Glu Ile Ile Ala Leu His Ser Ala His
                165                 170                 175

Asn Gln Gly Gly Ala Gln Leu Tyr Pro Asn Cys Ile Gln Ile Lys Val
            180                 185                 190

Val Gly Gly Lys Gly Ser Ala Val Pro Asn Gln Asn Phe Asp Leu Asn
        195                 200                 205

Lys Gly Tyr Thr Ser Asp His Pro Gly Leu Arg Phe Asn Leu Trp Gln
    210                 215                 220

Pro Phe Asn Asn Tyr Thr Ile Pro Gly Pro Glu Val Trp Lys Gly Val
225                 230                 235                 240

Val Val Ala Ser Asn Gly Thr Thr Asn Ser Thr Asn Leu Thr Asn
                245                 250                 255

Asn Thr Gly Thr Gly Phe Ala Asn Ser Thr Met Ala Thr Gly Glu Thr
            260                 265                 270

Arg Thr Glu Arg Ser Phe Met Thr Leu Thr Ala Ser His Ser Asp Thr
        275                 280                 285

Gly Val Pro Ala Lys Ser His Val Ala Val Ser Trp Thr Thr Ser
    290                 295                 300
```

Ala Ala Val Val Gly Ser Pro Ile Ser Val Thr Thr Thr Phe Ser Ser
305                 310                 315                 320

Phe Thr Thr Thr Pro Val Pro Thr Asn Ser Thr Gly Ala Tyr Leu Tyr
                325                 330                 335

Arg Tyr Lys

<210> SEQ ID NO 151
<211> LENGTH: 1005
<212> TYPE: DNA
<213> ORGANISM: Malbranchea cinnamomea

<400> SEQUENCE: 151

```
atgtcaccct ccttcaagtc cactgccatc ctcggagccg ttgctctggc cgcccgcgtg    60
cgcgcccacg gctacgtgtc tggaatcgtc gttgacggtg cttaccatgg cggttacatc   120
gtcgacaagt acccctacat gcccaaccca cccgatgtgg tcggctggtc gactacggcc   180
acggacctgg gcttcgtcgc ccctgacgcc tttggcgacc cggacatcat ctgccaccgg   240
gacggtgccc ccggtgccat ccacgccaaa gtcaacgccg gtgccaccat cgagctgcag   300
tggaacacct ggcccgaaag ccaccacggg cccgtcatcg actacctggc taactgcaac   360
ggtgactgct cgtccgtcga caagacctcg ctcaagttct tcaagatcag cgaggccggc   420
ctaaacgacg gctccaacgc cccggcag tgggcgtccg acgatctcat tgccaacaac   480
aacagctgga ctgtgaccat ccccaagtcg atcgccccgg gcaactacgt gctgcgccac   540
gagatcatcg ccctgcacag cgccggcaac cagaatggcg cgcagaacta cccccagtgc   600
ttcaacctcg agatcaccag caacggcagc gacaacccgg agggcgtgct gggaaccgag   660
ctgtacaagg ccgacgaccc gggcattctg ttcaacatct accagcccat ggactcgtac   720
ccgattcccg gccctgctct ctacaccggc ggctcttctc cctcccctaa tccgcccacc   780
tctacccagt cgcctgtgcc ccagcccacc cagtctcccc catcgggcag caaccccggc   840
aacggcaacg gcgacgacga caacgacaac ggcaacgaga ccccatcccc gtctctcccc   900
gtcgagatcc ctgacgacct gacctcgcgc gagctactcc ttgtggccca ggagatcatt   960
gcccgtctgc ttgagctgca gaatcagctg gtcgtctcga actaa              1005
```

<210> SEQ ID NO 152
<211> LENGTH: 334
<212> TYPE: PRT
<213> ORGANISM: Malbranchea cinnamomea

<400> SEQUENCE: 152

Met Ser Pro Ser Phe Lys Ser Thr Ala Ile Leu Gly Ala Val Ala Leu
1               5                   10                  15

Ala Ala Arg Val Arg Ala His Gly Tyr Val Ser Gly Ile Val Val Asp
                20                  25                  30

Gly Ala Tyr His Gly Gly Tyr Ile Val Asp Lys Tyr Pro Tyr Met Pro
            35                  40                  45

Asn Pro Pro Asp Val Val Gly Trp Ser Thr Thr Ala Thr Asp Leu Gly
        50                  55                  60

Phe Val Ala Pro Asp Ala Phe Gly Asp Pro Asp Ile Ile Cys His Arg
65                  70                  75                  80

Asp Gly Ala Pro Gly Ala Ile His Ala Lys Val Asn Ala Gly Ala Thr
                85                  90                  95

Ile Glu Leu Gln Trp Asn Thr Trp Pro Glu Ser His His Gly Pro Val
                100                 105                 110

```
Ile Asp Tyr Leu Ala Asn Cys Asn Gly Asp Cys Ser Ser Val Asp Lys
        115                 120                 125

Thr Ser Leu Lys Phe Phe Lys Ile Ser Glu Ala Gly Leu Asn Asp Gly
    130                 135                 140

Ser Asn Ala Pro Gly Gln Trp Ala Ser Asp Asp Leu Ile Ala Asn Asn
145                 150                 155                 160

Asn Ser Trp Thr Val Thr Ile Pro Lys Ser Ile Ala Pro Gly Asn Tyr
                165                 170                 175

Val Leu Arg His Glu Ile Ile Ala Leu His Ser Ala Gly Asn Gln Asn
                180                 185                 190

Gly Ala Gln Asn Tyr Pro Gln Cys Phe Asn Leu Glu Ile Thr Ser Asn
                195                 200                 205

Gly Ser Asp Asn Pro Glu Gly Val Leu Gly Thr Glu Leu Tyr Lys Ala
        210                 215                 220

Asp Asp Pro Gly Ile Leu Phe Asn Ile Tyr Gln Pro Met Asp Ser Tyr
225                 230                 235                 240

Pro Ile Pro Gly Pro Ala Leu Tyr Thr Gly Gly Ser Ser Pro Ser Pro
                245                 250                 255

Asn Pro Pro Thr Ser Thr Gln Ser Pro Val Pro Gln Pro Thr Gln Ser
                260                 265                 270

Pro Pro Ser Gly Ser Asn Pro Gly Asn Gly Asn Gly Asp Asp Asp Asn
        275                 280                 285

Asp Asn Gly Asn Glu Thr Pro Ser Pro Ser Leu Pro Val Glu Ile Pro
        290                 295                 300

Asp Asp Leu Thr Ser Arg Glu Leu Leu Leu Val Ala Gln Glu Ile Ile
305                 310                 315                 320

Ala Arg Leu Leu Glu Leu Gln Asn Gln Leu Val Val Ser Asn
                325                 330

<210> SEQ ID NO 153
<211> LENGTH: 1101
<212> TYPE: DNA
<213> ORGANISM: Talaromyces leycettanus

<400> SEQUENCE: 153
atgcatcaac acttccgata cactgcgctc ctgacagcgt tgctgtcagc atcaacccga      60
gtcgcatccc acggccatgt cagcaacatt gtcattaatg gcgttcccta tcaaggatgg     120
gatatcgatt ccatgcccta cgagtcagac ccaccagtgg ttgtcgcctg ggagacacct     180
aacacgtcaa acggtttcat taccccggat cagtacggta cgagtgatat tatctgccat     240
ctgaacgcaa ccaacgcaaa gggccatgcc gtcgttgctg ccggagacaa gatcagcatt     300
caatggactg cctggcccag ctcccaccac ggccctgtca tcagctacct ggccaactgt     360
ggcgccagct gtgagacagt cgacaaaacg acgttgcaat tctttaagat cgacaacatc     420
ggtttcatag atgactcttc cccccaggc atctgggcag ccgatcaatt ggaagcaaac     480
aacaacacct ggctcgtgga tcccccccg accatcgctc aggatacta cgtcctgcgc     540 aacgagatca tcgccctaca cggtgcagag aatcaggatg cgcccagaa ctatccgcag     600 tgcttcaatc tgcaggtcac cggctcgggt accgataaac ccgccggcgt tcttggaact     660
cagctctatt ctcccactga cccgggcatt ctcgtgaaca tttacacgag cctttcgacc     720
tacatcgtcc ccggtccaac cccgtacagt ggtgggtgt ccgtcgtgca gtctagctct     780
gctatcaccg cttctggaac cccggtgacg ggcactggcg gagttagccc aaccacggct     840
```

```
gctactacga cttcttcttc tcactccacg acttctacta ctaccgggcc cactgtaacc    900
tcgactagcc acactactac cactactact cctactaccc tcagaaccac gactacaact    960
gcagctggtg gtggtgcgac acagaccgtc tacggccaat gcggcggtag tggttggact   1020
ggcgcaactg cctgcgcagc cggagctact gcagcactc tgaatcccta ctatgcccaa   1080
tgccttccta ctggtgcttg a                                            1101
```

<210> SEQ ID NO 154
<211> LENGTH: 366
<212> TYPE: PRT
<213> ORGANISM: Talaromyces leycettanus

<400> SEQUENCE: 154

```
Met His Gln His Phe Arg Tyr Thr Ala Leu Leu Thr Ala Leu Leu Ser
1               5                  10                  15

Ala Ser Thr Arg Val Ala Ser His Gly His Val Ser Asn Ile Val Ile
            20                  25                  30

Asn Gly Val Pro Tyr Gln Gly Trp Asp Ile Asp Ser Met Pro Tyr Glu
        35                  40                  45

Ser Asp Pro Pro Val Val Ala Trp Glu Thr Pro Asn Thr Ser Asn
50                  55                  60

Gly Phe Ile Thr Pro Asp Gln Tyr Gly Thr Ser Asp Ile Ile Cys His
65                  70                  75                  80

Leu Asn Ala Thr Asn Ala Lys Gly His Ala Val Ala Ala Gly Asp
                85                  90                  95

Lys Ile Ser Ile Gln Trp Thr Ala Trp Pro Ser Ser His His Gly Pro
            100                 105                 110

Val Ile Ser Tyr Leu Ala Asn Cys Gly Ala Ser Cys Glu Thr Val Asp
        115                 120                 125

Lys Thr Thr Leu Gln Phe Phe Lys Ile Asp Asn Ile Gly Phe Ile Asp
130                 135                 140

Asp Ser Ser Pro Pro Gly Ile Trp Ala Ala Asp Gln Leu Glu Ala Asn
145                 150                 155                 160

Asn Asn Thr Trp Leu Val Glu Ile Pro Pro Thr Ile Ala Pro Gly Tyr
                165                 170                 175

Tyr Val Leu Arg Asn Glu Ile Ile Ala Leu His Gly Ala Glu Asn Gln
            180                 185                 190

Asp Gly Ala Gln Asn Tyr Pro Gln Cys Phe Asn Leu Gln Val Thr Gly
        195                 200                 205

Ser Gly Thr Asp Lys Pro Ala Gly Val Leu Gly Thr Gln Leu Tyr Ser
    210                 215                 220

Pro Thr Asp Pro Gly Ile Leu Val Asn Ile Tyr Thr Ser Leu Ser Thr
225                 230                 235                 240

Tyr Ile Val Pro Gly Pro Thr Pro Tyr Ser Gly Trp Val Ser Val Val
                245                 250                 255

Gln Ser Ser Ser Ala Ile Thr Ala Ser Gly Thr Pro Val Thr Gly Thr
            260                 265                 270

Gly Gly Val Ser Pro Thr Thr Ala Ala Thr Thr Ser Ser Ser His
        275                 280                 285

Ser Thr Thr Ser Thr Thr Thr Gly Pro Thr Val Thr Ser Thr Ser His
    290                 295                 300

Thr Thr Thr Thr Thr Thr Pro Thr Thr Leu Arg Thr Thr Thr Thr Thr
305                 310                 315                 320

Ala Ala Gly Gly Gly Ala Thr Gln Thr Val Tyr Gly Gln Cys Gly Gly
```

```
                    325                 330                 335
Ser Gly Trp Thr Gly Ala Thr Ala Cys Ala Ala Gly Ala Thr Cys Ser
                340                 345                 350

Thr Leu Asn Pro Tyr Tyr Ala Gln Cys Leu Pro Thr Gly Ala
            355                 360                 365
```

<210> SEQ ID NO 155
<211> LENGTH: 1091
<212> TYPE: DNA
<213> ORGANISM: Chaetomium thermophilum
<220> FEATURE:
<221> NAME/KEY: misc_feature
<222> LOCATION: (522)..(524)
<223> OTHER INFORMATION: n is a, c, g, or t

<400> SEQUENCE: 155

```
atgccttcct tcgcttcgaa gactctcatt tctgccctcg ccggcgctgc cagcgtcgcc      60
gctcacggcc acgtcaagaa cttcgtcatc aacggtctgt cgtaccaggc ctacgacccg     120
accgtcttcc cgtacatgca gaaccctccc atcgtcgccg gctggacggc ctccaacact     180
gacaacggct tcgtgggccc cgagtcctac tcgagccccg atatcatctg ccacaagtcg     240
gccacgaacg ccaagggcca tgccgtcatc aaggccggtg actctgtcta catccagtgg     300
gacacctggc cgagtcgca ccacggcccg gtcatcgact acctcgccag ctgcggcagc     360
gccggctgcg agacggtcga caagacccag ctcgagttct tcaagatcgc cgaggccggt     420
ctgattgacg gctcccaggc tcccggaaag tgggctgccg atcagctcat cgcccagaac     480
aactcgtggc tggtcaccat ccccgagaat atcaagccgc tnnnggctcc tacgtcctcc     540
gccacgagat catcgccctg cacagcgctg ccagaccaa cggtgcccag aactaccccg     600
tctgcatcaa cctcgaggtc actggtggcg gcagcgacgt tccctcgggt gtcaagggta     660
ctgagctcta caagcccacc gaccccggca tcctcatcaa catctaccag tcgctctcga     720
actacaccat ccctggccct gctctgatgc ccggcgccaa gccagtcacc cagcacacct     780
cagccatcat cggcagcacc accgccatca ctggcaccgc caccgctgct ccggccgcgc     840
cgacctcgac cgccgctgcc atcaccacca gctctgctaa tgccaacccc gccccgacca     900
ccacccgcgg caacgccaac cccgtcccga ctaccaccct ccgcacgagc accatcgctc     960
ctcagcccac tgctgccccc atccagaccc gacctccag cgtcggccgg ccccgcgcc    1020
cgacccgctg ccctggtctg acaacttca agcgcgctcg tcgccacgct cgtgaccttg    1080
ctgcccacta a                                                       1091
```

<210> SEQ ID NO 156
<211> LENGTH: 364
<212> TYPE: PRT
<213> ORGANISM: Chaetomium thermophilum
<220> FEATURE:
<221> NAME/KEY: misc_feature
<222> LOCATION: (174)..(176)
<223> OTHER INFORMATION: Xaa can be any naturally occurring amino acid

<400> SEQUENCE: 156

```
Met Pro Ser Phe Ala Ser Lys Thr Leu Ile Ser Ala Leu Ala Gly Ala
1               5                   10                  15

Ala Ser Val Ala Ala His Gly His Val Lys Asn Phe Val Ile Asn Gly
            20                  25                  30

Leu Ser Tyr Gln Ala Tyr Asp Pro Thr Val Phe Pro Tyr Met Gln Asn
        35                  40                  45
```

```
Pro Pro Ile Val Ala Gly Trp Thr Ala Ser Asn Thr Asp Asn Gly Phe
    50                  55                  60
Val Gly Pro Glu Ser Tyr Ser Ser Pro Asp Ile Ile Cys His Lys Ser
 65                  70                  75                  80
Ala Thr Asn Ala Lys Gly His Ala Val Ile Lys Ala Gly Asp Ser Val
                 85                  90                  95
Tyr Ile Gln Trp Asp Thr Trp Pro Glu Ser His His Gly Pro Val Ile
                100                 105                 110
Asp Tyr Leu Ala Ser Cys Gly Ser Ala Gly Cys Glu Thr Val Asp Lys
            115                 120                 125
Thr Gln Leu Glu Phe Phe Lys Ile Ala Glu Ala Gly Leu Ile Asp Gly
    130                 135                 140
Ser Gln Ala Pro Gly Lys Trp Ala Ala Asp Gln Leu Ile Ala Gln Asn
145                 150                 155                 160
Asn Ser Trp Leu Val Thr Ile Pro Glu Asn Ile Lys Pro Xaa Xaa Xaa
                165                 170                 175
Gly Ser Tyr Val Leu Arg His Glu Ile Ile Ala Leu His Ser Ala Gly
                180                 185                 190
Gln Thr Asn Gly Ala Gln Asn Tyr Pro Val Cys Ile Asn Leu Glu Val
            195                 200                 205
Thr Gly Gly Gly Ser Asp Val Pro Ser Gly Val Lys Gly Thr Glu Leu
    210                 215                 220
Tyr Lys Pro Thr Asp Pro Gly Ile Leu Ile Asn Ile Tyr Gln Ser Leu
225                 230                 235                 240
Ser Asn Tyr Thr Ile Pro Gly Pro Ala Leu Met Pro Gly Ala Lys Pro
                245                 250                 255
Val Thr Gln His Thr Ser Ala Ile Ile Gly Ser Thr Thr Ala Ile Thr
                260                 265                 270
Gly Thr Ala Thr Ala Pro Ala Ala Pro Thr Ser Thr Ala Ala Ala
            275                 280                 285
Ile Thr Thr Ser Ser Ala Asn Ala Asn Pro Ala Pro Thr Thr Thr Arg
    290                 295                 300
Gly Asn Ala Asn Pro Val Pro Thr Thr Thr Leu Arg Thr Ser Thr Ile
305                 310                 315                 320
Ala Pro Gln Pro Thr Ala Ala Pro Ile Gln Thr Pro Thr Ser Ser Val
                325                 330                 335
Gly Arg Pro Pro Arg Pro Thr Arg Cys Pro Gly Leu Asp Asn Phe Lys
            340                 345                 350
Arg Ala Arg Arg His Ala Arg Asp Leu Ala Ala His
    355                 360

<210> SEQ ID NO 157
<211> LENGTH: 1089
<212> TYPE: DNA
<213> ORGANISM: Trichoderma ressei

<400> SEQUENCE: 157
atgatccaga agctttccaa cctccttgtc accgcactgg cggtggctac tggcgttgtc      60
ggacatggac atattaatga cattgtcatc aacggggtgt ggtatcaggc ctatgatcct     120
acaacgtttc catacgagtc aaaccccccc atagtagtgg gctggacggc tgccgacctt     180
gacaacggta cgtgatcctc atctctatct gtacaacgct catgctaatc caactcaata     240
ggcttcgttt cacccgacgc ataccaaaac cctgacatca tctgccacaa gaatgctacg     300
aatgccaagg ggcacgcgtc tgtcaaggcc ggagacacta ttctcttcca gtgggtgcca     360
```

```
gttccatggc cgcaccctgg tcccattgtc gactacctgg ccaactgcaa tggtgactgc    420
gagaccgttg acaagacgac gcttgagttc ttcaagatcg atggcgttgg tctcctcagc    480
ggcggggatc cgggcacctg ggcctcagac gtgctgatct ccaacaacaa cacctgggtc    540
gtcaagatcc ccgacaatct tgcgccaggc aattacgtgc tccgccacga gatcatcgcg    600
ttacacagcg ccgggcaggc aaacggcgct cagaactacc ccagtgctt caacattgcc     660 gtctcaggct cgggttctct gcagcccagc ggcgttctag ggaccgacct ctatcacgcg    720
acggaccctg gtgttctcat caacatctac accagcccgc tcaactacat catccctgga    780
cctaccgtgg tatcaggcct gccaacgagt gttgcccagg ggagctccgc cgcgacggcc    840
accgccagcg ccactgttcc tggaggcggt agcggcccga ccagcagaac cacgacaacg    900
gcgaggacga cgcaggcctc aagcaggccc agctctacgc ctcccgcaac cacgtcggca    960
cctgctggcg gcccaacccca gactctgtac ggccagtgtg gtggcagcgg ttacagcggg   1020
cctactcgat gcgcgccgcc agccacttgc tctaccttga cccctacta cgcccagtgc     1080 cttaactag                                                            1089
```

<210> SEQ ID NO 158
<211> LENGTH: 344
<212> TYPE: PRT
<213> ORGANISM: Trichoderma ressei

<400> SEQUENCE: 158

```
Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
    130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240
```

```
Pro Gly Pro Thr Val Val Ser Gly Leu Pro Thr Ser Val Ala Gln Gly
            245                 250                 255

Ser Ser Ala Ala Thr Ala Thr Ala Ser Ala Thr Val Pro Gly Gly Gly
            260                 265                 270

Ser Gly Pro Thr Ser Arg Thr Thr Thr Ala Arg Thr Thr Gln Ala
            275                 280                 285

Ser Ser Arg Pro Ser Ser Thr Pro Pro Ala Thr Thr Ser Ala Pro Ala
290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
            325                 330                 335

Pro Tyr Tyr Ala Gln Cys Leu Asn
            340
```

<210> SEQ ID NO 159
<211> LENGTH: 759
<212> TYPE: DNA
<213> ORGANISM: Acrophialophora fusispora

<400> SEQUENCE: 159

```
atgcgcatag aagctatcac aggcctcgtg ctggcctcgg ccggtgcagt gtctgcccat      60
ggctgggtcg atgtctgggc tattggcggc aagaactaca caggcttcaa ccccacggtg     120
gcgccatggg tcccggatca gggcaccatt gcgtggccgg cctggaacac cgacacagga     180
ccggtgtaca gcaaggacgt caacaccaca gacatcatct gctcaatcaa tgccaccaac     240
gccaagatct actccgaccc catcgccgct gggaacgtca tcaacctgca ctggacggtg     300
tggccagact cacaccacgg gcccatcctg tcgtacctgg ccgcgtgcaa cggcgactgc     360
gccaaggccg acaagaccaa gctcaagtgg ttcaagattg cccatgccgg tcaaatcagc     420
ctgggcaccg gcggcggcca ggttggctac tgggccagcg acaagctgca agacgacaac     480
ggcacctggc ccgtcaccat tccggcctcc atcaagcccg gcaattacgt gctgcggaac     540
gagattattg ccctccattc ggcgtacgac gtcggcgccg cccagctcta cccgcagtgc     600
gttaatatca agatcacggg caacggccgc gtcacccctg ccggcgtggt gggaaccaag     660
ctctacaagg agaccgatcc tggcctgcat tataacatct ataacgacga gtctaagcct     720
gtctatcaga tccccggccc ggccttgtgt aagtgctaa                            759
```

<210> SEQ ID NO 160
<211> LENGTH: 252
<212> TYPE: PRT
<213> ORGANISM: Acrophialophora fusispora

<400> SEQUENCE: 160

```
Met Arg Ile Glu Ala Ile Thr Gly Leu Val Leu Ala Ser Ala Gly Ala
1               5                   10                  15

Val Ser Ala His Gly Trp Val Asp Val Trp Ala Ile Gly Gly Lys Asn
            20                  25                  30

Tyr Thr Gly Phe Asn Pro Thr Val Ala Pro Trp Val Pro Asp Gln Gly
        35                  40                  45

Thr Ile Ala Trp Pro Ala Trp Asn Thr Asp Thr Gly Pro Val Tyr Ser
    50                  55                  60

Lys Asp Val Asn Thr Thr Asp Ile Ile Cys Ser Ile Asn Ala Thr Asn
65                  70                  75                  80
```

Ala Lys Ile Tyr Ser Asp Pro Ile Ala Gly Asn Val Ile Asn Leu
            85                  90                  95

His Trp Thr Val Trp Pro Asp Ser His His Gly Pro Ile Leu Ser Tyr
        100                 105                 110

Leu Ala Ala Cys Asn Gly Asp Cys Ala Lys Ala Asp Lys Thr Lys Leu
            115                 120                 125

Lys Trp Phe Lys Ile Ala His Ala Gly Gln Ile Ser Leu Gly Thr Gly
        130                 135                 140

Gly Gly Gln Val Gly Tyr Trp Ala Ser Asp Lys Leu Gln Asp Asp Asn
145                 150                 155                 160

Gly Thr Trp Pro Val Thr Ile Pro Ala Ser Ile Lys Pro Gly Asn Tyr
                165                 170                 175

Val Leu Arg Asn Glu Ile Ile Ala Leu His Ser Ala Tyr Asp Val Gly
            180                 185                 190

Ala Ala Gln Leu Tyr Pro Gln Cys Val Asn Ile Lys Ile Thr Gly Asn
            195                 200                 205

Gly Arg Val Thr Pro Ala Gly Val Val Gly Thr Lys Leu Tyr Lys Glu
    210                 215                 220

Thr Asp Pro Gly Leu His Tyr Asn Ile Tyr Asn Asp Glu Ser Lys Pro
225                 230                 235                 240

Val Tyr Gln Ile Pro Gly Pro Ala Leu Cys Lys Cys
                245                 250

<210> SEQ ID NO 161
<211> LENGTH: 1035
<212> TYPE: DNA
<213> ORGANISM: Corynascus sepedonium

<400> SEQUENCE: 161

```
atgtctaaga cttctgctct ccttgctggc ctaacgggcg cggccctcgt cgctgcccac      60
gggcacgtca gccatatcat tgtcaacggt gtctactatg agaactacga ccccacgaca     120
cactggtacc agcccaaccc accaacagtc atcggctgga cggcagccca gcaggacaac     180
ggcttcatcg agcccaacaa ctttggcacg tcggacatca tctgccacaa gagcggttct     240
ccaggcggcg gtcacgctac cgtcgctgcg ggcgacaaga tcaacatcgt ctggactccg     300
gagtggcccg actcccatat cggcccggtc attgactacc tggctgcctg caacggtgac     360
tgcgagaccg taaacaagga gtcgctgcgc ttctttaaga ttgacgggc cggctatgac      420
aaggccgctg ccgctgggc cgccgagact ctgcgccaga acggcaacag ctggctcgtc     480
cagatcccgt ctgaccttaa ggctggcaac tacgtgctcc gccacgaaat catcgccctc     540
cacggcgctg aagcgccaa cggtgctcaa gcctaccgc agtgcatcaa ccttcgcgtg      600
acgggcggcg gcagcagcgt gcccagcggc gtggccggca cctcgctcta caaagcctcc     660
gacgcaggca tcctcttcaa ccctacgtc gcctctcccg attacccggt cccaggcccg     720
gcgctcattg ctggtgccgc cagctctatc gtacagagca cgtcggcagt gaccgctacc     780
gcctcggcca ccgctcccgg tgcggcggc gccaaccca accctacgcc caccaccacc     840
tcctcgagca atcccgcccc aagcaccacc ctcaggacaa ccacctcggc cgcgcaaacc     900
acgcccccgc ctaccaatgg caacgtccag acaaagtacg gtcagtgtgg tggtaggac     960
tggagcggcc caacggcgtg cgcggctggt tccagctgct cggtgctcaa cgactggtac    1020
tcccagtgcg tgtaa                                                    1035
```

<210>

<211> LENGTH: 344
<212> TYPE: PRT
<213> ORGANISM: Corynascus sepedonium

<400> SEQUENCE: 162

| | | | | | | | | | | | | | | |
|---|---|---|---|---|---|---|---|---|---|---|---|---|---|---|
| Met | Ser | Lys | Thr | Ser | Ala | Leu | Leu | Ala | Gly | Leu | Thr | Gly | Ala | Ala | Leu |
| 1 | | | | 5 | | | | | 10 | | | | | 15 | |

Val Ala Ala His Gly His Val

```
atgccttctt ctacctccaa gggtcttttc tccgccctca tgggcgcggc gtcggttgcc    60
gcccatggtc atgtcaccaa cattgtcatc aacggtgtgt cgtaccagaa ctacgacccg   120
accagcttcc cttacatgca gaacccgccg acggttgttg gctggacggc aagcaacact   180
gataacggct tcgtcgctcc tgatgcgttt gctagcggcg acatcatctg ccacagggac   240
gccaccaatg ctggtggtca tgccgtcgtt gctgctggtg acaaggtctt catccagtgg   300
gatacctggc tgagtcgca ccatggcccc gtccttgatt acctcgccag ctgcggtgac   360
gccggctgcg aaacggtcga caagaacact ctcgagttct tcaagatcgg cgaggctggc   420
ctgatcgacg gcagcagtgc tcccggcaag tgggcgtcgg accagctgat tgagaacaat   480
aactcgtgga tggttcagat ccctgccaac cttgcgcccg aaactatgt gctgcggcat    540
gagattattg ctttgcacag cgctgggcaa gctaacggtg cccaaaacta cccccagtgc   600
ttcaacctgc aagttaccgg ctccggcacg acaagcctg ccggtgtgct cggcaccgag    660
ctctacactc ccaccgacgc cggcatcttg gccaacatct acacctcgcc tgttcagtac   720
gagattcctg gcccggctct gatctcgggc gcttcggccg ttgaacagtc ctcctcggct   780
atcaccgcct ccgccagcgc tgagaccggc tccgccacag cacccctgc cggctctgcc    840
acggccgccc ccaccactac cactaccacg gctggctcgg atgctagcgc tacgccctcg   900
tcctcgtcca gctctggtgc gagcaccacc gccgagccca cccttcggc tactactacc    960
gccggcggca gcaccccgcg cccgacccgg tgccctggcc tgaagcgccg ccgccacgcc  1020
cgtgatgtca agctcgccct ctaa                                        1044
```

<210> SEQ ID NO 164
<211> LENGTH: 347
<212> TYPE: PRT
<213> ORGANISM: Corynascus sepedonium

<400> SEQUENCE: 164

```
Met Pro Ser Ser Thr Ser Lys Gly Leu Phe Ser Ala Leu Met Gly Ala
1               5                   10                  15

Ala Ser Val Ala Ala His Gly His Val Thr Asn Ile Val Ile Asn Gly
            20                  25                  30

Val Ser Tyr Gln Asn Tyr Asp Pro Thr Ser Phe Pro Tyr Met Gln Asn
        35                  40                  45

Pro Pro Thr Val Val Gly Trp Thr Ala Ser Asn Thr Asp Asn Gly Phe
    50                  55                  60

Val Ala Pro Asp Ala Phe Ala Ser Gly Asp Ile Ile Cys His Arg Asp
65                  70                  75                  80

Ala Thr Asn Ala Gly Gly His Ala Val Val Ala Ala Gly Asp Lys Val
                85                  90                  95

Phe Ile Gln Trp Asp Thr Trp Pro Glu Ser His His Gly Pro Val Leu
            100                 105                 110

Asp Tyr Leu Ala Ser Cys Gly Asp Ala Gly Cys Glu Thr Val Asp Lys
        115                 120                 125

Asn Thr Leu Glu Phe Phe Lys Ile Gly Glu Ala Gly Leu Ile Asp Gly
    130                 135                 140

Ser Ser Ala Pro Gly Lys Trp Ala Ser Asp Gln Leu Ile Glu Asn Asn
145                 150                 155                 160

Asn Ser Trp Met Val Gln Ile Pro Ala Asn Leu Ala Pro Gly Asn Tyr
                165                 170                 175

Val Leu Arg His Glu Ile Ile Ala Leu His Ser Ala Gly Gln Ala Asn
```

180                 185                 190
Gly Ala Gln Asn Tyr Pro Gln Cys Phe Asn Leu Gln Val Thr Gly Ser
            195                 200                 205

Gly Thr Asp Lys Pro Ala Gly Val Leu Gly Thr Glu Leu Tyr Thr Pro
        210                 215                 220

Thr Asp Ala Gly Ile Leu Ala Asn Ile Tyr Thr Ser Pro Val Gln Tyr
225                 230                 235                 240

Glu Ile Pro Gly Pro Ala Leu Ile Ser Gly Ala Ser Ala Val Glu Gln
                245                 250                 255

Ser Ser Ser Ala Ile Thr Ala Ser Ala Ser Ala Glu Thr Gly Ser Ala
            260                 265                 270

Thr Ala Pro Pro Ala Gly Ser Ala Thr Ala Ala Pro Thr Thr Thr Thr
        275                 280                 285

Thr Thr Ala Gly Ser Asp Ala Ser Ala Thr Pro Ser Ser Ser Ser Ser
        290                 295                 300

Ser Gly Ala Ser Thr Thr Ala Glu Pro Thr Pro Ser Ala Thr Thr Thr
305                 310                 315                 320

Ala Gly Gly Ser Thr Pro Arg Pro Thr Arg Cys Pro Gly Leu Lys Arg
                325                 330                 335

Arg Arg His Ala Arg Asp Val Lys Leu Ala Leu
            340                 345

<210> SEQ ID NO 165
<211> LENGTH: 1029
<212> TYPE: DNA
<213> ORGANISM: Myceliophthora thermophila

<400> SEQUENCE: 165
atgtccaagg cctctgctct cctcgctggc ctgacgggcg cggccctcgt cgctgcacat        60
ggccacgtca gccacatcgt cgtcaacggc gtctactaca ggaactacga ccccacgaca       120
gactggtacc agcccaaccc gccaacagtc atcggctgga cggcagccga tcaggataat       180
ggcttcgttg aacccaacag ctttggcacg ccagatatca tctgccacaa gagcgccacc       240
cccggcggcg ccacgctac cgttgctgcc ggagacaaga tcaacatcgt ctggaccccc       300
gagtggcccg aatcccacat cggccccgtc attgactacc tagccgcctg caacggtgac       360
tgcgagaccg tcgacaagtc gtcgctgcgc tggttcaaga ttgacggcgc cggctacgac       420
aaggccgccg ccgctgggc cgccgacgct ctgcgcgcca acggcaacag ctggctcgtc       480
cagatcccgt cggatctcaa ggccggcaac tacgtcctcc gccacgagat catcgccctc       540
cacggtgctc agagccccaa cggcgcccag gcctaccgc agtgcatcaa cctccgcgtc       600
accggcggcg gcagcaacct gcccagcggc gtcgccggca cctcgctgta caaggcgacc       660
gacccgggca tcctcttcaa ccccctacgtc tcctccccgg attacaccgt ccccggcccg       720
gccctcattg ccggcgccgc cagctcgatc gcccagagca cgtcggtcgc cactgccacc       780
ggcacggcca ccgttcccgg cggcggcggc gccaacccta ccgccaccac caccgccgcc       840
acctccgccg ccccgagcac cacctgagg acgaccacta cctcggccgc gcagactacc       900
gccccgccct ccggcgatgt gcagaccaag tacggccagt gtggtggcaa cggatggacg       960
ggcccgacgg tgtgcgcccc cggctcgagc tgctccgtcc tcaacgagtg gtactcccag      1020
tgtttgtaa                                                             1029

<210> SEQ ID NO 166
<211> LENGTH: 342

```
<212> TYPE: PRT
<213> ORGANISM: Myceliophthora thermophila

<400> SEQUENCE: 166

Met Ser Lys Ala Ser Ala Leu Leu Ala Gly Leu Thr Gly Ala Ala Leu
1               5                   10                  15

Val Ala Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Ser Asn Leu Pro
        195                 200                 205

Ser Gly Val Ala Gly Thr Ser Leu Tyr Lys Ala Thr Asp Pro Gly Ile
210                 215                 220

Leu Phe Asn Pro Tyr Val Ser Pro Asp Tyr Thr Val Pro Gly Pro
225                 230                 235                 240

Ala Leu Ile Ala Gly Ala Ser Ser Ile Ala Gln Ser Thr Ser Val
            245                 250                 255

Ala Thr Ala Thr Gly Thr Ala Thr Val Pro Gly Gly Gly Ala Asn
            260                 265                 270

Pro Thr Ala Thr Thr Ala Thr Ser Ala Ala Pro Ser Thr Thr
            275                 280                 285

Leu Arg Thr Thr Thr Ser Ala Ala Gln Thr Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
            340

<210> SEQ ID NO 167
<211> LENGTH: 765
<212> TYPE: DNA
<213> ORGANISM: Talaromyces emersonii

<400> SEQUENCE: 167
```

```
atgctgtctt cgaaggctcc tgtcacccct gcctttgcag gcctcgctgg ccttctgtcc      60
gccccactgg tcaaggccca tggttttgtc cagggcattg tcatcggtga ccaattctac     120
agcgggtaca tcgtcaacga gttccctac gaatccaacc cacccccgt catcggctgg      180
gccacgacag ccaccgacct gggcttcgtc gacggcactg aataccaagg accagacatc     240
atctgccacc ggaatgcgac gcccgcgctg ctgacagccc ccgtggccgc cggcggcacc     300
gtcgagctgc agtggacgcc ctggccgtcc agccaccacg gccggtcat cacgtacctg      360
gccaactgca acggcaactg ctcgaccgtc gacaagacgc agctggagtt cttcaagatc     420
gaccagtcgg gcctgatcaa cgacactgac ccgccgggca cctgggcgtc cgacaacctc     480
atcgccaaca caacagctg gaccgtgacc atccccagca ccctcgagcc gggcaactac     540
gtgctgcgcc acgagatcat cgccctgcac tcggcgggca caaagacgg cgcccagaac     600
tacccccagt gcatcaacat cgaggtcacg ggcggcggct cggtcgagcc gacgggcacg     660
ctgggcgagg atctctacca cgacacggac ccgggcattc tgatcgacat ttacgagccg     720
attgcgacgt ataccattcc aggaccgcct gagccgacgt tctag                    765
```

<210> SEQ ID NO 168
<211> LENGTH: 254
<212> TYPE: PRT
<213> ORGANISM: Talaromyces emersonii

<400> SEQUENCE: 168

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
            20                  25                  30

Ile Val Ile Gly Asp Gln Phe Tyr Ser Gly Tyr Ile Val Asn Glu Phe
        35                  40                  45

Pro Tyr Glu Ser Asn Pro Pro Val Ile Gly Trp Ala Thr Thr Ala
    50                  55                  60

Thr Asp Leu Gly Phe Val Asp Gly Thr Glu Tyr Gln Gly Pro Asp Ile
65                  70                  75                  80

Ile Cys His Arg Asn Ala Thr Pro Ala Leu Leu Thr Ala Pro Val Ala
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Asn Gly Asn Cys Ser
        115                 120                 125

Thr Val Asp Lys Thr Gln Leu Glu Phe Phe Lys Ile Asp Gln Ser Gly
    130                 135                 140

Leu Ile Asn Asp Thr Asp Pro Pro Gly Thr Trp Ala Ser Asp Asn Leu
145                 150                 155                 160

Ile Ala Asn Asn Ser Trp Thr Val Thr Ile Pro Ser Thr Leu Glu
                165                 170                 175

Pro Gly Asn Tyr Val Leu Arg His Glu Ile Ile Ala Leu His Ser Ala
            180                 185                 190

Gly Asn Lys Asp Gly Ala Gln Asn Tyr Pro Gln Cys Ile Asn Ile Glu
        195                 200                 205

Val Thr Gly Gly Gly Ser Val Glu Pro Thr Gly Thr Leu Gly Glu Asp
    210                 215                 220

Leu Tyr His Asp Thr Asp Pro Gly Ile Leu Ile Asp Ile Tyr Glu Pro
225                 230                 235                 240
```

Ile Ala Thr Tyr Thr Ile Pro Gly Pro Pro Glu Pro Thr Phe
                245                    250

<210> SEQ ID NO 169
<211> LENGTH: 3060
<212> TYPE: DNA
<213> ORGANISM: Aspergillus fumigatus

<400> SEQUENCE: 169

```
atgagattcg gttggctcga ggtggccgct ctgacggccg cttctgtagc caatgcccag      60
gtttgtgatg ctttcccgtc attgtttcgg atatagttga caatagtcat ggaaataatc     120
aggaattggc tttctctcca ccattctacc cttcgccttg ggctgatggc cagggagagt     180
gggcagatgc ccatcgacgc gccgtcgaga tcgtttctca gatgacactg gcggagaagg     240
ttaaccttac aacgggtact gggtgggttg cgacttttt gttgacagtg agctttcttc     300
actgaccatc tacacagatg gaaatggac cgatgcgtcg gtcaaaccgg cagcgttccc     360
aggtaagctt gcaattctgc aacaacgtgc aagtgtagtt gctaaaacgc ggtggtgcag     420
acttggtatc aactggggtc tttgtggcca ggattcccct ttgggtatcc gtttctgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660
gctggggcct gctgctggtc ctctcggcaa atacccggac ggcggcagaa tctgggaagg     720
cttctctcct gatccggttc tcactggtgt acttttcgcc gaaactatca agggtatcca     780
agacgcgggt gtgattgcta ctgccaagca ttacattctg aatgaacagg agcatttccg     840
acaggttggc gaggcccagg gatatggtta caacatcacg gagacgatca gctccaacgt     900
ggatgacaag accatgcacg agttgtacct ttggtgagta gttgacactg caaatgagga     960
ccttgattga tttgactgac ctggaatgca ggcccttgc agatgctgtg cgcggtaaga    1020
ttttccgtag acttgacctc gcgacgaaga atcgctgac gaaccatcgt agctggcgtt    1080
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt ccccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtgggt gctaacggct gccccgaccg cggctgtgat    1680
aacggcactc ttgctatggc ctggggtagt ggtactgcca acttccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt ttttaaccaa ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
```

-continued

```
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccect cctgaaggct ggcggcgctc ctggtggtaa ccctacccct    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag    3060
```

<210> SEQ ID NO 170
<211> LENGTH: 863
<212> TYPE: PRT
<213> ORGANISM: Aspergillus fumigatus

<400> SEQUENCE: 170

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
```

```
                195                 200                 205
Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620
```

-continued

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
            850                 855                 860

<210> SEQ ID NO 171
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 171
cacaactggg gatccatgac tttgtccaag atcacttcca          40

<210> SEQ ID NO 172
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 172
ggcctccgcg gccgcttaag cgttgaacag tgcaggacca          40

<210> SEQ ID NO 173
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 173
cacaactggg gatccatgac tttgtccaag atcacttcca         40

<210> SEQ ID NO 174
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 174
ggcctccgcg gccgcttaag cgttgaacag tgcaggacca         40

<210> SEQ ID NO 175
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 175
cacaactggg gatccatgct gtcttcgacg actcgcaccc         40

<210> SEQ ID NO 176
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 176
ggcctccgcg gccgcctaga acgtcggctc aggcggcccc         40

<210> SEQ ID NO 177
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 177
ctggggatcc atgtcctttt ccaagat                      27

<210> SEQ ID NO 178
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 178
ctccgcggcc gcttaaccag tatacagag                    29

<210> SEQ ID NO 179
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 179
actcaattta cctctatcca cactt                        25

<210> SEQ ID NO 180
<211> LENGTH: 25
<212> TYPE: DNA

<213> ORGANISM: Artificial Sequence
<220> FEATURE:
<223> OTHER INFORMATION: Artificial DNA Primer

<400> SEQUENCE: 180
gaattgtgag cggataacaa tttca                                     25

<210> SEQ ID NO 181
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 181
cggactgcgc accatgctgt cttcgacgac tcgcac                         36

<210> SEQ ID NO 182
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 182
tcgccacgga gcttatcgac ttcttctaga acgtc                          35

<210> SEQ ID NO 183
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 183
acaagaatac tgatcctggc atctggtttg acatctactc ggatctgag           49

<210> SEQ ID NO 184
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 184
ctcagatccg agtagatgtc aaaccagatg ccaggatcag tattcttgt           49

<210> SEQ ID NO 185
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 185
atcatcgccc ttcactctgc gtttaacctg aacggcgcgc agaac               45

<210> SEQ ID NO 186
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 186
gttctgcgcg ccgttcaggt taaacgcaga gtgaagggcg atgat               45

<210> SEQ ID NO 187
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 187
gaagtttgtc aagatcgccg ctaagggctt gatcgacggc tccaac        46

<210> SEQ ID NO 188
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 188
gttggagccg tcgatcaagc ccttagcggc gatcttgaca aacttc        46

<210> SEQ ID NO 189
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 189
cttgttaacc aatacccta catggaaaac cctcccgaca ccattgcc        48

<210> SEQ ID NO 190
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 190
ggcaatggtg tcgggagggt tttccatgta ggggtattgg ttaacaag        48

<210> SEQ ID NO 191
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 191
ctcccgacac cattgcctgg gccaccaccg ccaccgacct cg        42

<210> SEQ ID NO 192
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 192
cgaggtcggt ggcggtggtg gcccaggcaa tggtgtcggg ag        42

<210> SEQ ID NO 193
<211> LENGTH: 46
<212> TYPE: DNA
<213> ORGANISM: Artificial Sequence
<220> FEATURE:

<223> OTHER INFORMATION: Artificial DNA Primer

<400> SEQUENCE: 193
acagatcgaa ttccagtgga cgaagtggcc agagtctcac catgga  46

<210> SEQ ID NO 194
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 194
acagatcgaa ttccagtgga cgaagtggcc agagtctcac catgga  46

<210> SEQ ID NO 195
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 195
ccagtggacg aagtggccaa agtctcacca tggaccg  37

<210> SEQ ID NO 196
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 196
cggtccatgg tgagactttg gccacttcgt ccactgg  37

<210> SEQ ID NO 197
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 197
ctggcatctg gtttgacatc tacggcgatc tgagcggtgg ataccct  47

<210> SEQ ID NO 198
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 198
agggtatcca ccgctcagat cgccgtagat gtcaaaccag atgccag  47

<210> SEQ ID NO 199
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 199
atcatcgccc ttcactctgc gtttaacctg aacggcgcgc agaac  45

```
<210> SEQ ID NO 200
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 200
gttctgcgcg ccgttcaggt taaacgcaga gtgaagggcg atgat          45

<210> SEQ ID NO 201
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 201
cacgagatca tcgcccttca caccgcgggt aacctgaacg gcgc            44

<210> SEQ ID NO 202
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 202
gcgccgttca ggttacccgc ggtgtgaagg gcgatgatct cgtg            44

<210> SEQ ID NO 203
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 203
atcatcgccc ttcactctgc gtttaacctg aacggcgcgc agaac          45

<210> SEQ ID NO 204
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 204
cggctccaac ccacctggta tctgggcttc cgatgaactg atcg            44

<210> SEQ ID NO 205
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 205
atcatcgccc ttcactctgc gtttaacctg aacggcgcgc agaac          45

<210> SEQ ID NO 206
<211> LENGTH: 44
<212> TYPE: DNA
<213> ORGANISM: Artificial Sequence
<220> FEATURE:
<223> OTHER INFORMATION: Artificial DNA Primer
```

```
<400> SEQUENCE: 206
cggctccaac ccacctggta tctgggcttc cgatgaactg atcg                44

<210> SEQ ID NO 207
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 207
cggcaccggc taccagaccc cggatattat ctgccacaga gacgc               45

<210> SEQ ID NO 208
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 208
atcatcgccc ttcactctgc gtttaacctg aacggcgcgc agaac               45

<210> SEQ ID NO 209
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 209
cggctccaac ccacctggta tctgggcttc cgatgaactg atcg                44

<210> SEQ ID NO 210
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 210
ccagtgtttc aacatccaaa tcaccggtcc tggcagtgct caggg               45

<210> SEQ ID NO 211
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 211
ccattcctgc ctgctatgcc cccggaaact acgtcc                         36

<210> SEQ ID NO 212
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 212
cctggtcctg cactgttcaa ctgctaagcg gcc                            33

<210> SEQ ID NO 213
<211> LENGTH: 43
```

```
<212> TYPE: DNA
<213> ORGANISM: Artificial Sequence
<220> FEATURE:
<223> OTHER INFORMATION: Artificial DNA Primer

<400> SEQUENCE: 213
tggaccgtca ccattcccaa ctgcgtcgcc cccggcaact acg                43

<210> SEQ ID NO 214
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 214
cgtagttgcc gggggcgacg cagttgggaa tggtgacggt cca                43

<210> SEQ ID NO 215
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 215
ccggggccgc ctgagccgac gtgctaggcg gccgcggagg ccacc              45

<210> SEQ ID NO 216
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 216
ggtggcctcc gcggccgcct agcacgtcgg ctcaggcggc cccgg              45

<210> SEQ ID NO 217
<211> LENGTH: 27
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (10)..(10)
<223> OTHER INFORMATION: N=DEOXYURIDINE

<400> SEQUENCE: 217
atgcagcgcn gccataacca tgagtga                                  27

<210> SEQ ID NO 218
<211> LENGTH: 28
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (10)..(10)
<223> OTHER INFORMATION: N=DEOXYURIDINE

<400> SEQUENCE: 218
agcgctgcan aattctctta ctgtcatg                                 28

<210> SEQ ID NO 219
```

```
<211> LENGTH: 36
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 219
aattaagncc tcagcgtgat ttaaaacgcc attgct                          36

<210> SEQ ID NO 220
<211> LENGTH: 41
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 220
acttaatnaa accctcagcg cagttaggtt ggtgttcttc t                    41

<210> SEQ ID NO 221
<211> LENGTH: 29
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (11)..(11)
<223> OTHER INFORMATION: N=DEOXYURIDINE

<400> SEQUENCE: 221
agctcaagga nacctacagt tattcgaaa                                  29

<210> SEQ ID NO 222
<211> LENGTH: 35
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (11)..(11)
<223> OTHER INFORMATION: N=DEOXYURIDINE

<400> SEQUENCE: 222
atccttgagc ngtttcctgt gtgaaattgt tatcc                           35

<210> SEQ ID NO 223
<211> LENGTH: 37
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=DEOXYURIDINE

<400> SEQUENCE: 223
atctcctcng ctggtctggt taagccagcc ccgacac                         37
```

```
<210> SEQ ID NO 224
<211> LENGTH: 27
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=DEOXYURIDINE

<400> SEQUENCE: 224
agaggagana atactctgcg ctccgcc                                          27

<210> SEQ ID NO 225
<211> LENGTH: 32
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=DEOXYURIDINE

<400> SEQUENCE: 225
gggtttaanc ctcacacagg aaacagctat ga                                    32

<210> SEQ ID NO 226
<211> LENGTH: 46
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (12)..(12)
<223> OTHER INFORMATION: N=DEOXYURIDINE

<400> SEQUENCE: 226
agtgtctgcg ancgctctca ctgcccccag ttgtgtatat agagga                     46

<210> SEQ ID NO 227
<211> LENGTH: 36
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (12)..(12)
<223> OTHER INFORMATION: N=DEOXYURIDINE

<400> SEQUENCE: 227
atcgcagaca cngctggcgg tagacaatca atccat                                36

<210> SEQ ID NO 228
<211> LENGTH: 32
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=DEOXYURIDINE

<400> SEQUENCE: 228
ggacttaang gatctaagat gagctcatgg ct                                    32
```

<210> SEQ ID NO 229
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 229
acgccattgc tatgatgctt gaag                                              24

<210> SEQ ID NO 230
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 230
tggtgaggtg ctatcgtcct t                                                 21

<210> SEQ ID NO 231
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 231
cttcctgtag gtgcaccgaa g                                                 21

<210> SEQ ID NO 232
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 232
acagaacgat atcggacctc g                                                 21

<210> SEQ ID NO 233
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 233
tcgttatgtt aagtcttcta tca                                               23

<210> SEQ ID NO 234
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 234
agagctcgaa gttcctccga g                                                 21

<210> SEQ ID NO 235
<211> LENGTH: 22
<212> TYPE: DNA
<213> ORGANISM: Artificial Sequence
<220> FEATURE:
<223> OTHER INFORMATION: Artificial DNA Primer

```
<400> SEQUENCE: 235
tatcacgagg ccctttcgtc tc                                              22

<210> SEQ ID NO 236
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 236
tccgtcggct cctctccttc gt                                              22

<210> SEQ ID NO 237
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 237
tgcatatcct ctgacagtat atga                                            24

<210> SEQ ID NO 238
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 238
cagtgaagag ggcagtcgat agt                                             23

<210> SEQ ID NO 239
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 239
acgaggaaca tggctatctg ga                                              22

<210> SEQ ID NO 240
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 240
tcagctcatt ctgggaggtg gga                                             23

<210> SEQ ID NO 241
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 241
actccaggat cctttaaatc ca                                              22

<210> SEQ ID NO 242
```

-continued

```
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 242
actggcaagg gatgccatgc t                                           21

<210> SEQ ID NO 243
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 243
tgatcatata accaattgcc ct                                          22

<210> SEQ ID NO 244
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 244
agttgtgtat atagaggatt ga                                          22

<210> SEQ ID NO 245
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 245
tggtccttcg ctcgtgatgt gga                                         23

<210> SEQ ID NO 246
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 246
agtcctcagc gttaccggca                                             20

<210> SEQ ID NO 247
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 247
accctcagct gtgtccggga                                             20

<210> SEQ ID NO 248
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 248
```
tggtatgtga acgccagtct g                                           21

<210> SEQ ID NO 249
<211> LENGTH: 28
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 249
agagcganat gtcctttttcc aagataat                                   28

<210> SEQ ID NO 250
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 250
tctgcgantt agtgatggtg gtgatgatga ccagtataca gaggaggac             49

<210> SEQ ID NO 251
<211> LENGTH: 28
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 251
agagcganat gctgtcttcg acgactcg                                    28

<210> SEQ ID NO 252
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 252
tctgcganct agtgatggtg gtgatgatgg aacgtcggct caggcggcc             49

<210> SEQ ID NO 253
<211> LENGTH: 33
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 253
agagcganat gtctgttgct aagtttgctg gtg                33

<210> SEQ ID NO 254
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 254
tctgcgantt agtgatggtg gtgatgatgg gcggagaggt cacgggcgt                49

<210> SEQ ID NO 255
<211> LENGTH: 32
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 255
agagcganat gccttctact aaagtcgctg cc                32

<210> SEQ ID NO 256
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 256
tctgcgantc agtgatggtg gtgatgatga aggacagtag tggtgatga                49

<210> SEQ ID NO 257
<211> LENGTH: 40
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

<400> SEQUENCE: 257
agagcganat gccttctttc gcctccaaga ctctcctttc                40

<210> SEQ ID NO 258
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=DEOXYURIDINE

```
<400> SEQUENCE: 258
tctgcgantc agtgatggtg gtgatgatgg tttgcctcct cagcccctc       49

<210> SEQ ID NO 259
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 259
cccagttatc aactaccttg                                       20

<210> SEQ ID NO 260
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 260
ctcaatttac ctctatccac                                       20

<210> SEQ ID NO 261
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 261
tataaccaat tgccctcatc                                       20

<210> SEQ ID NO 262
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 262
gcaccgtcga gctgcagtgg                                       20

<210> SEQ ID NO 263
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 263
ccttgccaac tgcaatggtg                                       20

<210> SEQ ID NO 264
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 264
ggactgcgca ccatgccttc tactaaag                              28

<210> SEQ ID NO 265
```

```
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 265
gccacggagc ttaattaatc aaaggacagt agtg                               34

<210> SEQ ID NO 266
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 266
caatggcaat tgttctaccg                                               20

<210> SEQ ID NO 267
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 267
cgacggcagc tcggcgcccg                                               20

<210> SEQ ID NO 268
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 268
gcatttatca gggttattgt ctcatgagcg g                                  31

<210> SEQ ID NO 269
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 269
gctgataaat ctggagccgg tgagcg                                        26

<210> SEQ ID NO 270
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 270
ccagaccagc agaggagata atactctgcg                                    30

<210> SEQ ID NO 271
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 271
```

| caaggatacc tacagttatt cgaaacctcc tg | 32 |

<210> SEQ ID NO 272
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 272

| gtggctggcc atggcttcgt tatcaacatc gtgattgatg gtaaaaagt | 49 |

<210> SEQ ID NO 273
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 273

| aacgaagcca tggccagcca ctagagaagc aga | 33 |

<210> SEQ ID NO 274
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 274

| gttatggcgg gtatctagtg aacatctatc catacatgtc caatcctcc | 49 |

<210> SEQ ID NO 275
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 275

| gttcactaga tacccgccat aactgtcgat tgtca | 35 |

<210> SEQ ID NO 276
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 276

| gttatggcgg gtatctagtg aacgtctatc catacatgtc caatcctcc | 49 |

<210> SEQ ID NO 277
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 277

| gttcactaga tacccgccat aactgtcgat tgtca | 35 |

<210> SEQ ID NO 278
<211> LENGTH: 49
<212> TYPE: DNA

```
<213> ORGANISM: Artificial Sequence
<220> FEATURE:
<223> OTHER INFORMATION: Artificial DNA Primer

<400> SEQUENCE: 278
tgctccgtgc aatggtgatt gtaggactgt ggataagacc caattagaa         49

<210> SEQ ID NO 279
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 279
acaatcacca ttgcacggag caaggtagtt gataa                        35

<210> SEQ ID NO 280
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 280
attagaattc ttcaaaattg ccgaggaggg tctcatcaat gatgacaatc c      51

<210> SEQ ID NO 281
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 281
ctcggcaatt ttgaagaatt ctaattgggt cttatcc                      37

<210> SEQ ID NO 282
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 282
attagaattc ttcaaaattg ccgagaaagg tctcatcaat gatgacaatc c      51

<210> SEQ ID NO 283
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 283
ctcggcaatt ttgaagaatt ctaattgggt cttatcc                      37

<210> SEQ ID NO 284
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 284
attagaattc ttcaaaattg ccgagctggg tctcatcaat gatgacaatc c      51
```

<210> SEQ ID NO 285
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 285
ctcggcaatt ttgaagaatt ctaattgggt cttatcc                                37

<210> SEQ ID NO 286
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 286
gatagcagcc aacaacagct gggtcgtcac cattccaacc acaattgc                    48

<210> SEQ ID NO 287
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 287
ccagctgttg ttggctgcta tcagattgtc tgaag                                  35

<210> SEQ ID NO 288
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 288
gatagcagcc aacaacagct gggaggtcac cattccaacc acaattgc                    48

<210> SEQ ID NO 289
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 289
ccagctgttg ttggctgcta tcagattgtc tgaag                                  35

<210> SEQ ID NO 290
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 290
ggcatgagat tattgctctt cacaaagctc agaaccagga tggtgcc                     47

<210> SEQ ID NO 291
<211> LENGTH: 36
<212> TYPE: DNA
<213> ORGANISM: Artificial Sequence
<220> FEATURE:

<223> OTHER INFORMATION: Artificial DNA Primer

<400> SEQUENCE: 291
gtgaagagca ataatctcat gcctcagaac atagtt                                    36

<210> SEQ ID NO 292
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 292
ggcatgagat tattgctctt cacttcgctc agaaccagga tggtgcc                        47

<210> SEQ ID NO 293
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 293
gtgaagagca ataatctcat gcctcagaac atagtt                                    36

<210> SEQ ID NO 294
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 294
ggcatgagat tattgctctt cacactgctc agaaccagga tggtgcc                        47

<210> SEQ ID NO 295
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 295
gtgaagagca ataatctcat gcctcagaac atagtt                                    36

<210> SEQ ID NO 296
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 296
ggcatgagat tattgctctt cactatgctc agaaccagga tggtgcc                        47

<210> SEQ ID NO 297
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 297
gtgaagagca ataatctcat gcctcagaac atagtt                                    36

-continued

```
<210> SEQ ID NO 298
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 298
gcccagaact atccccagtg cgtcaatctg caggtcactg gaggtg            46

<210> SEQ ID NO 299
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 299
gcactgggga tagttctggg caccatcctg gt                           32

<210> SEQ ID NO 300
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 300
tggaggtggt tctgataacc ctgagggaac tcttggaacg gcactc            46

<210> SEQ ID NO 301
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 301
agggttatca gaaccacctc cagtgacctg cag                          33

<210> SEQ ID NO 302
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 302
cctgctggaa ctcttggaac gtgcctctac cacgataccg atcctg            46

<210> SEQ ID NO 303
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 303
cgttccaaga gttccagcag ggttatcaga acc                          33

<210> SEQ ID NO 304
<211> LENGTH: 46
<212> TYPE: DNA
<213> ORGANISM: Artificial Sequence
<220> FEATURE:
<223> OTHER INFORMATION: Artificial DNA Primer
```

<400> SEQUENCE: 304
cctgctggaa ctcttggaac ggagctctac cacgataccg atcctg      46

<210> SEQ ID NO 305
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 305
cgttccaaga gttccagcag ggttatcaga acc      33

<210> SEQ ID NO 306
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 306
cctgctggaa ctcttggaac gcagctctac cacgataccg atcctg      46

<210> SEQ ID NO 307
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 307
cgttccaaga gttccagcag ggttatcaga acc      33

<210> SEQ ID NO 308
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 308
catccctggt cctcctctgt atagggtca tcatcaccac catcact      47

<210> SEQ ID NO 309
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 309
atacagagga ggaccaggga tgatatagct ggaaa      35

<210> SEQ ID NO 310
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 310
ctacagcggg tacatcgtca acgtcttccc ctacgaatcc aacccac      47

<210> SEQ ID NO 311
<211> LENGTH: 33

<212> TYPE: DNA
<213> ORGANISM: Artificial Sequence
<220> FEATURE:
<223> OTHER INFORMATION: Artificial DNA Primer

<400> SEQUENCE: 311
gttgacgatg tacccgctgt agctgttggg agt                           33

<210> SEQ ID NO 312
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 312
gtcgacggca caggatacca acagccggac atcatctgcc accg               44

<210> SEQ ID NO 313
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 313
ttggtatcct gtgccgtcga cgaagcccag g                             31

<210> SEQ ID NO 314
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 314
cgccgtgcaa cggcaactgc cgcaccgtcg acaagacgac gctg               44

<210> SEQ ID NO 315
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 315
gcagttgccg ttgcacggcg ccaggtaggt g                             31

<210> SEQ ID NO 316
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 316
cgtcgatggt agcgagtatg ctcaggccga catcatttgc cacaaga            47

<210> SEQ ID NO 317
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 317
agcatactcg ctaccatcga cgaaacccaa gtcg                              34

<210> SEQ ID NO 318
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 318
cgtcgatggt agcgagtatg ctaccgccga catcatttgc cacaaga               47

<210> SEQ ID NO 319
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 319
agcatactcg ctaccatcga cgaaacccaa gtcg                              34

<210> SEQ ID NO 320
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 320
ctcgagtttt tcaagattga cgagtgcggt ctcatcaacg acgacgac              48

<210> SEQ ID NO 321
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 321
ctcgtcaatc ttgaaaaact cgaggtcggt cttgg                             35

<210> SEQ ID NO 322
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 322
ctcgagtttt tcaagattga cgagggtggt ctcatcaacg acgacgac              48

<210> SEQ ID NO 323
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 323
ctcgtcaatc ttgaaaaact cgaggtcggt cttgg                             35

<210> SEQ ID NO 324
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 324
acgacgacga cgtccccggt atctgggcca gtgataactt gatcg      45

<210> SEQ ID NO 325
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 325
accggggacg tcgtcgtcgt tgatgagacc g      31

<210> SEQ ID NO 326
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 326
gatcgccaac aacaacagct gggtcgtgac catcccctct gacattg      47

<210> SEQ ID NO 327
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 327
ccagctgttg ttgttggcga tcaagttatc actgg      35

<210> SEQ ID NO 328
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 328
gatcgccaac aacaacagct ggttcgtgac catcccctct gacattg      47

<210> SEQ ID NO 329
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 329
ccagctgttg ttgttggcga tcaagttatc actgg      35

<210> SEQ ID NO 330
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 330
tggactgtga ccatcccctc tcgtattgcg gctggcaact acgtc      45

<210> SEQ ID NO 331
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 331
agaggggatg gtcacagtcc agctgttgtt gtt                            33

<210> SEQ ID NO 332
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 332
gtcacgaaat cattgcccctt cacaaggctg gtaacaagga tggtgctc            48

<210> SEQ ID NO 333
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 333
gtgaagggca atgatttcgt gacggaggac gtag                           34

<210> SEQ ID NO 334
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 334
gtcacgaaat cattgcccctt cacaccgctg gtaacaagga tggtgctc            48

<210> SEQ ID NO 335
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 335
gtgaagggca atgatttcgt gacggaggac gtag                           34

<210> SEQ ID NO 336
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 336
gtcacgaaat cattgcccctt cactacgctg gtaacaagga tggtgctc            48

<210> SEQ ID NO 337
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 337
gtgaagggca atgatttcgt gacggaggac gtag						34

<210> SEQ ID NO 338
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 338
gctcagaact accctcagtg catcaacttg aaggtcactg gcggc						45

<210> SEQ ID NO 339
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 339
gcactgaggg tagttctgag caccatcctt gtt						33

<210> SEQ ID NO 340
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 340
gctcagaact accctcagtg cgtcaacttg aaggtcactg gcggc						45

<210> SEQ ID NO 341
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 341
gcactgaggg tagttctgag caccatcctt gtt						33

<210> SEQ ID NO 342
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 342
ccttctggca ctgctggtga gatgctgtac aaggacaccg atgctg						46

<210> SEQ ID NO 343
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 343
ctcaccagca gtgccagaag gagcgagatc ac						32

<210> SEQ ID NO 344

```
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 344
ccttctggca ctgctggtga gcagctgtac aaggacaccg atgctg            46

<210> SEQ ID NO 345
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 345
ctcaccagca gtgccagaag gagcgagatc ac                            32

<210> SEQ ID NO 346
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 346
actgctggtg agagcctgta ccgtgacacc gatgctggta tcctc               45

<210> SEQ ID NO 347
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 347
gtacaggctc tcaccagcag tgccagaagg ag                             32

<210> SEQ ID NO 348
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 348
ctcctacgat attcccggac ctcccatgta caacgctacc tccagct              47

<210> SEQ ID NO 349
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 349
aggtccggga atatcgtagg aggaaagaga ctgg                            34

<210> SEQ ID NO 350
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 350
```

|   |   |
|---|---|
| caaaacatcg ttatcgacgg taaattttaa gcagtgatgc atccattatt aa | 52 |

<210> SEQ ID NO 351
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 351

|   |   |
|---|---|
| tttaccgtcg ataacgatgt tttgcacaaa accatg | 36 |

<210> SEQ ID NO 352
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 352

|   |   |
|---|---|
| agttactctg gataccttgt gaatatcttc ccctacgagt ccaaccca | 48 |

<210> SEQ ID NO 353
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 353

|   |   |
|---|---|
| attcacaagg tatccagagt aactgatttt tttgtaag | 38 |

<210> SEQ ID NO 354
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 354

|   |   |
|---|---|
| agttactctg gataccttgt gaatgtcttc ccctacgagt ccaaccca | 48 |

<210> SEQ ID NO 355
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 355

|   |   |
|---|---|
| attcacaagg tatccagagt aactgatttt tttgtaag | 38 |

<210> SEQ ID NO 356
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 356

|   |   |
|---|---|
| tgtgaatcag ttcccctacg agcttaaccc accagctgtt attgggt | 47 |

<210> SEQ ID NO 357
<211> LENGTH: 34
<212> TYPE: DNA

<213> ORGANISM: Artificial Sequence
<220> FEATURE:
<223> OTHER INFORMATION: Artificial DNA Primer

<400> SEQUENCE: 357
ctcgtagggg aactgattca caaggtatcc agag                                    34

<210> SEQ ID NO 358
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 358
ccaccagctg ttattgggtg gtgcacaact gcaaccgacc tggga                        45

<210> SEQ ID NO 359
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 359
ccacccaata acagctggtg ggttggactc gt                                      32

<210> SEQ ID NO 360
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 360
ccaccagctg ttattgggtg ggagacaact gcaaccgacc tggga                        45

<210> SEQ ID NO 361
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 361
ccacccaata acagctggtg ggttggactc gt                                      32

<210> SEQ ID NO 362
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 362
ctagactttg tcaagattga ccaatgcggt ttgatcgacg atactaccc                    49

<210> SEQ ID NO 363
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 363
ttggtcaatc ttgacaaagt ctagcttagt cttatcc                                 37

<210> SEQ ID NO 364
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 364
acgatactac cccccgggt atctgggctt ccgacaaact tatcg                45

<210> SEQ ID NO 365
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 365 acccggggg gtagtatcgt cgatcaaacc ac                               32

<210> SEQ ID NO 366
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 366
gctgccaaca acagctggac ttgcactatc ccctccacca tcgcg                45

<210> SEQ ID NO 367
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 367
agtccagctg ttgttggcag cgataagttt gtcg                            34

<210> SEQ ID NO 368
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 368
gctgccaaca acagctggac tcttactatc ccctccacca tcgcg                45

<210> SEQ ID NO 369
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 369
agtccagctg ttgttggcag cgataagttt gtcg                            34

<210> SEQ ID NO 370
<211> LENGTH: 46
<212> TYPE: DNA
<213> ORGANISM: Artificial Sequence
<220> FEATURE:

```
<223> OTHER INFORMATION: Artificial DNA Primer

<400> SEQUENCE: 370
ccaacaacag ctggactgta actcttccct ccaccatcgc gcctgg          46

<210> SEQ ID NO 371
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 371
agttacagtc cagctgttgt tggcagcgat aagtt                      35

<210> SEQ ID NO 372
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 372
ctggactgta actatcccct cccgcatcgc gcctggaaac tacgttt         47

<210> SEQ ID NO 373
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 373
ggaggggata gttacagtcc agctgttgtt ggc                        33

<210> SEQ ID NO 374
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 374
gccacgaaat cattgctctt cacaaggctg gaaacgcaga cggtgc          46

<210> SEQ ID NO 375
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 375
gtgaagagca atgatttcgt ggcgcaaaac gtagt                      35

<210> SEQ ID NO 376
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 376
gccacgaaat cattgctctt cactttgctg gaaacgcaga cggtgc          46
```

```
<210> SEQ ID NO 377
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 377
gtgaagagca atgatttcgt ggcgcaaaac gtagt                            35

<210> SEQ ID NO 378
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 378
gccacgaaat cattgctctt cacaccgctg gaaacgcaga cggtgc                46

<210> SEQ ID NO 379
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 379
gtgaagagca atgatttcgt ggcgcaaaac gtagt                            35

<210> SEQ ID NO 380
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 380
gccacgaaat cattgctctt cactacgctg gaaacgcaga cggtgc                46

<210> SEQ ID NO 381
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 381
gtgaagagca atgatttcgt ggcgcaaaac gtagt                            35

<210> SEQ ID NO 382
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 382
tgcccaaaac taccctcaat gcgtcaactt ggagatcacc ggcagc                46

<210> SEQ ID NO 383
<211> LENGTH: 32
<212> TYPE: DNA
<213> ORGANISM: Artificial Sequence
<220> FEATURE:
<223> OTHER INFORMATION: Artificial DNA Primer
```

<400> SEQUENCE: 383
gcattgaggg tagttttggg caccgtctgc gt                                    32

<210> SEQ ID NO 384
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 384
gcagcggaac cgccgctccc gagggtaccg ctggcgaaaa gctc                       44

<210> SEQ ID NO 385
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 385
gggagcggcg gttccgctgc cggtgatctc                                       30

<210> SEQ ID NO 386
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 386
accgctggcg aaaagctcta ccgctctact gaccccggta tcttgg                     46

<210> SEQ ID NO 387
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 387
gtagagcttt tcgccagcgg taccagaggg ag                                    32

<210> SEQ ID NO 388
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 388
gacctacgtt attcccggac cacccctgtg gagcggtgct gccaa                      45

<210> SEQ ID NO 389
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 389
tggtccggga ataacgtagg tcgacaagga ttgg                                  34

<210> SEQ ID NO 390
<211> LENGTH: 46

```
<212> TYPE: DNA
<213> ORGANISM: Artificial Sequence
<220> FEATURE:
<223> OTHER INFORMATION: Artificial DNA Primer

<400> SEQUENCE: 390
taccagggtt acgatccgac catcttccct tacatgcaga acccgc          46

<210> SEQ ID NO 391
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 391
ggtcggatcg taaccctggt acgagacccc g                           31

<210> SEQ ID NO 392
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 392
taccagggtt acgatccgac cgtcttccct tacatgcaga acccgc           46

<210> SEQ ID NO 393
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 393
ggtcggatcg taaccctggt acgagacccc g                           31

<210> SEQ ID NO 394
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 394
ccgacctcct tcccttacat gctcaacccg cccatcgtgg tcgg             44

<210> SEQ ID NO 395
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 395
catgtaaggg aaggaggtcg gatcgtaacc ctg                         33

<210> SEQ ID NO 396
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 396
```
ttgccccgga tgccttcgcc accggcgata tcatctgcca caaga          45

<210> SEQ ID NO 397
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 397
ggcgaaggca tccggggcaa caaagccgtt g          31

<210> SEQ ID NO 398
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 398
cgagttcttc aagatcgacg agtgcggcct ggtcgacggc agctc          45

<210> SEQ ID NO 399
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 399
ctcgtcgatc ttgaagaact cgagcttggt cttg          34

<210> SEQ ID NO 400
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 400
cgagttcttc aagatcgacg agggcggcct ggtcgacggc agctc          45

<210> SEQ ID NO 401
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 401
ctcgtcgatc ttgaagaact cgagcttggt cttg          34

<210> SEQ ID NO 402
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 402
acggcagctc ggcgcccggt atctggggct ccgaccagct cat          43

<210> SEQ ID NO 403
<211> LENGTH: 28
<212> TYPE: DNA
<213> ORGANISM: Artificial Sequence

```
<220> FEATURE:
<223> OTHER INFORMATION: Artificial DNA Primer

<400> SEQUENCE: 403
accgggcgcc gagctgccgt cgaccagg                                            28

<210> SEQ ID NO 404
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 404
gccaacaaca actcgtggct cctcgagatc ccgcccacca tcgc                          44

<210> SEQ ID NO 405
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 405
gagccacgag ttgttgttgg cgatgagctg gt                                       32

<210> SEQ ID NO 406
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 406
cctacaccgt cccggggccg ccgctcatct ccggcgccgt cag                           43

<210> SEQ ID NO 407
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 407 cggcccccggg acggtgtagg tgatcgggg                                          29

<210> SEQ ID NO 408
<211> LENGTH: 884
<212> TYPE: DNA
<213> ORGANISM: Talaromyces thermophilus

<400> SEQUENCE: 408
atgaaagccc ccagcgctgc gtcgatcctc cttcctttcc ttgcgagcat cacccgtacc          60
tctgcccacg ggttcgtctc caatatcgtc attaatggtg tctcgtatcg gggctggctc         120
cccaatgaag acccctataa acctgagccc ccgattggcg tgggttggga gacgcccaac         180
ctgagcaacg gcttcgtgac gcccgaagaa gcgttgaccg atgcgatcgt ctgccacaag         240
gaggccaagc cggcccgcgg ctatgccagc gtcgcagccg cgacaagat ctatatccaa          300 tggcagccga ttccatggcc ggagtctcac catggtgcgt tagactctct cattgttttg         360
cagtcaagcc tcgcccaact gacaacattc tcttccaagg acccgtcctg gactatctgg         420 cccccttgcaa cggcgactgc cagaacgtca acaagtccag cctggagttt ttcaagatcg        480
```

```
acggcaaagg actcatcgac ggctcctccc cgccgggctt ctgggccgac gacgaactta    540
tcgccaacgg caacggctgg ctggtccaga tccccgagga catcaagccg ggcaactacg    600
tgctgcgaca tgagatcatc gccttgcatg agggattcaa ccagaacggc gcccagctgt    660
atccccagtg cttcaacctg cagattacgg gatctggcac cgttgagccg agggaacgc     720 ccgccacgga gctgtattcg cccaccgacc cgggcattct ggtcgacatc tacaacccct    780
tgagcacgta tgtggtgccg ggccccacgc tcatcccaca ggcggttgag atcgaacagt    840
cttcgtcggc ggttacggcg acagggacgc caacgccggc ttaa                    884
```

<210> SEQ ID NO 409
<211> LENGTH: 272
<212> TYPE: PRT
<213> ORGANISM: Talaromyces thermophilus

<400> SEQUENCE: 409

```
Met Lys Ala Pro Ser Ala Ala Ser Ile Leu Leu Pro Phe Leu Ala Ser
1               5                   10                  15

Ile Thr Arg Thr Ser Ala His Gly Phe Val Ser Asn Ile Val Ile Asn
            20                  25                  30

Gly Val Ser Tyr Arg Gly Trp Leu Pro Asn Glu Asp Pro Tyr Lys Pro
        35                  40                  45

Glu Pro Pro Ile Gly Val Gly Trp Glu Thr Pro Asn Leu Ser Asn Gly
    50                  55                  60

Phe Val Thr Pro Glu Glu Ala Leu Thr Asp Ala Ile Val Cys His Lys
65                  70                  75                  80

Glu Ala Lys Pro Ala Arg Gly Tyr Ala Ser Val Ala Ala Gly Asp Lys
                85                  90                  95

Ile Tyr Ile Gln Trp Gln Pro Ile Pro Trp Pro Glu Ser His His Gly
            100                 105                 110

Pro Val Leu Asp Tyr Leu Ala Pro Cys Asn Gly Asp Cys Gln Asn Val
        115                 120                 125

Asn Lys Ser Ser Leu Glu Phe Phe Lys Ile Asp Gly Lys Gly Leu Ile
    130                 135                 140

Asp Gly Ser Ser Pro Pro Gly Phe Trp Ala Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Gly Phe Asn
            180                 185                 190

Gln Asn Gly Ala Gln Leu Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
                245                 250                 255

Glu Gln Ser Ser Ser Ala Val Thr Ala Thr Gly Thr Pro Thr Pro Ala
            260                 265                 270
```

<210> SEQ ID NO 410
<211> LENGTH: 885
<212> TYPE: DNA
<213> ORGANISM: Talaromyces thermophilus

<400> SEQUENCE: 410

```
atgaagggct ccagcgctgc gtcggtgctt cttgctctcc tcgcgggcat tacccgtacc      60
tctgcgcacg ggtatgtctc caacattgtt gtcaacggcg tctactatcg aggctggctc     120
cccggcgaag accctataaa ccctgacccc ccgatcggcg tgggctggga cacgcccaac     180
ctgggcaacg gcttcgtgac gcctgaagaa gcgtcgaccg atgccatcat ctgccacaag     240
gaggccaagc cggcccgcgg ccatgccacc gtgaaagccg gcgacaagat ctacatccaa     300
tggcagccga tccctggcc ggagtcccac cacggtgcgt agcatttcct tgagactctg      360
attgttgcat tccagtctca cccactaaca atacttctag gccccgtcct cgactatctg     420
gccgcttgca acggcgactg cgagaccgtc gacaagacca gcctgcggtt cttcaagatc     480
tccaacaagg gtctcatcga cggctcttcc ccgccgggct actgggctga cgatcagctc     540
atcgagaacg gtaacggatg gctggttcag attcccgagg acatcaagcc gggcaactac     600
gtgctgcgac acgagatcat cgctttgcac gcagcgggca acccgaacgg cgcccagctg     660
tatccgcagt gcttcaacct gcatattacg ggttccggca ccgtcgagcc gcagggaata     720
ccagccaccg agctgtactc gcccgatgac ccgggcattc tgatcaacat ctaccagccc     780
ttgaccacgt atgaggtgcc gggcccgacg cccatcccac aggcggttga gattgagcag     840
tcttcgtccg cgattaccgc gactggaacg ccaacgccgg catga                     885
```

<210> SEQ ID NO 411
<211> LENGTH: 272
<212> TYPE: PRT
<213> ORGANISM: Talaromyces thermophilus

<400> SEQUENCE: 411

```
Met Lys Gly Ser Ser Ala Ala Ser Val Leu Leu Ala Leu Leu Ala Gly
1               5                   10                  15

Ile Thr Arg Thr Ser Ala His Gly Tyr Val Ser Asn Ile Val Val Asn
            20                  25                  30

Gly Val Tyr Tyr Arg Gly Trp Leu Pro Gly Glu Asp Pro Tyr Asn Pro
        35                  40                  45

Asp Pro Pro Ile Gly Val Gly Trp Glu Thr Pro Asn Leu Gly Asn Gly
    50                  55                  60

Phe Val Thr Pro Glu Glu Ala Ser Thr Asp Ala Ile Ile Cys His Lys
65                  70                  75                  80

Glu Ala Lys Pro Ala Arg Gly His Ala Thr Val Lys Ala Gly Asp Lys
                85                  90                  95

Ile Tyr Ile Gln Trp Gln Pro Ile Pro Trp Pro Glu Ser His His Gly
            100                 105                 110

Pro Val Leu Asp Tyr Leu Ala Ala Cys Asn Gly Asp Cys Glu Thr Val
        115                 120                 125

Asp Lys Thr Ser Leu Arg Phe Phe Lys Ile Ser Asn Lys Gly Leu Ile
    130                 135                 140

Asp Gly Ser Ser Pro Pro Gly Tyr Trp Ala Asp Asp Gln Leu Ile Glu
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Ala Ala Gly Asn
            180                 185                 190

Pro Asn Gly Ala Gln Leu Tyr Pro Gln Cys Phe Asn Leu His Ile Thr
        195                 200                 205
```

-continued

| | | | | | | | | | | | | | |
|---|---|---|---|---|---|---|---|---|---|---|---|---|---|
| Gly | Ser | Gly | Thr | Val | Glu | Pro | Gln | Gly | Ile | Pro | Ala | Thr | Glu | Leu | Tyr |
| | 210 | | | | | 215 | | | | | 220 | | | | |
| Ser | Pro | Asp | Asp | Pro | Gly | Ile | Leu | Ile | Asn | Ile | Tyr | Gln | Pro | Leu | Thr |
| 225 | | | | | 230 | | | | | 235 | | | | | 240 |
| Thr | Tyr | Glu | Val | Pro | Gly | Pro | Thr | Pro | Ile | Pro | Gln | Ala | Val | Glu | Ile |
| | | | | 245 | | | | | 250 | | | | | 255 | |
| Glu | Gln | Ser | Ser | Ser | Ala | Ile | Thr | Ala | Thr | Gly | Thr | Pro | Thr | Pro | Ala |
| | | | 260 | | | | | 265 | | | | | 270 | | |

GH61 POLYPEPTIDE VARIANTS AND POLYNUCLEOTIDES ENCODING SAME

CROSS-REFERENCE TO RELATED APPLICATIONS

This application is a 35 U.S.C. 371 national application of PCT/US2013/038477, filed on Apr. 26, 2013, which claims priority from U.S. provisional application Ser. No. 61/639,648, filed on Apr. 27, 2012. The contents of these applications are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to GH61 polypeptide variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2005/074647, WO 2008/148131, and WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 and WO 2012/149344 disclose isolated GH61 polypeptides having cellulolytic enhancing activity and the polynucleotides thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses an isolated GH61 polypeptide having cellulolytic enhancing activity and the polynucleotide thereof from *Aspergillus fumigatus*. WO 2011/005867 discloses an isolated GH61 polypeptide having cellulolytic enhancing activity and the polynucleotide thereof from *Penicillium pinophilum*. WO 2011/039319 discloses an isolated GH61 polypeptide having cellulolytic enhancing activity and the polynucleotide thereof from *Thermoascus* sp. WO 2011/041397 discloses an isolated GH61 polypeptide having cellulolytic enhancing activity and the polynucleotide thereof from *Penicillium* sp. WO 2011/041504 discloses isolated GH61 polypeptides having cellulolytic enhancing activity and the polynucleotides thereof from *Thermoascus crustaceus*. WO 2012/030799 discloses isolated GH61 polypeptides having cellulolytic enhancing activity and the polynucleotides thereof from *Aspergillus aculeatus*. WO 2012/113340 discloses isolated GH61 polypeptides having cellulolytic enhancing activity and the polynucleotides thereof from *Thermomyces lanuginosus*. WO 2012/122477 discloses isolated GH61 polypeptides having cellulolytic enhancing activity and the polynucleotides thereof from *Aurantiporus alborubescens, Trichophaea saccata*, and *Penicillium thomii*. WO 2012/135659 discloses an isolated GH61 polypeptide having cellulolytic enhancing activity and the polynucleotide thereof from *Talaromyces stipitatus*. WO 2012/146171 discloses isolated GH61 polypeptides having cellulolytic enhancing activity and the polynucleotides thereof from *Humicola insolens*. WO 2012/101206 discloses isolated GH61 polypeptides having cellulolytic enhancing activity and the polynucleotides thereof from *Malbranchea cinnamomea, Talaromyces leycettanus*, and *Chaetomium thermophilum*. WO 2013/043910 discloses isolated GH61 polypeptides having cellulolytic enhancing activity and the polynucleotides thereof from *Acrophialophora fusispora* and *Corynascus sepedonium*.

WO 2012/044835 and WO 2012/044836 disclose GH61 polypeptide variants having cellulolytic enhancing activity with improved thermal activity and thermostability.

There is a need in the art for GH61 polypeptides having cellulolytic enhancing activity with increased thermostability as a component of enzyme compositions for use in the degradation of lignocellulose at high temperatures.

The present invention provides GH61 polypeptide variants with increased thermostability.

SUMMARY OF THE INVENTION

The present invention relates to isolated GH61 polypeptide variants, comprising a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variants have cellulolytic enhancing activity.

The present invention also relates to isolated polynucleotides encoding the variants; nucleic acid constructs, vectors, and host cells comprising the polynucleotides; and methods of producing the variants.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIG. 1 shows the genomic DNA sequence (SEQ ID NO: 29) and the deduced amino acid sequence (SEQ ID NO: 30) of an *Aspergillus fumigatus* gene encoding a GH61B polypeptide having cellulolytic enhancing activity.

DEFINITIONS

Figure 2:
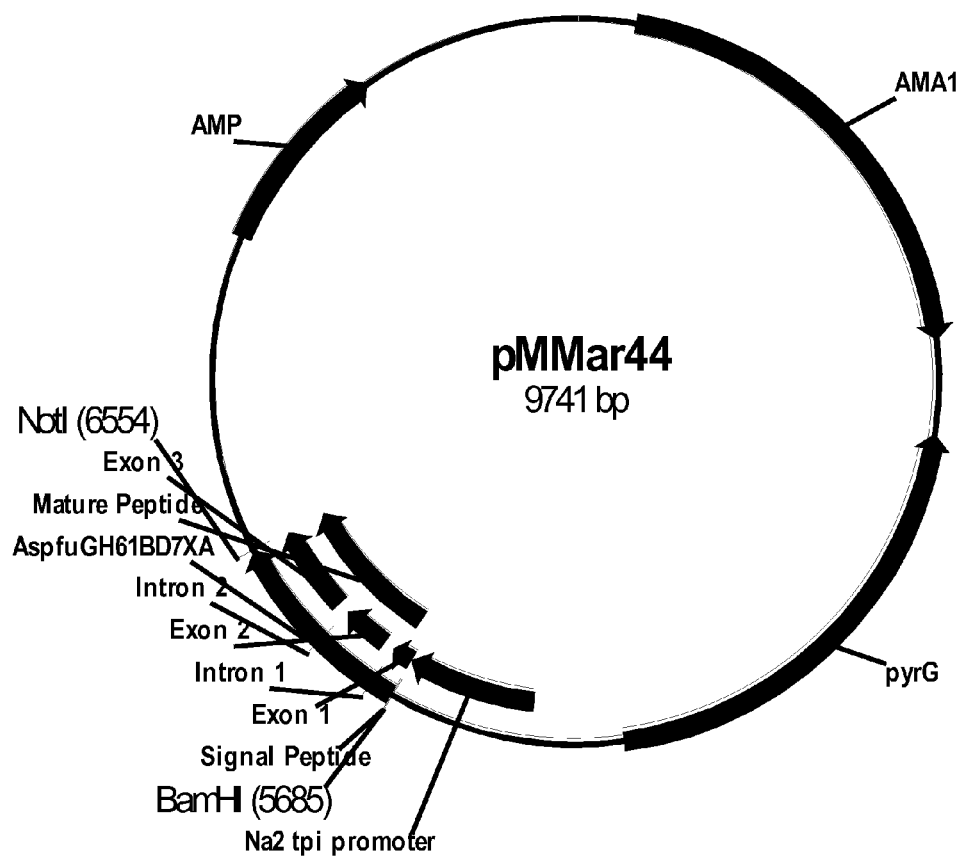
FIG. 2 shows a restriction map of pMMar44.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, beta-xylosidase activity is preferably determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is preferably determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed pretreated corn stover (PCS), 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, *Biochem. J.* 280: 309-316, and Henrissat, and Bairoch, 1996, *Biochem. J.* 316: 695-696. The enzymes in this family were originally classified as a glycoside hydrolase family based on measurement of very weak endo-1,4-beta-D-glucanase activity in one family member. The GH61s have recently been classified as lytic polysaccharide monooxygenases (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061).

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of the mature polypeptide thereof, wherein the fragment has cellulolytic enhancing activity. In one aspect, a fragment contains at least 85% of the amino acid residues, e.g., at least 90% of the amino acid residues or at least 95% of the amino acid residues of the mature polypeptide of a GH61 polypeptide.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property includes, but is not limited to, increased thermostability.

Increased thermostability: The term "increased thermostability" means a higher retention of cellulolytic enhancing activity of a GH61 polypeptide variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

The increased thermostability of the variant relative to the parent can be determined by differential scanning calorimetry (DSC) using methods standard in the art (see, for example, Sturtevant, 1987, *Annual Review of Physical Chemistry* 38: 463-488; Example 9). The increased thermostability of the variant relative to the parent can also be determined using protein thermal unfolding analysis (see, for example, Example 10 herein). The increased thermostability of the variant relative to the parent can also be determined using any enzyme assay known in the art for GH61 polypeptides having cellulolytic enhancing activity to measure residual activity after a temperature treatment. See for example, WO 2005/074647, WO 2008/148131 WO 2005/074656, WO 2010/065830, WO 2007/089290, WO 2009/085935, WO 2009/085859, WO 2009/085864, WO 2009/085868, and WO 2008/151043, which are incorporated herein by reference. Alternatively, the increased thermostability of the variant relative to the parent can be determined using any application assay for the variant where the performance of the variant is compared to the parent. For example, the application assays described in Example 5 can be used.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 326 of SEQ ID NO: 2 based on the SignalP 3.0 program (Bendtsen et al., 2004, *J. Mol. Biol.* 340: 783-795) that predicts amino acids 1 to 19 of SEQ ID NO: 2 are a signal peptide. In another aspect, the mature polypeptide is amino acids 18 to 239 of SEQ ID NO: 4 based on the SignalP program that predicts amino acids 1 to 17 of SEQ ID NO: 4 are a signal peptide. In another aspect, the mature polypeptide is amino acids 20 to 258 of SEQ ID NO: 6 based on the SignalP program that predicts amino acids 1 to 19 of SEQ ID NO: 6 are a signal peptide. In another aspect, the mature polypeptide is amino acids 19 to 226 of SEQ ID NO: 8 based on the SignalP program that predicts amino acids 1 to 18 of SEQ ID NO: 8 are a signal peptide. In another aspect, the mature polypeptide is amino acids 20 to 304 of SEQ ID NO: 10 based on the SignalP program that predicts amino acids 1 to 19 of SEQ ID NO: 10 are a signal peptide. In another aspect, the mature polypeptide is amino acids 16 to 317 of SEQ ID NO: 12 based on the SignalP program that predicts amino acids 1 to 15 of SEQ ID NO: 12 are a signal peptide. In another aspect, the mature polypeptide is amino acids 22 to 249 of SEQ ID NO: 14 based on the SignalP program that predicts amino acids 1 to 21 of SEQ ID NO: 14 are a signal peptide. In another aspect, the mature polypeptide is amino acids 20 to 249 of SEQ ID NO: 16 based on the SignalP program that predicts amino acids 1 to 19 of SEQ ID NO: 16 are a signal peptide. In another aspect, the mature polypeptide is amino acids 18 to 232 of SEQ ID NO: 18 based on the SignalP program that predicts amino acids 1 to 17 of SEQ ID NO: 18 are a signal peptide. In another aspect, the mature polypeptide is amino acids 16 to 235 of SEQ ID NO: 20 based on the SignalP program that predicts amino acids 1 to 15 of SEQ ID NO: 20 are a signal peptide. In another aspect, the mature polypeptide is amino acids 19 to 323 of SEQ ID NO: 22 based on the SignalP program that predicts amino acids 1 to 18 of SEQ ID NO: 22 are a signal peptide. In another aspect, the mature polypeptide is amino acids 16 to 310 of SEQ ID NO: 24 based on the SignalP program that predicts amino acids 1 to 15 of SEQ ID NO: 24 are a signal peptide. In another aspect, the mature polypeptide is amino acids 20 to 246 of SEQ ID NO: 26 based on the SignalP program that predicts amino acids 1 to 19 of SEQ ID NO: 26 are a signal peptide. In another aspect, the mature polypeptide is amino acids 22 to 354 of SEQ ID NO: 28 based on the SignalP program that predicts amino acids 1 to 21 of SEQ ID NO: 28 are a signal peptide. In another aspect, the mature polypeptide is amino acids 22 to 250 of SEQ ID NO: 30 based on the SignalP program that predicts amino acids 1 to 21 of SEQ ID NO: 30 are a signal peptide. In another aspect, the mature polypeptide is amino acids 22 to 322 of SEQ ID NO: 32 based on the SignalP program that predicts amino acids 1 to 21 of SEQ ID NO: 32 are a signal peptide. In another aspect, the mature polypeptide is amino acids 24 to 444 of SEQ ID NO: 34 based on the SignalP program that predicts amino acids 1 to 23 of SEQ ID NO: 34 are a signal peptide. In another aspect, the mature polypeptide is amino acids 26 to 253 of SEQ ID NO: 36 based on the SignalP program that predicts amino acids 1 to 25 of SEQ ID NO: 36 are a signal peptide. In another aspect, the mature polypeptide is amino acids 18 to 246 of SEQ ID NO: 38 based on the SignalP program that predicts amino acids 1 to 17 of SEQ ID NO: 38 are a signal peptide. In another aspect, the mature polypeptide is amino acids 20 to 334 of SEQ ID NO: 40 based on the SignalP program that predicts amino acids 1 to 19 of SEQ ID NO: 40 are a signal peptide. In another aspect, the mature polypeptide is amino acids 18 to 227 of SEQ ID NO: 42 based on the SignalP program that predicts amino acids 1 to 17 of SEQ ID NO: 42 are a signal peptide. In another aspect, the mature polypeptide is amino acids 20 to 223 of SEQ ID NO: 44 based on the SignalP program that predicts amino acids 1 to 19 of SEQ ID NO: 44 are a signal peptide. In another aspect, the mature polypeptide is amino acids 22 to 368 of SEQ ID NO: 46 based on the SignalP program that predicts amino acids 1 to 21 of SEQ ID NO: 46 are a signal peptide. In another aspect, the mature polypeptide is amino acids 25 to 330 of SEQ ID NO: 48 based on the SignalP program that predicts amino acids 1 to 24 of SEQ ID NO: 48 are a signal peptide. In another aspect, the mature polypeptide is amino acids 17 to 236 of SEQ ID NO: 50 based on the SignalP program that predicts amino acids 1 to 16 of SEQ ID NO: 50 are a signal peptide. In another aspect, the mature polypeptide is amino acids 19 to 250 of SEQ ID NO: 52 based on the SignalP program that predicts amino acids 1 to 18 of SEQ ID NO: 52 are a signal peptide. In another aspect, the mature polypeptide is amino acids 23 to 478 of SEQ ID NO: 54 based on the SignalP program that predicts amino acids 1 to 22 of SEQ ID NO: 54 are a signal peptide. In another aspect, the mature polypeptide is amino acids 17 to 230 of SEQ ID NO: 56 based on the SignalP program that predicts amino acids 1 to 16 of SEQ ID NO: 56 are a signal peptide. In another aspect, the mature polypeptide is amino acids 20 to 257 of SEQ ID NO: 58 based on the SignalP program that predicts amino acids 1 to 19 of SEQ ID NO: 58 are a signal peptide. In another aspect, the mature polypeptide is amino acids 23 to 251 of SEQ ID NO: 60 based on the SignalP program that predicts amino acids 1 to 22 of SEQ ID NO: 60 are a signal peptide. In another aspect, the mature polypeptide is amino acids 19 to 349 of SEQ ID NO: 62 based on the SignalP program that predicts amino acids 1 to 18 of SEQ ID NO: 62 are a signal peptide. In another aspect, the mature polypeptide is amino acids 24 to 436 of SEQ ID NO: 64 based on the SignalP program that predicts amino acids 1 to 23 of SEQ ID NO: 64 are a signal peptide. In another aspect, the mature polypeptide is amino acids 21 to 344 of SEQ ID NO: 66 based on the SignalP program that predicts amino acids 1 to 23 of SEQ ID NO: 66 are a signal peptide. In another aspect, the mature polypeptide is amino acids 26 to 400 of SEQ ID NO: 68 based on the SignalP program that predicts amino acids 1 to 25 of SEQ ID NO: 68 are a signal peptide. In another aspect, the mature polypeptide is amino acids 21 to 389 of SEQ ID NO: 70 based on the SignalP program that predicts amino acids 1 to 20 of SEQ ID NO: 70 are a signal peptide. In another aspect, the mature polypeptide is amino acids 22 to 406 of SEQ ID NO: 72 based on the SignalP program that predicts amino acids 1 to 21 of SEQ ID NO: 72 are a signal peptide. In another aspect, the mature polypeptide is amino acids 20 to 427 of SEQ ID NO: 74 based on the SignalP program that predicts amino acids 1 to 19 of SEQ ID NO: 74 are a signal peptide. In another aspect, the mature polypeptide is amino acids 18 to 267 of SEQ ID NO: 76 based on the SignalP program that predicts amino acids 1 to 17 of SEQ ID NO: 76 are a signal peptide. In another aspect, the mature polypeptide is amino acids 21 to 273 of SEQ ID NO: 78 based on the SignalP program that predicts amino acids 1 to 20 of SEQ ID NO: 78 are a signal peptide. In another aspect, the mature polypeptide is amino acids 21 to 322 of SEQ ID NO: 80 based on the SignalP program that predicts amino acids 1 to 20 of SEQ ID NO: 80 are a signal peptide. In another aspect, the mature polypeptide is amino acids 18 to 234 of SEQ ID NO: 82 based on the SignalP program that predicts amino acids 1 to 17 of SEQ ID NO: 82 are a signal peptide. In another aspect, the mature polypeptide is amino acids 24 to 233 of SEQ ID NO: 84 based on the SignalP program that predicts amino acids 1 to 23 of SEQ ID NO: 84 are a signal peptide. In another aspect, the mature polypeptide is amino acids 17 to 237 of SEQ ID NO: 86 based on the SignalP program that predicts amino acids 1 to 16 of SEQ ID NO: 86 are a signal peptide. In another aspect, the mature polypeptide is amino acids 20 to 484 of SEQ ID NO: 88 based on the SignalP program that predicts amino acids 1 to 19 of SEQ ID NO: 88 are a signal peptide. In another aspect, the mature polypeptide is amino acids 22 to 320 of SEQ ID NO: 90 based on the SignalP program that predicts amino acids 1 to 21 of SEQ ID NO: 90 are a signal peptide. In another aspect, the mature polypeptide is amino acids 23 to 272 of SEQ ID NO: 92 based on the SignalP program that predicts amino acids 1 to 22 of SEQ ID NO: 92 are a signal peptide. In another aspect, the mature polypeptide is amino acids 22 to 327 of SEQ ID NO: 94 based on the SignalP program that predicts amino acids 1 to 21 of SEQ ID NO: 94 are a signal peptide. In another aspect, the mature polypeptide is amino acids 23 to 274 of SEQ ID NO: 96 based on the SignalP program that predicts amino acids 1 to 22 of SEQ ID NO: 96 are a signal peptide. In another aspect, the mature polypeptide is amino acids 18 to 227 of SEQ ID NO: 98 based on the SignalP program that predicts amino acids 1 to 17 of SEQ ID NO: 98 are a signal peptide. In another aspect, the mature polypeptide is amino acids 17 to 257 of SEQ ID NO: 100 based on the SignalP program that predicts amino acids 1 to 16 of SEQ ID NO: 100 are a signal peptide. In another aspect, the mature polypeptide is amino acids 20 to 246 of SEQ ID NO: 102 based on the SignalP program that predicts amino acids 1 to 19 of SEQ ID NO: 102 are a signal peptide. In another aspect, the mature polypeptide is amino acids 28 to 265 of SEQ ID NO: 104 based on the SignalP program that predicts amino acids 1 to 27 of SEQ ID NO: 104 are a signal peptide. In another aspect, the mature polypeptide is amino acids 16 to 310 of SEQ ID NO: 106 based on the SignalP program that predicts amino acids 1 to 15 of SEQ ID NO: 106 are a signal peptide. In another aspect, the mature polypeptide is amino acids 21 to 354 of SEQ ID NO: 108 based on the SignalP program that predicts amino acids 1 to 20 of SEQ ID NO: 108 are a signal peptide. In another aspect, the mature polypeptide is amino acids 22 to 267 of SEQ ID NO: 110 based on the SignalP program that predicts amino acids 1 to 21 of SEQ ID NO: 110 are a signal peptide. In another aspect, the mature polypeptide is amino acids 16 to 237 of SEQ ID NO: 112 based on the SignalP program that predicts amino acids 1 to 15 of SEQ ID NO: 112 are a signal peptide. In another aspect, the mature polypeptide is amino acids 20 to 234 of SEQ ID NO: 114 based on the SignalP program that predicts amino acids 1 to 19 of SEQ ID NO: 114 are a signal peptide. In another aspect, the mature polypeptide is amino acids 18 to 226 of SEQ ID NO: 116 based on the SignalP program that predicts amino acids 1 to 17 of SEQ ID NO: 116 are a signal peptide. In another aspect, the mature polypeptide is amino acids 17 to 231 of SEQ ID NO: 118 based on the SignalP program that predicts amino acids 1 to 16 of SEQ ID NO: 118 are a signal peptide. In another aspect, the mature polypeptide is amino acids 22 to 248 of SEQ ID NO: 120 based on the SignalP program that predicts amino acids 1 to 21 of SEQ ID NO: 120 are a signal peptide. In another aspect, the mature polypeptide is amino acids 18 to 233 of SEQ ID NO: 122 based on the SignalP program that predicts amino acids 1 to 17 of SEQ ID NO: 122 are a signal peptide. In another aspect, the mature polypeptide is amino acids 21 to 243 of SEQ ID NO: 124 based on the SignalP program that predicts amino acids 1 to 20 of SEQ ID NO: 124 are a signal peptide. In another aspect, the mature polypeptide is amino acids 21 to 363 of SEQ ID NO: 126 based on the SignalP program that predicts amino acids 1 to 20 of SEQ ID NO: 126 are a signal peptide. In another aspect, the mature polypeptide is amino acids 20 to 296 of SEQ ID NO: 128 based on the SignalP program that predicts amino acids 1 to 19 of SEQ ID NO: 128 are a signal peptide. In another aspect, the mature polypeptide is amino acids 16 to 318 of SEQ ID NO: 130 based on the SignalP program that predicts amino acids 1 to 15 of SEQ ID NO: 130 are a signal peptide. In another aspect, the mature polypeptide is amino acids 19 to 259 of SEQ ID NO: 132 based on the SignalP program that predicts amino acids 1 to 18 of SEQ ID NO: 132 are a signal peptide. In another aspect, the mature polypeptide is amino acids 20 to 325 of SEQ ID NO: 134 based on the SignalP program that predicts amino acids 1 to 19 of SEQ ID NO: 134 are a signal peptide. In another aspect, the mature polypeptide is amino acids 19 to 298 of SEQ ID NO: 136 based on the SignalP program that predicts amino acids 1 to 18 of SEQ ID NO: 136 are a signal peptide. In another aspect, the mature polypeptide is amino acids 20 to 298 of SEQ ID NO: 138 based on the SignalP program that predicts amino acids 1 to 19 of SEQ ID NO: 138 are a signal peptide. In another aspect, the mature polypeptide is amino acids 22 to 344 of SEQ ID NO: 140 based on the SignalP program that predicts amino acids 1 to 21 of SEQ ID NO: 140 are a signal peptide. In another aspect, the mature polypeptide is amino acids 20 to 330 of SEQ ID NO: 142 based on the SignalP program that predicts amino acids 1 to 19 of SEQ ID NO: 142 are a signal peptide. In another aspect, the mature polypeptide is amino acids 19 to 216 of SEQ ID NO: 144 based on the SignalP program that predicts amino acids 1 to 18 of SEQ ID NO: 144 are a signal peptide. In another aspect, the mature polypeptide is amino acids 18 to 490 of SEQ ID NO: 146 based on the SignalP program that predicts amino acids 1 to 17 of SEQ ID NO: 146 are a signal peptide. In another aspect, the mature polypeptide is amino acids 21 to 306 of SEQ ID NO: 148 based on the SignalP program that predicts amino acids 1 to 20 of SEQ ID NO: 148 are a signal peptide. In another aspect, the mature polypeptide is amino acids 22 to 339 of SEQ ID NO: 150 based on the SignalP program that predicts amino acids 1 to 21 of SEQ ID NO: 150 are a signal peptide. In another aspect, the mature polypeptide is amino acids 23 to 334 of SEQ ID NO: 152 based on the SignalP program that predicts amino acids 1 to 22 of SEQ ID NO: 152 are a signal peptide. In another aspect, the mature polypeptide is amino acids 24 to 366 of SEQ ID NO: 154 based on the SignalP program that predicts amino acids 1 to 23 of SEQ ID NO: 154 are a signal peptide. In another aspect, the mature polypeptide is amino acids 21 to 364 of SEQ ID NO: 156 based on the SignalP program that predicts amino acids 1 to 20 of SEQ ID NO: 156 are a signal peptide. In another aspect, the mature polypeptide is amino acids 22 to 344 of SEQ ID NO: 158 based on the SignalP program that predicts amino acids 1 to 21 of SEQ ID NO: 158 are a signal peptide. In another aspect, the mature polypeptide is amino acids 20 to 252 of SEQ ID NO: 160 based on the SignalP program that predicts amino acids 1 to 19 of SEQ ID NO: 160 are a signal peptide. In another aspect, the mature polypeptide is amino acids 20 to 344 of SEQ ID NO: 162 based on the SignalP program that predicts amino acids 1 to 19 of SEQ ID NO: 162 are a signal peptide. In another aspect, the mature polypeptide is amino acids 22 to 347 of SEQ ID NO: 164 based on the SignalP program that predicts amino acids 1 to 21 of SEQ ID NO: 164 are a signal peptide. In another aspect, the mature polypeptide is amino acids 20 to 342 of SEQ ID NO: 166 based on the SignalP program that predicts amino acids 1 to 19 of SEQ ID NO: 166 are a signal peptide. In another aspect, the mature polypeptide is amino acids 27 to 254 of SEQ ID NO: 168 based on the SignalP program that predicts amino acids 1 to 26 of SEQ ID NO: 168 are a signal peptide. In another aspect, the mature polypeptide is amino acids 23 to 272 of SEQ ID NO: 409 based on the SignalP program that predicts amino acids 1 to 22 of SEQ ID NO: 409 are a signal peptide. In another aspect, the mature polypeptide is amino acids 23 to 272 of SEQ ID NO: 411 based on the SignalP program that predicts amino acids 1 to 22 of SEQ ID NO: 411 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 388 to 1332 of SEQ ID NO: 1 based on the SignalP 3.0 program (Bendtsen et al., 2004, supra) that predicts nucleotides 330 to 387 of SEQ ID NO: 1 encode a signal peptide. In another aspect, the mature polypeptide coding sequence is nucleotides 98 to 821 of SEQ ID NO: 3 based on the SignalP program that predicts nucleotides 47 to 97 of SEQ ID NO: 3 encode a signal peptide. In another aspect, the mature polypeptide coding sequence is nucleotides 126 to 978 of SEQ ID NO: 5 based on the SignalP program that predicts nucleotides 69 to 125 of SEQ ID NO: 5 encode a signal peptide. In another aspect, the mature polypeptide coding sequence is nucleotides 55 to 678 of SEQ ID NO: 7 or the genomic DNA sequence thereof based on the SignalP program that predicts nucleotides 1 to 54 of SEQ ID NO: 7 encode a signal peptide. In another aspect, the mature polypeptide coding sequence is nucleotides 58 to 912 of SEQ ID NO: 9 or the genomic DNA sequence thereof based on the SignalP program that predicts nucleotides 1 to 57 of SEQ ID NO: 9 encode a signal peptide. In another aspect, the mature polypeptide coding sequence is nucleotides 46 to 951 of SEQ ID NO: 11 or the genomic DNA sequence thereof based on the SignalP program that predicts nucleotides 1 to 45 of SEQ ID NO: 11 encode a signal peptide. In another aspect, the mature polypeptide coding sequence is nucleotides 64 to 796 of SEQ ID NO: 13 based on the SignalP program that predicts nucleotides 1 to 63 of SEQ ID NO: 13 encode a signal peptide. In another aspect, the mature polypeptide coding sequence is nucleotides 77 to 766 of SEQ ID NO: 15 based on the SignalP program that predicts nucleotides 20 to 76 of SEQ ID NO: 15 or the genomic DNA sequence thereof encode a signal peptide. In another aspect, the mature polypeptide coding sequence is nucleotides 52 to 921 of SEQ ID NO: 17 based on the SignalP program that predicts nucleotides 1 to 51 of SEQ ID NO: 17 encode a signal peptide. In another aspect, the mature polypeptide coding sequence is nucleotides 46 to 851 of SEQ ID NO: 19 based on the SignalP program that predicts nucleotides 1 to 45 of SEQ ID NO: 19 encode a signal peptide. In another aspect, the mature polypeptide coding sequence is nucleotides 55 to 1239 of SEQ ID NO: 21 based on the SignalP program that predicts nucleotides 1 to 54 of SEQ ID NO: 21 encode a signal peptide. In another aspect, the mature polypeptide coding sequence is nucleotides 46 to 1250 of SEQ ID NO: 23 based on the SignalP program that predicts nucleotides 1 to 45 of SEQ ID NO: 23 encode a signal peptide. In another aspect, the mature polypeptide coding sequence is nucleotides 58 to 811 of SEQ ID NO: 25 based on the SignalP program that predicts nucleotides 1 to 57 of SEQ ID NO: 25 encode a signal peptide. In another aspect, the mature polypeptide coding sequence is nucleotides 64 to 1112 of SEQ ID NO: 27 based on the SignalP program that predicts nucleotides 1 to 63 of SEQ ID NO: 27 encode a signal peptide. In another aspect, the mature polypeptide coding sequence is nucleotides 64 to 859 of SEQ ID NO: 29 based on the SignalP program that predicts nucleotides 1 to 63 of SEQ ID NO: 29 encode a signal peptide. In another aspect, the mature polypeptide coding sequence is nucleotides 64 to 1018 of SEQ ID NO: 31 based on the SignalP program that predicts nucleotides 1 to 63 of SEQ ID NO: 31 encode a signal peptide. In another aspect, the mature polypeptide coding sequence is nucleotides 70 to 1483 of SEQ ID NO: 33 based on the SignalP program that predicts nucleotides 1 to 69 of SEQ ID NO: 33 encode a signal peptide. In another aspect, the mature polypeptide coding sequence is nucleotides 76 to 832 of SEQ ID NO: 35 based on the SignalP program that predicts nucleotides 1 to 75 of SEQ ID NO: 35 encode a signal peptide. In another aspect, the mature polypeptide coding sequence is nucleotides 52 to 875 of SEQ ID NO: 37 based on the SignalP program that predicts nucleotides 1 to 51 of SEQ ID NO: 37 encode a signal peptide. In another aspect, the mature polypeptide coding sequence is nucleotides 58 to 1250 of SEQ ID NO: 39 based on the SignalP program that predicts nucleotides 1 to 57 of SEQ ID NO: 39 encode a signal peptide. In another aspect, the mature polypeptide coding sequence is nucleotides 52 to 795 of SEQ ID NO: 41 based on the SignalP program that predicts nucleotides 1 to 51 of SEQ ID NO: 41 encode a signal peptide. In another aspect, the mature polypeptide coding sequence is nucleotides 58 to 974 of SEQ ID NO: 43 based on the SignalP program that predicts nucleotides 1 to 57 of SEQ ID NO: 43 encode a signal peptide. In another aspect, the mature polypeptide coding sequence is nucleotides 64 to 1104 of SEQ ID NO: 45 based on the SignalP program that predicts nucleotides 1 to 63 of SEQ ID NO: 45 encode a signal peptide. In another aspect, the mature polypeptide coding sequence is nucleotides 73 to 990 of SEQ ID NO: 47 based on the SignalP program that predicts nucleotides 1 to 72 of SEQ ID NO: 47 encode a signal peptide. In another aspect, the mature polypeptide coding sequence is nucleotides 49 to 1218 of SEQ ID NO: 49 based on the SignalP program that predicts nucleotides 1 to 48 of SEQ ID NO: 49 encode a signal peptide. In another aspect, the mature polypeptide coding sequence is nucleotides 55 to 930 of SEQ ID NO: 51 based on the SignalP program that predicts nucleotides 1 to 54 of SEQ ID NO: 51 encode a signal peptide. In another aspect, the mature polypeptide coding sequence is nucleotides 67 to 1581 of SEQ ID NO: 53 based on the SignalP program that predicts nucleotides 1 to 66 of SEQ ID NO: 53 encode a signal peptide. In another aspect, the mature polypeptide coding sequence is nucleotides 49 to 865 of SEQ ID NO: 55 based on the SignalP program that predicts nucleotides 1 to 48 of SEQ ID NO: 55 encode a signal peptide. In another aspect, the mature polypeptide coding sequence is nucleotides 58 to 1065 of SEQ ID NO: 57 based on the SignalP program that predicts nucleotides 1 to 57 of SEQ ID NO: 57 encode a signal peptide. In another aspect, the mature polypeptide coding sequence is nucleotides 67 to 868 of SEQ ID NO: 59 based on the SignalP program that predicts nucleotides 1 to 66 of SEQ ID NO: 59 encode a signal peptide. In another aspect, the mature polypeptide coding sequence is nucleotides 55 to 1099 of SEQ ID NO: 61 based on the SignalP program that predicts nucleotides 1 to 54 of SEQ ID NO: 61 encode a signal peptide. In another aspect, the mature polypeptide coding sequence is nucleotides 70 to 1483 of SEQ ID NO: 63 based on the SignalP program that predicts nucleotides 1 to 69 of SEQ ID NO: 63 encode a signal peptide. In another aspect, the mature polypeptide coding sequence is nucleotides 61 to 1032 of SEQ ID NO: 65 based on the SignalP program that predicts nucleotides 1 to 60 of SEQ ID NO: 65 encode a signal peptide. In another aspect, the mature polypeptide coding sequence is nucleotides 76 to 1200 of SEQ ID NO: 67 based on the SignalP program that predicts nucleotides 1 to 75 of SEQ ID NO: 67 encode a signal peptide. In another aspect, the mature polypeptide coding sequence is nucleotides 61 to 1167 of SEQ ID NO: 69 based on the SignalP program that predicts nucleotides 1 to 60 of SEQ ID NO: 69 encode a signal peptide. In another aspect, the mature polypeptide coding sequence is nucleotides 64 to 1218 of SEQ ID NO: 71 based on the SignalP program that predicts nucleotides 1 to 63 of SEQ ID NO: 71 encode a signal peptide. In another aspect, the mature polypeptide coding sequence is nucleotides 58 to 1281 of SEQ ID NO: 73 based on the SignalP program that predicts nucleotides 1 to 57 of SEQ ID NO: 73 encode a signal peptide. In another aspect, the mature polypeptide coding sequence is nucleotides 52 to 801 of SEQ ID NO: 75 based on the SignalP program that predicts nucleotides 1 to 51 of SEQ ID NO: 75 encode a signal peptide. In another aspect, the mature polypeptide coding sequence is nucleotides 61 to 819 of SEQ ID NO: 77 based on the SignalP program that predicts nucleotides 1 to 60 of SEQ ID NO: 77 encode a signal peptide. In another aspect, the mature polypeptide coding sequence is nucleotides 61 to 966 of SEQ ID NO: 79 based on the SignalP program that predicts nucleotides 1 to 60 of SEQ ID NO: 79 encode a signal peptide. In another aspect, the mature polypeptide coding sequence is nucleotides 52 to 702 of SEQ ID NO: 81 or the genomic DNA sequence thereof based on the SignalP program that predicts nucleotides 1 to 51 of SEQ ID NO: 81 encode a signal peptide. In another aspect, the mature polypeptide coding sequence is nucleotides 70 to 699 of SEQ ID NO: 83 or the genomic DNA sequence thereof based on the SignalP program that predicts nucleotides 1 to 69 of SEQ ID NO: 83 encode a signal peptide. In another aspect, the mature polypeptide coding sequence is nucleotides 49 to 711 of SEQ ID NO: 85 or the genomic DNA sequence thereof based on the SignalP program that predicts nucleotides 1 to 48 of SEQ ID NO: 85 encode a signal peptide. In another aspect, the mature polypeptide coding sequence is nucleotides 76 to 1452 of SEQ ID NO: 87 based on the SignalP program that predicts nucleotides 1 to 75 of SEQ ID NO: 87 encode a signal peptide. or In another aspect, the mature polypeptide coding sequence is nucleotides 64 to 1018 of SEQ ID NO: 89 based on the SignalP program that predicts nucleotides 1 to 63 of SEQ ID NO: 89 encode a signal peptide. In another aspect, the mature polypeptide coding sequence is nucleotides 67 to 869 of SEQ ID NO: 91 based on the SignalP program that predicts nucleotides 1 to 66 of SEQ ID NO: 91 encode a signal peptide. In another aspect, the mature polypeptide coding sequence is nucleotides 64 to 1036 of SEQ ID NO: 93 based on the SignalP program that predicts nucleotides 1 to 63 of SEQ ID NO: 93 encode a signal peptide. In another aspect, the mature polypeptide coding sequence is nucleotides 67 to 878 of SEQ ID NO: 95 based on the SignalP program that predicts nucleotides 1 to 66 of SEQ ID NO: 95 encode a signal peptide. In another aspect, the mature polypeptide coding sequence is nucleotides 52 to 818 of SEQ ID NO: 97 based on the SignalP program that predicts nucleotides 1 to 51 of SEQ ID NO: 97 encode a signal peptide. In another aspect, the mature polypeptide coding sequence is nucleotides 49 to 1117 of SEQ ID NO: 99 based on the SignalP program that predicts nucleotides 1 to 48 of SEQ ID NO: 99 encode a signal peptide. In another aspect, the mature polypeptide coding sequence is nucleotides 58 to 875 of SEQ ID NO: 101 based on the SignalP program that predicts nucleotides 1 to 57 of SEQ ID NO: 101 encode a signal peptide. In another aspect, the mature polypeptide coding sequence is nucleotides 82 to 1064 of SEQ ID NO: 103 based on the SignalP program that predicts nucleotides 1 to 81 of SEQ ID NO: 103 encode a signal peptide. In another aspect, the mature polypeptide coding sequence is nucleotides 46 to 1032 of SEQ ID NO: 105 based on the SignalP program that predicts nucleotides 1 to 45 of SEQ ID NO: 105 encode a signal peptide. In another aspect, the mature polypeptide coding sequence is nucleotides 61 to 1062 of SEQ ID NO: 107 based on the SignalP program that predicts nucleotides 1 to 60 of SEQ ID NO: 107 encode a signal peptide. In another aspect, the mature polypeptide coding sequence is nucleotides 64 to 801 of SEQ ID NO: 109 based on the SignalP program that predicts nucleotides 1 to 63 of SEQ ID NO: 109 encode a signal peptide. In another aspect, the mature polypeptide coding sequence is nucleotides 46 to 840 of SEQ ID NO: 111 based on the SignalP program that predicts nucleotides 1 to 45 of SEQ ID NO: 111 encode a signal peptide. In another aspect, the mature polypeptide coding sequence is nucleotides 58 to 702 of SEQ ID NO: 113 based on the SignalP program that predicts nucleotides 1 to 57 of SEQ ID NO: 113 encode a signal peptide. In another aspect, the mature polypeptide coding sequence is nucleotides 52 to 750 of SEQ ID NO: 115 based on the SignalP program that predicts nucleotides 1 to 51 of SEQ ID NO: 115 encode a signal peptide. In another aspect, the mature polypeptide coding sequence is nucleotides 49 to 851 of SEQ ID NO: 117 based on the SignalP program that predicts nucleotides 1 to 48 of SEQ ID NO: 117 encode a signal peptide. In another aspect, the mature polypeptide coding sequence is nucleotides 64 to 860 of SEQ ID NO: 119 based on the SignalP program that predicts nucleotides 1 to 63 of SEQ ID NO: 119 encode a signal peptide. In another aspect, the mature polypeptide coding sequence is nucleotides 52 to 830 of SEQ ID NO: 121 based on the SignalP program that predicts nucleotides 1 to 51 of SEQ ID NO: 121 encode a signal peptide. In another aspect, the mature polypeptide coding sequence is nucleotides 61 to 925 of SEQ ID NO: 123 based on the SignalP program that predicts nucleotides 1 to 60 of SEQ ID NO: 123 encode a signal peptide. In another aspect, the mature polypeptide coding sequence is nucleotides 61 to 1089 of SEQ ID NO: 125 based on the SignalP program that predicts nucleotides 1 to 60 of SEQ ID NO: 125 encode a signal peptide. In another aspect, the mature polypeptide coding sequence is nucleotides 58 to 1083 of SEQ ID NO: 127 based on the SignalP program (that predicts nucleotides 1 to 57 of SEQ ID NO: 127 encode a signal peptide. In another aspect, the mature polypeptide coding sequence is nucleotides 46 to 1029 of SEQ ID NO: 129 based on the SignalP program that predicts nucleotides 1 to 45 of SEQ ID NO: 129 encode a signal peptide. In another aspect, the mature polypeptide coding sequence is nucleotides 55 to 1110 of SEQ ID NO: 131 based on the SignalP program that predicts nucleotides 1 to 54 of SEQ ID NO: 131 encode a signal peptide. In another aspect, the mature polypeptide coding sequence is nucleotides 58 to 1100 of SEQ ID NO: 133 based on the SignalP program that predicts nucleotides 1 to 57 of SEQ ID NO: 133 encode a signal peptide. In another aspect, the mature polypeptide coding sequence is nucleotides 55 to 1036 of SEQ ID NO: 135 based on the SignalP program that predicts nucleotides 1 to 54 of SEQ ID NO: 135 encode a signal peptide. In another aspect, the mature polypeptide coding sequence is nucleotides 58 to 1022 of SEQ ID NO: 137 based on the SignalP program that predicts nucleotides 1 to 57 of SEQ ID NO: 137 encode a signal peptide. In another aspect, the mature polypeptide coding sequence is nucleotides 64 to 1032 of SEQ ID NO: 139 based on the SignalP program that predicts nucleotides 1 to 63 of SEQ ID NO: 139 encode a signal peptide. In another aspect, the mature polypeptide coding sequence is nucleotides 58 to 1054 of SEQ ID NO: 141 based on the SignalP program that predicts nucleotides 1 to 57 of SEQ ID NO: 141 encode a signal peptide. In another aspect, the mature polypeptide coding sequence is nucleotides 55 to 769 of SEQ ID NO: 143 based on the SignalP program that predicts nucleotides 1 to 54 of SEQ ID NO: 143 encode a signal peptide. In another aspect, the mature polypeptide coding sequence is nucleotides 52 to 1533 of SEQ ID NO: 145 based on the SignalP program that predicts nucleotides 1 to 51 of SEQ ID NO: 145 encode a signal peptide. In another aspect, the mature polypeptide coding sequence is nucleotides 61 to 918 of SEQ ID NO: 147 based on the SignalP program that predicts nucleotides 1 to 60 of SEQ ID NO: 147 encode a signal peptide. In another aspect, the mature polypeptide coding sequence is nucleotides 64 to 1089 of SEQ ID NO: 149 based on the SignalP program that predicts nucleotides 1 to 63 of SEQ ID NO: 149 encode a signal peptide. In another aspect, the mature polypeptide coding sequence is nucleotides 67 to 1002 of SEQ ID NO: 151 based on the SignalP program that predicts nucleotides 1 to 66 of SEQ ID NO: 151 encode a signal peptide. In another aspect, the mature polypeptide coding sequence is nucleotides 70 to 1098 of SEQ ID NO: 153 based on the SignalP program that predicts nucleotides 1 to 69 of SEQ ID NO: 153 encode a signal peptide. In another aspect, the mature polypeptide coding sequence is nucleotides 61 to 1088 of SEQ ID NO: 155 based on the SignalP program that predicts nucleotides 1 to 60 of SEQ ID NO: 155 encode a signal peptide. In another aspect, the mature polypeptide coding sequence is nucleotides 64 to 1086 of SEQ ID NO: 157 based on the SignalP program that predicts nucleotides 1 to 63 of SEQ ID NO: 157 encode a signal peptide. In another aspect, the mature polypeptide coding sequence is nucleotides 58 to 756 of SEQ ID NO: 159 based on the SignalP program that predicts nucleotides 1 to 57 of SEQ ID NO: 159 encode a signal peptide. In another aspect, the mature polypeptide coding sequence is nucleotides 58 to 1032 of SEQ ID NO: 161 based on the SignalP program that predicts nucleotides 1 to 57 of SEQ ID NO: 161 encode a signal peptide. In another aspect, the mature polypeptide coding sequence is nucleotides 64 to 1041 of SEQ ID NO: 163 based on the SignalP program that predicts nucleotides 1 to 63 of SEQ ID NO: 163 encode a signal peptide. In another aspect, the mature polypeptide coding sequence is nucleotides 58 to 1026 of SEQ ID NO: 165 based on the SignalP program that predicts nucleotides 1 to 57 of SEQ ID NO: 165 encode a signal peptide. In another aspect, the mature polypeptide coding sequence is nucleotides 79 to 762 of SEQ ID NO: 167 based on the SignalP program that predicts nucleotides 1 to 78 of SEQ ID NO: 167 encode a signal peptide. In another aspect, the mature polypeptide coding sequence is nucleotides 67 to 881 of SEQ ID NO: 408 based on the SignalP program that predicts nucleotides 1 to 66 of SEQ ID NO: 408 encode a signal peptide. In another aspect, the mature polypeptide coding sequence is nucleotides 67 to 882 of SEQ ID NO: 410 based on the SignalP program that predicts nucleotides 1 to 66 of SEQ ID NO: 410 encode a signal peptide. The term "mature polypeptide coding sequence" herein shall be understood to include the cDNA sequence of the genomic DNA sequence or the genomic DNA sequence of the cDNA sequence.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or doublestranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent GH61 polypeptide: The term "parent" or "parent GH61 polypeptide" means a GH61 polypeptide to which an alteration, i.e., a substitution, insertion, and/or deletion, at one or more (e.g., several) positions, is made to produce the GH61 polypeptide variants of the present invention. The parent may be a naturally occurring (wild-type) polypeptide or a variant or fragment thereof.

Polypeptide having cellulolytic enhancing activity: The term "polypeptide having cellulolytic enhancing activity" means a GH61 polypeptide or variant thereof that catalyzes the enhancement of the hydrolysis of a cellulosic material by enzyme having cellulolytic activity, i.e., a cellulase. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide or variant thereof for 1-7 days at a suitable temperature, such as 40° C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS) In one aspect, GH61 polypeptide enhancing activity is determined using a mixture of CELLUCLAST® 1.5L (Novozymes A/S, Bagsværd, Denmark) in the presence of 2-3% of total protein weight $Aspergillus$ $oryzae$ beta-glucosidase (recombinantly produced in $Aspergillus$ $oryzae$ according to WO 02/095014) or 2-3% of total protein weight $Aspergillus$ $fumigatus$ beta-glucosidase (recombinantly produced in $Aspergillus$ $oryzae$ as described in WO 02/095014) of cellulase protein loading is used as the source of the cellulolytic activity.

Another assay for determining the cellulolytic enhancing activity of a GH61 polypeptide or variant thereof is to incubate the GH61 polypeptide or variant with 0.5% phosphoric acid swollen cellulose (PASO), 100 mM sodium acetate pH 5, 1 mM $MnSO_4$, 0.1% gallic acid, 0.025 mg/ml of $Aspergillus$ $fumigatus$ beta-glucosidase, and 0.01% TRITON® X100 for 24-96 hours at 40° C. followed by determination of the glucose released from the PASO.

The GH61 polypeptides or variants thereof having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, $J. Mol. Biol.$ 48: 443-453) as implemented in the Needle program of the EMBOSS package (EMBOSS: The European Molecular Biology Open Software Suite, Rice et al., 2000, $Trends Genet.$ 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence, wherein the subsequence encodes a fragment having cellulolytic enhancing activity. In one aspect, a subsequence contains at least 85% of the nucleotides, e.g., at least 90% of the nucleotides or at least 95% of the nucleotides of the mature polypeptide coding sequence of a GH61 polypeptide.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellulolytic enhancing activity of their parent GH61 polypeptides.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type GH61 polypeptide: The term "wild-type" GH61 polypeptide means a GH61 polypeptide naturally produced by a microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Conventions for Designation of Variants

For purposes of the present invention, the mature polypeptide disclosed in SEQ ID NO: 30 is used to determine the corresponding amino acid residue in another GH61 polypeptide. The amino acid sequence of another GH61 polypeptide is aligned with the mature polypeptide disclosed in SEQ ID NO: 30, and based on the alignment, the amino acid position number corresponding to any amino acid residue in the mature polypeptide disclosed in SEQ ID NO: 30 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 30 wherein position 1 is the first amino acid of the signal peptide (i.e., Met) and position 22 is His of SEQ ID NO: 30.

For example, the position corresponding to position 105 of the *Aspergillus fumigatus* GH61 polypeptide (SEQ ID NO: 30) is position 109 in the *Penicillium emersonii* GH61 polypeptide (SEQ ID NO: 36), position 105 in the *Thermoascus aurantiacus* GH61 polypeptide (SEQ ID NO: 14), and position 103 in the *Aspergillus aculeatus* GH61 polypeptide (SEQ ID NO: 68); the position corresponding to position 188 of the *Aspergillus fumigatus* GH61 polypeptide is position 192 in the *Penicillium emersonii* GH61 polypeptide, position 188 in the *Thermoascus aurantiacus* GH61 polypeptide, and position 186 in the *Aspergillus aculeatus* GH61 polypeptide; the position corresponding to position 154 of the *Aspergillus fumigatus* GH61 polypeptide is position 152 in the *Aspergillus aculeatus* GH61 polypeptide; and the position corresponding to position 189 of the *Aspergillus fumigatus* GH61 polypeptide is position 193 in the *Penicillium emersonii* GH61 polypeptide and position 187 in the *Aspergillus aculeatus* GH61 polypeptide.

Identification of the corresponding amino acid residue in another GH61 polypeptide can be determined by an alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another GH61 polypeptide has diverged from the mature polypeptide of SEQ ID NO: 30 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the GH61 polypeptide variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411 Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
| --- | --- |
| 195 | 195 195a 195b |
| G | G - K - A |

Multiple Substitutions.

Variants comprising multiple substitutions are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Substitutions.

Where different substitutions can be introduced at a position, the different substitutions are separated by a comma, e.g., "Arg170Tyr, Glu" represents a substitution of arginine at position 170 with tyrosine or glutamic acid. Thus, "Tyr167Gly, Ala+Arg170Gly, Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated GH61 polypeptide variants, comprising a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variants have cellulolytic enhancing activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent GH61 polypeptide.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In one aspect, the number of substitutions in the variants of the present invention is 1-28, e.g., 1, 2, 3, 4, 5, 6, 7, 8, 9, 10, 11, 12, 13, 14, 15, 16, 17, 18, 19, 20, 21, 22, 23, 24, 25, 26, 27, and 28 substitutions.

In another aspect, a variant comprises a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eight positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at nine positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at ten positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eleven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twelve positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at thirteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at fourteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at fifteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at sixteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at seventeen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at eighteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at nineteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-one positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at twenty-seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250. In another aspect, a variant comprises a substitution at each position corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250.

In another aspect, the variant comprises or consists of a substitution at a position corresponding to position 26. In another aspect, the amino acid at a position corresponding to position 26 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution S26I of the mature polypeptide of SEQ ID NO: 30.

In another aspect, the variant comprises or consists of a substitution at a position corresponding to position 32. In another aspect, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu or Ser. In another aspect, the variant comprises or consists of the substitution G32E or G32S of the mature polypeptide of SEQ ID NO: 30.

In another aspect, the variant comprises or consists of a substitution at a position corresponding to position 34. In another aspect, the amino acid at a position corresponding to position 34 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant comprises or consists of the substitution Y34F of the mature polypeptide of SEQ ID NO: 30.

In another aspect, the variant comprises or consists of a substitution at a position corresponding to position 40. In another aspect, the amino acid at a position corresponding to position 40 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution V40A of the mature polypeptide of SEQ ID NO: 30.

In another aspect, the variant comprises or consists of a substitution at a position corresponding to position 41. In another aspect, the amino acid at a position corresponding to position 41 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the substitution N41T of the mature polypeptide of SEQ ID NO: 30.

In another aspect, the variant comprises or consists of a substitution at a position corresponding to position 42. In another aspect, the amino acid at a position corresponding to position 42 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Glu, or Val. In another aspect, the variant comprises or consists of the substitution Q42I, Q42E, or Q42V of the mature polypeptide of SEQ ID NO: 30.

In another aspect, the variant comprises or consists of a substitution at a position corresponding to position 47. In another aspect, the amino acid at a position corresponding to position 47 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, or Arg. In another aspect, the variant comprises or consists of the substitution S47E, S47L, or S47R of the mature polypeptide of SEQ ID NO: 30.

In another aspect, the variant comprises or consists of a substitution at a position corresponding to position 56. In another aspect, the amino acid at a position corresponding to position 56 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Glu, or Thr. In another aspect, the variant comprises or consists of the substitution S56C, S56E, or S56T of the mature polypeptide of SEQ ID NO: 30.

In another aspect, the variant comprises or consists of a substitution at a position corresponding to position 72. In another aspect, the amino acid at a position corresponding to position 72 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln or Thr. In another aspect, the variant comprises or consists of the substitution S72Q or S72T of the mature polypeptide of SEQ ID NO: 30.

In another aspect, the variant comprises or consists of a substitution at a position corresponding to position 102. In another aspect, the amino acid at a position corresponding to position 102 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys or Pro. In another aspect, the variant comprises or consists of the substitution T102K or T102P of the mature polypeptide of SEQ ID NO: 30.

In another aspect, the variant comprises or consists of a substitution at a position corresponding to position 123. In another aspect, the amino acid at a position corresponding to position 123 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution A123R of the mature polypeptide of SEQ ID NO: 30.

In another aspect, the variant comprises or consists of a substitution at a position corresponding to position 138. In another aspect, the amino acid at a position corresponding to position 138 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Glu, Gly, Lys, Leu, or Met. In another aspect, the variant comprises or consists of the substitution Q138C, Q138E, Q138G, Q138K, Q138L, or Q138M of the mature polypeptide of SEQ ID NO: 30.

In another aspect, the variant comprises or consists of a substitution at a position corresponding to position 149. In another aspect, the amino acid at a position corresponding to position 149 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution V149I of the mature polypeptide of SEQ ID NO: 30.

In another aspect, the variant comprises or consists of a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution D152S of the mature polypeptide of SEQ ID NO: 30.

In another aspect, the variant comprises or consists of a substitution at a position corresponding to position 163. In another aspect, the amino acid at a position corresponding to position 163 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Phe, or Val. In another aspect, the variant comprises or consists of the substitution T163E, T163F, or T163V of the mature polypeptide of SEQ ID NO: 30.

In another aspect, the variant comprises or consists of a substitution at a position corresponding to position 164. In another aspect, the amino acid at a position corresponding to position 164 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys or Leu. In another aspect, the variant comprises or consists of the substitution V164C or V164L of the mature polypeptide of SEQ ID NO: 30.

In another aspect, the variant comprises or consists of a substitution at a position corresponding to position 166. In another aspect, the amino acid at a position corresponding to position 166 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution I166L of the mature polypeptide of SEQ ID NO: 30.

In another aspect, the variant comprises or consists of a substitution at a position corresponding to position 169. In another aspect, the amino acid at a position corresponding to position 169 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg or Cys. In another aspect, the variant comprises or consists of the substitution S169R or S169C of the mature polypeptide of SEQ ID NO: 30. In another aspect, the variant comprises or consists of the substitution S173C of the mature polypeptide of SEQ ID NO: 36. The position in the *Penicillium* sp. (*emersonii*) GH61 mature polypeptide corresponding to position 169 in the *A. fumigatus* GH61 mature polypeptide is position 173.

In another aspect, the variant comprises or consists of a substitution at a position corresponding to position 186. In another aspect, the amino acid at a position corresponding to position 186 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe, Lys, Thr, or Tyr. In another aspect, the variant comprises or consists of the substitution S186F, S186K, S186T, or S186Y of the mature polypeptide of SEQ ID NO: 30.

In another aspect, the variant comprises or consists of a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile or Val. In another aspect, the variant comprises or consists of the substitution F200I or F200V of the mature polypeptide of SEQ ID NO: 30.

In another aspect, the variant comprises or consists of a substitution at a position corresponding to position 207. In another aspect, the amino acid at a position corresponding to position 207 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises or consists of the substitution G207P of the mature polypeptide of SEQ ID NO: 30.

In another aspect, the variant comprises or consists of a substitution at a position corresponding to position 213. In another aspect, the amino acid at a position corresponding to position 213 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu. In another aspect, the variant comprises or consists of the substitution S213E of the mature polypeptide of SEQ ID NO: 30.

In another aspect, the variant comprises or consists of a substitution at a position corresponding to position 219. In another aspect, the amino acid at a position corresponding to position 219 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Met, Gln, or Cys. In another aspect, the variant comprises or consists of the substitution S219E, S219M, S219Q, or S219C of the mature polypeptide of SEQ ID NO: 30.

In another aspect, the variant comprises or consists of a substitution at a position corresponding to position 222. In another aspect, the amino acid at a position corresponding to position 222 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution K222R of the mature polypeptide of SEQ ID NO: 30.

In another aspect, the variant comprises or consists of a substitution at a position corresponding to position 234. In another aspect, the amino acid at a position corresponding to position 234 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly or Lys. In another aspect, the variant comprises or consists of the substitution S234G or S234K of the mature polypeptide of SEQ ID NO: 30.

In another aspect, the variant comprises or consists of a substitution at a position corresponding to position 246. In another aspect, the amino acid at a position corresponding to position 246 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the variant comprises or consists of the substitution A246P of the mature polypeptide of SEQ ID NO: 30.

In another aspect, the variant comprises or consists of a substitution at a position corresponding to position 249. In another aspect, the amino acid at a position corresponding to position 249 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Arg, or Cys. In another aspect, the variant comprises or consists of the substitution N249Q, N249R, or N249C of the mature polypeptide of SEQ ID NO: 30. In another aspect, the variant comprises or consists of the substitution F253C of the mature polypeptide of SEQ ID NO: 36. The position in the *Penicillium* sp. (*emersonii*) GH61 mature polypeptide corresponding to position 249 in the *A. fumigatus* GH61 mature polypeptide is position 253.

In another aspect, the variant comprises or consists of a substitution at a position corresponding to position 250. In another aspect, the amino acid at a position corresponding to position 250 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant comprises or consists of the substitution A250C of the mature polypeptide of SEQ ID NO: 30.

In another aspect, the variant comprises or consists of one or more (e.g., several) substitutions selected from the group consisting of S261; G32E, S; Y34F; V40A; N41T; Q42I, E, V; S47E, L, R; S56C, E, T; S72Q, T; T102K, P; A123R; Q138C, E, G, K, L, M; V149I ; D152S; T163E, F, V; V164C, L; I166L; S169R, C; S186F, K, T, Y; F200I, V; G207P; S213E; S219E, M, Q, C; K222R; S234G, K; A246P; N249Q, R, C; and A250C; or the one or more (e.g., several) substitutions selected from the group consisting of S261; G32E, S; Y34F; V40A; N41T; Q42I, E, V; S47E, L, R; S56C, E, T; S72Q, T; T102K, P; A123R; Q138C, E, G, K, L, M; V149I ; D152S; T163E, F, V; V164C, L; I166L; S169R, C; S186F, K, T, Y; F200I, V; G207P; S213E; S219E, M, Q, C; K222R; S234G, K; A246P; N249Q, R, C; and A250C at positions corresponding to the mature polypeptide of SEQ ID NO: 30 in other GH61 polypeptides described herein.

In each of the aspects below, the variant comprises or consists of the one or more (e.g., several) substitutions described below at positions corresponding to SEQ ID NO: 30 in other GH61 polypeptides described herein.

In another aspect, the variant comprises or consists of the substitutions S173C+F253C of the mature polypeptide of SEQ ID NO: 36. In another aspect, the variant comprises or consists of the substitutions L111V+D152S+M155L+ A162W+Q138K+K229W of the mature polypeptide of SEQ ID NO: 30. In another aspect, the variant comprises or consists of the substitutions L111V+D152S+M155L+ A162W+S47E+K229W of the mature polypeptide of SEQ ID NO: 30. In another aspect, the variant comprises or consists of the substitutions L111V+D152S+M155L+ A162W+S56A+K229W of the mature polypeptide of SEQ ID NO: 30. In another aspect, the variant comprises or consists of the substitutions L111V+D152S+M155L+ A162W+T102K+K229W of the mature polypeptide of SEQ ID NO: 30. In another aspect, the variant comprises or consists of the substitutions L111V+D152S+M155L+

A162W+S186T+K$_{229}$W of the mature polypeptide of SEQ ID NO: 30. In another aspect, the variant comprises or consists of the substitutions L111V+D152S+M155L+A162W+K229W+S234G of the mature polypeptide of SEQ ID NO: 30. In another aspect, the variant comprises or consists of the substitutions L111V+D152S+M155L+A162W+T102K+E105K+K229W of the mature polypeptide of SEQ ID NO: 30. In another aspect, the variant comprises or consists of the substitutions L111V+D152S+M155L+A162W+Q138K+G188F+K229W of the mature polypeptide of SEQ ID NO: 30. In another aspect, the variant comprises or consists of the substitutions L111V+D152S+M155L+A162W+Q138K+V149I+G188F+K229W of the mature polypeptide of SEQ ID NO: 30. In another aspect, the variant comprises or consists of the substitutions L111V+D152S+M155L+A162W+S169C+G188F+K229W+A250C of the mature polypeptide of SEQ ID NO: 30. In another aspect, the variant comprises or consists of the substitutions L111V+D152S+M155L+A162W+S72T+Q138K+V149I+G188F+K229W of the mature polypeptide of SEQ ID NO: 30. In another aspect, the variant comprises or consists of the substitutions L111V+D152S+M155L+A162W+Q138K+V149I+G188F+G207P+K229W of the mature polypeptide of SEQ ID NO: 30.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

The variants of the present invention may further or even further comprise a substitution at one or more (e.g., several) positions corresponding to positions 111, 152, 155, and 162 of the mature polypeptide of SEQ ID NO: 30, wherein the variants have cellulolytic enhancing activity (WO 2012/044835).

In one aspect, the number of additional substitutions above in the variants of the present invention is 1-4, such as 1, 2, 3, or 4 substitutions.

In another aspect, the variant further or even further comprises a substitution at one or more (e.g., several) positions corresponding to positions 111, 152, 155, and 162. In another aspect, the variant further or even further comprises a substitution at two positions corresponding to any of positions 111, 152, 155, and 162. In another aspect, the variant further or even further comprises a substitution at three positions corresponding to any of positions 111, 152, 155, and 162. In another aspect, the variant further or even further comprises a substitution at each position corresponding to positions 111, 152, 155, and 162.

In another aspect, the variant further or even further comprises a substitution at a position corresponding to position 111. In another aspect, the amino acid at a position corresponding to position 111 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution L111V of the mature polypeptide of SEQ ID NO: 30.

In another aspect, the variant further or even further comprises a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant further or even further comprises the substitution D152S of the mature polypeptide of SEQ ID NO: 30.

In another aspect, the variant further or even further comprises a substitution at a position corresponding to position 155. In another aspect, the amino acid at a position corresponding to position 155 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution M155L of the mature polypeptide of SEQ ID NO: 30.

In another aspect, the variant further or even further comprises a substitution at a position corresponding to position 162. In another aspect, the amino acid at a position corresponding to position 162 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the variant further or even further comprises the substitution A162W of the mature polypeptide of SEQ ID NO: 30.

In another aspect, the variant further or even further comprises one or more (e.g., several) substitutions selected from the group consisting of L111V, D152S, M155L, and A162W of the mature polypeptide of SEQ ID NO: 30, or the one or more (e.g., several) substitutions selected from the group consisting of L111V, D152S, M155L, and A162W at positions corresponding to the mature polypeptide of SEQ ID NO: 30 in other GH61 polypeptides described herein.

The variants of the present invention may further or even further comprise a substitution at one or more (e.g., several) positions corresponding to positions 96, 98, 200, 202, and 204 of the mature polypeptide of SEQ ID NO: 30, wherein the variants have cellulolytic enhancing activity (WO 2012/044836).

In one aspect, the number of additional substitutions above in the variants of the present invention is 1-5, such as 1, 2, 3, 4, or 5 substitutions.

In another aspect, the variant further or even further comprises a substitution at one or more (e.g., several) positions corresponding to positions 96, 98, 200, 202, and 204. In another aspect, the variant further or even further comprises a substitution at two positions corresponding to any of positions 96, 98, 200, 202, and 204. In another aspect, the variant further or even further comprises a substitution at three positions corresponding to any of positions 96, 98, 200, 202, and 204. In another aspect, the variant further or even further comprises a substitution at four positions corresponding to any of positions 96, 98, 200, 202, and 204. In another aspect, the variant further or even further comprises a substitution at each position corresponding to positions 96, 98, 200, 202, and 204.

In another aspect, the variant further or even further comprises a substitution at a position corresponding to position 96. In another aspect, the amino acid at a position corresponding to position 96 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution I96V of the mature polypeptide of SEQ ID NO: 30.

In another aspect, the variant further or even further comprises a substitution at a position corresponding to position 98. In another aspect, the amino acid at a position corresponding to position 98 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution F98L of the mature polypeptide of SEQ ID NO: 30.

In another aspect, the variant further or even further comprises a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further or even further comprises the substitution F200I of the mature polypeptide of SEQ ID NO: 30.

In another aspect, the variant further or even further comprises a substitution at a position corresponding to position 202. In another aspect, the amino acid at a position corresponding to position 202 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution I202L of the mature polypeptide of SEQ ID NO: 30.

In another aspect, the variant further or even further comprises a substitution at a position corresponding to position 204. In another aspect, the amino acid at a position corresponding to position 204 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further or even further comprises the substitution I204V of the mature polypeptide of SEQ ID NO: 30.

In another aspect, the variant further or even further comprises one or more (e.g., several) substitutions selected from the group consisting of I96V, F98L, F200I, I202L, and I204V, or the one or more (e.g., several) substitutions selected from the group consisting of I96V, F98L, F200I, I202L, and I204V at positions corresponding to SEQ ID NO: 30 in other GH61 polypeptides described herein.

The variants of the present invention may further or even further comprise a substitution at one or more (e.g., several) positions corresponding to positions 105, 154, 188, 189, 216, and 229 of the mature polypeptide of SEQ ID NO: 30, wherein the variants have cellulolytic enhancing activity.

In one aspect, the number of additional substitutions above in the variants of the present invention is 1-6, e.g., 1, 2, 3, 4, 5, or 6 substitutions.

In another aspect, a variant further or even further comprises a substitution at one or more (e.g., several) positions corresponding to positions 105, 154, 188, 189, 216, and 229. In another aspect, a variant further or even further comprises a substitution at two positions corresponding to any of positions 105, 154, 188, 189, 216, and 229. In another aspect, a variant further or even further comprises a substitution at three positions corresponding to any of positions 105, 154, 188, 189, 216, and 229. In another aspect, a variant further or even further comprises a substitution at four positions corresponding to any of positions 105, 154, 188, 189, 216, and 229. In another aspect, a variant further or even further comprises a substitution at five positions corresponding to any of positions 105, 154, 188, 189, 216, and 229. In another aspect, a variant further or even further comprises a substitution at each position corresponding to positions 105, 154, 188, 189, 216, and 229.

In another aspect, the variant further or even further comprises a substitution at a position corresponding to position 105. In another aspect, the amino acid at a position corresponding to position 105 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro or Lys. In another aspect, the variant further or even further comprises of the substitution E105P or E105K of the mature polypeptide of SEQ ID NO: 30.

In another aspect, the variant further or even further comprises a substitution at a position corresponding to position 154. In another aspect, the amino acid at a position corresponding to position 154 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further or even further comprises the substitution E154L of the mature polypeptide of SEQ ID NO: 30.

In another aspect, the variant further or even further comprises a substitution at a position corresponding to position 188. In another aspect, the amino acid at a position corresponding to position 188 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or Trp. In another aspect, the variant further or even further comprises the substitution G188A or G188W of the mature polypeptide of SEQ ID NO: 30.

In another aspect, the variant further or even further comprises a substitution at a position corresponding to position 189. In another aspect, the amino acid at a position corresponding to position 189 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another aspect, the variant further or even further comprises the substitution N189K of the mature polypeptide of SEQ ID NO: 30.

In another aspect, the variant further or even further comprises a substitution at a position corresponding to position 216. In another aspect, the amino acid at a position corresponding to position 216 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or Tyr. In another aspect, the variant further or even further comprises the substitution A216L or A216Y of the mature polypeptide of SEQ ID NO: 30.

In another aspect, the variant further or even further comprises a substitution at a position corresponding to position 229. In another aspect, the amino acid at a position corresponding to position 229 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, His, Ile, or Tyr. In another aspect, the variant further or even further comprises the substitution A229W, A229H, A229I, or A229Y of the mature polypeptide of SEQ ID NO: 30.

In another aspect, the variant further or even further comprises one or more (e.g., several) substitutions selected from the group consisting of E105P, K; E154L; G188A, W; N189K; A216L, Y; and A229W, H, I, Y, of the mature polypeptide of SEQ ID NO: 30, or the one or more (e.g., several) substitutions selected from the group consisting of E105P, K; E154L; G188A, W; N189K; A216L, Y; and A229W, H, I, Y at positions corresponding to the mature polypeptide of SEQ ID NO: 30 in other GH61 polypeptides described herein.

The variants may consist of at least 85% of the amino acid residues, e.g., at least 90% of the amino acid residues or at least 95% of the amino acid residues of the mature polypeptides of the corresponding parent GH61 polypeptides.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in GH61 polypeptides correspond to positions 22, 107, 194, and/or 196 of the mature polypeptide of SEQ ID NO: 30.

In an embodiment, the variants have increased thermostability compared to their parent GH61 polypeptides.

In one aspect, the thermostability of the variant relative to the parent is determined at pH 3.0 and 45° C. In another aspect, the thermostability of the variant relative to the parent is determined at pH 3.0 and 50° C. In another aspect, the thermostability of the variant relative to the parent is determined at pH 3.0 and 55° C. In another aspect, the thermostability of the variant relative to the parent is determined at pH 3.0 and 60° C. In another aspect, the thermostability of the variant relative to the parent is determined at pH 3.0 and 62° C. In another aspect, the thermostability of the variant relative to the parent is determined at pH 3.0 and 65° C. In another aspect, the thermostability of the variant relative to the parent is determined at pH 3.0 and 68° C. In another aspect, the thermostability of the variant relative to the parent is determined at pH 3.0 and 70° C. In another aspect, the thermostability of the variant relative to the parent is determined at pH 3.0 and 72° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C. In another aspect, the thermostability of the variant relative to the parent is determined at pH 3.0 and 95° C.

In another aspect, the thermostability of the variant relative to the parent is determined at pH 3.5 and 45° C. In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 62° C. In another aspect, the thermostability of the variant relative to the parent is determined at pH 3.5 and 65° C. In another aspect, the thermostability of the variant relative to the parent is determined at pH 3.5 and 68° C. In another aspect, the thermostability of the variant relative to the parent is determined at pH 3.5 and 70° C. In another aspect, the thermostability of the variant relative to the parent is determined at pH 3.5 and 72° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90° C. In another aspect, the thermostability of the variant relative to the parent is determined at pH 3.5 and 95° C.

In another aspect, the thermostability of the variant relative to the parent is determined at pH 4.0 and 45° C. In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 62° C. In another aspect, the thermostability of the variant relative to the parent is determined at pH 4.0 and 65° C. In another aspect, the thermostability of the variant relative to the parent is determined at pH 4.0 and 68° C. In another aspect, the thermostability of the variant relative to the parent is determined at pH 4.0 and 70° C. In another aspect, the thermostability of the variant relative to the parent is determined at pH 4.0 and 72° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C. In another aspect, the thermostability of the variant relative to the parent is determined at pH 4.0 and 95° C.

In another aspect, the thermostability of the variant relative to the parent is determined at pH 4.5 and 45° C. In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 62° C. In another aspect, the thermostability of the variant relative to the parent is determined at pH 4.5 and 65° C. In another aspect, the thermostability of the variant relative to the parent is determined at pH 4.5 and 68° C. In another aspect, the thermostability of the variant relative to the parent is determined at pH 4.5 and 70° C. In another aspect, the thermostability of the variant relative to the parent is determined at pH 4.5 and 72° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C. In another aspect, the thermostability of the variant relative to the parent is determined at pH 4.5 and 95° C.

In another aspect, the thermostability of the variant relative to the parent is determined at pH 5.0 and 45° C. In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 62° C. In another aspect, the thermostability of the variant relative to the parent is determined at pH 5.0 and 65° C. In another aspect, the thermostability of the variant relative to the parent is determined at pH 5.0 and 68° C. In another aspect, the thermostability of the variant relative to the parent is determined at pH 5.0 and 70° C. In another aspect, the thermostability of the variant relative to the parent is determined at pH 5.0 and 72° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C. In another aspect, the thermostability of the variant relative to the parent is determined at pH 5.0 and 95° C.

In another aspect, the thermostability of the variant relative to the parent is determined at pH 5.5 and 45° C. In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 62° C. In another aspect, the thermostability of the variant relative to the parent is determined at pH 5.5 and 65° C. In another aspect, the thermostability of the variant relative to the parent is determined at pH 5.5 and 68° C. In another aspect, the thermostability of the variant relative to the parent is determined at pH 5.5 and 70° C. In another aspect, the thermostability of the variant relative to the parent is determined at pH 5.5 and 72° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C. In another aspect, the thermostability of the variant relative to the parent is determined at pH 5.5 and 95° C.

In another aspect, the thermostability of the variant relative to the parent is determined at pH 6.0 and 45° C. In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 62° C. In another aspect, the thermostability of the variant relative to the parent is determined at pH 6.0 and 65° C. In another aspect, the thermostability of the variant relative to the parent is determined at pH 6.0 and 68° C. In another aspect, the thermostability of the variant relative to the parent is determined at pH 6.0 and 70° C. In another aspect, the thermostability of the variant relative to the parent is determined at pH 6.0 and 72° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C. In another aspect, the thermostability of the variant relative to the parent is determined at pH 6.0 and 95° C.

In another aspect, the thermostability of the variant relative to the parent is determined at pH 6.5 and 45° C. In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 62° C. In another aspect, the thermostability of the variant relative to the parent is determined at pH 6.5 and 65° C. In another aspect, the thermostability of the variant relative to the parent is determined at pH 6.5 and 68° C. In another aspect, the thermostability of the variant relative to the parent is determined at pH 6.5 and 70° C. In another aspect, the thermostability of the variant relative to the parent is determined at pH 6.5 and 72° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C. In another aspect, the thermostability of the variant relative to the parent is determined at pH 6.5 and 95° C.

In another aspect, the thermostability of the variant relative to the parent is determined at pH 7.0 and 45° C. In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 62° C. In another aspect, the thermostability of the variant relative to the parent is determined at pH 7.0 and 65° C. In another aspect, the thermostability of the variant relative to the parent is determined at pH 7.0 and 68° C. In another aspect, the thermostability of the variant relative to the parent is determined at pH 7.0 and 70° C. In another aspect, the thermostability of the variant relative to the parent is determined at pH 7.0 and 72° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C. In another aspect, the thermostability of the variant relative to the parent is determined at pH 7.0 and 95° C.

In another aspect, the thermostability of the variant relative to the parent is determined at pH 7.5 and 45° C. In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 62° C. In another aspect, the thermostability of the variant relative to the parent is determined at pH 7.5 and 65° C. In another aspect, the thermostability of the variant relative to the parent is determined at pH 7.5 and 68° C. In another aspect, the thermostability of the variant relative to the parent is determined at pH 7.5 and 70° C. In another aspect, the thermostability of the variant relative to the parent is determined at pH 7.5 and 72° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C. In another aspect, the thermostability of the variant relative to the parent is determined at pH 7.5 and 95° C.

In another aspect, the thermostability of the variant relative to the parent is determined at pH 8.0 and 45° C. In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 62° C. In another aspect, the thermostability of the variant relative to the parent is determined at pH 8.0 and 65° C. In another aspect, the thermostability of the variant relative to the parent is determined at pH 8.0 and 68° C. In another aspect, the thermostability of the variant relative to the parent is determined at pH 8.0 and 70° C. In another aspect, the thermostability of the variant relative to the parent is determined at pH 8.0 and 72° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C. In another aspect, the thermostability of the variant relative to the parent is determined at pH 8.0 and 95° C.

In another aspect, the thermostability of the variant relative to the parent is determined at pH 8.5 and 45° C. In another aspect, the thermostability of the variant relative to the parent is determined at pH 8.5 and 50° C. In another aspect, the thermostability of the variant relative to the parent is determined at pH 8.5 and 55° C. In another aspect, the thermostability of the variant relative to the parent is determined at pH 8.5 and 60° C. In another aspect, the thermostability of the variant relative to the parent is determined at pH 8.5 and 62° C. In another aspect, the thermostability of the variant relative to the parent is determined at pH 8.5 and 65° C. In another aspect, the thermostability of the variant relative to the parent is determined at pH 8.5 and 68° C. In another aspect, the thermostability of the variant relative to the parent is determined at pH 8.5 and 70° C. In another aspect, the thermostability of the variant relative to the parent is determined at pH 8.5 and 72° C. In another aspect, the thermostability of the variant relative to the parent is determined at pH 8.5 and 75° C. In another aspect, the thermostability of the variant relative to the parent is determined at pH 8.5 and 80° C. In another aspect, the thermostability of the variant relative to the parent is determined at pH 8.5 and 85° C. In another aspect, the thermostability of the variant relative to the parent is determined at pH 8.5 and 90° C. In another aspect, the thermostability of the variant relative to the parent is determined at pH 8.5 and 95° C.

In another aspect, the thermostability of the variant relative to the parent is determined at pH 9.0 and 45° C. In another aspect, the thermostability of the variant relative to the parent is determined at pH 9.0 and 50° C. In another aspect, the thermostability of the variant relative to the parent is determined at pH 9.0 and 55° C. In another aspect, the thermostability of the variant relative to the parent is determined at pH 9.0 and 60° C. In another aspect, the thermostability of the variant relative to the parent is determined at pH 9.0 and 62° C. In another aspect, the thermostability of the variant relative to the parent is determined at pH 9.0 and 65° C. In another aspect, the thermostability of the variant relative to the parent is determined at pH 9.0 and 68° C. In another aspect, the thermostability of the variant relative to the parent is determined at pH 9.0 and 70° C. In another aspect, the thermostability of the variant relative to the parent is determined at pH 9.0 and 72° C. In another aspect, the thermostability of the variant relative to the parent is determined at pH 9.0 and 75° C. In another aspect, the thermostability of the variant relative to the parent is determined at pH 9.0 and 80° C. In another aspect, the thermostability of the variant relative to the parent is determined at pH 9.0 and 85° C. In another aspect, the thermostability of the variant relative to the parent is determined at pH 9.0 and 90° C. In another aspect, the thermostability of the variant relative to the parent is determined at pH 9.0 and 95° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 20 minutes. In each of the aspects above, the thermostability of the variant relative to the parent can be determined by incubating the variant and parent for 25 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes. A time period longer than 60 minutes can also be used.

In one aspect, the thermostability of the variant having cellulolytic enhancing activity is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to more thermostable than the parent.

Parent GH61 Polypeptides

The parent GH61 polypeptide may be any GH61 polypeptide having cellulolytic enhancing activity.

The parent GH61 polypeptide may be (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or (ii) the full-length complement of (i); or (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In one aspect, the parent has a sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellulolytic enhancing activity.

In one embodiment, the amino acid sequence of the parent differs by up to 10 amino acids, e.g., 1, 2, 3, 4, 5, 6, 7, 8, 9, or 10 from the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent comprises or consists of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another embodiment, the parent is a fragment containing at least 85% of the amino acid residues, e.g., at least 90% of the amino acid residues or at least 95% of the amino acid residues of the mature polypeptide of a GH61 polypeptide.

In another embodiment, the parent is an allelic variant of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or the full-length complements thereof (Sambrook et al., 1989, *Molecular Cloning, A Laboratory Manual*, 2d edition, Cold Spring Harbor, N.Y.).

The polynucleotide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or subsequences thereof, as well as the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, or fragments thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or subsequences thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410; (ii) the mature polypeptide coding sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In another embodiment, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; the mature polypeptide thereof; or a fragment thereof.

In another embodiment, the nucleic acid probe is SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

In another aspect, the parent is encoded by a polynucleotide having a sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one embodiment, the parent is secreted extracellularly.

The parent may be a bacterial GH61 polypeptide. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* GH61 polypeptide, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* GH61 polypeptide.

In one embodiment, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* GH61 polypeptide.

The parent may be a fungal GH61 polypeptide. For example, the parent may be a yeast GH61 polypeptide such as a *Candida, Kluyveromyces, Pichia, Saccharomyces, Schizosaccharomyces,* or *Yarrowia* GH61 polypeptide; or a filamentous fungal GH61 polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* GH61 polypeptide.

In another embodiment, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* GH61 polypeptide.

In another embodiment, the parent is an *Acremonium cellulolyticus, Aspergillus aculeatus, Aspergillus awamori, Aspergillus foetidus, Aspergillus fumigatus, Aspergillus japonicus, Aspergillus lentulus, Aspergillus nidulans, Aspergillus niger, Aspergillus oryzae, Aspergillus terreus, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fennellia nivea, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium pinophilum, Penicillium purpurogenum, Phanerochaete chrysosporium, Talaromyces leycettanus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* GH61 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a GH61 polypeptide variant having cellulolytic enhancing activity, comprising: (a) introducing into a parent GH61 polypeptide a substitution at one or more (e.g., several) positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity; and optionally (b) recovering the variant. In one aspect, the methods further or even further comprise introducing into the parent GH61 polypeptide a substitution at one or more (e.g., several) positions corresponding to positions 111, 152, 155, and 162 of the mature polypeptide of SEQ ID NO: 30, wherein the variant has cellulolytic enhancing activity. In another aspect, the methods further or even further comprise introducing into the parent GH61 polypeptide a substitution at one or more (e.g., several) positions corresponding to positions 96, 98, 200, 202, and 204 of the mature polypeptide of SEQ ID NO: 30, wherein the variant has cellulolytic enhancing activity. In another aspect, the methods further or even further comprise introducing into the parent GH61 polypeptide a substitution at one or more (e.g., several) positions corresponding to positions 105, 154, 188, 189, 216, and 229 of the mature polypeptide of SEQ ID NO: 30, wherein the variant has cellulolytic enhancing activity, The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding GH61 polypeptide variants of the present invention.

Nucleic Acid Constructs

The present invention also relates to nucleic acid constructs comprising a polynucleotide encoding a GH61 polypeptide variant of the present invention operably linked to one or more control sequences that direct the expression of the coding sequence in a suitable host cell under conditions compatible with the control sequences.

The polynucleotide may be manipulated in a variety of ways to provide for expression of a GH61 polypeptide variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the GH61 polypeptide variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the GH61 polypeptide variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the GH61 polypeptide variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the GH61 polypeptide variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a GH61 polypeptide variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a GH61 polypeptide variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the GH61 polypeptide variant and the signal peptide sequence is positioned next to the N-terminus of the propeptide sequence.

It may also be desirable to add regulatory sequences that regulate expression of the GH61 polypeptide variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a GH61 polypeptide variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* daI genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system. The vector preferably contains an element(s) that permits integration of the vector into the host cell's genome or autonomous replication of the vector in the cell independent of the genome.

For integration into the host cell genome, the vector may rely on the polynucleotide's sequence encoding the GH61 polypeptide variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and AA/SI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a GH61 polypeptide variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a GH61 polypeptide variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a GH61 polypeptide variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a GH61 polypeptide variant, comprising: (a) cultivating a recombinant host cell of the present invention under conditions conducive for production of the variant; and optionally (b) recovering the variant.

The host cells are cultivated in a nutrient medium suitable for production of the GH61 polypeptide variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The GH61 polypeptide variant may be detected using methods known in the art that are specific for the variant. These detection methods include, but are not limited to, use of specific antibodies, formation of an enzyme product, or disappearance of an enzyme substrate. For example, an enzyme assay may be used to determine the activity of the variant. A specific assay for GH61 proteins is to incubate the GH61 polypeptide variants with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X100 for 24-96 hours at 40° C. followed by an assay of this reaction to determine the glucose released from the PASC. See the assay described in Example 5.

The GH61 polypeptide variants may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The GH61 polypeptide variants may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the GH61 polypeptide variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the cellulolytic enhancing activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, a GH61 polypeptide, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the GH61 polypeptide variants having cellulolytic enhancing activity, or compositions thereof.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technol.* 100: 10-18; Mosier et al., 2005, *Bioresource Technol.* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, countercurrent reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a GH61 polypeptide variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a GH61 polypeptide having cellulolytic enhancing activity. In another aspect, the enzyme composition comprises an endoglucanase and a GH61 polypeptide having cellulolytic enhancing activity. In another aspect, the enzyme composition comprises a cellobiohydrolase and a GH61 polypeptide having cellulolytic enhancing activity. In another aspect, the enzyme composition comprises a beta-glucosidase and a GH61 polypeptide having cellulolytic enhancing activity. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II In another aspect, the enzyme composition comprises an endoglucanase, a GH61 polypeptide having cellulolytic enhancing activity, and a cellobiohydrolase. In another aspect, the enzyme composition comprises an endoglucanase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a GH61 polypeptide having cellulolytic enhancing activity. In another aspect, the enzyme composition comprises a beta-glucosidase, a GH61 polypeptide having cellulolytic enhancing activity, and a cellobiohydrolase. In another aspect, the enzyme composition comprises a beta-glucosidase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and a GH61 polypeptide having cellulolytic enhancing activity. In another aspect, the enzyme composition comprises an endoglucanase, a beta-glucosidase, a GH61 polypeptide having cellulolytic enhancing activity, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another preferred aspect, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises an oxidoreductase. In another preferred aspect, the oxidoreductase is a catalase. In another preferred aspect, the oxidoreductase is a laccase. In another preferred aspect, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and the GH61 polypeptide variants depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a GH61 polypeptide variant to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a GH61 polypeptide variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, for example, site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram-negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

The polypeptide having enzyme activity may also be a fungal polypeptide, and more preferably a yeast polypeptide such as a *Candida, Kluyveromyces, Pichia, Saccharomyces,*

Schizosaccharomyces, or Yarrowia polypeptide having enzyme activity; or more preferably a filamentous fungal polypeptide such as an Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella, or Xylaria polypeptide having enzyme activity.

In one aspect, the polypeptide is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis polypeptide having enzyme activity.

In another aspect, the polypeptide is an Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride, or Trichophaea saccata polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), SPEZYME™ CP (Genencor Int.), ACCELERASE™ TR10 (DuPont), FILTRASE® NL (DSM); METHAPLUS® S/L 100 (DSM), ROHAMENT™ 7069 W (Rohm GmbH), or ALTERNAFUEL® CMAX3™ (Dyadic International, Inc.). The cellulase enzymes are added in amounts effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, Acidothermus cellulolyticus endoglucanase (WO 91/05039; WO 93/15186; U.S. Pat. No. 5,275,944; WO 96/02551; U.S. Pat. No. 5,536,655; WO 00/70031; WO 05/093050), Erwinia carotovara endoglucanase (Saarilahti et al., 1990, Gene 90: 9-14), Thermobifida fusca endoglucanase III (WO 05/093050), and Thermobifida fusca endoglucanase V (WO 05/093050).

Examples of fungal endoglucanases that can be used in the present invention, include, but are not limited to, Trichoderma reesei endoglucanase I (Penttila et al., 1986, Gene 45: 253-263, Trichoderma reesei Cel7B endoglucanase I (GenBank:M15665), Trichoderma reesei endoglucanase II (Saloheimo et al., 1988, Gene 63:11-22), Trichoderma reesei Cel5A endoglucanase II (GenBank: M19373), Trichoderma reesei endoglucanase III (Okada et al., 1988, Appl. Environ. Microbiol. 64: 555-563, GenBank: AB003694), Trichoderma reesei endoglucanase V (Saloheimo et al., 1994, Molecular Microbiology 13: 219-228, GenBank:Z33381), Aspergillus aculeatus endoglucanase (Ooi et al., 1990, Nucleic Acids Research 18: 5884), Aspergillus kawachii endoglucanase (Sakamoto et al., 1995, Current Genetics 27: 435-439), Fusarium oxysporum endoglucanase (GenBank:L29381), Humicola grisea var. thermoidea endoglucanase (GenBank:AB003107), Melanocarpus albomyces endoglucanase (GenBank:MAL515703), Neurospora crassa endoglucanase (GenBank:XM_324477), Humicola insolens endoglucanase V, Myceliophthora thermophila CBS117.65 endoglucanase, Thermoascus aurantiacus endoglucanase I (GenBank:AF487830), and Trichoderma reesei strain No. VTT-D-80133 endoglucanase (GenBank:M15665).

Examples of cellobiohydrolases useful in the present invention include, but are not limited to, Aspergillus aculeatus cellobiohydrolase II (WO 2011/059740), Chaetomium thermophilum cellobiohydrolase I, Chaetomium thermophilum cellobiohydrolase II, Humicola insolens cellobiohydrolase I, Myceliophthora thermophila cellobiohydrolase II (WO 2009/042871), Penicillium occitanis cellobiohydrolase I (GenBank:AY690482), Talaromyces emersonii cellobiohydrolase I (GenBank:AF439936), Thielavia hyrcanie cellobiohydrolase II (WO 2010/141325), Thielavia terrestris cellobiohydrolase II (CEL6A, WO 2006/074435), Trichoderma reesei cellobiohydrolase I, Trichoderma reesei cellobiohydrolase II, and Trichophaea saccata cellobiohydrolase II (WO 2010/057086).

Examples of beta-glucosidases useful in the present invention include, but are not limited to, beta-glucosidases from Aspergillus aculeatus (Kawaguchi et al., 1996, Gene 173: 287-288), Aspergillus fumigatus (WO 2005/047499), Aspergillus niger (Dan et al., 2000, J. Biol. Chem. 275: 4973-4980), Aspergillus oryzae (WO 02/095014), Penicillium brasilianum IBT 20888 (WO 2007/019442 and WO 2010/088387), Thielavia terrestris (WO 2011/035029), and Trichophaea saccata (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used as a component of the enzyme composition.

Examples of GH61 polypeptides useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, and WO 2009/085868), *Aspergillus fumigatus* (WO 2010/138754), *Penicillium pinophilum* (WO 2011/005867), *Thermoascus* sp. (WO 2011/039319), *Penicillium* sp. (WO 2011/041397), *Thermoascus crustaceous* (WO 2011/041504), *Aspergillus aculeatus* (WO 2012/125925), *Thermomyces lanuginosus* (WO 2012/113340, WO 12/129, 699, and WO 2012/130964), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206).

In one aspect, the GH61 polypeptide variant and GH61 polypeptide having cellulolytic enhancing activity is used in the presence of a soluble activating divalent metal cation according to WO 2008/151043, e.g., manganese or copper.

In another aspect, the GH61 polypeptide variant and GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/13095), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8x212), and *Talaromyces thermophilus* GH11 (WO 2012/13095).

Examples of acetylxylan esterases useful in the processes of the present invention include, but are not limited to, acetylxylan esterases from *Aspergillus aculeatus* (WO 2010/

108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus fumigatus* catalase, *Aspergillus lentilus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, and Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. nae-*

*dodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another preferred aspect, the fermentation product is an alkane. The alkane may be an unbranched or a branched alkane. The alkane can be, but is not limited to, pentane, hexane, heptane, octane, nonane, decane, undecane, or dodecane.

In another preferred aspect, the fermentation product is a cycloalkane. The cycloalkane can be, but is not limited to, cyclopentane, cyclohexane, cycloheptane, or cyclooctane.

In another preferred aspect, the fermentation product is an alkene. The alkene may be an unbranched or a branched alkene. The alkene can be, but is not limited to, pentene, hexene, heptene, or octene.

In another preferred aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another preferred aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another preferred aspect, the fermentation product is isoprene.

In another preferred aspect, the fermentation product is a ketone. It will be understood that the term "ketone" encompasses a substance that contains one or more ketone moieties. The ketone can be, but is not limited to, acetone.

In another preferred aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The present invention also relates to detergent compositions comprising a GH61 polypeptide variant of the present invention and a surfactant. A GH61 polypeptide variant of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In one aspect, the present invention also relates to methods for cleaning or washing a hard surface or laundry, the method comprising contacting the hard surface or the laundry with a detergent composition of the present invention.

In a specific aspect, the present invention provides a detergent additive comprising a GH61 polypeptide variant of the invention. The detergent additive as well as the detergent composition may comprise one or more (e.g., several) enzymes selected from the group consisting of an amylase, arabinase, cutinase, carbohydrase, cellulase, galactanase, laccase, lipase, mannanase, oxidase, pectinase, peroxidase, protease, and xylanase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases:

Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a GH61 polypeptide variant of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A GH61 polypeptide variant having cellulolytic enhancing activity of the present invention may also be incorporated in the detergent formulations disclosed in WO 97/07202, which is hereby incorporated by reference.

Plants

The present invention also relates to isolated plants, e.g., a transgenic plant, plant part, or plant cell, comprising a polynucleotide of the present invention so as to express and produce a GH61 polypeptide variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences (Sticklen, 2008, *Nature Reviews* 9: 433-443), is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Strains

*Aspergillus oryzae* strain PFJO218 (amy⁻, alp⁻, Npl⁻, CPA⁻, KA⁻, pyrG⁻, ku70⁻; U.S. Patent Application 20100221783) was used as an expression host for the GH61 polypeptide variants.

*Aspergillus oryzae* strain COLs1300 was also used as an expression host for GH61 polypeptide variants. *A. niger* COLs1300 (amyA, amyB, amyC, alpA, nprA, kusA, niaD, niiA, amdS+) was created from *A. oryzae* PFJ0220 (EP 2 147 107 B1) by deleting the promoter and 5' part of both the nitrite reductase (niiA) gene and nitrate reductase (niaD) gene.

Media and Reagents

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, 3 g of citric acid, and deionized water to 1 liter.

COLs1300 protoplasting cultivating medium was composed of 100 ml of sucrose medium and 1 ml of 1 M urea.

COLs1300 protoplasting solution was composed of 80 mg of GLUCANEX® (Novozymes A/S, Bagsvaerd, Denmark), 0.5 mg/ml of chitinase (Sigma Chemical Co., Inc., St. Louis, Mo., USA), 10 ml of 1.2 M $MgSO_4$, and 100 µl of 1 M $NaH_2PO_4$ pH 5.8.

COVE-N-Gly plates were composed of 50 ml of COVE salt solution, 218 g of sorbitol, 10 g of glycerol, 2.02 g of $KNO_3$, 25 g of Noble agar, and deionized water to 1 liter.

COVE-N-Gly plates with 10 mM uridine were composed of 50 ml of COVE salt solution, 218 g of sorbitol, 10 g of glycerol, 2.02 g of $KNO_3$, 25 g of Noble agar, and deionized water to 1 liter; uridine was then added at a concentration of 10 mM to individual plates.

COVE salt solution was composed of 26 g of KCl, 26 g of $MgSO_4.7H_2O$, 76 g of $KH_2PO_4$, 50 ml of COVE trace elements solution, and deionized water to 1 liter.

COVE trace elements solution was composed of 40 mg of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

LB agar were composed of 5 g of starch (Merck, Whitehouse Station, N.J., USA), 37 g of LB agar (Sigma Chemical Co., Inc., St. Louis, Mo., USA), and deionized water to 1 liter.

LB+Amp agar plates were composed of LB agar supplemented with 150 µg of ampicillin per ml.

M400 medium was composed of 50 g of maltodextrin, 2 g of $MgSO_4.7H_2O$, 2 g of $KH_2PO_4$, 4 g of citric acid, 8 g of yeast extract, 2 g of urea, 0.5 ml of AMG trace metals solution, 0.5 g of $CaCl_2$, and deionized water to 1 liter; adjusted with NaOH to pH 6. After pH adjustment 0.7 ml of antifoam was added.

Magnificent broth was composed of 50 g of Magnificent Broth powder (MacConnell Research Corp. San Diego, Calif., USA) and deionized water to 1 liter.

MaltV1 medium was composed of 20 g of maltose, 10 g of Bacto Peptone, 1 g of yeast extract, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, 0.48 g of citric acid, 19.52 g of 2-(N-morpholino)ethanesulfonic acid (MES), and deionized water to 1 liter; adjusted with NaOH to pH 5.5.

MDU2BP medium (pH 5.0) was composed of 135 g of maltose, 3 g of $MgSO_4.7H_2O$, 3 g of NaCl, 6 g of $K_2SO_4$, 36 g of $KH_2PO_4$, 21 g of yeast extract, 6 g of urea, 1.5 ml of AMG trace metals solution, and deionized water up to 1 liter.

PEG solution was composed of 6 g of polyethylene glycol 4000 (PEG 4000), 100 µl of 1 M Tris pH 7.5, 100 µl of 1 M $CaCl_2$, and deionized water to 10 ml.

Protoplasting cultivation medium was composed of 92 ml of transformation sucrose medium, 2 ml of 1 M uridine, 1 ml of 1 M $NaNO_3$, and 10 ml of YP medium.

Protoplasting solution was composed of 15 ml of 1.2 M $MgSO_4$, 150 µl of 1 M $NaH_2PO_4$ (pH 5.8), 100 mg of GLUCANEX® (Novozymes A/S, Bagsvaerd, Denmark), and 10 mg of chitinase (Sigma Chemical Co., Inc., St. Louis, Mo., USA).

ST solution was composed of 1.5 ml of 2 M sorbitol, 500 µl of 1 M Tris pH 7.5, and deionized water to 5 ml.

STC solution was composed of 60 ml of 2 M sorbitol, 1 ml of 1 M Tris pH 7.5, 1 ml of 1 M $CaCl_2$, and deionized water to 100 ml.

Sucrose medium was composed of 20 ml of COVE salt solution, 342 g of sucrose, and deionized water to 1 liter.

Sucrose agar plates were composed of 20 ml of *Trichoderma* trace metals solution, 20 g of Noble agar, 342 g of sucrose, and deionized water to 1 liter.

TAE buffer was composed of 40 mM 2-amino-2-hydroxymethyl-propane-1,3-diol, 20 mM glacial acetic acid, and 2 mM ethylenediaminetetraacetic acid at pH 8.0.

TBE buffer was composed of 10.8 g of Tris base, 5.5 g of boric acid, and 0.74 g of EDTA (pH 8) in deionized water to 1 liter.

TE buffer was composed of 10 mM Tris-0.1 mM EDTA pH 8.

Top agar was composed of 500 ml of sucrose medium, 5 g of low melting agarose, and 10 ml of 20 mM Tris pH 7.5.

Transformation sucrose medium was composed of 70 ml of 1 M sucrose and 20 ml of COVE salt solution.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

2XYT agar plates were composed of 16 g of tryptone, 10 g of yeast extract, 5 g of NaCl, 15 g of Bacto agar, and deionized water to 1 liter.

2XYT+Amp agar plates were composed of 2XYT agar supplemented with 100 μg of ampicillin per ml.

YP medium was composed of 10 g of Bacto yeast extract, 20 g of Bacto peptone, and deionized water to 1 liter.

Plasmid pEN12376 (U.S. Patent Application 20060234340) containing the AMA sequence for autonomous maintenance in *Aspergillus* was digested with Bam HI and Not I to linearize the plasmid and remove an 8 bp fragment. The digested plasmid was purified using a PCR Purification Kit (QIAGEN Inc., Valencia, Calif., USA).

The *Aspergillus fumigatus* GH61B polypeptide coding sequence (FIG. 1; SEQ ID NO: 29 [genomic DNA sequence] and SEQ ID NO: 30 [deduced amino acid sequence]), mutated *Aspergillus fumigatus* GH61 B polypeptide coding sequence (WO 2012/044835), *Penicillium emersonii* GH61A polypeptide coding sequence (SEQ ID NO: 35 [genomic DNA sequence] and SEQ ID NO: 36 [deduced amino acid sequence]), and *Thermoascus aurantiacus* GH61A polypeptide coding sequence (SEQ ID NO: 13 [genomic DNA sequence] and SEQ ID NO: 14 [deduced amino acid sequence]) were amplified from source plasmids described below using the primers shown in Table 1. Bold letters represent coding sequence. The remaining sequences are homologous to insertion sites of pEN12376 for expression of the GH61 polypeptide coding sequences.

TABLE 1

| GH61 Polypeptide origin | Source Template | Plasmid | Primer ID | Primer Sequence |
|---|---|---|---|---|
| *Aspergillus fumigatus* GH61B | pAG43 (WO 2010/138754) | pMMar44 | AspfuGH61Bp ENI2376F_2 | CACAACTGGGGATCCATGACT TTGTCCAAGATCACTTCCA (SEQ ID NO: 171) |
| | | | AspfuGH61Bp EN12376R_2 | GGCCTCCGCGGCCGCTTAAG CGTTGAACAGTGCAGGACCA (SEQ ID NO: 172) |
| Mutated *Aspergillus fumigatus* GH61B | pTH230 (WO 2012/044835) | pMMar49 | AfumGH61SD MB3pENI3376 F | CACAACTGGGGATCCATGACT TTGTCCAAGATCACTTCCA (SEQ ID NO: 173) |
| | | | AfumGH61SD MB3pENI3376 R | GGCCTCCGCGGCCGCTTAAG CGTTGAACAGTGCAGGACCA (SEQ ID NO: 174) |
| *Penicillium emersonii* GH61A | pDM286 | pMMar45 | PenemGH61p ENI2376F | CACAACTGGGGATCCATGCTG TCTTCGACGACTCGCACCC (SEQ ID NO: 175) |
| | | | PenemGH61p ENI2376R | GGCCTCCGCGGCCGCCTAGA ACGTCGGCTCAGGCGGCCCC (SEQ ID NO: 176) |
| *Thermoascus aurantiacus* GH61A | pDZA2 (WO 2005/074656) | pDFng113 | TaGH61aBaM H1tagF | CTGGGGATCCATGTCCTTTTC CAAGAT (SEQ ID NO: 177) |
| | | | TaGH61aNcoI tagR | CTCCGCGGCCGCTTAACCAGT ATACAGAG (SEQ ID NO: 178) |

Example 1: Construction of Expression Vectors pMMar44, pMMar49, pMMar45, and pDFng113

Plasmid pMMar44 was constructed as described below for expression of the *Aspergillus fumigatus* GH61B polypeptide, and generation of mutant gene libraries. Additionally, plasmids pMMar49, pMMar45, and pDFng113 were constructed as described below for expression of the *Aspergillus fumigatus* GH61B polypeptide variants (WO 2012/044835). *Penicillium* sp. (*emersonii*) GH61A polypeptide (hereinafter *Penicillium emersonii* GH61A polypeptide), and *Thermoascus aurantiacus* GH61A polypeptide, respectively, and generation of variants.

Construction of plasmid pMMar44 containing the *Aspergillus fumigatus* GH61 B polypeptide coding sequence is described below. The *Aspergillus fumigatus* GH61B polypeptide coding sequence was amplified from plasmid pAG43 (WO 2010/138754) using the primers shown in Table 1 with overhangs designed for cloning into plasmid pENI2376.

Fifty picomoles of each of the primers listed in Table 1 were used in a PCR composed of 90 ng of pAG43, 1× ADVANTAGE® 2 PCR Buffer (Clontech Laboratories, Inc., Mountain View, Calif., USA), 1 μl of a blend of dATP, dTTP, dGTP, and dCTP, each at 10 mM, and 1× ADVANTAGE® 2 DNA Polymerase Mix (Clontech Laboratories, Inc., Mountain View, Calif., USA) in a final volume of 50 μl. The amplification was performed using an EPPENDORF® MASTERCYCLER® 5333 (Eppendorf Scientific, Inc., Westbury, N.Y., USA) programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit (QIAGEN Inc., Valencia, Calif., USA).

The homologous ends of the 862 bp PCR product and digested pENI2376 were joined together using an IN-FUSION™ ADVANTAGE® PCR Cloning Kit (Clontech Laboratories, Inc., Mountain View, Calif., USA). A total of 63 ng of the 862 bp PCR product and 200 ng of the Bam HI/Not I digested pENI2376 were used in a reaction composed of 4 µl of 5×IN-FUSION™ reaction buffer (Clontech Laboratories, Inc., Mountain View, Calif., USA) and 2 µl of IN-FUSION™ enzyme (Clontech Laboratories, Inc., Mountain View, Calif., USA) in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells (Stratagene, La Jolla, Calif., USA) according to the manufacturer's instructions. *E. coli* transformants were selected on 2XYT+Amp agar plates. Plasmid DNA from several of the resulting *E. coli* transformants was prepared using a BIOROBOT® 9600 (QIAGEN Inc., Valencia, Calif., USA). The *Aspergillus fumigatus* GH61B polypeptide coding sequence insert was confirmed by DNA sequencing using a Model 3130xL Genetic Analyzer (Applied Biosystems®, Life Technologies, Grand Island, N.Y., USA) and dye-terminator chemistry from a BigDye® Terminator v3.1 Cycle Sequencing Kit (Applied Biosystems®, Life Technologies). Sequencing primers used for verification of the gene insert and sequence are shown below.

```
Primer 996271:
                                      (SEQ ID NO: 179)
ACTCAATTTACCTCTATCCACACTT Primer pALLO2 3':
                                      (SEQ ID NO: 180)
GAATTGTGAGCGGATAACAATTTCA
```

A plasmid containing the correct *A. fumigatus* GH61B polypeptide coding sequence was selected and designated pMMar44 (FIG. 2).

Construction of plasmid pMMar49 containing eight base-pair changes resulted in four amino acid mutations of the *Aspergillus fumigatus* GH61B polypeptide (WO 2012/044835) is described below. The mutated *Aspergillus fumigatus* GH61 B polypeptide coding sequence (WO 2012/044835) was amplified from plasmid pTH230 using the primers shown in Table 1 with overhangs designed for cloning into plasmid pEN12376.

Fifty picomoles of each of the primers listed in Table 1 were used in a PCR composed of 100 ng of pTH230, 1× ADVANTAGE® 2 PCR Buffer (Clontech Laboratories, Inc., Mountain View, Calif., USA), 1 µl of a blend of dATP, dTTP, dGTP, and dCTP, each at 10 mM, and 1× ADVANTAGE® 2 DNA Polymerase Mix (Clontech Laboratories, Inc., Mountain View, Calif., USA) in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit.

The homologous ends of the 862 bp PCR product and the digested pEN12376 were joined together using an IN-FUSION™ ADVANTAGE® PCR Cloning Kit. A total of 90 ng of the 862 bp PCR product and 220 ng of the Bam HI/Not I digested pEN12376 were used in a reaction composed of 4 µl of 5×IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The mutated *Aspergillus fumigatus* GH61 B polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 3:
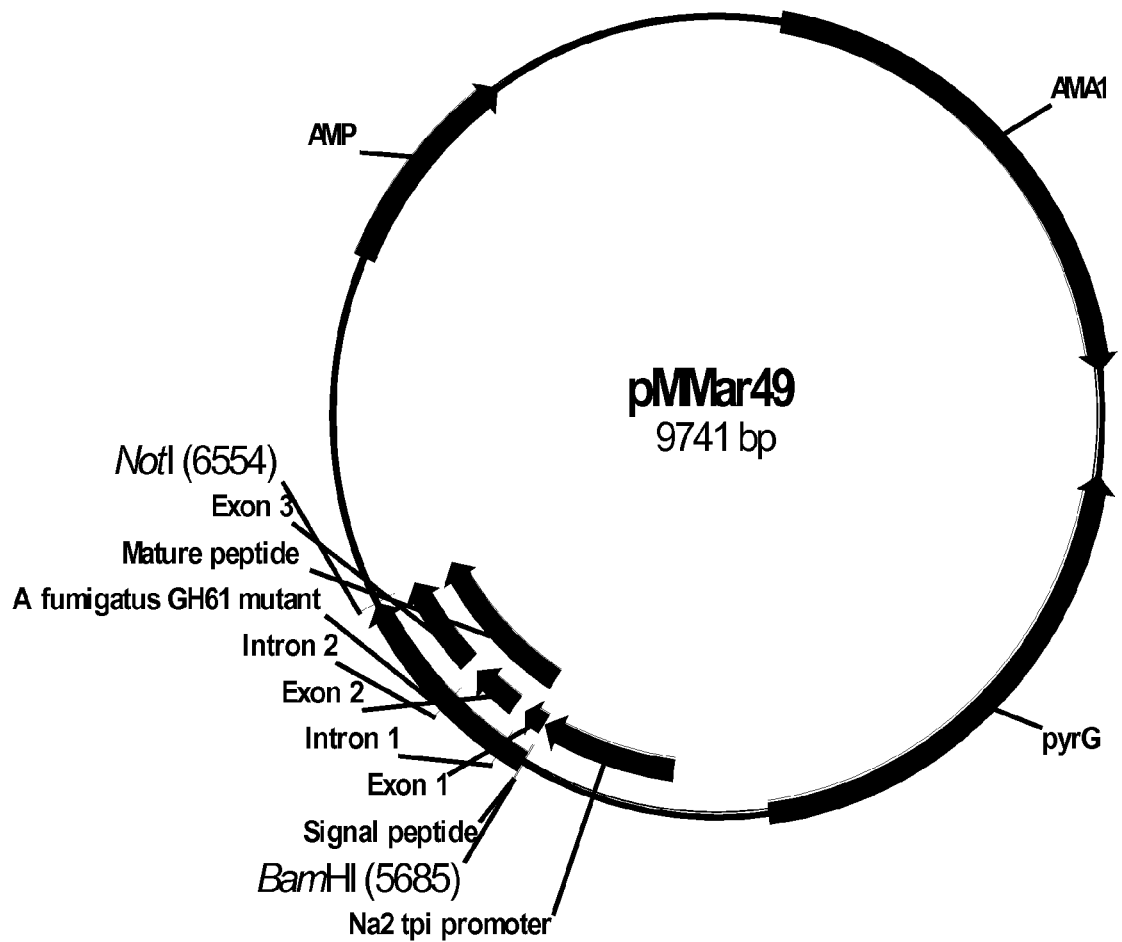
FIG. 3 shows a restriction map of pMMar49.

A plasmid containing the correct mutated *A. fumigatus* GH61B polypeptide coding sequence was selected and designated pMMar49 (FIG. 3).

Construction of plasmid pMMar45 containing the *Penicillium emersonii* GH61A polypeptide coding sequence is described below. The *Penicillium emersonii* GH61A polypeptide coding sequence was amplified from plasmid pDM286 containing the *Penicillium* emersonii GH61A polypeptide coding sequence using the primers shown in Table 1 with overhangs designed for cloning into plasmid pEN12376.

Plasmid pDM286 was constructed according to the following protocol. The *P. emersonii* GH61A polypeptide gene was amplified from plasmid pGH61D23Y4 (WO 2011/041397) using PHUSION™ High-Fidelity Hot Start DNA Polymerase (Finnzymes Oy, Espoo, Finland) and gene-specific forward and reverse primers shown below. The region in italics represents vector homology to the site of insertion.

```
Forward primer:
                                      (SEQ ID NO: 181)
5'-CGGACTGCGCACCATGCTGTCTTCGACGACTCGCAC-3'

Reverse primer:
                                      (SEQ ID NO: 182)
5'-TCGCCACGGAGCTTATCGACTTCTTCTAGAACGTC-3'
```

The amplification reaction contained 30 ng of plasmid pGH61 D23Y4, 50 µmoles of each of the primers listed above, 1 µl of a 10 mM blend of dATP, dTTP, dGTP, and dCTP, 1× PHUSION™ High-Fidelity Hot Start DNA Polymerase buffer (Finnzymes Oy, Espoo, Finland) and 1 unit of PHUSION™ High-Fidelity Hot Start DNA Polymerase in a final volume of 50 µl.

The amplification reaction was incubated in an EPPENDORF® MASTERCYCLER® 5333 epgradient S (Eppendorf Scientific, Inc., Westbury, N.Y., USA) programmed for 1 cycle at 98° C. for 30 seconds; 35 cycles each at 98° C. for 10 seconds, 60° C. for 30 seconds, and 72° C. for 30 seconds, and 1 cycle at 72° C. for 10 minutes.

PCR products were separated by 1% agarose gel electrophoresis using TAE buffer. A 0.87 kb fragment was excised from the gel and extracted using a NUCLEOSPIN® Extract II Kit (Macherey-Nagel, Inc., Bethlehem, Pa., USA).

Plasmid pMJ09 (US 2005/0214920 A1) was digested with Nco I and Pac I, and after digestion, the digested vector was isolated by 1.0% agarose gel electrophoresis using TBE buffer where an approximately 7.1 kb fragment was excised from the gel and extracted using a QIAQUICK® Gel Extraction Kit. The 0.87 kb PCR product was inserted into Nco I/Pac I-digested pMJ09 using an IN-FUSION™ ADVANTAGE® PCR Cloning Kit according to the manufacturer's protocol. The IN-FUSION™ reaction was composed of 1×IN-FUSION™ Reaction buffer, 180 ng of Not I/Pac I digested plasmid pMJ09, 108 ng of the 0.87 kb PCR product, and 1 µl of IN-FUSION™ Enzyme in a 10 µl reaction volume. The reaction was incubated for 15 minutes at 37° C. and then for 15 minutes at 50° C. To the reaction 40 µl of TE were added and 2 µl were used to transform ONE SHOT® TOP10 competent cells (Invitrogen, Carlsbad, Calif., USA) according to the manufacturer's protocol. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer and dye-terminator chemistry from a BigDye® Terminator v3.1 Cycle Sequencing Kit. One clone containing the insert with no PCR errors was identified and designated plasmid pDM286. Plasmid pDM286 can be digested with Pme I to generate an approximately 5.4 kb fragment for *T. reesei* transformation. This 5.4 kb fragment contains the expression cassette [*T. reesei* Cel7A cellobiohydrolase (CBHl) promoter, P. emersonii glycosyl hydrolase 61A (GH61A) gene, *T. reesei* Cel7A cellobiohydrolase (CBHl) terminator], and *Aspergillus nidulans* acetamidase (amdS) gene.

For construction of pMMar45, 50 picomoles of each of the primers listed in Table 1 were used in a PCR composed of 120 ng of pDM286, 1× EXPAND® PCR Buffer (Roche Diagnostics, Inc., Indianapolis, Ind., USA), 1 µl of a blend of dATP, dTTP, dGTP, and dCTP, each at 10 mM, and 1× EXPAND® DNA Polymerase Mix (Roche Diagnostics, Inc., Indianapolis, Ind., USA) in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 762 bp PCR product band was excised from the gel and extracted using a QIAQUICK® Gel Extraction Kit.

The homologous ends of the 762 bp PCR product and the Bam HI/Not I digested pEN12376 were joined together using an IN-FUSION™ ADVANTAGE® PCR Cloning Kit. A total of 90 ng of the 762 bp PCR product and 200 ng of the digested pENI2376 were used in a reaction composed of 4 µl of 5×IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The P. emersonii GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 4:
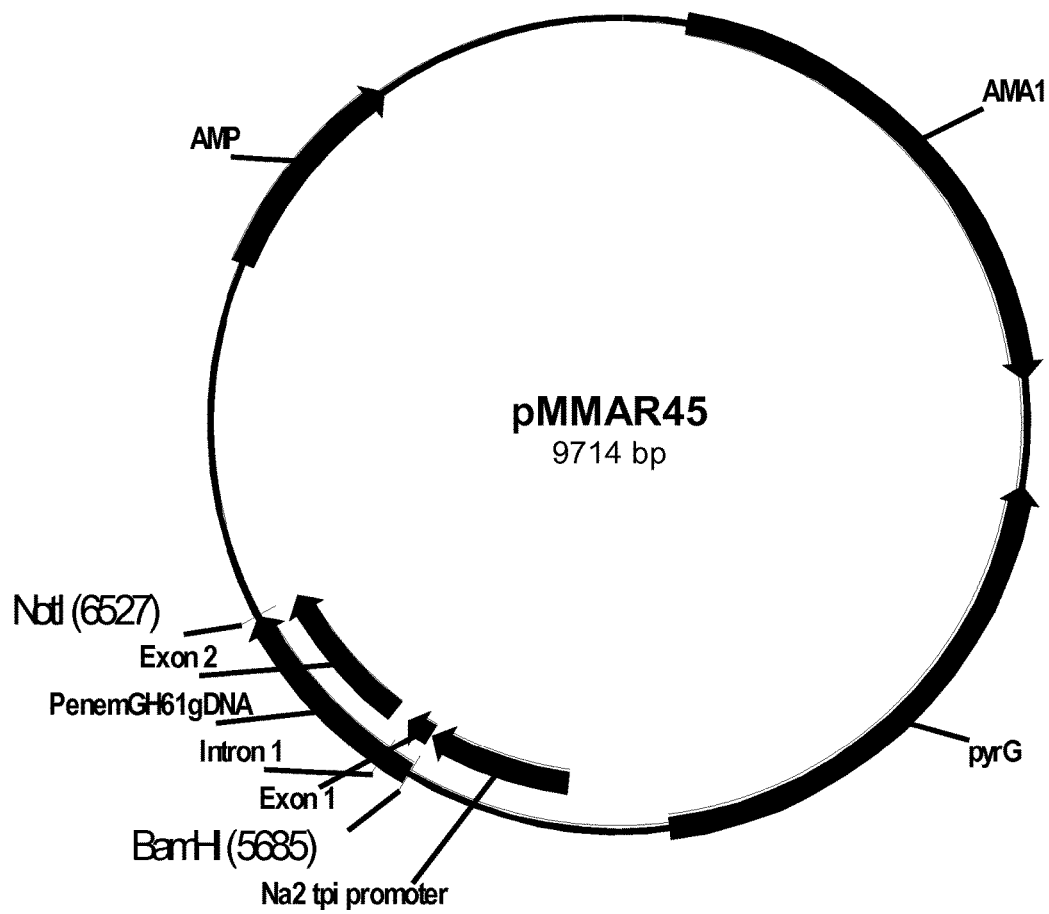
FIG. 4 shows a restriction map of pMMar45.

A plasmid containing the correct P. emersonii GH61A polypeptide coding sequence was selected and designated pMMar45 (FIG. 4).

Construction of plasmid pDFng113 containing the *Thermoascus aurantiacus* GH61A polypeptide coding sequence is described below. The *Thermoascus aurantiacus* GH61A polypeptide coding sequence was amplified from plasmid pDZA2 (WO 2005/074656) using the primers shown in Table 1 with overhangs designed for cloning into plasmid pENI2376.

Fifty picomoles of each of the primers listed in Table 1 were used in a PCR composed of 100 ng of pDZA2, 1× EXPAND® PCR Buffer, 1 µl of a blend of dATP, dTTP, dGTP, and dCTP, each at 10 mM, and 1× EXPAND® DNA Polymerase Mix in a final volume of 50 µl. The amplification reaction was performed using an EPPENDORF® MASTERCYCLER® 5333 programmed for 1 cycle at 94° C. for 2 minutes; 30 cycles each at 94° C. for 15 seconds, 59.9° C. for 30 seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 822 bp PCR product band was excised from the gel and extracted using a QIAQUICK® Gel Extraction Kit.

The homologous ends of the 822 bp PCR product and the Bam HI/Not I digested pENI2376 were joined together using an IN-FUSION™ ADVANTAGE® PCR Cloning Kit. A total of 37 ng of the 799 bp PCR product and 200 ng of the digested pENI2376 were used in a reaction composed of 4 µl of 5×IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 50 µl with TE buffer and 2 µl of the reaction were transformed into *E. coli* XL10-GOLD® Ultracompetent Cells (Stratagene, La Jolla, Calif., USA) according to the manufacturer's instructions. *E. coli* transformants were selected on 2XYT+Amp agar plates. Plasmid DNA from several of the resulting *E. coli* transformants was prepared using a BIOROBOT® 9600. The *T. aurantiacus* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers 996271 and pALLO2 3' were used for verification of the gene insert and sequence.

Figure 5:
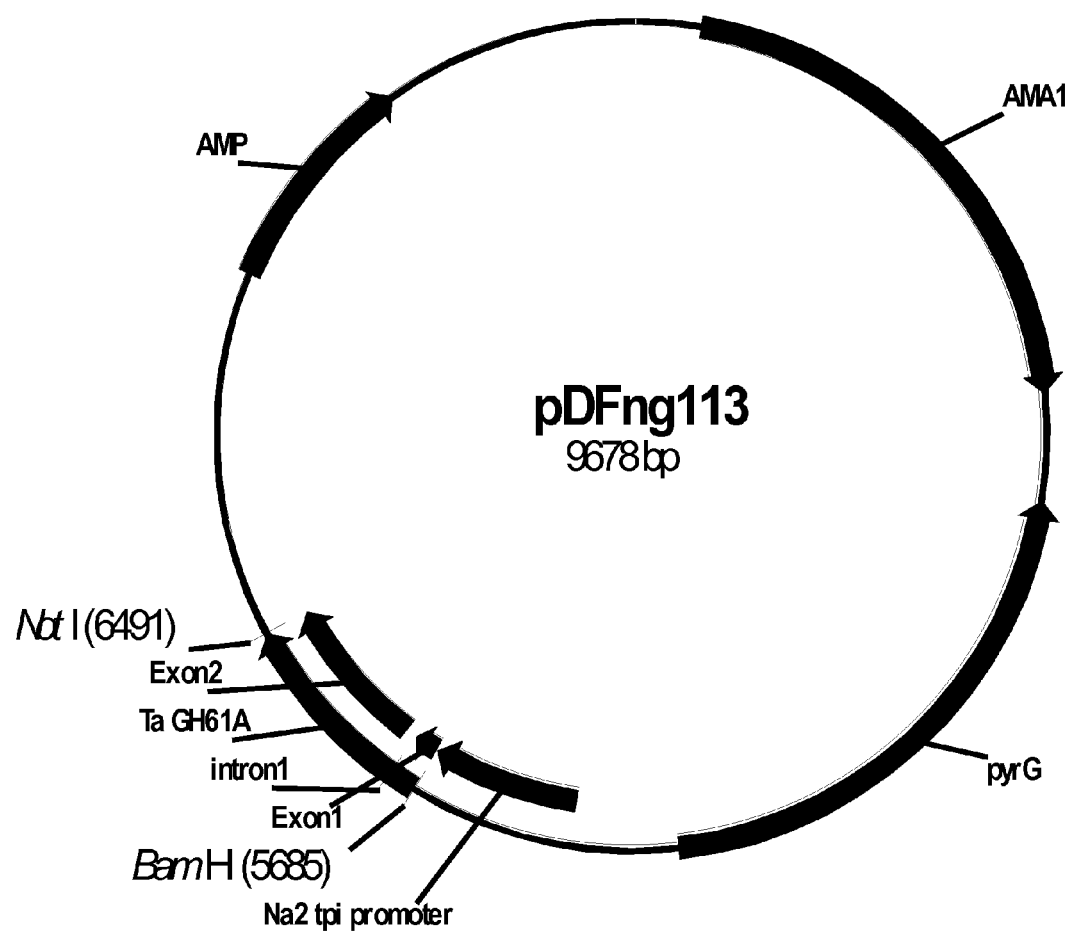
FIG. 5 shows a restriction map of pDFng113.

A plasmid containing the correct *T. aurantiacus* GH61A polypeptide coding sequence was selected and designated pDFng113 (FIG. 5).

Example 2: Construction of an *Aspergillus fumigatus* GH61B Polypeptide Site Saturation Library A site saturation library of the *Aspergillus fumigatus* GH61B polypeptide coding sequence was synthesized by GeneArt AG (Regensburg, Germany). An average of 16.8 mutations per position was synthesized for a total of 165 residues, excluding the most conserved residues, resulting in a total of 2768 mutants. *E. coli* DH10B (Invitrogen, Carlsbad, Calif., USA) strains containing mutant plasmids with known mutations were arrayed in 96 well plates as 50 µl glycerol stocks, and stored at −80° C.

DNA was generated from a thawed GeneArt plate by using a sterile 96 well replicator to stamp the GeneArt plate onto a 2XYT agar plate containing 100 µg/ml of ampicillin. The agar plate was incubated overnight at 37° C. Resulting colonies from the agar plate were used to inoculate a 96 deep well block with each well containing 1 ml of Magnificent broth supplemented with 400 µg of ampicillin per ml. The block was covered with an airpore breathable lid and then incubated in a humidified box at 37° C. overnight at 350 rpm. The block was centrifuged at 1100×g for 10 minutes and the supernatant discarded. Plasmids were extracted from the cell pellets using a BIOROBOT® 9600.

Example 3: Expression of the Wild-Type and Variants of the *A. fumigatus* GH61B Polypeptide and *P. emersonii* GH61A Polypeptide in *Aspergillus oryzae* PFJO218

*Aspergillus oryzae* PFJO218 was inoculated onto a COVE-N-Gly plate with 10 mM uridine and incubated at 34° C. until confluent. Spores were collected from the plate by washing with 8 ml of 0.01% TWEEN® 20. One ml of the spore suspension was used to inoculate 103 ml of the Protoplasting cultivation medium in a 500 ml polycarbonate shake flask. The shake flask was incubated at 30° C. with agitation at 180 rpm for 17-20 hours. Mycelia were filtered through a funnel lined with MIRACLOTH® (Calbiochem, La Jolla, Calif., USA) and washed with 200 ml of 0.6 M $MgSO_4$. Washed mycelia were resuspended in 15 ml of Protoplasting solution in a 125 ml sterile polycarbonate shake flask and incubated on ice for 5 minutes. One ml of a solution of 12 mg of bovine serum albumin per ml of deionized water was added to the shake flask and the shake flask was then incubated at 37° C. with mixing at 70 rpm for 1-3 hours until protoplasting was complete. The mycelia/protoplast mixture was filtered through a funnel lined with MIRACLOTH® into a 50 ml conical tube and overlayed with 5 ml of ST solution. The 50 ml conical tube was centrifuged at 1050×g for 15 minutes with slow acceleration/deceleration. After centrifugation, the liquid was separated into 3 phases. The interphase which contained the protoplasts was transferred to a new 50 ml conical tube. Two volumes of STC solution were added to the protoplasts followed by a brief centrifugation at 1050×g for 5 minutes. The supernatant was discarded. The protoplasts were washed twice with 20 ml of STC with resuspension of the protoplast pellet, centrifugation at 1050×g for 10 minutes, and decanting of the supernatant each time. After the final decanting, the protoplast pellet was resuspended in STC at a concentration of $1×10^8$/ml. Protoplasts were frozen at −80° C. until transformation.

A 1.3 µl volume of each mutant plasmid was used to transform 3.5 µl of *A. oryzae* PFJO218 protoplasts with 3.5 µl of PEG solution per well in a 24 well plate. Plasmid pMMar44 or pMMar45 (Table 1) was also transformed as above into *A. oryzae* PFJO218 protoplasts to provide broth comprising the *A. fumigatus* or *P. emersonii* wild-type GH61 polypeptides. The 24 well plate was incubated at 37° C. stationary for 30 minutes followed by addition of 28.6 µl of Transformation sucrose medium containing 10 mM $NaNO_3$ and 14.3 µl of STC. The 24 well plate was then placed in a humidified box at 37° C. stationary for 7 days. On day 7, 1 ml of MaltV1 medium was added to each well. The plate was returned to the humidified box at 39° C. stationary and incubated for an additional 5 days. At least 550 µl of broth for each variant or the wild-type *A. fumigatus* or *P. emersonii* GH61 polypeptide were harvested using a pipette to remove the mycelia mat and aspirate the liquid, for assay using PASC as a substrate. Mutant plasmids resulting in variants with improved thermostability using a PASC assay (Example 5) were transformed again and retested using the protocols described above.

Some of the variants were spore-purified for further characterization. After a 7 day incubation of the transformation and prior to the addition of 1 ml of MaltV1 expression medium, a loop was swiped over the initial growth from the transformation to collect spores in the well. The spores were then streaked onto a COVE-N-Gly plate and incubated at 37° C. for approximately 36 hours. Single individual transformants were excised from the plate and transferred onto fresh COVE-N-Gly plates. The plates were stored at 34° C. until confluent. Once confluent, a loop dipped in 0.01% TWEEN® 20 was swiped over the spores which was then used to inoculate a 24 well plate with each well containing 1 ml of MaltV1 expression medium. The 24 well plate was placed in a humidified box at 39° C. Samples were harvested on the fifth day by removing the mycelia mat and pipetting up the broth.

Example 4: Preparation of *Aspergillus fumigatus* Beta-Glucosidase

*Aspergillus fumigatus* NN055679 Cel3A beta-glucosidase (SEQ ID NO: 169 [DNA sequence] and SEQ ID NO: 170 [deduced amino acid sequence]) was recombinantly prepared according to WO 2005/047499 using *Aspergillus oryzae* as a host.

The filtered broth was adjusted to pH 8.0 with 20% sodium acetate, which made the solution turbid. To remove the turbidity, the solution was centrifuged (20000×g for 20 minutes), and the supernatant was filtered through a 0.2 µm filtration unit (Nalgene, Rochester, N.Y., USA). The filtrate was diluted with deionized water to reach the same conductivity as 50 mM Tris/HCl, pH 8.0. The adjusted enzyme solution was applied to a Q SEPHAROSE® Fast Flow column (GE Healthcare, Piscataway, N.J., USA) equilibrated with 50 mM Tris-HCl pH 8.0 and eluted with a linear gradient from 0 to 500 mM sodium chloride. Fractions were pooled and treated with VA (w/v) activated charcoal to remove color from the beta-glucosidase pool. The charcoal was removed by filtration of the suspension through a 0.2 µm filtration unit (Nalgene, Rochester, N.Y., USA). The filtrate was adjusted to pH 5.0 with 20% acetic acid and diluted 10 times with deionized water. The adjusted filtrate was applied to a SP SEPHAROSE® Fast Flow column (GE Healthcare, Piscataway, N.J., USA) equilibrated with 10 mM succinic acid pH 5.0 and eluted with a linear gradient from 0 to 500 mM sodium chloride. Protein concentration was determined using a Microplate BCA™ Protein Assay Kit (Thermo Fischer Scientific, Waltham, Mass., USA) in which bovine serum albumin was used as a protein standard.

Example 5: Screening of *Aspergillus fumigatus* GH61B and *Penicillium emersonii* GH61A Polypeptide Variant Libraries Using a BIOMEK® FX Laboratory Automation Workstation (Beckman Coulter, Fullerton, Calif., USA) with a DYAD® Thermal Cycler (Bio-Rad Laboratories, Inc., Richmond, Calif., USA), 80 µl of each broth sample from the library plates of the *Aspergillus fumigatus* GH61B variants and parent (wild-type) polypeptide grown in MaltV1 medium (Example 3) were mixed with 20 µl of 1 M sodium acetate-10 mM MnSO$_4$ pH 5.0 buffer. Depending on the library, the samples were then heat challenged at 62° C., 65° C., 68° C., 72° C., or 75° C. for 20 minutes and compared to ambient temperature controls. After the heat challenge, the broth samples were diluted 1.25, 2.5, 6.25, and 15.625-fold in 2 mM MnSO$_4$-200 mM sodium acetate pH 5 and 12.5 µl of the dilutions were then transferred to 384-well polypropylene assay plates containing 25 µl of 1% phosphoric acid swollen cellulose (PASC) and 12.5 µl of a cofactor solution (400 mM sodium acetate pH 5, 4 mM MnSO$_4$, 0.4% gallic acid, 0.1 mg/ml of *Aspergillus fumigatus* beta-glucosidase, and 0.04% TRITON® X100). The plates were heat-sealed using an ALPS-300™ (Abgene, Epsom, United Kingdom) with a plastic sheet and incubated at 40° C. for 4 days.

Background glucose concentration of the buffer-treated broth samples was determined prior to incubation by performing a glucose assay using the following reagents per liter: 0.9951 g of ATP, 0.5176 g of NAD, 0.5511 g of MgSO$_4$.7H$_2$O, 20.9 g of MOPS, 1000 units of hexokinase, 1000 units of glucose-6-phosphate dehydrogenase, and 0.01% TRITON® X-100, pH 7.5. The BIOMEK® FX Laboratory Automation Workstation was used for this assay. Four 2-fold serial dilutions were performed in 384-well polystyrene plates using water as diluent. Five µl of the dilutions were added to a new 384-well polystyrene plate, followed by addition of 60 µl of the above reagents. The plate was incubated at ambient temperature (22° C.±2° C.) for 30 to 45 minutes. Relative fluorescent units (RFU) were determined using a DTX 880 plate reader (Beckman Coulter, Fullerton, Calif., USA) with excitation at 360 nm and emission at 465 nm and compared to glucose standards (1 mg/ml and 0.125 mg/ml) diluted in the same plate as the samples. At the end of four days, the 40° C. incubated PASC plates were analyzed for glucose concentration using the glucose assay described above. Any background glucose was subtracted from the appropriate samples and then residual activity was calculated by comparing the glucose released in the PASC assay of the ambient sample treatment to the glucose released in the PASC assay of the heat challenged sample. Only data that fits in the linear part of the curve (defined as less than or equal to 1 mg/ml glucose produced in an assay containing 5 mg/ml PASC) was used in the calculation. The formula for calculating the residual activity of the heat treatment was as follows: (mg/ml glucose produced for heat treated sample/mg/ml glucose produced for ambient treated sample)×100%. Improved variants were those having a higher % residual activity as compared to wild-type *A. fumigatus* GH61A polypeptide broth from MaltV1 medium in at least one heat treatment condition. MICROSOFT® EXCEL® (Microsoft Corporation, Redmond, Wash., USA) was used for all calculations.

Example 6: Thermostability of *Aspergillus fumigatus* GH61B Variants Measured by Residual Activity After Heat Treatment Based on the residual activity ratios as described in Example 5, screening of libraries constructed in the previous Examples generated the results listed in Table 2.

Table 2 shows average % Residual Activity (from 3-5 samples of each variant and the wild-type control) after treatment at 62, 65, or 68° C. The parent *Aspergillus fumigatus* GH61B polypeptide showed decreased residual activity of 56%, 35%, and 12% when the temperature was increased from 62° C. to 65° C. to 68° C., respectively. The increase in thermostability of the *Aspergillus fumigatus* GH61 B polypeptide variants ranged from 1.02- to 1.3-fold increase when treated at 62° C., 1.06- to 1.7-fold increase when treated at 65° C., and 1.3- to 3.8-fold increase when treated at 68° C. compared to the wild-type *A. fumigatus* GH61 polypeptide. The results showed that improvements were most significant when treated at 68° C.

TABLE 2

Variants with improved thermostability at 62, 65, or 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| Parent (Wild-Type) | 56% | 13% | 35% | 16% | 12% | 10% |
| S26I | 71% | 8% | 59% | 15% | 36% | 17% |
| G32E | 64% | 21% | 50% | 24% | 28% | 20% |
| G32S | 67% | 17% | 50% | 20% | 33% | 15% |
| Y34F | 50% | 6% | 38% | 9% | 25% | 21% |
| V40A | 46% | 10% | 35% | 7% | 22% | 7% |
| N41T | 59% | 21% | 56% | 22% | 41% | 30% |
| Q42E | 60% | 20% | 43% | 15% | 27% | 19% |
| Q42I | 48% | 7% | 50% | 16% | 41% | 33% |
| Q42V | 62% | 22% | 47% | 14% | 28% | 14% |
| S47R | 58% | 13% | 41% | 17% | 18% | 11% |
| S47E | 58% | 11% | 47% | 11% | 22% | 4% |
| S47L | 52% | 13% | 42% | 7% | 18% | 6% |
| S56T | 53% | 8% | 41% | 15% | 19% | 15% |
| S56E | 59% | 9% | 40% | 12% | 22% | 16% |
| S56C | 55% | 10% | 38% | 15% | 16% | 14% |
| S72Q | 57% | 6% | 45% | 8% | 31% | 21% |
| S72T | 60% | 13% | 45% | 7% | 25% | 12% |
| T102K | 60% | 2% | 44% | 10% | 26% | 7% |
| T102P | 55% | 7% | 42% | 9% | 33% | 18% |
| A123R | 52% | 7% | 39% | 9% | 17% | 15% |
| Q138C | 67% | 13% | 51% | 16% | 35% | 15% |

TABLE 2-continued

Variants with improved thermostability at 62, 65, or 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| Q138E | 63% | 15% | 58% | 10% | 46% | 11% |
| Q138K | 69% | 11% | 58% | 8% | 46% | 13% |
| Q138L | 69% | 11% | 56% | 16% | 39% | 17% |
| Q138M | 62% | 12% | 55% | 11% | 34% | 21% |
| Q138G | 53% | 11% | 47% | 13% | 29% | 21% |
| V149I | 53% | 2% | 43% | 4% | 28% | 11% |
| D152S | 64% | 7% | 59% | 8% | 39% | 17% |
| T163V | 60% | 13% | 50% | 5% | 24% | 3% |
| T163F | 61% | 15% | 47% | 8% | 20% | 5% |
| T163E | 59% | 13% | 43% | 8% | 21% | 4% |
| V164C | 58% | 12% | 48% | 7% | 24% | 3% |
| V164L | 56% | 9% | 40% | 5% | 16% | 1% |
| I166L | 59% | 16% | 45% | 11% | 17% | 3% |
| S169R | 45% | 9% | 48% | 14% | 38% | 29% |
| S186K | 47% | 8% | 41% | 9% | 38% | 22% |
| S186F | 46% | 11% | 38% | 11% | 28% | 15% |
| S186T | 46% | 23% | 35% | 25% | 31% | 29% |
| S186Y | 45% | 19% | 37% | 16% | 32% | 20% |
| F200I | 42% | 13% | 40% | 13% | 32% | 15% |
| F200V | 48% | 14% | 45% | 19% | 32% | 31% |
| G207P | 60% | 12% | 40% | 17% | 20% | 14% |
| S213E | 50% | 12% | 35% | 11% | 18% | 8% |
| S219C | 45% | 9% | 35% | 4% | 27% | 6% |
| S219E | 47% | 12% | 39% | 7% | 28% | 8% |
| S219M | 48% | 9% | 42% | 13% | 31% | 18% |
| S219Q | 49% | 12% | 41% | 30% | 31% | 31% |
| K222R | 61% | 14% | 50% | 24% | 35% | 35% |
| S234K | 52% | 22% | 36% | 21% | 17% | 26% |
| S234G | 68% | 13% | 45% | 18% | 27% | 27% |
| A246P | 56% | 7% | 43% | 11% | 26% | 15% |
| N249Q | 67% | 14% | 52% | 16% | 36% | 20% |
| N249R | 61% | 19% | 46% | 20% | 32% | 22% |

Example 7: Thermostability of *Aspergillus fumigatus* GH61B Polypeptide Combinatorial Variants Plasmid pLSBF09-3 was constructed as a template for subsequent *Aspergillus fumigatus* GH61B combinatorial variants. This plasmid was constructed by performing a single site-directed mutagenesis reaction on pMMar49 (Example 1) using a QUIKCHANGE® II XL Site-Directed Mutagenesis Kit (Stratagene, La Jolla, Calif., USA). Two mutagenic primers were designed to insert the desired mutation. The PCR was composed of 125 ng of each primer, approximately 25 ng of template plasmid, 1× QUIKCHANGE® reaction buffer (Stratagene, La Jolla, Calif., USA), 3 µl of QUIKSOLUTION® (Stratagene, La Jolla, Calif., USA), 1 µl of XL dNTP mix, and 1 µl of 2.5 U/µl Pfu ULTRA™ enzyme (Stratagene, La Jolla, Calif., USA) in a final volume of 50 µl. The amplification reaction was performed using an EPPENDORF® MASTERCYCLER® thermocycler programmed for a 95° C. hot start; 1 cycle at 95° C. for 1 minute; 18 cycles each at 95° C. for 50 seconds, 60° C. for 50 seconds, and 68° C. for 10 minutes; and a 4° C. hold. One microliter of Dpn I was directly added to the amplification reaction and incubated at 37° C. for 1 hour. A 2 µl volume of the Dpn I digested reaction was used to transform *E. coli* XL10-GOLD® Ultracompetent Cells according to the manufacturer's instructions. *E. coli* transformants were selected on 2XYT+Amp agar plates. One of the clones with the desired mutation was designated pLSBF09-3. Using pLSBF09-3 as a template, two additional combinatorial plasmids were constructed. Plasmids pDFng146 and pDFng148 were each mutagenized as described above. The primers used in these reactions are shown in Table 3.

TABLE 3

| Plasmid | Mutations | Parent Plasmid | Oligo ID # | Sequence |
|---|---|---|---|---|
| pLSBF09-3 | L111V, D152S, M155L, A162W, K229W | pMMar49 | 615628 | ACAAGAATACTGATCC TGGCATCTGGTTTGAC ATCTACTCGGATCTGA G (SEQ ID NO: 183) |
| | | | 615632 | CTCAGATCCGAGTAGA TGTCAAACCAGATGCC AGGATCAGTATTCTTG T (SEQ ID NO: 184) |
| pDFng146 | L111V, D152S, M155L, A162W, G188F, K229W | pLSBF09-3 | 1200378 | ATCATCGCCCTTCACT CTGCGTTTAACCTGAA CGGCGCGCAGAAC (SEQ ID NO: 185) |
| | | | 1200379 | GTTCTGCGCGCCGTTC AGGTTAAACGCAGAGT GAAGGGCGATGAT (SEQ ID NO: 186) |
| pDFng148 | L111V, D152S, M155L, A162W, Q138K, K229W | pLSBF09-3 | 1200382 | GAAGTTTGTCAAGATC GCCGCTAAGGGCTTGA TCGACGGCTCCAAC (SEQ ID NO: 187) |
| | | | 1200383 | GTTGGAGCCGTCGATC AAGCCCTTAGCGGCGA TCTTGACAAACTTC (SEQ ID NO: 188) |

Seven variants (pLSBF15, 17, 18, 20, 22, 53, and pDFNG145) of the *Aspergillus fumigatus* GH61B polypeptide were constructed by adding a single amino acid mutation on top of pLSBF09-3 or pDFng148 using a QUIKCHANGE® II XL Site-Directed Mutagenesis Kit). The site directed mutagenesis method described above was used in the construction of these mutants as well. Primers used in these reactions are shown in Table 4.

Four additional variants (pLSBF47, 48, 49, and 54) of *Aspergillus fumigatus* GH61B were constructed via multi-site-directed mutagenesis of pDFng146 or pDFng148 using a QUIKCHANGE® Lightning Multi Site-Directed Mutagenesis Kit (Stratagene, La Jolla, Calif., USA). One mutagenic primer was designed for each desired mutation. One hundred ng of each primer (Table 4) were used in a PCR containing approximately 100 ng of template plasmid, 1× QUIKCHANGE® Lightning Multi Buffer (Stratagene, La Jolla, Calif., USA), 0.5 µl of QUIKSOLUTION® (Stratagene, La Jolla, Calif., USA), 1 µl of dNTP mix, and 1 µl of QUIKCHANGE® Lightning Multi enzyme blend (Stratagene, La Jolla, Calif., USA) in a final volume of 25 µl. The amplification reaction was performed using an EPPENDORF® MASTERCYCLER® thermocycler programmed for a 95° C. hot start; 1 cycle at 95° C. for 2 minutes; 30 cycles each at 95° C. for 20 seconds, 55° C. for 30 seconds, and 65° C. for 5 minutes; 1 cycle at 65° C. for 5 minutes, and a 4° C. hold. One microliter of Dpn I was directly added to the amplification reaction and incubated at 37° C. for 5 minutes. A 1.5 µl volume of the Dpn I digested reaction was transformed into *E. coli* XL10-GOLD® Ultracompetent Cells according to the manufacturer's instructions. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer and dye-terminator chemistry from a BigDye® Terminator v3.1 Cycle Sequencing Kit. One of the clones with the desired mutations was designated as each plasmid listed below. The *A. fumigatus* GH61A polypeptide variants were expressed using *Aspergillus oryzae* PFJO218 as host was performed according to the procedure described in Example 3.

TABLE 4

| Plasmid | Mutations | Parent Plasmid | Oligo ID | #Sequence |
|---|---|---|---|---|
| pLSBF15 | L111V, D152S, M155L, A162W, S47E, K229W | pLSBF09-3 | 1200265 | CTTGTTAACCAATACCCCTACATGGAAA ACCCTCCCGACACCATTGCC (SEQ ID NO: 189) |
| | | | 1200266 | GGCAATGGTGTCGGGAGGGTTTTCCAT GTAGGGGTATTGGTTAACAAG (SEQ ID NO: 190) |
| pLSBF17 | L111V, D152S, M155L, A162W, S56A, K229W | pLSBF09-3 | 1200269 | CTCCCGACACCATTGCCTGGGCCACCA CCGCCACCGACCTCG (SEQ ID NO: 191) |
| | | | 1200270 | CGAGGTCGGTGGCGGTGGTGGCCCAG GCAATGGTGTCGGGAG (SEQ ID NO: 192) |
| pLSBF18 | L111V, D152S, M155L, A162W, T102K, K229W | pLSBF09-3 | 1200271 | ACAGATCGAATTCCAGTGGACGAAGTG GCCAGAGTCTCACCATGGA (SEQ ID NO: 193) |
| | | | 1200272 | ACAGATCGAATTCCAGTGGACGAAGTG GCCAGAGTCTCACCATGGA (SEQ ID NO: 194) |
| pLSBF20 | L111V, D152S, M155L, A162W, T102K, E105K, K229W | pLSBF09-3 | 1200275 | CCAGTGGACGAAGTGGCCAAAGTCTCA CCATGGACCG (SEQ ID NO: 195) |
| | | | 1200276 | CGGTCCATGGTGAGACTTTGGCCACTT CGTCCACTGG (SEQ ID NO: 196) |
| pLSBF22 | L111V, D152S, M155L, A162W, K229W, S234G | pLSBF09-3 | 1200279 | CTGGCATCTGGTTTGACATCTACGGCG ATCTGAGCGGTGGATACCCT (SEQ ID NO: 197) |
| | | | 1200280 | AGGGTATCCACCGCTCAGATCGCCGTA GATGTCAAACCAGATGCCAG (SEQ ID NO: 198) |
| pLSBF53 | L111V, D152S, M155L, A162W, Q138K, G188F, K229W | pDFng148 | 1200378 | ATCATCGCCCTTCACTCTGCGTTTAACC TGAACGGCGCGCAGAAC (SEQ ID NO: 199) |
| | | | 1200379 | GTTCTGCGCGCCGTTCAGGTTAAACGC AGAGTGAAGGGCGATGAT (SEQ ID NO: 200) |
| pDFng145 | L111V, D152S, M155L, A162W, S186T, K229W | pLSBF09-3 | 1200376 | CACGAGATCATCGCCCTTCACACCGCG GGTAACCTGAACGGCGC (SEQ ID NO: 201) |
| | | | 1200377 | GCGCCGTTCAGGTTACCCGCGGTGTG AAGGGCGATGATCTCGTG (SEQ ID NO: 202) |

TABLE 4-continued

| Plasmid | Mutations | Parent Plasmid | Oligo ID | #Sequence |
|---|---|---|---|---|
| pLSBF47 | L111V, D152S, M155L, A162W, Q138K, V149I, G188F, K229W | pDFng148 | 1200378 | ATCATCGCCCTTCACTCTGCGTTTAACC TGAACGGCGCGCAGAAC (SEQ ID NO: 203) |
|  |  |  | 1201840 | CGGCTCCAACCCACCTGGTATCTGGGC TTCCGATGAACTGATCG (SEQ ID NO: 204) |
| pLSBF48 | L111V, D152S, M155L, A162W, S72T, Q138K, V149I, G188F, K229W | pDFng148 | 1200378 | ATCATCGCCCTTCACTCTGCGTTTAACC TGAACGGCGCGCAGAAC (SEQ ID NO: 205) |
|  |  |  | 1201840 | CGGCTCCAACCCACCTGGTATCTGGGC TTCCGATGAACTGATCG (SEQ ID NO: 206) |
|  |  |  | 1201841 | CGGCACCGGCTACCAGACCCCGGATA TTATCTGCCACAGAGACGC (SEQ ID NO: 207) |
| pLSBF49 | L111V, D152S, M155L, A162W, Q138K, V149I, G188F, G207P, K229W | pDFng148 | 1200378 | ATCATCGCCCTTCACTCTGCGTTTAACC TGAACGGCGCGCAGAAC (SEQ ID NO: 208) |
|  |  |  | 1201840 | CGGCTCCAACCCACCTGGTATCTGGGC TTCCGATGAACTGATCG (SEQ ID NO: 209) |
|  |  |  | 1201842 | CCAGTGTTTCAACATCCAAATCACCGG TCCTGGCAGTGCTCAGGG (SEQ ID NO: 210) |
| pLSBF54 | L111V, D152S, M155L, A162W, S169C, G188F, K229W, A250C | pDFng146 | 1201386 | CCATTCCTGCCTGCTATGCCCCCGGAA ACTACGTCC (SEQ ID NO: 211) |
|  |  |  | 1201390 | CCTGGTCCTGCACTGTTCAACTGCTAA GCGGCC (SEQ ID NO: 212) |

Based on the residual activity ratios determined according to Example 5, screening of libraries constructed in the previous Examples generated the results listed in Table 5. Table 5 shows an average % Residual Activity (2-199 samples for each of the combinatorial variants and 34-179 samples for the wild-type GH61 polypeptide after treatment at any of 65° C., 68° C., 72° C., or 75° C.

The parent wild-type *A. fumigatus* GH61 polypeptide showed decreased residual activity of 40%, 24%, 0% and 0% when the temperature of treatment was increased from 65° C. to 68° C. to 72° C. to 75° C., respectively. The thermostability of the *Aspergillus fumigatus* GH61B polypeptide combinatorial variants ranged from 0.8-fold (decrease) to 1.4-fold increase at 65° C., no increase to 2-fold increase at 68° C. compared to the wild-type *A. fumigatus* GH61 polypeptide. Since wild-type GH61 polypeptide has no residual activity at 72° C., the other variant (L111V, D152S, M155L, A162W) was used for comparison at 72° C. and 75° C. In these cases, the variants ranged from no increase to 4.4-fold increase at 72° C., and 4-fold to 33-fold increase at 75° C. The results showed that improvements were most significant at the 75° C. treatment for those measured at 75° C., otherwise they were most significant at 72° C. where the wild-type had no measurable residual activity.

TABLE 5

*Aspergillus fumigatus* GH61B polypeptide variants with improved thermostability at 65° C., 68° C., 72° C. or 75° C. treatment

| Mutations | Avg % Res. Act. 65° C. | Standard Deviation | Avg % Res. Act. 68° C. | Standard Deviation | Avg % Res. Act. 72° C. | Standard Deviation | Avg % Res. Act. 75° C. | Standard Deviation |
|---|---|---|---|---|---|---|---|---|
| L111V, D152S, M155L, A162W | 55% | 16% | 49% | 21% | 10% | 7% | 1% | 7% |
| L111V, D152S, M155L, A162W, Q138K, G188F, K229W | 51% | 7% | NA | NA | 44% | 1% | 30% | 5% |
| L111V, D152S, M155L, A162W, Q138K, V149I, G188F, G207P, K229W | 47% | 9% | NA | NA | 42% | 9% | 32% | 12% |

TABLE 5-continued

Aspergillus fumigatus GH61B polypeptide variants with improved thermostability at 65° C., 68° C., 72° C. or 75° C. treatment

| Mutations | Avg % Res. Act. 65° C. | Standard Deviation | Avg % Res. Act. 68° C. | Standard Deviation | Avg % Res. Act. 72° C. | Standard Deviation | Avg % Res. Act. 75° C. | Standard Deviation |
|---|---|---|---|---|---|---|---|---|
| L111V, D152S, M155L, A162W, S72T, Q138K, V149I, G188F, K229W | 50% | 4% | NA | NA | 41% | 6% | 31% | 8% |
| L111V, D152S, M155L, A162W, S169C, G188F, K229W, A250C | 39% | 12% | NA | NA | 37% | 14% | 33% | 12% |
| L111V, D152S, M155L, A162W, Q138K, V149I, G188F, K229W | 49% | 6% | NA | NA | 36% | 19% | 28% | 14% |
| L111V, D152S, M155L, A162W, Q138K, K229W | 49% | 12% | 35% | 11% | 26% | 8% | 4% | 5% |
| L111V, D152S, M155L, A162W, K229W, S234G | 34% | 15% | 32% | 9% | 20% | 4% | NA | NA |
| L111V, D152S, M155L, A162W, T102K, E105K, K229W | 37% | 24% | 33% | 21% | 19% | 10% | NA | NA |
| L111V, D152S, M155L, A162W, S186T, K229W | 33% | 14% | 32% | 11% | 18% | 3% | NA | NA |
| L111V, D152S, M155L, A162W, T102K, K229W | 36% | 16% | 33% | 16% | 18% | 11% | NA | NA |
| L111V, D152S, M155L, A162W, S47E, K229W | 32% | 21% | 27% | 24% | 11% | 13% | NA | NA |
| L111V, D152S, M155L, A162W, S56A, K229W | 34% | 28% | 25% | 18% | 11% | 3% | NA | NA |
| Wild-Type | 40% | 18% | 24% | 21% | 0% | 0% | 0% | 0% |

Example 8: Purification of *Aspergillus fumigatus* GH61B and *Penicillium emersonii* GH61 Polypeptide Variants Expression and purification of the wild-type *Aspergillus fumigatus* GH61B and *Penicillium emersonii* GH61 polypeptides was conducted as previously described in WO 2012/044835.

Strains expressing *Aspergillus fumigatus* GH61 B and *Penicillium emersonii* GH61 polypeptide variants, generated as described in Examples 7 and 11, were cultured in shake flasks to generate material as described below for purification Following isolation of single colonies, the *Aspergillus oryzae* PFJO218 transformants were cultured for 4 days at 34° C. on COVE-N-Gly plates in preparation for larger scale fermentation. Spores were recovered from each plate using 0.01% TWEEN® 20. Each spore suspension (500 µl) was inoculated into 25 ml of M400 medium in 125 ml plastic shake flasks. The transformants were fermented for 3 days at 39° C. with agitation at 150 rpm and the broths were collected and filtered using 0.22 µm filters. The filtered culture broths were then concentrated by centrifugal ultrafiltration using VIVACELL® 100 5 kDa MWCO centrifugal concentration devices (Sartorius Stedim, Goettingen, Germany) and then buffer exchanged into 20 mM Tris-HCl pH 8.0.

The concentrated and buffer exchanged *Aspergillus fumigatus* GH61B and *Penicillium emersonii* GH61 polypeptide variants were further purified by one of two chromatographic methods. In one method, the concentrated and buffer exchanged broths were then each applied to a MONO Q® HR 16/10 column (GE Healthcare, Piscataway, N.J., USA) equilibrated with 20 mM Tris-HCl pH 8.0. Bound proteins were eluted with a linear gradient of 0-500 mM sodium chloride in 20 mM Tris-HCl pH 8.0. Fractions were analyzed by SDS-PAGE using a CRITERION® Stain-Free Tris-HCl 8-16% SDS-PAGE gel (Bio-Rad Laboratories, Inc., Hercules, Calif., USA), pooled based on the abundance of an approximately 25 kDa band, and concentrated using VIVASPIN® 5 kDa MWCO centrifugal concentration devices (GE Healthcare, Buckinghamshire, United Kingdom). Alternatively, the concentrated and desalted broths were then each applied to a HILOAD® 26/60 SUPERDEX® 75 (GE Healthcare, Piscataway, N.J., USA) size exclusion column equilibrated with 20 mM Tris-HCl pH 8.0 and 150 mM NaCl. Applied proteins were eluted isocratically using 20 mM Tris-HCl pH 8.0 and 150 mM NaCl as the mobile phase. Fractions were analyzed by SDS-PAGE using a CRITERION® Stain-Free Tris-HCl 8-16% SDS-PAGE gel, pooled based on the abundance of an approximately 25 kDa band, and concentrated using VIVASPIN® 5 kDa MWCO centrifugal concentration devices and then buffer exchanged into 20 mM MES pH 6.0.

Protein concentrations were determined using a Microplate BCA™ Protein Assay Kit in which bovine serum albumin was used as a protein standard.

Example 9: Determination of Tm (Melting Temperature) of the *Aspergillus fumigatus* Wild-Type GH61B Polypeptide and *Aspergillus fumigatus* GH61B Polypeptide Variants by Differential Scanning Calorimetry The thermostabilities of the *A. fumigatus* wild-type GH61B polypeptide and the *Aspergillus fumigatus* GH61B polypeptide variants, which were purified as described in Example 8, were determined by Differential Scanning calorimetry (DSC) using a VP Differential Scanning calorimeter (MicroCal Inc., GE Healthcare, Piscataway, N.J., USA). The melting temperature, Tm (° C.), was taken as the top of denaturation peak (major endothermic peak) in thermograms (Cp vs. T) obtained after heating a 1 mg protein per ml solution of the enzyme in 50 mM sodium acetate pH 5.0, 100 μM CuSO$_4$, or a 1 mg protein per ml solution of the enzyme in 50 mM sodium acetate pH 5.0, 10 mM EDTA pH 5.0, at a constant programmed heating rate. One ml of sample and reference-solutions were degassed at 25° C. using a ThermoVac (MicroCal Inc., GE Healthcare, Piscataway, N.J., USA) prior to loading of sample and reference cells of the calorimeter. Sample and reference (reference: degassed water) solutions were manually loaded into the DSC and thermally pre-equilibrated to 25° C. before the DSC scan was performed from 25° C. to 95° C. at a scan rate of 90 K/hour. Denaturation temperatures were determined at an accuracy of approximately +/−1° C. The results of the thermostability determinations of the *A. fumigatus* GH61 B polypeptide variants are shown in Table 6.

TABLE 6

Melting temperatures (° C.) of the *A. fumigatus* GH61B polypeptide and variants of the *A. fumigatus* GH61B polypeptide, as determined by differential scanning calorimetry

| Mutations | Tm + 100 μm CuSO$_4$ | Tm + 10 mM EDTA pH 5 |
|---|---|---|
| WT | 69 | 59 |
| S186K | 77 | n.d. |
| S234K | 73 | n.d. |
| L111V, D152S, M155L, A162W, Q138K, K229W | n.d. | 69 |

Example 10: Determination of Tm (Melting Temperature) of the *Aspergillus fumigatus* Wild-Type GH61B Polypeptide and *Aspergillus fumigatus* GH61B Polypeptide Variants by Protein Thermal Unfolding Analysis Protein thermal unfolding of the *Aspergillus fumigatus* GH61B polypeptide variants was monitored using SYPRO® Orange Protein Stain (Invitrogen, Naerum, Denmark) using a StepOnePlus™ Real-Time PCR System (Applied Biosystems Inc., Foster City, Calif., USA). In a 96-well white PCR-plate, 15 μl of a protein sample (prepared as described in Example 8) in 100 mM sodium acetate pH 5.0 was mixed (1:1) with Sypro Orange (resulting concentration=10×; stock solution=5000× in DMSO) in 20 mM EDTA. The plate was sealed with an optical PCR seal. The PCR instrument was set at a scan-rate of 76° C. per hour, starting at 25° C. and finishing at 96° C. Fluorescence was monitored every 20 seconds using a built-in LED blue light for excitation and ROX-filter (610 nm, emission). Tm-values were calculated as the maximum value of the first derivative (dF/dK) (Gregory et al., 2009, *J. Biomol. Screen.* 14: 700). The results of the thermostability determinations are shown in Table 7.

TABLE 7

Melting temperatures (° C.) of the *A. fumigatus* GH61B polypeptide and variants determined by thermal unfolding analysis

| Mutations | Tm |
|---|---|
| Wild-Type | 59 |
| Q138E | 61 |
| Q138L | 62 |
| D152S | 65 |

Example 11: Construction of *Penicillium emersonii* GH61A Polypeptide Variants

Variant plasmid pLSBF10 was constructed through two sequential single site-directed mutagenesis reactions on pMMar45 (Example 1) using a QUIKCHANGE® II XL Site-Directed Mutagenesis Kit. Two mutagenic primers were designed to insert each desired mutation. A total of 125 ng of each primer was used in a PCR containing approximately 25 ng of template plasmid, 1× QUIKCHANGE® reaction buffer, 3 μl of QUIKSOLUTION®, 1 μl of XL dNTP mix (provided in the QUIKCHANGE® 11 XL Site-Directed Mutagenesis Kit), and 1 μl of 2.5 U/μl Pfu Ultra enzyme in a final volume of 50 μl. The PCR was performed using an EPPENDORF® MASTERCYCLER® thermocycler programmed for a 95° C. hot start; 1 cycle at 95° C. for 1 minute; 18 cycles each at 95° C. for 50 seconds, 60° C. for 50 seconds, and 68° C. for 10 minutes; and a 4° C. hold. One microliter of Dpn I was directly added to the amplification reaction and incubated at 37° C. for 1 hour. A 2 μl volume of the Dpn I digested reaction was used to transform *E. coli* XL10-GOLD® Ultracompetent Cells according to the manufacturer's instructions. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer and dye-terminator chemistry from a BigDye® Terminator v3.1 Cycle Sequencing Kit. One of the clones with the desired 2 mutations was designated as pLSBF10. The primers used in this reaction can be found below in Table 8.

A summary of the primers used for the site-directed mutagenesis and the variant (S173C, F253C) obtained are shown in Table 8.

The resulting mutant plasmid DNA was prepared using a BIOROBOT® 9600. Each mutant plasmid was sequenced using a 3130×1 Genetic Analyzer to verify the substitutions. The sequencing primers 996271 and pALLO2 3' were used for verification.

TABLE 8

| Plasmid | Mutation(s) | Parent Plasmid | Oligo ID # | Sequence |
|---|---|---|---|---|
| pLSBF10 | S173C, F253C | pMMar45 | 615942 | TGGACCGTCACCATTCCCA ACTGCGTCGCCCCCGGCAA CTACG (SEQ ID NO: 213) |
| | | | 615943 | CGTAGTTGCCGGGGGCGAC GCAGTTGGGAATGGTGACG GTCCA (SEQ ID NO: 214) |

TABLE 8-continued

| Plasmid | Muta-tion(s) | Parent Plasmid | Oligo ID # | Sequence |
|---|---|---|---|---|
| | | | 615944 | CCGGGGCCGCCTGAGCCGA CGTGCTAGGCGGCCGCGGA GGCCACC (SEQ ID NO: 215) |
| | | | 615945 | GGTGGCCTCCGCGGCCGCC TAGCACGTCGGCTCAGGCG GCCCCGG (SEQ ID NO: 216) |

The *P. emersonii* GH61A polypeptide variants were expressed using *Aspergillus oryzae* PFJO218 as host was performed according to the procedure described in Example 3.

Example 12: Thermostability of the *P. emersonii* Wild-Type GH61A Polypeptide and *P. emersonii* GH61A Polypeptide Variant Based on the residual activity ratios determined according to Example 5, screening of libraries constructed in the previous Examples generated the results listed in Table 9. Table 9 shows an average % Residual Activity (from 2-14 samples each for the combinatorial variants and 14 samples of wild-type after treatment at any of 65° C., 68° C., 72° C. or, 75° C.

The parent wild-type *P. emersonii* GH61A polypeptide showed decreased residual activity of 45%, 18% and 1% when the temperature of treatment was increased from 65° C. to to 72° C. to 75° C., respectively (68° C. was not tested). The thermostability of the *P. emersonii* GH61A polypeptide combinatorial variant (S173C, F253C) ranged from 0.8-fold (decrease) to 2.2-fold increase at 72° C., and 30-fold compared to the wild-type *P. emersonii* GH61A polypeptide at 75° C.

TABLE 9

Penicillium emersonii GH61A polypeptide variants with improved thermostability at 65° C., 68° C., 72° C. or 75° C. treatment

| Mutations | Avg % Res. Act. 65° C. | Standard Deviation | Avg % Res. Act. 68° C. | Standard Deviation | Avg % Res. Act. 72° C. | Standard Deviation | Avg % Res. Act. 75° C. | Standard Deviation |
|---|---|---|---|---|---|---|---|---|
| Wild-Type | 45% | 7% | NA | NA | 18% | 7% | 1% | 5% |
| S173C, F253C | 38% | 6% | 49% | 8% | 40% | 19% | 30% | 6% |

Example 13: Determination of Tm (Melting Temperature) of the *P. emersonii* Wild-Type GH61A Polypeptide and *P. emersonii* GH61A Polypeptide Variant by Differential Scanning Calorimetry The thermostabilities of the P. emersonii wild-type GH61A polypeptide and the *P. emersonii* GH61A polypeptide variant (S173C, F253C), purified as described in Example 8, were determined by Differential Scanning calorimetry (DSC) using a VP Differential Scanning calorimeter as described in Example 9. The results of the thermostability determination of the *P. emersonii* GH61A polypeptide variant are shown in Table 10.

TABLE 10

Melting temperatures (° C.) of the *P. emersonii* wild-type GH61A polypeptide and *P. emersonii* GH61A polypeptide and variant of *P. emersonii* GH61A polypeptide, as determined by differential scanning calorimetry

| Enzyme Sample | Tm + 100 um CuSO4 pH 5 | Tm + 10 mM EDTA pH 5 |
|---|---|---|
| Wild-Type | 82 | 74 |
| S173C, F253C | 87 | 77 |

Example 14: Determination of Tm (Melting Temperature) of the *P. emersonii* Wild-Type GH61A Polypeptide and *P. emersonii* GH61A Polypeptide Variant by Protein Thermal Unfolding Analysis Protein thermal unfolding of the *Penicillium emersonii* GH61A polypeptide variant (S173C, F253C) was monitored using SYPRO® Orange Protein Stain and was performed using a StepOnePlus™ Real-Time PCR System as described as Example 10. The culture broths of *P. emersonii* GH61A wild-type polypeptide and P. emersonii GH61A polypeptide variant were prepared as described in Example 11. The results of the thermostability determination are shown in Table 11.

TABLE 11

Melting temperature (° C.) of *Penicillium emersonii* GH61A polypeptide variants by protein thermal unfolding analysis

| Mutations | Tm |
|---|---|
| Wild-Type | 64 |
| S173C, F253C | 69 |

Example 15: Construction of Expression Vectors pDFng153-4, pDFng154-17, pDFng155-33, pDFng156-37, and pDFng157-51

Figure 6:
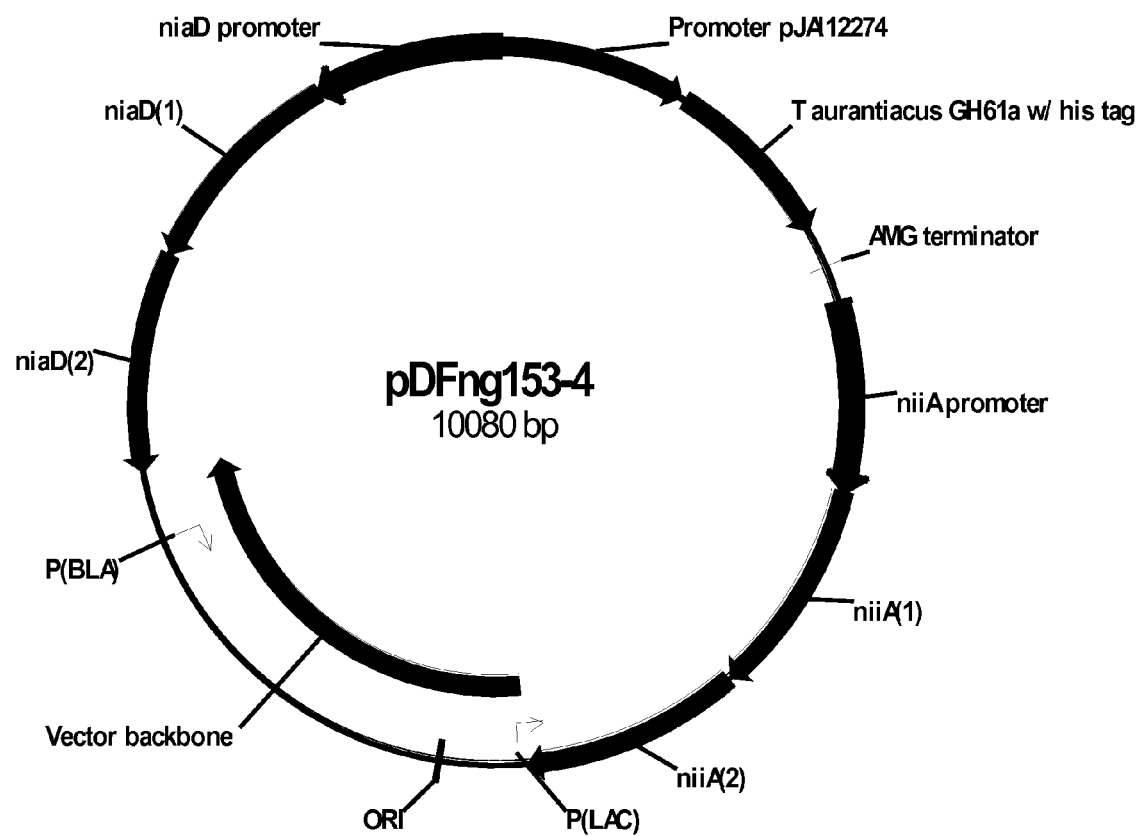
FIG. 6 shows a restriction map of pDFng153-4.
Figure 7:
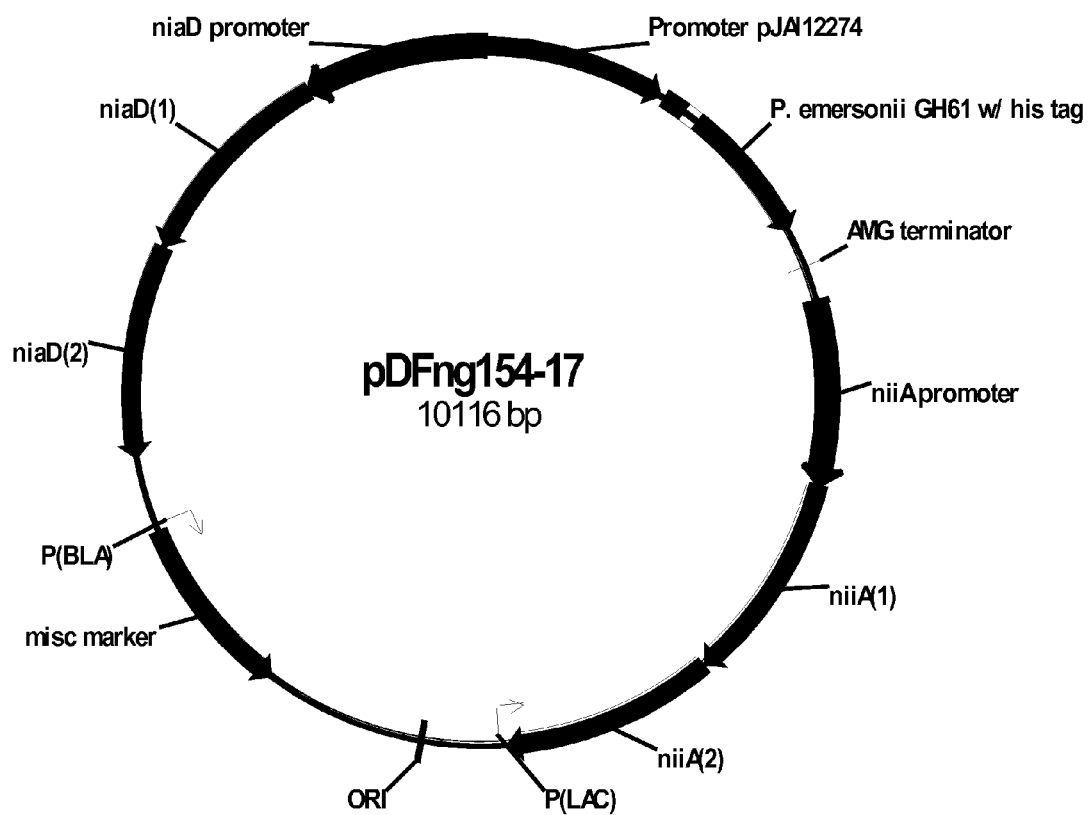
FIG. 7 shows a restriction map of pDFng154-17.
Figure 8:
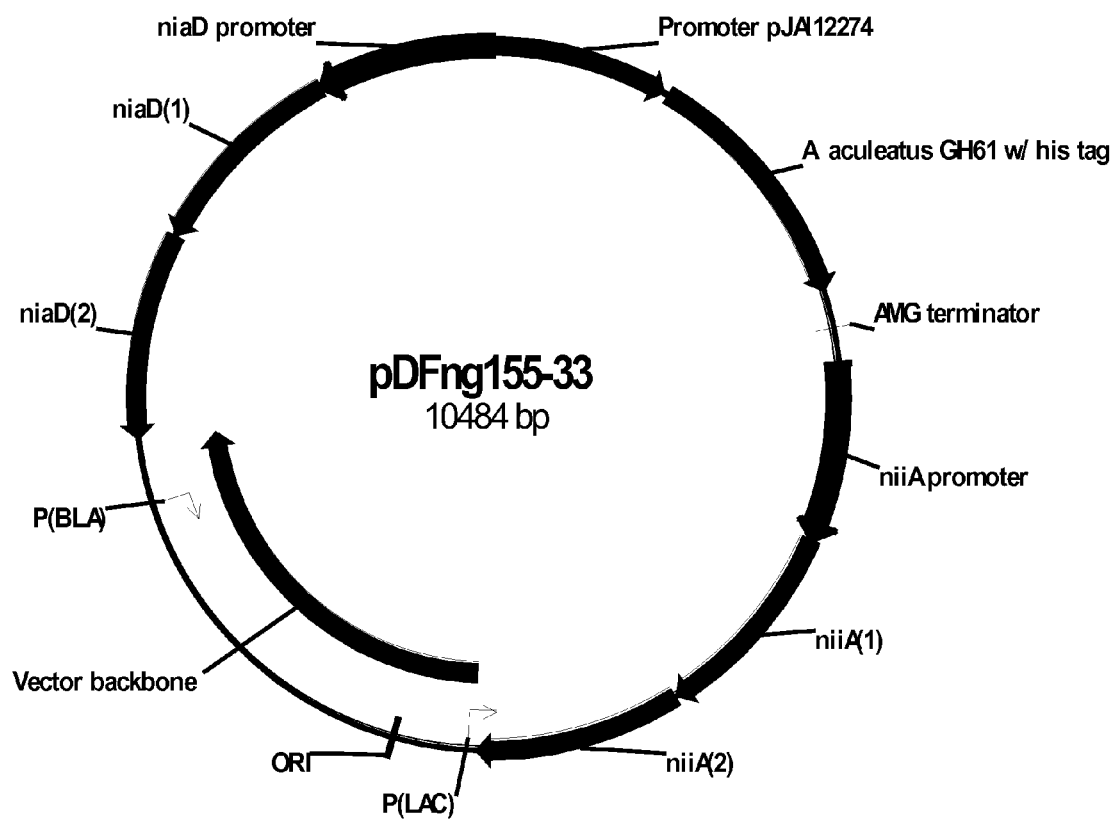
FIG. 8 shows a restriction map of pDFng155-33.
Figure 9:
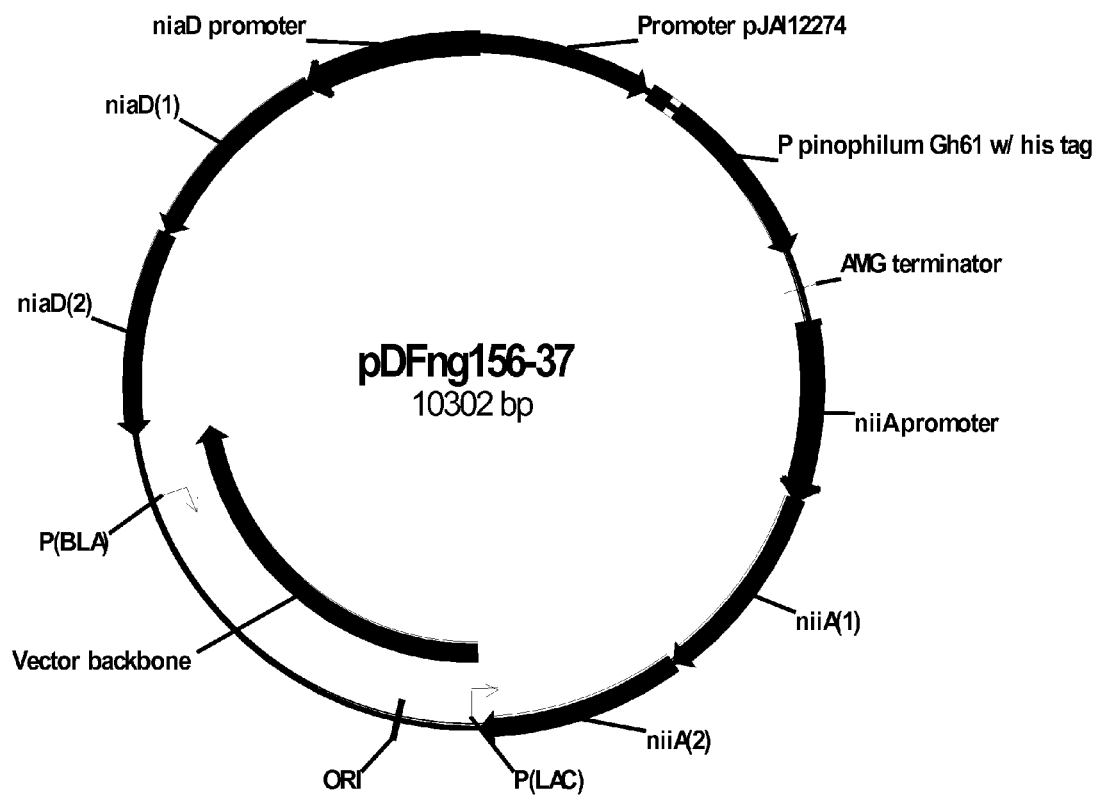
FIG. 9 shows a restriction map of pDFng156-37.
Figure 10:
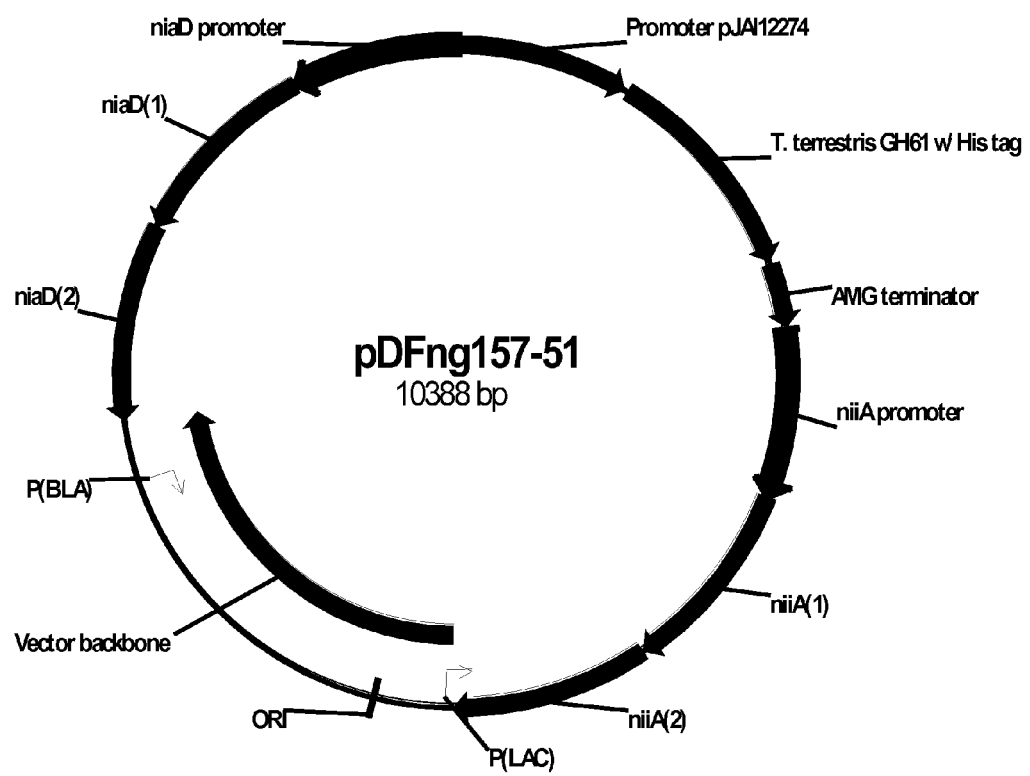
FIG. 10 shows a restriction map of pDFng157-51.
Figure 11:
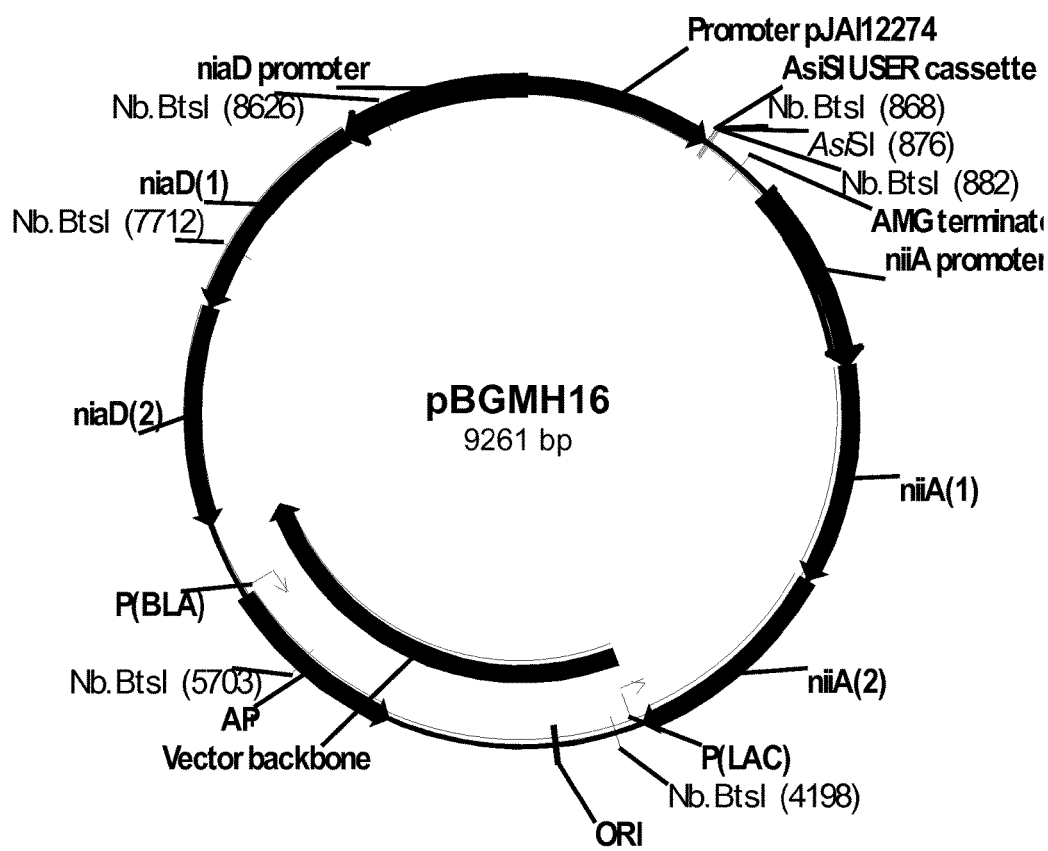
FIG. 11 shows a restriction map of pBGMH16.

Plasmids pDFng153-4 (FIG. 6), pDFng154-17 (FIG. 7), pDFng155-33 (FIG. 8), and pDFng156-37 (FIG. 9), and pDFng157-51 (FIG. 10) were constructed as described below for expression of the *Thermoascus aurantiacus* GH61A polypeptide, *Penicillium emersonii* GH61A polypeptide, *Aspergillus aculeatus* GH61 polypeptide, *Penicillium pinophilum* GH61 polypeptide, and *Thielavia terrestris* GH61 polypeptide, respectively, and generation of the variants listed in Table 12. The plasmids were constructed using plasmid pBGMH16 (FIG. 11).

Plasmid pBGMH16 was constructed according to the protocol described below. A Nb.Btsl recognition site in pUC19 was removed by PCR using the primer pair BGMH24 and BGMH25 shown below followed by the uracil-specific excision reagent USER™ based cloning (New England BioLabs, Ipswich, Mass., USA). Plasmid pUC19 is described in Yanisch-Perron et al., 1985, *Gene* 33(1): 103-19.

```
Primer BGMH24:
                                    (SEQ ID NO: 217)
ATGCAGCGCUGCCATAACCATGAGTGA Primer BGMH25:
                                    (SEQ ID NO: 218)
AGCGCTGCAUAATTCTCTTACTGTCATG
```

Underlined sequence is used in the USER™ assisted fusion of the PCR fragment creating pBGMH13. USER™ (Uracil-Specific Excision Reagent) Enzyme (New England Biolabs, Ipswich, Mass., USA) generates a single nucleotide gap at the location of a uracil. USER™ Enzyme is a mixture of Uracil DNA glycosylase (UDG) and the DNA glycosylase-lyase endonuclease VIII. UDG catalyzes the excision of a uracil base, forming an abasic (apyrimidinic) site while leaving the phosphodiester backbone intact. The lyase activity of endonuclease VIII cleaves the phosphodiester backbone at the 3' and 5' sides of the basic site so that base-free deoxyribose is released.

The amplification reaction was composed of 100 ng of each primer, 10 ng of pUC19, 1×PfuTurbo® $C_x$ Reaction Buffer (Stratagene, La Jolla, Calif., USA), 2.5 µl of a blend of dATP, dTTP, dGTP, and dCTP, each at 10 mM, and 2.5 units of PfuTurbo® $C_X$ Hot Start DNA Polymerase (Stratagene, La Jolla, Calif., USA) in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 3 minutes; and a final elongation at 72° C. for 7 minutes. Five µl of 10× NEBuffer 4 (New England Biolabs, Inc., Ipswich, Mass., USA) and 20 units of Dpn I were added and incubated at 37° C. for 1 hour. The Dpn I was inactivated at 80° C. for 20 minutes. A total of 100 ng of the PCR product and 1 unit of USER™ enzyme in a total volume of 10 µl were incubated 20 minutes at 37° C. followed by 20 minutes at 25° C. Ten µl were transformed into ONE SHOT® TOP10 competent cells. *E. coli* transformants were selected on LB+Amp agar plates and plasmid DNA was prepared using QIAPREP® Spin Miniprep Kit (QIAGEN Inc., Valencia, Calif., USA). The resulting plasmid pBGMH13 was confirmed by sequencing using an Applied Biosystems Model 3730XL Automated DNA Sequencer using version 3.1 BIG-DYE™ terminator chemistry (Applied Biosystems, Inc., Foster City, Calif., USA).

Plasmid pBGMH14 contains part of pBGMH13 as vector backbone and a Pac I/Nt.BbvCl USER™ cassette (Hansen et al., 2011, *Appl. Environ. Microbiol.* 77(9): 3044-51) which is flanked by part of the *A. oryzae* niaD gene on one side and part of the *A. oryzae* niiA gene on the other side. The Pac I/Nt.BbvCl USER™ cassette can be linearized with Pac I and Nt.BbvCl and a PCR product with compatible overhangs can be cloned into this site (New England Biolabs, Ipswich, Mass., USA).

An *Aspergillus oryzae* niiA fragment was generated using primers BGMH27 and BGMH29 shown below. The primer pair BGMH28 and BGMH32 shown below was used to amplify the *Aspergillus oryzae* niaD gene region and primer pair BGMH30 and BGMH31 shown below was used to amplify the plasmid backbone region.

```
Primer BGMH 27:
                                    (SEQ ID NO: 219)
AATTAAGUCCTCAGCGTGATTTAAAACGCCATTGCT Primer BGMH 28:
                                    (SEQ ID NO: 220)
ACTTAATUAAACCCTCAGCGCAGTTAGGTTGGTGTTCTTCT Primer BGMH 29:
                                    (SEQ ID NO: 221)
AGCTCAAGGAUACCTACAGTTATTCGAAA Primer BGMH 30:
                                    (SEQ ID NO: 222)
ATCCTTGAGCUGTTTCCTGTGTGAAATTGTTATCC Primer BGMH 31:
                                    (SEQ ID NO: 223)
ATCTCCTCUGCTGGTCTGGTTAAGCCAGCCCCGACAC Primer BGMH 32:
                                    (SEQ ID NO: 224)
AGAGGAGAUAATACTCTGCGCTCCGCC
```

Underlined sequence was used in the USER™ assisted fusion of the three fragments. The sequence marked in bold was used to introduce a PacI/Nt.BbvCl USER™ cassette (Hansen et al., 2011, supra) between the niiA and niaD fragments.

Genomic DNA from *A. oryzae* BECH2 (WO 00/39322) was purified using a FASTDNA™ 2 ml SPIN Kit for Soil (MP Biomedicals, Santa Ana, Calif., USA).

Each PCR was composed of 100 ng of each primer, template DNA (pBGMH13 or *A. oryzae* $BECH_2$ genomic DNA), 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCRs were performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 4 minutes; and a final elongation at 72° C. for 10 minutes. Where template DNA was a plasmid, 5 µl of 10× NEBuffer 4 and 20 units of Dpn I were added and incubated at 37° C. for 1 hour. The Dpn I was inactivated at 80° C. for 20 minutes. Fifty ng of each of the PCR products and 1 unit of USER™ enzyme in a total volume of 10 µl were incubated for 20 minutes at 37° C. followed by 20 minutes at 25° C. Then 10 µl were transformed into ONE SHOT® TOP10 competent cells. The three fragments were fused by uracil-specific excision reagent based cloning (Nour-Eldin et al., 2010, *Methods Mol. Biol.* 643: 185-200). *E. coli* transformants were selected on LB+Amp agar plates and plasmid DNA was prepared using QIAPREP® Spin Miniprep Kit. Plasmid pBGMH14 was confirmed by sequencing using an Applied Biosystems Model 3730XL Automated DNA Sequencer using version 3.1 BIG-DYE™ terminator chemistry. Promoter P13amy is a derivative of the NA2-tpi promoter from pJaL676 (WO 2003/008575). The *A. niger* AMG terminator used is described by Christensen et al., 1988, *Nature Biotechnology* 6: 141-1422. The P13amy promoter and AMG terminator were cloned into the Pac 1/Nt.BbvCl USER™ cassette in pBGMH14. The primers shown below were designed so that an Asi SI/Nb.Btsl USER™ cassette (Hansen et al., 2011, supra) was introduced between the promoter and terminator.

Primer BGMH 49:
(SEQ ID NO: 225)
<u>GGGTTTAAU</u>CCTCACACAGGAAACAGCTATGA

Primer BGMH 50:
(SEQ ID NO: 226)
AGTGTCTGCGAUCGCTCTCACTGCCCCCAGTTGTGTATATAGAGGA Primer BGMH 51:
(SEQ ID NO: 227)
ATCGCAGACACUGCTGGCGGTAGACAATCAATCCAT Primer BGMH 52:
(SEQ ID NO: 228)
<u>GGACTTAAU</u>GGATCTAAGATGAGCTCATGGCT Underlined sequence was used in the USER™ assisted fusion of the two fragments into a Pac I/Nt.BbvCI digested pBGMH14. The sequence marked in bold was used to introduce a AsiSI/Nb.BtsI USER™ cassette (Hansen et al., 2011, supra) between the promoter and terminator.

The primer pair BGMH49 and BGMH50 was used to amplify promoter P13amy and the primer pair BGMH51 and BGMH52 was used to amplify the AMG terminator. The PCR was composed of 100 ng of each primer, template DNA, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 45 seconds; and a final elongation at 72° C. for 3 minutes. Then 5 µl of 10× NEBuffer 4 and 20 units of Dpn I were added and incubated at 37° C. for 1 hour. The Dpn I was inactivated at 80° C. for 20 minutes.

The two fragments were fused into Pac I/Nt.BbvCI digested pBGMH14 by USER™ based cloning method in a reaction composed of 10 ng of Pac I/Nt.BbvCI digested pBGMH14, 50 ng of each of the two PCR products, and 1 unit of USER™ enzyme in a total volume of 10 µl. The reaction was incubated at 37° C. for 20 minutes followed by 20 minutes at 25° C. Then 10 µl were transformed into ONE SHOT® TOP10 competent cells. *E. coli* transformants were selected on LB+Amp agar plates and plasmid DNA was prepared using QIAPREP® Spin Miniprep Kit. Plasmid pBGMH16 was confirmed by sequencing.

DNA sequence was verified by Sanger sequencing with an Applied Biosystems Model 3730XL Automated DNA Sequencer using version 3.1 BIG-DYE™ terminator chemistry. Sequencing primers used for verification of niiA, niaD, the P13amy promoter, AsiSI/Nb.BtsI USER™ cassette, and AMG terminator sequence in BGMH16 are shown below.

| | | |
|---|---|---|
| BGMH 36 | ACGCCATTGCTATGATGCTTGAAG | (SEQ ID NO: 229) |
| BGMH 37 | TGGTGAGGTGCTATCGTCCTT | (SEQ ID NO: 230) |
| BGMH 38 | CTTCCTGTAGGTGCACCGAAG | (SEQ ID NO: 231) |
| BGMH 39 | ACAGAACGATATCGGACCTCG | (SEQ ID NO: 232) |
| BGMH 40 | TCGTTATGTTAAGTCTTCTATCA | (SEQ ID NO: 233) |
| BGMH 41 | AGAGCTCGAAGTTCCTCCGAG | (SEQ ID NO: 234) |
| BGMH 42 | TATCACGAGGCCCTTTCGTCTC | (SEQ ID NO: 235) |
| BGMH 43 | TCCGTCGGCTCCTCTCCTTCGT | (SEQ ID NO: 236) |
| BGMH 44 | TGCATATCCTCTGACAGTATATGA | (SEQ ID NO: 237) |
| BGMH 45 | CAGTGAAGAGGGCAGTCGATAGT | (SEQ ID NO: 238) |
| BGMH 46 | ACGAGGAACATGGCTATCTGGA | (SEQ ID NO: 239) |
| BGMH 47 | TCAGCTCATTCTGGGAGGTGGGA | (SEQ ID NO: 240) |
| BGMH 48 | ACTCCAGGATCCTTTAAATCCA | (SEQ ID NO: 241) |
| BGMH 53 | ACTGGCAAGGGATGCCATGCT | (SEQ ID NO: 242) |
| BGMH 54 | TGATCATATAACCAATTGCCCT | (SEQ ID NO: 243) |
| BGMH 55 | AGTTGTGTATATAGAGGATTGA | (SEQ ID NO: 244) |
| BGMH 56 | TGGTCCTTCGCTCGTGATGTGGA | (SEQ ID NO: 245) |
| BGMH 57 | AGTCCTCAGCGTTACCGGCA | (SEQ ID NO: 246) |
| BGMH 58 | ACCCTCAGCTGTGTCCGGGA | (SEQ ID NO: 247) |
| BGMH 59 | TGGTATGTGAACGCCAGTCTG | (SEQ ID NO: 248) |

Plasmid pBGMH16 contains flanking regions designed to repair the niiA gene and niaD gene in *Aspergillus oryzae* COLs1300. Plasmid pBGMH16 was digested with Asi Si and Nb. Bts I to linearize the plasmid and create single stranded overhangs so that a PCR product with compatible overhangs can be cloned into this site by USER™ cloning (New England Biolabs, Inc., Ipswich, Mass., USA). The digested plasmid was purified using a DNA Purification Kit (QIAGEN Inc., Valencia, Calif., USA) according to the manufacturer's instructions.

The *T. aurantiacus* GH61A polypeptide coding sequence (SEQ ID NO: 13 [genomic DNA sequence] and SEQ ID NO: 14 [deduced amino acid sequence]), *P. emersonii* GH61A polypeptide coding sequence (SEQ ID NO: 35 [genomic DNA sequence] and SEQ ID NO: 36 [deduced amino acid sequence]), *A. aculeatus* GH61 polypeptide coding sequence (SEQ ID NO: 67 [genomic DNA sequence] and SEQ ID NO: 68 [deduced amino acid sequence]), *P. pinophilum* GH61 polypeptide coding sequence (SEQ ID NO: 31 [genomic DNA sequence] and SEQ ID NO: 32 [deduced amino acid sequence]), and *T. terrestris* GH61 polypeptide coding sequence (SEQ ID NO: 45 [genomic DNA sequence; cDNA was used herein] and SEQ ID NO: 46 [deduced amino acid sequence]) were amplified from source plasmids described below using the primers shown in Table 12. Bold letters represent coding sequence. The single deoxyuridine (U) residue inserted into each primer is the U that is excised from the PCR products using the USER™ enzyme (New England Biolabs, Inc., Ipswich, Mass., USA) to obtain overhangs for the insertion site. The underline letters represent a His tag. The remaining sequences are homologous to insertion sites of pBGMH16 for expression of the GH61 polypeptides.

into *E. coli* XL10-GOLD® Super Competent Cells according to the manufacturer's instructions. *E. coli* transformants were selected on 2XYT+Amp agar plates. Plasmid DNA

TABLE 12

| GH61 origin | Source Template | Plasmid | Primer ID | Primer Sequence |
|---|---|---|---|---|
| *Thermoascus aurantiacus* GH61A | pDFng113 Example 1 | pDFng153-4 | TaGH61_USERtagF | AGAGCGA(U)ATGTCCTTTTCCAAGATAAT (SEQ ID NO: 249) |
| | | | TaGH61_USER_HIStagR | TCTGCGA(U)TTAGTGATGGTGGTGATGAT GACCAGTATACAGAGGAGGAC (SEQ ID NO: 250) |
| *Penicillium emersonii* GH61A | pMMar45 Example 1 | pDFng154-17 | PeGH61_USERtagF | AGAGCGA(U)ATGCTGTCTTCGACGACTCG (SEQ ID NO: 251) |
| | | | PeGH61_USER_HIStagR | TCTGCGA(U)CTAGTGATGGTGGTGATGAT GGAACGTCGGCTCAGGCGGCC (SEQ ID NO: 252) |
| *Aspergillus aculeatus* GH61 | Xyz1566 (WO 2012/ 030799) | pDFng155-33 | AaGH61_USERtagF | AGAGCGA(U)ATGTCTGTTGCTAAGTTTGC TGGTG (SEQ ID NO: 253) |
| | | | AaGH61_USER_HIStagR | TCTGCGA(U)TTAGTGATGGTGGTGATGAT GGGCGGAGAGGTCACGGGCGT (SEQ ID NO: 254) |
| *Penicillium pinophilum* GH61 | pSMai215 (Example 15) | pDFng156-37 | PpGH61_USERtagF | AGAGCGA(U)ATGCCTTCTACTAAAGTCGC TGCC (SEQ ID NO: 255) |
| | | | PpGH61_USER_HIStagR | TCTGCGA(U)TCAGTGATGGTGGTGATGAT GAAGGACAGTAGTGGTGATGAT (SEQ ID NO: 256) |
| *Thielavia terrestris* GH61 | pAG68 (WO 2011/ 035027) | pDFng157-51 | TtGH61_USERtagF | AGAGCGA(U)ATGCCTTCTTTCGCCTCCAA GACTCTCCTTTC (SEQ ID NO: 257) |
| | | | TtGH61_USER_HIStagR | TCTGCGA(U)TCAGTGATGGTGGTGATGAT GGTTTGCCTCCTCAGCCCCTC (SEQ ID NO: 258 ID NO) |

Construction of plasmid pDFng153-4 containing the *Thermoascus aurantiacus* GH61A polypeptide coding sequence is described below. The *T. aurantiacus* GH61A polypeptide coding sequence was amplified from plasmid pDFng113 using the primers shown in Table 12 with overhangs designed for cloning into plasmid pBGMH16. The amplification was composed of 100 ng of each primer listed in Table 12, 30 ng of pDFng113, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 57.7° C. for 30 seconds, and 72° C. for 1.5 minutes; and a final elongation at 72° C. for 10 minutes. The heat block then went to a 10° C. soak cycle.

The PCR solution was analyzed by 0.7% agarose gel electrophoresis using TBE buffer where an approximately 894 bp PCR product band was observed. The PCR solution was then digested with 1 µl of Dpn 1 and 4.5 µl of NEBuffer 4 at 37° C. overnight and purified using a QIAGEN® Purification Kit according to the manufacturer's instructions.

The homologous ends of the 894 bp PCR product and the Asi SI and Nb.BtsI digested pBGMH16 were joined together in a reaction composed of 10 µl of the PCR containing the 894 bp PCR product, 1 µl of the Asi SI and Nb.BtsI digested plasmid pBGMH16, and 1 µl of USER™ enzyme. The reaction was incubated for 15 minutes at 37° C., followed by 15 minutes at 25° C. Ten µl of the reaction were transformed from several of the resulting *E. coli* transformants was prepared using a BIOROBOT® 9600. The *T. aurantiacus* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers shown below were used for verification of the gene insert and sequence.

```
Primer TaGH61seqF:
                            (SEQ ID NO: 259)
CCCAGTTATCAACTACCTTG Primer pBGMH16seqF:
                            (SEQ ID NO: 260)
CTCAATTTACCTCTATCCAC Primer pBGMH16seqR:
                            (SEQ ID NO: 261)
TATAACCAATTGCCCTCATC
```

A plasmid containing the correct *T. aurantiacus* GH61A polypeptide coding sequence was selected and designated pDFng153-4.

Construction of plasmid pDFng154-17 containing the *Penicillium emersonii* GH61A polypeptide coding sequence is described below. The *P. emersonii* GH61A polypeptide coding sequence was amplified from plasmid pMMar45 using the primers shown in Table 12 with overhangs designed for cloning into plasmid pBGMH16. The amplification was composed of 100 ng of each primer listed in Table 12, 30 ng of pMMar45, 1×PfuTurbo® $C_x$ Reaction Buffer, 2.5 µl of a blend of dATP, dTTP, dGTP, and dCTP, each at 10 mM, and 2.5 units of PfuTurbo® C$_x$ Hot Start DNA Polymerase in a final volume of 50 µl. The amplification was performed using an EPPENDORF® MASTERCYCLER® 5333 programmed for 1 cycle at 95° C. for 2 minutes; 30 cycles each at 95° C. for 30 seconds, 64.1° C. for 30 seconds, and 72° C. for 1.5 minutes; and a final elongation at 72° C. for 10 minutes. The heat block then went to a 10° C. soak cycle.

The PCR solution was analyzed by 0.7% agarose gel electrophoresis using TBE buffer where an approximately 930 bp PCR product band was observed. The PCR solution was then digested with 1 µl of Dpn 1 and 4.5 µl of NEBuffer 4 at 37° C. overnight and purified using a QIAGEN® Purification Kit according to the manufacturer's instructions.

The homologous ends of the 930 bp PCR product and the Asi SI and Nb.BtsI digested pBGMH16 were joined together in a reaction composed of 10 µl of the PCR solution containing the 930 bp PCR product, 1 µl of the Asi SI and Nb.BtsI digested pBGMH16, and 1 µl of USER™ enzyme. The reaction was incubated for 15 minutes at 37° C., followed by 15 minutes at 25° C. Ten µl of the reaction were transformed into E. coli XL10-GOLD® Super Competent Cells according to the manufacturer's instructions. E. coli transformants were selected on 2XYT+Amp agar plates. Plasmid DNA from several of the resulting E. coli transformants was prepared using a BIOROBOT® 9600. The P. emersonii GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer PeGH61seqF shown below were used for verification of the gene insert and sequence.

```
PeGH61seqF:
                                   (SEQ ID NO: 261)
            GCACCGTCGAGCTGCAGTGG
```

A plasmid containing the correct P. emersonii GH61A polypeptide coding sequence was selected and designated pDFng154-17.

Construction of plasmid pDFng155-33 containing the Aspergillus aculeatus GH61A polypeptide coding sequence is described below. The A. aculeatus GH61A polypeptide coding sequence was amplified from plasmid Xyz1566 (WO 2012/030799 Example 3) using primers shown in Table 12 with overhangs designed for cloning into plasmid pBGMH16. The amplification reaction was composed of 100 ng of each primer listed in Table 12, 30 ng of plasmid Xyz1566, 1×PfuTurbo® C$_x$ Reaction Buffer, 2.5 µl of a blend of dATP, dTTP, dGTP, and dCTP, each at 10 mM, and 2.5 units of PfuTurbo® C$_x$ Hot Start DNA Polymerase in a final volume of 50 µl. The amplification was performed using an EPPENDORF® MASTERCYCLER® 5333 programmed for 1 cycle at 95° C. for 2 minutes; 30 cycles each at 95° C. for 30 seconds, 63.4° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.3 kb PCR product band was observed. The PCR product solution was then digested with 1 µl of Dpn 1 and 4.5 µl of NEBuffer 4 at 37° C. overnight and purified using a QIAGEN® Purification Kit according to the manufacturer's instructions.

The homologous ends of the 1.3 kb PCR product and the digested pBGMH16 were joined together in a reaction composed of 10 µl of the PCR containing the 1.3 kb PCR product, 1 µl of the digested pBGMH16, and 1 µl of USER™ enzyme. The reaction was incubated for 15 minutes at 37° C., followed by 15 minutes at 25° C. Ten µl of the reaction were transformed into E. coli XL10-GOLD® Super Competent Cells according to the manufacturer's instructions. E. coli transformants were selected on 2XYT+Amp agar plates. Plasmid DNA from several of the resulting E. coli transformants was prepared using a BIOROBOT® 9600. The A. aculeatus GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer AaGH61seqF shown below were used for verification of the gene insert and sequence.

```
Primer AaGH61seqF:
                                   (SEQ ID NO: 263)
            CCTTGCCAACTGCAATGGTG
```

A plasmid containing the correct A. aculeatus GH61A polypeptide coding sequence was selected and designated pDFng155-33.

Plasmid pSMai215 was used to provide the DNA template of the Penicillium pinophilum GH61A gene for construction of pDFng156-37. Plasmid pSMai215 was constructed as described below. Two synthetic oligonucleotide primers shown below were designed to PCR amplify the Penicillium pinophilum GH61A polypeptide gene. An IN-FUSION™ PCR Cloning Kit was used to clone the fragment directly into the expression vector pMJ09 (WO 2005/047499). Bold letters represent coding sequence. The remaining sequence is homologous to the insertion sites of pMJ09.

```
Forward primer:
                                   (SEQ ID NO: 264)
  5'-GGACTGCGCACCATGCCTTCTACTAAAG-3'

Reverse primer:
                                   (SEQ ID NO: 265)
  5'-GCCACGGAGCTTAATTAATCAAAGGACAGTAGTG-3'
```

Fifty picomoles of each of the primers above were used in a PCR composed of 10 ng of pPin7, 1× EXPAND® High Fidelity PCR buffer with MgCl$_2$ (Roche Diagnostics Corporation, Indianapolis, Ind., USA), 0.25 mM each of dATP, dTTP, dGTP, and dCTP, and 2.6 units of EXPAND® High Fidelity Enzyme Mix (Roche Diagnostics Corporation, Indianapolis, Ind., USA), in a final volume of 50 µl. The amplification was performed using an EPPENDORF® MASTERCYCLER® 5333 epgradient S programmed for 1 cycle at 98° C. for 3 minute; 30 cycles each at 98° C. for 30 seconds, 59° C. for 30 seconds, and 72° C. for 1 minute; and a final elongation at 72° C. for 15 minutes. The heat block then went to a 4° C. soak cycle. The reaction products were isolated by 1% agarose gel electrophoresis in TAE buffer where an approximately 1.05 kb product band was observed on the gel. The PCR product solution was purified using a MINELUTE® Gel Extraction Kit.

Plasmid pMJ09 (WO 2005/047499) was digested with Nco I and Pac I, isolated by 1.0% agarose gel electrophoresis in TAE buffer, excised from the gel, and extracted using a QIAQUICK® Gel Extraction Kit (QIAGEN Inc., Valencia, Calif., USA) according to the manufacturer's instructions.

The 1.05 kb gene fragment and the digested vector were ligated together using an IN-FUSION™ PCR Cloning Kit (Clontech Laboratories Inc., Mountain View, Calif., USA) resulting in pSMai215. The ligation reaction (20 µl) was composed of 1×IN-FUSION™ Buffer, 1×BSA, 1 µl of IN-FUSION™ enzyme (diluted 1:10), 100 ng of the gel-purified Nco I/Pac I digested pMJ09, and 42 ng of the purified 1.05 kb PCR product. The reaction was incubated at 37° C. for 15 minutes follow by 50° C. for 15 minutes. After diluting the reaction mix with 50 µl of TE buffer (pH 8), 2.5 µl of the reaction were transformed into *E. coli* XL10 SOLOPACK® Gold Supercompetent cells. The *E. coli* transformation reactions were spread onto $2XYT_{amp}$ agar plates. An *E. coli* transformant containing pSMai215 was detected by restriction digestion and plasmid DNA was prepared using a BIOROBOT® 9600. The *Penicillium pinophilum* GH61A insert in pSMai215 was confirmed by DNA sequencing.

Construction of plasmid pDFng156-37 containing the *Penicillium pinophilum* GH61A polypeptide coding sequence is described below. The *P. pinophilum* GH61A polypeptide coding sequence was amplified from plasmid pSMai215 using the primers shown in Table 12 with overhangs designed for cloning into plasmid pBGMH16. The amplification reaction was composed of 100 ng of each primer listed in Table 12, 30 ng of plasmid pSMai215, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 61.2° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.1 kb PCR product band was observed. The PCR product solution was then digested with 1 µl of Dpn 1 and 4.5 µl of NEB4 buffer at 37° C. overnight and purified using a QIAGEN® Purification Kit.

The homologous ends of the 1.1 kb PCR product and the digested pBGMH16 were joined together in a reaction composed of 10 µl of the PCR containing the 1.1 kb PCR product, 1 µl of the digested pBGMH16, and 1 µl of USER™ enzyme. The reaction was incubated at 37° C. for 15 minutes, followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *P. pinophilum* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer PpGH61seqF shown below were used for verification of the gene insert and sequence.

```
Primer PpGH61seqF:
                              (SEQ ID NO: 266)
CAATGGCAATTGTTCTACCG
```

A plasmid containing the correct *P. pinophilum* GH61A polypeptide coding sequence was selected and designated pDFng156-37.

Construction of plasmid pDFng157-51 containing the *Thielavia terrestris* GH61 polypeptide coding sequence is described below. The *T. terrestris* GH61 polypeptide coding sequence was amplified from plasmid pAG68 using the primers shown in Table 12 with overhangs designed for cloning into plasmid pBGMH16. The amplification reaction was composed of 100 ng of each primer listed in Table 12, 30 ng of plasmid pAG68, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase in a final volume of 50 µl. The PCR was performed using an EPPENDORF® MASTERCYCLER® 5333 programmed for 1 cycle at 95° C. for 2 minutes; 30 cycles each at 95° C. for 30 seconds, 61.2° C. for 30 seconds, and 72° C. for 1.5 minutes; and a final elongation at 72° C. for 10 minutes. The heat block then went to a 10° C. soak cycle.

The PCR product solution was analyzed by 0.7% agarose gel electrophoresis using TBE buffer where an approximately 1.2 kb PCR product band was observed. The PCR product solution was then digested with 1 µl of Dpn 1 and 4.5 µl of NEB4 buffer at 37° C. overnight and purified using a QIAGEN® Purification Kit according to the manufacturer's instructions The homologous ends of the 1.2 kb PCR product and the digested pBGMH16 were joined together in a reaction composed of 10 µl of the PCR containing the 1.1 kb PCR product, 1 µl of the digested pBGMH16, and 1 µl of USER™ enzyme. The reaction was incubated at 37° C. for 15 minutes, followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *T. terrestris* GH61A polypeptide coding sequence insert was confirmed by DNA sequencing using a Model 3130xL Genetic Analyzer and dye-terminator chemistry from a BigDye® Terminator v3.1 Cycle Sequencing Kit. The sequencing primers pBGMH16seqF and pBGMH16seqR and primer TtGH61seqF shown below were used for verification of the gene insert and sequence.

```
Primer TtGH61seqF:
                              (SEQ ID NO: 267)
CGACGGCAGCTCGGCGCCCG
```

A plasmid containing the correct *T. terrestris* GH61 polypeptide coding sequence was selected and designated pDFng157-51.

Example 16: Construction of *Thermoascus aurantiacus* GH61 Polypeptide Variants

The *Thermoascus aurantiacus* GH61 polypeptide variants were constructed by SOE-PCR (Splicing by Overhang Extension Polymerase Chain Reaction) with plasmid pDFng153-4. In brief, the first PCR used forward primer EbZn NiaD Fwd and a mutation specific reverse primer (Table 13). The second PCR used reverse primer EbZn NiiA Rev and a mutation specific forward primer (Table 13) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

```
Primer EbZn NiaD Fwd:
                              (SEQ ID NO: 268)
5'-GCATTTATCAGGGTTATTGTCTCATGAGCGG-3'

Primer EbZn NiiA Rev:
                              (SEQ ID NO: 269)
5'-GCTGATAAATCTGGAGCCGGTGAGCG-3'

Primer BGMH110V2F:
                              (SEQ ID NO: 270)
5'-CCAGACCAGCAGAGGAGATAATACTCTGCG-3'

Primer BGMH109V2R:
                              (SEQ ID NO: 271)
5'-CAAGGATACCTACAGTTATTCGAAACCTCCTG-3'
```

The first PCRs for the *T. aurantiacus* GH61 polypeptide variants contained 0.2 picomole of the EbZn NiaD Fwd primer, 0.2 picomole of the reverse primer listed in Table 13, 10 ng of template (pDFng153-4), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient (Eppendorf Scientific, Inc., Westbury, N.Y., USA) programmed for 1 cycle at 98° C. for 2 minutes; 35 cycles each at 98° C. for 25 seconds, 66° C. for 30 seconds, and 72° C. for 5 minute; and a final elongation at 72° C. for 10 minutes. The heat block then went to a 10° C. hold stage.

The second SOE-PCRs for the *T. aurantiacus* GH61 variants contained 0.2 picomole of the forward primer listed in Table 13, 0.2 picomole of the EbZn NiiA Rev primer, 10 ng of template (pDFng153-4), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minute; and a final elongation at 72° C. for 10 minutes. The heat block then went to a 10° C. hold stage.

Each PCR product was analyzed by 1.0% agarose electrophoresis using TAE buffer where a 4.1 to 5.3 kb (as specified in Table 13) PCR product band was observed indicating proper amplification. The remaining 45 microliters were then treated with 10 units of Dpn 1 and 1×NEB4 to remove the remaining wild-type template. The reaction was incubated for 4 hours at 37° C. and then purified using a MINELUTE® 96 UF Purification Kit (QIAGEN Inc., Valencia, Calif., USA). The purified PCR products were resuspended in deionized water to a final volume equal to 20 µl. The concentration of each fragment was measured using a NanoDrop 2000 (Thermo Scientific, Wilmington, Del., USA).

The third SOE-PCR for the *T. aurantiacus* GH61 variants contained 50 to 100 ng of each fragment produced in the first and second PCRs, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow the overlapping nucleotides to splice before amplification.

The wild-type fragment was produced using conditions similar to the third PCR. The reaction was composed of 10 ng of template (pDFng153-4), 0.2 picomole of primer BGMH110V2F, 0.2 picomole of primer BGMH109V2R, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 13

| Template Backbone | Amino Acid Substitution | Primer ID | Primer Direction | Primer Sequence | PCR fragment size (kb) |
|---|---|---|---|---|---|
| Thermoascus aurantiacus GH61 | Q26I | 1203249 | Fwd | GTGGCTGGCCATGGCTTCGT TATCAACATCGTGATTGATG GTAAAAAGT (SEQ ID NO: 272) | 5.3 |
| | | 1203250 | Rev | AACGAAGCCATGGCCAGCCA CTAGAGAAGCAGA (SEQ ID NO: 273) | 4.1 |
| Thermoascus aurantiacus GH61 | Q42I | 1203262 | Fwd | GTTATGGCGGGTATCTAGTG AACATCTATCCATACATGTC CAATCCTCC (SEQ ID NO: 274) | 5.2 |
| | | 1203261 | Rev | GTTCACTAGATACCCGCCAT AACTGTCGATTGTCA (SEQ ID NO: 275) | 4.2 |

TABLE 13-continued

| Template Backbone | Amino Acid Substitution | Primer ID | Primer Direction | Primer Sequence | PCR fragment size (kb) |
|---|---|---|---|---|---|
| Thermoascus aurantiacus GH61 | Q42V | 1203263 | Fwd | GTTATGGCGGGTATCTAGTG AACGTCTATCCATACATGTC CAATCCTCC (SEQ ID NO: 277) | 5.2 |
| | | 1203261 | Rev | GTTCACTAGATACCCGCCAT AACTGTCGATTGTCA (SEQ ID NO: 278) | 4.2 |
| Thermoascus aurantiacus GH61 | S123R | 1203276 | Fwd | TGCTCCGTGCAATGGTGATT GTAGGACTGTGGATAAGACC CAATTAGAA (SEQ ID NO: 279) | 4.9 |
| | | 1203277 | Rev | ACAATCACCATTGCACGGAG CAAGGTAGTTGATAA (SEQ ID NO: 280) | 4.5 |
| Thermoascus aurantiacus GH61 | S138E | 1203280 | Fwd | ATTAGAATTCTTCAAAATTG CCGAGGAGGGTCTCATCAAT GATGACAATCC (SEQ ID NO: 281) | 4.9 |
| | | 1203279 | Rev | CTCGGCAATTTTGAAGAATT CTAATTGGGTCTTATCC (SEQ ID NO: 282) | 4.5 |
| Thermoascus aurantiacus GH61 | S138K | 1203281 | Fwd | ATTAGAATTCTTCAAAATTG CCGAGAAAGGTCTCATCAAT GATGACAATCC (SEQ ID NO: 283) | 4.9 |
| | | 1203279 | Rev | CTCGGCAATTTTGAAGAATT CTAATTGGGTCTTATCC (SEQ ID NO: 284) | 4.5 |
| Thermoascus aurantiacus GH61 | S138L | 1203282 | Fwd | ATTAGAATTCTTCAAAATTG CCGAGCTGGGTCTCATCAAT GATGACAATCC (SEQ ID NO: 285) | 4.9 |
| | | 1203279 | Rev | CTCGGCAATTTTGAAGAATT CTAATTGGGTCTTATCC (SEQ ID NO: 286) | 4.5 |
| Thermoascus aurantiacus GH61 | T163V | 1203285 | Fwd | GATAGCAGCCAACAACAGCT GGGTCGTCACCATTCCAACC ACAATTGC (SEQ ID NO: 287) | 4.8 |
| | | 1203286 | Rev | CCAGCTGTTGTTGGCTGCTA TCAGATTGTCTGAAG (SEQ ID NO: 288) | 4.6 |
| Thermoascus aurantiacus GH61 | T163E | 1203288 | Fwd | GATAGCAGCCAACAACAGCT GGGAGGTCACCATTCCAACC ACAATTGC (SEQ ID NO: 289) | 4.8 |
| | | 1203289 | Rev | CCAGCTGTTGTTGGCTGCTA TCAGATTGTCTGAAG (SEQ ID NO: 290) | 4.6 |
| Thermoascus aurantiacus GH61 | S186K | 1203297 | Fwd | GGCATGAGATTATTGCTCTT CACAAAGCTCAGAACCAGGA TGGTGCC (SEQ ID NO: 291) | 4.8 |
| | | 1203298 | Rev | GTGAAGAGCAATAATCTCAT GCCTCAGAACATAGTT (SEQ ID NO: 292) | 4.6 |
| Thermoascus aurantiacus GH61 | S186F | 1203299 | Fwd | GGCATGAGATTATTGCTCTT CACTTCGCTCAGAACCAGGA TGGTGCC (SEQ ID NO: 293) | 4.8 |
| | | 1203298 | Rev | GTGAAGAGCAATAATCTCAT GCCTCAGAACATAGTT (SEQ ID NO: 294) | 4.6 |

TABLE 13-continued

| Template Backbone | Amino Acid Substitution | Primer ID | Primer Direction | Primer Sequence | PCR fragment size (kb) |
|---|---|---|---|---|---|
| Thermoascus aurantiacus GH61 | S186T | 1203300 | Fwd | GGCATGAGATTATTGCTCTT CACACTGCTCAGAACCAGGA TGGTGCC (SEQ ID NO: 295) | 4.8 |
| | | 1203298 | Rev | GTGAAGAGCAATAATCTCAT GCCTCAGAACATAGTT (SEQ ID NO: 296) | 4.6 |
| Thermoascus aurantiacus GH61 | S186Y | 1203301 | Fwd | GGCATGAGATTATTGCTCTT CACTATGCTCAGAACCAGGA TGGTGCC (SEQ ID NO: 297) | 4.8 |
| | | 1203298 | Rev | GTGAAGAGCAATAATCTCAT GCCTCAGAACATAGTT (SEQ ID NO: 298) | 4.6 |
| Thermoascus aurantiacus GH61 | I200V | 1203302 | Fwd | GCCCAGAACTATCCCCAGTG CGTCAATCTGCAGGTCACTG GAGGTG (SEQ ID NO: 299) | 4.7 |
| | | 1203303 | Rev | GCACTGGGGATAGTTCTGGG CACCATCCTGGT (SEQ ID NO: 300) | 4.7 |
| Thermoascus aurantiacus GH61 | A213E | 1203306 | Fwd | TGGAGGTGGTTCTGATAACC CTGAGGGAACTCTTGGAACG GCACTC (SEQ ID NO: 301) | 4.7 |
| | | 1203307 | Rev | AGGGTTATCAGAACCACCTC CAGTGACCTGCAG (SEQ ID NO: 302) | 4.7 |
| Thermoascus aurantiacus GH61 | A219C | 1203308 | Fwd | CCTGCTGGAACTCTTGGAAC GTGCCTCTACCACGATACCG ATCCTG (SEQ ID NO: 303) | 4.7 |
| | | 1203309 | Rev | CGTTCCAAGAGTTCCAGCAG GGTTATCAGAACC (SEQ ID NO: 304) | 4.7 |
| Thermoascus aurantiacus GH61 | A219E | 1203310 | Fwd | CCTGCTGGAACTCTTGGAAC GGAGCTCTACCACGATACCG ATCCTG (SEQ ID NO: 305) | 4.7 |
| | | 1203309 | Rev | CGTTCCAAGAGTTCCAGCAG GGTTATCAGAACC (SEQ ID NO: 306) | 4.7 |
| Thermoascus aurantiacus GH61 | A219Q | 1203312 | Fwd | CCTGCTGGAACTCTTGGAAC GCAGCTCTACCACGATACCG ATCCTG (SEQ ID NO: 307) | 4.7 |
| | | 1203309 | Rev | CGTTCCAAGAGTTCCAGCAG GGTTATCAGAACC (SEQ ID NO: 308) | 4.7 |
| Thermoascus aurantiacus GH61 | T248R | 1203320 | Fwd | CATCCCTGGTCCTCCTCTGT ATAGGGGTCATCATCACCAC CATCACT (SEQ ID NO: 309) | 4.6 |
| | | 1203319 | Rev | ATACAGAGGAGGACCAGGGA TGATATAGCTGGAAA (SEQ ID NO: 310) | 4.8 |

Example 17: Construction of *Penicillium emersonii* GH61 Polypeptide Variants

The *Penicillium emersonii* GH61 polypeptide variants were constructed by SOE-PCR (Splicing by Overhang Extension Polymerase Chain Reaction) with plasmid pDFng154-17. In brief, the first PCR used forward primer EbZn NiaD Fwd and a mutation specific reverse primer (Table 14). The second PCR used reverse primer EbZn NiiA Rev and a mutation specific forward primer (Table 14) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the P. emersonii GH61 polypeptide variants contained 0.2 picomole of the EbZn NiaD Fwd primer, 0.2 picomole of the reverse primer listed in Table 14, 10 ng of template (pDFng154-17), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minute; and a final elongation at 72° C. for 10 minutes. The heat block then went to a 10° C. hold stage.

The second PCRs for the P. emersonii GH61 variants contained 0.2 picomole of the forward primer listed in Table 14, 0.2 picomole of the EbZn NiiA Rev primer, 10 ng of template (pDFng154-17), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.2 to 5.2 kb (as specified in Table 14) PCR product band was observed indicating proper amplification. The remaining 45 microliters were then treated with 10 units of Dpn 1 and 1×NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the P. emersonii GH61 variants contained 50 to 100 ng of each fragment produced in the first and second PCRs, 4 nanomoles each dATP, dTTP, dGTP, and dCTP, 1× ADVANTAGE® GC-Melt Buffer (Clontech Laboratories, Inc., Mountain View, Calif., USA), and 2.5 units of ADVANTAGE® GC Genomic LA Polymerase (Clontech Laboratories, Inc., Mountain View, Calif., USA) in a final reaction volume of 50 µl. The amplification was performed using an EPPENDORF® MASTERCYCLER® Gradient programmed for 1 cycle at 94° C. for 1 minutes; 35 cycles each at 94° C. for 30 seconds, 66° C. for 30 seconds, and 72° C. for 10 minutes; and a final elongation at 72° C. for 10 minutes. The heat block then went to a 10° C. hold stage. Primer BGMH110V2F primer (0.4 picomole) and primer BGMH109V2R (0.4 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng154-17), 0.4 picomole of primer BGMH110V2F, 0.4 picomole of primer BGMH109V2R, 1 nanomole each dATP, dTTP, dGTP, and dCTP, 1× ADVANTAGE® GC-Melt Buffer, and 2.5 units of ADVANTAGE® GC Genomic LA Polymerase in a final reaction volume of 50 µl. The amplification was performed using an EPPENDORF® MASTERCYCLER® Gradient programmed for 1 cycle at 94° C. for 1 minutes; 35 cycles each at 94° C. for 30 seconds, 66° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the Aspergillus oryzae COLs1300 strain as described in Example 21.

TABLE 14

| Template Backbone | Amino Acid Substitution | Primer ID | Primer Direction | Primer Sequence | PCR fragment size (kb) |
|---|---|---|---|---|---|
| Penicillium emersonii GH61 | S46V | 1203486 | Fwd | CTACAGCGGGTACATCGTCAA CGTCTTCCCCTACGAATCCAA CCCAC (SEQ ID NO: 311) | 5.2 |
|  |  | 1203484 | Rev | GTTGACGATGTACCCGCTGTA GCTGTTGGGAGT (SEQ ID NO: 312) | 4.2 |
| Penicillium emersonii GH61 | G76Q | 1203493 | Fwd | GTCGACGGCACAGGATACCAA CAGCCGGACATCATCTGCCAC CG (SEQ ID NO: 313) | 5.1 |
|  |  | 1203494 | Rev | TTGGTATCCTGTGCCGTCGAC GAAGCCCAGG (SEQ ID NO: 314) | 4.3 |
| Penicillium emersonii GH61 | S127R | 1203496 | Fwd | CGCCGTGCAACGGCAACTGCC GCACCGTCGACAAGACGACGC TG (SEQ ID NO: 315) | 4.9 |
|  |  | 1203497 | Rev | GCAGTTGCCGTTGCACGGCGC CAGGTAGGTG (SEQ ID NO: 316) | 4.5 |

Example 18: Construction of *Aspergillus aculeatus* GH61 Polypeptide Variants

The *Aspergillus aculeatus* GH61 polypeptide variants were constructed by SOE-PCR (Splicing by Overhang Extension Polymerase Chain Reaction) with plasmid pDFng155-33. In brief, the first PCR used forward primer EbZn NiaD Fwd and a mutation specific reverse primer (Table 15). The second PCR used reverse primer EbZn NiiA Rev and a mutation specific forward primer (Table 15) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *A. aculeatus* GH61 polypeptide variants contained 0.2 picomole of the EbZn NiaD Fwd primer, 0.2 picomole of the reverse primer listed in Table 15, 10 ng of template (pDFng155-33), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

The second PCRs for the *A. aculeatus* GH61 variants contained 0.2 picomole of the forward primer listed in Table 15, 0.2 picomole of the EbZn NiiA Rev primer, 10 ng of template (pDFng155-33), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.6 to 5.1 kb (as specified in Table 15) PCR product band was observed indicating proper amplification. The remaining 45 microliters were then treated with 10 units of Dpn 1 and 1×NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *A. aculeatus* GH61 variants contained 50 to 100 ng of each fragment produced in the first and second PCRs, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng155-33), 0.2 picomole of primer BGMH110V2F, 0.2 picomole of primer BGMH109V2R, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 15

| Template Backbone | Amino Acid Substitution | Primer ID | Primer Direction | Primer Sequence | PCR fragment size (kb) |
|---|---|---|---|---|---|
| *Aspergillus aculeatus* GH61 | D70Q | 1203194 | Fwd | CGTCGATGGTAGCGAGTATG CTCAGGCCGACATCATTTGC CACAAGA (SEQ ID NO: 317) | 5.6 |
| | | 1203195 | Rev | AGCATACTCGCTACCATCGA CGAAACCCAAGTCG (SEQ ID NO: 318) | 4.1 |
| *Aspergillus aculeatus* GH61 | D70T | 1203196 | Fwd | CGTCGATGGTAGCGAGTATG CTACCGCCGACATCATTTGC CACAAGA (SEQ ID NO: 319) | 5.6 |
| | | 1203195 | Rev | AGCATACTCGCTACCATCGA CGAAACCCAAGTCG (SEQ ID NO: 320) | 4.1 |

TABLE 15-continued

| Template Backbone | Amino Acid Substitution | Primer ID | Primer Direction | Primer Sequence | PCR fragment size (kb) |
|---|---|---|---|---|---|
| Aspergillus aculeatus GH61 | S136C | 1203202 | Fwd | CTCGAGTTTTTCAAGATTGA CGAGTGCGGTCTCATCAACG ACGACGAC (SEQ ID NO: 321) | 5.4 |
| | | 1203203 | Rev | CTCGTCAATCTTGAAAAACT CGAGGTCGGTCTTGG (SEQ ID NO: 322) | 4.3 |
| Aspergillus aculeatus GH61 | S136G | 1203208 | Fwd | CTCGAGTTTTTCAAGATTGA CGAGGGTGGTCTCATCAACG ACGACGAC (SEQ ID NO: 323) | 5.4 |
| | | 1203203 | Rev | CTCGTCAATCTTGAAAAACT CGAGGTCGGTCTTGG (SEQ ID NO: 324) | 4.3 |
| Aspergillus aculeatus GH61 | T147I | 1203209 | Fwd | ACGACGACGACGTCCCCGGT ATCTGGGCCAGTGATAACTT GATCG (SEQ ID NO: 325) | 5.3 |
| | | 1203210 | Rev | ACCGGGGACGTCGTCGTCGT TGATGAGACCG (SEQ ID NO: 326) | 4.4 |
| Aspergillus aculeatus GH61 | T161V | 1203211 | Fwd | GATCGCCAACAACAACAGCT GGGTCGTGACCATCCCCTCT GACATTG (SEQ ID NO: 327) | 5.3 |
| | | 1203212 | Rev | CCAGCTGTTGTTGTTGGCGA TCAAGTTATCACTGG (SEQ ID NO: 328) | 4.4 |
| Aspergillus aculeatus GH61 | T161F | 1203213 | Fwd | GATCGCCAACAACAACAGCT GGTTCGTGACCATCCCCTCT GACATTG (SEQ ID NO: 329) | 5.3 |
| | | 1203212 | Rev | CCAGCTGTTGTTGTTGGCGA TCAAGTTATCACTGG (SEQ ID NO: 330) | 4.4 |
| Aspergillus aculeatus GH61 | D167R | 1203220 | Fwd | TGGACTGTGACCATCCCCTC TCGTATTGCGGCTGGCAACT ACGTC (SEQ ID NO: 331) | 5.3 |
| | | 1203221 | Rev | AGAGGGGATGGTCACAGTCC AGCTGTTGTTGTT (SEQ ID NO: 332) | 4.4 |
| Aspergillus aculeatus GH61 | S184K | 1203222 | Fwd | GTCACGAAATCATTGCCCTT CACAAGGCTGGTAACAAGGA TGGTGCTC (SEQ ID NO: 333) | 5.2 |
| | | 1203223 | Rev | GTGAAGGGCAATGATTTCGT GACGGAGGACGTAG (SEQ ID NO: 334) | 4.5 |
| Aspergillus aculeatus GH61 | S184T | 1203225 | Fwd | GTCACGAAATCATTGCCCTT CACACCGCTGGTAACAAGGA TGGTGCTC (SEQ ID NO: 335) | 5.2 |
| | | 1203223 | Rev | GTGAAGGGCAATGATTTCGT GACGGAGGACGTAG (SEQ ID NO: 336) | 4.5 |
| Aspergillus aculeatus GH61 | S184Y | 1203226 | Fwd | GTCACGAAATCATTGCCCTT CACTACGCTGGTAACAAGGA TGGTGCTC (SEQ ID NO: 337) | 5.2 |
| | | 1203223 | Rev | GTGAAGGGCAATGATTTCGT GACGGAGGACGTAG (SEQ ID NO: 338) | 4.5 |

TABLE 15-continued

| Template Backbone | Amino Acid Substitution | Primer ID | Primer Direction | Primer Sequence | PCR fragment size (kb) |
|---|---|---|---|---|---|
| Aspergillus aculeatus GH61 | L198I | 1203227 | Fwd | GCTCAGAACTACCCTCAGTG CATCAACTTGAAGGTCACTG GCGGC (SEQ ID NO: 339) | 5.2 |
| | | 1203228 | Rev | GCACTGAGGGTAGTTCTGAG CACCATCCTTGTT (SEQ ID NO: 340) | 4.5 |
| Aspergillus aculeatus GH61 | L198V | 1203229 | Fwd | GCTCAGAACTACCCTCAGTG CGTCAACTTGAAGGTCACTG GCGGC (SEQ ID NO: 341) | 5.2 |
| | | 1203228 | Rev | GCACTGAGGGTAGTTCTGAG CACCATCCTTGTT (SEQ ID NO: 342) | 4.5 |
| Aspergillus aculeatus GH61 | S217M | 1203237 | Fwd | CCTTCTGGCACTGCTGGTGA GATGCTGTACAAGGACACCG ATGCTG (SEQ ID NO: 343) | 5.1 |
| | | 1203235 | Rev | CTCACCAGCAGTGCCAGAAG GAGCGAGATCAC (SEQ ID NO: 344) | 4.6 |
| Aspergillus aculeatus GH61 | S217Q | 1203238 | Fwd | CCTTCTGGCACTGCTGGTGA GCAGCTGTACAAGGACACCG ATGCTG (SEQ ID NO: 345) | 5.1 |
| | | 1203235 | Rev | CTCACCAGCAGTGCCAGAAG GAGCGAGATCAC (SEQ ID NO: 346) | 4.6 |
| Aspergillus aculeatus GH61 | K220R | 1203239 | Fwd | ACTGCTGGTGAGAGCCTGTA CCGTGACACCGATGCTGGTA TCCTC (SEQ ID NO: 347) | 5.1 |
| | | 1203240 | Rev | GTACAGGCTCTCACCAGCAG TGCCAGAAGGAG (SEQ ID NO: 348) | 4.6 |
| Aspergillus aculeatus GH61 | A243P | 1203244 | Fwd | CTCCTACGATATTCCCGGAC CTCCCATGTACAACGCTACC TCCAGCT (SEQ ID NO: 349) | 5.0 |
| | | 1203245 | Rev | AGGTCCGGGAATATCGTAGG AGGAAAGAGACTGG (SEQ ID NO: 350) | 4.7 |

Example 19: Construction of *Penicillium pinophilum* GH61 Polypeptide Variants

The *Penicillium pinophilum* GH61 polypeptide variants were constructed by SOE-PCR (Splicing by Overhang Extension Polymerase Chain Reaction) with plasmid pDFng156-37. In brief, the first PCR used forward primer EbZn NiaD Fwd and a mutation specific reverse primer (Table 16). The second PCR used reverse primer EbZn NiiA Rev and a mutation specific forward primer (Table 16) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *P. pinophilum* GH61 polypeptide variants contained 0.2 picomole of the EbZn NiaD Fwd primer, 0.2 picomole of the reverse primer listed in Table 16, 10 ng of template (pDFng156-37), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 μl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

The second PCRs for the *P. pinophilum* GH61 variants contained 0.2 picomole of the forward primer listed in Table 16, 0.2 picomole of the EbZn NiiA Rev primer, 10 ng of template (pDFng156-37), 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 μl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.1 to 5.5 kb (as specified in Table 16) PCR product band was observed indicating proper amplification. The remaining 45 microliters were then treated with 10 units of Dpn 1 and 1×NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *P. pinophilum* GH61 variants contained 50 to 100 ng of each fragment produced in the first and second PCRs, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.2 picomole) and primer BGMH109V2R (0.2 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng156-37), 0.2 picomole of primer BGMH110V2F, 0.2 picomole of primer BGMH109V2R, 1 nanomole each dATP, dTTP, dGTP, and dCTP, 1× PHUSION® High-Fidelity Buffer, and 0.7 unit of PHUSION® High-Fidelity DNA Polymerase in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each SOE-PCR product was analyzed by 1.0% agarose electrophoresis using TAE buffer where an approximately 8 kb PCR product band was observed indicating proper amplification. The remaining 45 µl of each SOE-PCR product then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 16

| Template Backbone | Amino Acid Substitution | Primer ID | Primer Direction | Primer Sequence | PCR fragment size (kb) |
|---|---|---|---|---|---|
| *Penicillium pinophilum* GH61 | S34F | 1203326 | Fwd | CAAAACATCGTTATCGACG GTAAATTTTAAGCAGTGAT GCATCCATTATTAA (SEQ ID NO: 351) | 5.5 |
| | | 1203327 | Rev | TTTACCGTCGATAACGATG TTTTGCACAAAACCATG (SEQ ID NO: 352) | 4.1 |
| *Penicillium pinophilum* GH61 | Q42I | 1203334 | Fwd | AGTTACTCTGGATACCTTG TGAATATCTTCCCCTACGA GTCCAACCCA (SEQ ID NO: 353) | 5.4 |
| | | 1203333 | Rev | ATTCACAAGGTATCCAGAG TAACTGATTTTTTTGTAAG (SEQ ID NO: 354) | 4.2 |
| *Penicillium pinophilum* GH61 | Q42V | 1203335 | Fwd | AGTTACTCTGGATACCTTG TGAATGTCTTCCCCTACGA GTCCAACCCA (SEQ ID NO: 355) | 5.4 |
| | | 1203333 | Rev | ATTCACAAGGTATCCAGAG TAACTGATTTTTTTGTAAG (SEQ ID NO: 356) | 4.2 |
| *Penicillium pinophilum* GH61 | S47L | 1203338 | Fwd | TGTGAATCAGTTCCCCTAC GAGCTTAACCCACCAGCTG TTATTGGGT (SEQ ID NO: 357) | 5.4 |
| | | 1203337 | Rev | CTCGTAGGGGAACTGATTC ACAAGGTATCCAGAG (SEQ ID NO: 358) | 4.2 |
| *Penicillium pinophilum* GH61 | A56C | 1203340 | Fwd | CCACCAGCTGTTATTGGGT GGTGCACAACTGCAACCGA CCTGGGA (SEQ ID NO: 359) | 5.4 |
| | | 1203341 | Rev | CCACCCAATAACAGCTGGT GGGTTGGACTCGT (SEQ ID NO: 360) | 4.2 |

TABLE 16-continued

| Template Backbone | Amino Acid Substitution | Primer ID | Primer Direction | Primer Sequence | PCR fragment size (kb) |
|---|---|---|---|---|---|
| Penicillium pinophilum GH61 | A56E | 1203342 | Fwd | CCACCAGCTGTTATTGGGT GGGAGACAACTGCAACCGA CCTGGGA (SEQ ID NO: 361) | 5.4 |
| | | 1203341 | Rev | CCACCCAATAACAGCTGGT GGGTTGGACTCGT (SEQ ID NO: 362) | 4.2 |
| Penicillium pinophilum GH61 | G138C | 1203353 | Fwd | CTAGACTTTGTCAAGATTG ACCAATGCGGTTTGATCGA CGATACTACCC (SEQ ID NO: 363) | 5.1 |
| | | 1203354 | Rev | TTGGTCAATCTTGACAAAG TCTAGCTTAGTCTTATCC (SEQ ID NO: 364) | 4.5 |
| Penicillium pinophilum GH61 | T149I | 1203359 | Fwd | ACGATACTACCCCCCCGGG TATCTGGGCTTCCGACAAA CTTATCG (SEQ ID NO: 365) | 5.1 |
| | | 1203360 | Rev | ACCCGGGGGGGTAGTATCG TCGATCAAACCAC (SEQ ID NO: 366) | 4.5 |
| Penicillium pinophilum GH61 | V164C | 1203365 | Fwd | GCTGCCAACAACAGCTGGA CTTGCACTATCCCCTCCAC CATCGCG (SEQ ID NO: 367) | 5.1 |
| | | 1203366 | Rev | AGTCCAGCTGTTGTTGGCA GCGATAAGTTTGTCG (SEQ ID NO: 368) | 4.5 |
| Penicillium pinophilum GH61 | V164L | 1203367 | Fwd | GCTGCCAACAACAGCTGGA CTCTTACTATCCCCTCCAC CATCGCG (SEQ ID NO: 369) | 5.1 |
| | | 1203366 | Rev | AGTCCAGCTGTTGTTGGCA GCGATAAGTTTGTCG (SEQ ID NO: 370) | 4.5 |
| Penicillium pinophilum GH61 | I166L | 1203368 | Fwd | CCAACAACAGCTGGACTGT AACTCTTCCCTCCACCATC GCGCCTGG (SEQ ID NO: 372) | 5.0 |
| | | 1203369 | Rev | AGTTACAGTCCAGCTGTTG TTGGCAGCGATAAGTT (SEQ ID NO: 372) | 4.6 |
| Penicillium pinophilum GH61 | T169R | 1203370 | Fwd | CTGGACTGTAACTATCCCC TCCCGCATCGCGCCTGGAA ACTACGTTT (SEQ ID NO: 373) | 5.0 |
| | | 1203371 | Rev | GGAGGGGATAGTTACAGTC CAGCTGTTGTTGGC (SEQ ID NO: 374) | 4.6 |
| Penicillium pinophilum GH61 | S186K | 1203372 | Fwd | GCCACGAAATCATTGCTCT TCACAAGGCTGGAAACGCA GACGGTGC (SEQ ID NO: 375) | 5.0 |
| | | 1203373 | Rev | GTGAAGAGCAATGATTTCG TGGCGCAAAACGTAGT (SEQ ID NO: 376) | 4.6 |
| Penicillium pinophilum GH61 | S186F | 1203374 | Fwd | GCCACGAAATCATTGCTCT TCACTTTGCTGGAAACGCA GACGGTGC (SEQ ID NO: 377) | 5.0 |
| | | 1203373 | Rev | GTGAAGAGCAATGATTTCG TGGCGCAAAACGTAGT (SEQ ID NO: 378) | 4.6 |

TABLE 16-continued

| Template Backbone | Amino Acid Substitution | Primer ID | Primer Direction | Primer Sequence | PCR fragment size (kb) |
|---|---|---|---|---|---|
| Penicillium pinophilum GH61 | S186T | 1203375 | Fwd | GCCACGAAATCATTGCTCT TCACACCGCTGGAAACGCA GACGGTGC (SEQ ID NO: 379) | 5.0 |
| | | 1203373 | Rev | GTGAAGAGCAATGATTTCG TGGCGCAAAACGTAGT (SEQ ID NO: 380) | 4.6 |
| Penicillium pinophilum GH61 | S186Y | 1203376 | Fwd | GCCACGAAATCATTGCTCT TCACTACGCTGGAAACGCA GACGGTGC (SEQ ID NO: 381) | 5.0 |
| | | 1203373 | Rev | GTGAAGAGCAATGATTTCG TGGCGCAAAACGTAGT (SEQ ID NO: 382) | 4.6 |
| Penicillium pinophilum GH61 | I200V | 1203377 | Fwd | TGCCCAAAACTACCCTCAA TGCGTCAACTTGGAGATCA CCGGCAGC (SEQ ID NO: 383) | 4.9 |
| | | 1203378 | Rev | GCATTGAGGGTAGTTTTGG GCACCGTCTGCGT (SEQ ID NO: 384) | 4.7 |
| Penicillium pinophilum GH61 | S213E | 1203381 | Fwd | GCAGCGGAACCGCCGCTCC CGAGGGTACCGCTGGCGAA AAGCTC (SEQ ID NO: 385) | 4.9 |
| | | 1203382 | Rev | GGGAGCGGCGGTTCCGCTG CCGGTGATCTC (SEQ ID NO: 386) | 4.7 |
| Penicillium pinophilum GH61 | T222R | 1203388 | Fwd | ACCGCTGGCGAAAAGCTCT ACCGCTCTACTGACCCCGG TATCTTGG (SEQ ID NO: 387) | 4.9 |
| | | 1203389 | Rev | GTAGAGCTTTTCGCCAGCG GTACCAGAGGGAG (SEQ ID NO: 388) | 4.7 |
| Penicillium pinophilum GH61 | T245P | 1203393 | Fwd | GACCTACGTTATTCCCGGA CCACCCCTGTGGAGCGGTG CTGCCAA (SEQ ID NO: 389) | 4.8 |
| | | 1203394 | Rev | TGGTCCGGGAATAACGTAG GTCGACAAGGATTGG (SEQ ID NO: 390) | 4.8 |

Example 20: Construction of *Thielavia terrestris* GH61 Polypeptide Variants

The *Thielavia terrestris* GH61 polypeptide variants were constructed by SOE-PCR (Splicing by Overhang Extension Polymerase Chain Reaction) with plasmid pDFng157-51. In brief, the first PCR used forward primer EbZn NiaD Fwd and a mutation specific reverse primer (Table 17). The second PCR used reverse primer EbZn NiiA Rev and a mutation specific forward primer (Table 17) containing the sequence coding for the altered amino acid. The mutation specific forward and reverse primers contained 15-20 overlapping nucleotides. The third PCR used the overlapping nucleotides to splice together the fragments produced in the first and second reaction. Finally, using a nested forward primer BGMH110V2F and a nested reverse primer BGMH109V2R, the spliced fragment was amplified by PCR.

The first PCRs for the *T. terrestris* GH61 polypeptide variants contained 0.2 picomole of the EbZn NiaD Fwd primer, 0.4 picomole of the reverse primer listed in Table 17, 10 ng of template (pDFng157-51), 4 nanomoles each dATP, dTTP, dGTP, and dCTP, 1× ADVANTAGE® GC-Melt Buffer, and 2.5 units of ADVANTAGE® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 5 minutes; and a final elongation at 72° C. for 10 minutes. The heat block then went to a 10° C. hold stage.

The second PCRs for the *T. terrestris* GH61 variants contained 0.2 picomole of the forward primer listed in Table 17, 0.4 picomole of the EbZn NiiA Rev primer, 10 ng of template (pDFng157-51), 4 nanomoles each dATP, dTTP, dGTP, and dCTP, 1× Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 5 minutes; and a final elongation at 72° C. for 10 minutes. The heat block then went to a 10° C. hold stage.

Each PCR product was analyzed by 1.0% agarose electrophoresis using TAE buffer where a 4.1 to 5.6 kb (as specified in Table 17) PCR product band was observed indicating proper amplification. The remaining 45 microliters were then treated with 10 units of Dpn 1 and 1×NEB4 to remove the remaining wild-type template. The reaction was incubated for 4 hours at 37° C. and then purified using a MINELUTE® 96 UF Purification Kit. The purified PCR products were resuspended in deionized water to a final volume equal to 20 µl. The concentration of each fragment was measured using a NanoDrop 2000.

The third SOE-PCR for the *T. terrestris* GH61 variants contained 50 to 100 ng of each fragment produced in the first and second PCRs, 4 nanomoles each dATP, dTTP, dGTP, and dCTP, 1× Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 10 minutes; and a final elongation at 72° C. for 10 minutes. The heat block then went to a 10° C. hold stage. Primer BGMH110V2F primer (0.4 picomole) and primer BGMH109V2R (0.4 picomole) were added during the annealing/elongation step of the fifth cycle to allow for the overlapping nucleotides to splice before amplification.

The wild-type fragment was produced using conditions similar to the third PCR. The reaction was composed of 10 ng of template (pDFng157-51), 0.4 picomole of primer BGMH110V2F, 0.4 picomole of primer BGMH109V2R, 1 nanomole each dATP, dTTP, dGTP, and dCTP, 1× Advantage® GC-Melt Buffer, and 2.5 units of Advantage® GC Genomic LA Polymerase in a final reaction volume of 50 µl. The amplification was performed using an EPPENDORF® MASTERCYCLER® Gradient programmed for 1 cycle at 94° C. for 1 minute; 35 cycles each at 94° C. for 30 seconds, 66° C. for 30 seconds, and 72° C. for 10 minutes; and a final elongation at 72° C. for 10 minutes. The heat block then went to a 10° C. hold stage.

Each SOE-PCR product solution was analyzed by 1.0% agarose electrophoresis using TAE buffer where an approximately 8 kb PCR product band was observed indicating proper amplification. The remaining 45 µl of each SOE-PCR product was then purified using a MINELUTE® 96 UF Purification Kit. The purified PCR products were resuspended in deionized water to a final volume equal to 20 µl. The concentration of each fragment was measured using a NanoDrop 2000. The entire volume was then transformed into the *Aspergillus oryzae* COLs1300 strain as described in Example 21.

TABLE 17

| Template Backbone | Amino Acid Substitution | Primer ID | Primer Direction | Primer Sequence | PCR fragment size (kb) |
|---|---|---|---|---|---|
| *Thielavia terrestris* GH61 | S42I | 1203409 | Fwd | TACCAGGGTTACGATCCGACCAT CTTCCCTTACATGCAGAACCCGC (SEQ ID NO: 391) | 5.6 |
| | | 1203408 | Rev | GGTCGGATCGTAACCCTGGTACG AGACCCCG (SEQ ID NO: 392) | 4.1 |
| *Thielavia terrestris* GH61 | S42V | 1203410 | Fwd | TACCAGGGTTACGATCCGACCGT CTTCCCTTACATGCAGAACCCGC (SEQ ID NO: 393) | 5.6 |
| | | 1203408 | Rev | GGTCGGATCGTAACCCTGGTACG AGACCCCG (SEQ ID NO: 394) | 4.1 |
| *Thielavia terrestris* GH61 | Q47L | 1203413 | Fwd | CCGACCTCCTTCCCTTACATGCT CAACCCGCCCATCGTGGTCGG (SEQ ID NO: 395) | 5.5 |
| | | 1203412 | Rev | CATGTAAGGGAAGGAGGTCGGAT CGTAACCCTG (SEQ ID NO: 396) | 4.2 |
| *Thielavia terrestris* GH61 | S72T | 1203421 | Fwd | TTGCCCCGGATGCCTTCGCCACC GGCGATATCATCTGCCACAAGA (SEQ ID NO: 397) | 5.4 |
| | | 1203420 | Rev | GGCGAAGGCATCCGGGGCAACAA AGCCGTTG (SEQ ID NO: 398) | 4.3 |
| *Thielavia terrestris* GH61 | V139C | 1203427 | Fwd | CGAGTTCTTCAAGATCGACGAGT GCGGCCTGGTCGACGGCAGCTC (SEQ ID NO: 399) | 5.3 |
| | | 1203428 | Rev | CTCGTCGATCTTGAAGAACTCGA GCTTGGTCTTG (SEQ ID NO: 400) | 4.4 |
| *Thielavia terrestris* GH61 | V139G | 1203433 | Fwd | CGAGTTCTTCAAGATCGACGAGG GCGGCCTGGTCGACGGCAGCTC (SEQ ID NO: 401) | 5.3 |
| | | 1203428 | Rev | CTCGTCGATCTTGAAGAACTCGA GCTTGGTCTTG (SEQ ID NO: 402) | 4.4 |

TABLE 17-continued

| Template Backbone | Amino Acid Substitution | Primer ID | Primer Direction | Primer Sequence | PCR fragment size (kb) |
|---|---|---|---|---|---|
| Thielavia terrestris GH61 | V150I | 1203434 | Fwd | ACGGCAGCTCGGCGCCCGGTATC TGGGGCTCCGACCAGCTCAT (SEQ ID NO: 403) | 5.2 |
| | | 1203435 | Rev | ACCGGGCGCCGAGCTGCCGTCGA CCAGG (SEQ ID NO: 404) | 4.5 |
| Thielavia terrestris GH61 | V165L | 1203442 | Fwd | GCCAACAACAACTCGTGGCTCCT CGAGATCCCGCCCACCATCGC (SEQ ID NO: 405) | 5.2 |
| | | 1203441 | Rev | GAGCCACGAGTTGTTGTTGGCGA TGAGCTGGT (SEQ ID NO: 406) | 4.5 |
| Thielavia terrestris GH61 | A426P | 1203469 | Fwd | CCTACACCGTCCCGGGGCCGCCG CTCATCTCCGGCGCCGTCAG (SEQ ID NO: 407) | 4.9 |
| | | 1203470 | Rev | CGGCCCCGGGACGGTGTAGGTGA TCGGGG (SEQ ID NO: 408) | 4.8 |

Example 21: Expression of the *T. aurantiacus* GH61A, *P. emersonii* GH61A, *A. aculeatus* GH61, *Penicillium pinophilum* GH61, and *Thielavia terrestris* GH61 Polypeptides Variants in *Aspergillus oryzae* COLs1300

*Aspergillus oryzae* COLs1300 was inoculated onto a COVE-N-Gly plate containing 10 mM urea and incubated at 34° C. until confluent. Spores were collected from the plate by washing with 10 ml of YP medium. The whole spore suspension was used to inoculate 100 ml of COL1300 protoplasting cultivation medium in a 500 ml polycarbonate shake flask. The shake flask was incubated at 30° C. with agitation at 200 rpm for 16-20 hours. Mycelia were filtered through a funnel lined with MIRACLOTH® and washed with 200 ml of 0.6 M MgSO$_4$. Washed mycelia were resuspended in 20 ml of COLs1300 protoplasting solution in a 125 ml sterile polycarbonate shake flask and incubated at room temperature for 3 minutes. One ml of a solution of 12 mg of BSA per ml of deionized water was added to the shake flask and the shake flask was then incubated at 37° C. with mixing at 65 rpm for 100-150 minutes until protoplasting was complete. The mycelia/protoplast mixture was filtered through a funnel lined with MIRACLOTH® in to a 50 ml conical tube and overlayed with 5 ml of ST solution. The 50 ml conical tube was centrifuged at 1050×g for 15 minutes with slow acceleration/deceleration. After centrifugation, the liquid was separated in 3 phases. The interphase which contained the protoplasts was transferred to a new 50 ml conical tube. Two volumes of STC solution were added to the protoplasts followed by centrifugation at 1050×g for 5 minutes. The supernatant was discarded and the protoplasts were washed twice with 5 ml of STC solution with resuspension of the protoplast pellet, centrifugation at 1050×g for 5 minutes, and decanting of the supernatant each time. After the final decanting, the protoplast pellet was resuspended in STC solution at a concentration of 5×10$^7$/ml. Protoplasts were frozen at −80° C. until transformation.

A 15 μl volume of each mutant fragment, as described in Examples 16-20, was used to transform 100 μl of *A. oryzae* COLs1300 protoplasts in a 15 ml round bottom tube. After an initial incubation at room temperature for 15 minutes, 300 μl of PEG solution was added to the 15 ml round bottom tube containing the transformation mixture. The reaction was incubated for an additional 15 minutes at room temperature. Six ml of melted top agar was added to the reaction and the whole mixture was poured evenly onto a sucrose agar plate supplemented with 10 mM NaNO$_3$ and left at room temperature until the top agar was set. The plates were incubated at 37° C. for 4-6 days. Resulting transformants were picked using sterile inoculating loops and transferred to plates containing COVE-N-gly medium and incubated at 34° C. for approximately 4 days (until sporulation). Spores were inoculated into a deep well 48 well plate containing 0.5 ml of MDU2BP medium incubated at 34° C. for 3 days, stationary in a humidified box. Samples were harvested on the third day by removing the mycelia mat.

Example 22: Determination of Tm (Melting Temperature) of *T. aurantiacus* GH61A, *P. emersonii* GH61A, *A. aculeatus* GH61, *Penicillium pinophilum* GH61, and *Thielavia terrestris* GH61 Variants by Protein Thermal Unfolding Analysis Protein thermal unfolding of the *Thermoascus aurantiacus* GH61A, *Penicillium emersonii* GH61A, *Aspergillus aculeatus* GH61, *Penicillium pinophilum* GH61, *Thielavia terrestris* GH61 variants was determined by protein thermal unfolding analysis described according to Example 10. The broths of the variants, and wild-type polypeptides thereof were prepared as described in Example 21. Average reading of triplicate broths from one to five transformants for each variant was determined, and the increase in Tm for each variant is shown in Table 18.

TABLE 18

Increase of melting temperatures (° C.) of *T. aurantiacus* GH61A, *P. emersonii* GH61A, *A. aculeatus* GH61, *P. pinophilum* GH61, and *T. terrestris* GH61 polypeptides variants comparing to wild-type polypeptide as determined by protein thermal unfolding analysis

| Wild-Type *T. aurantiacus* GH61A | | Wild-Type Tm (° C.) 73.0 |
|---|---|---|
| | Mutation | Δ ° C. |
| *T. aurantiacus* GH61A | Q26I | 3 |
| *T. aurantiacus* GH61A | Q42I | 2 |
| *T. aurantiacus* GH61A | Q42V | 2 |

TABLE 18-continued

Increase of melting temperatures (° C.) of *T. aurantiacus* GH61A, *P. emersonii* GH61A, *A. aculeatus* GH61, *P. pinophilum* GH61, and *T. terrestris* GH61 polypeptides variants comparing to wild-type polypeptide as determined by protein thermal unfolding analysis

| | Mutation | Δ ° C. |
|---|---|---|
| *T. aurantiacus* GH61A | S123R | 2 |
| *T. aurantiacus* GH61A | S138E | 3 |
| *T. aurantiacus* GH61A | S138K | 3 |
| *T. aurantiacus* GH61A | S138L | 3 |
| *T. aurantiacus* GH61A | T163V | 3 |
| *T. aurantiacus* GH61A | T163E | 3 |
| *T. aurantiacus* GH61A | S186K | 3 |
| *T. aurantiacus* GH61A | S186F | 3 |
| *T. aurantiacus* GH61A | S186T | 3 |
| *T. aurantiacus* GH61A | S186Y | 3 |
| *T. aurantiacus* GH61A | I200V | 3 |
| *T. aurantiacus* GH61A | A213E | 3 |
| *T. aurantiacus* GH61A | A219C | 3 |
| *T. aurantiacus* GH61A | A219E | 3 |
| *T. aurantiacus* GH61A | A219Q | 3 |
| *T. aurantiacus* GH61A | T248R | 3 |

| Wild-Type *P. emersonii* GH61A | Wild-Type Tm (° C.) 67.2 |
|---|---|

| | Mutation | Δ ° C. |
|---|---|---|
| *P. emersonii* GH61A | S46V | 2 |
| *P. emersonii* GH61A | G76Q | 1 |
| *P. emersonii* GH61A | S127R | 1 |

| Wild-Type *A. aculeatus* GH61 | Wild-Type Tm (° C.) 44.8 |
|---|---|

| | Mutation | Δ ° C. |
|---|---|---|
| *A. aculeatus* GH61 | D70Q | 1 |
| *A. aculeatus* GH61 | D70T | 2 |
| *A. aculeatus* GH61 | S136C | 2 |
| *A. aculeatus* GH61 | S136G | 1 |
| *A. aculeatus* GH61 | T147I | 3 |
| *A. aculeatus* GH61 | T161V | 2 |
| *A. aculeatus* GH61 | T161F | 2 |
| *A. aculeatus* GH61 | D167R | 5 |
| *A. aculeatus* GH61 | S184K | 2 |
| *A. aculeatus* GH61 | S184T | 2 |
| *A. aculeatus* GH61 | S184Y | 3 |
| *A. aculeatus* GH61 | L198I | 2 |
| *A. aculeatus* GH61 | L198V | 1 |
| *A. aculeatus* GH61 | S217M | 2 |
| *A. aculeatus* GH61 | S217Q | 2 |
| *A. aculeatus* GH61 | K220R | 2 |
| *A. aculeatus* GH61 | A243P | 3 |

| Wild-Type *P. pinophilum* GH61 | Wild-Type Tm (° C.) 55.4 |
|---|---|

| | Mutation | Δ ° C. |
|---|---|---|
| *P. pinophilum* GH61 | S34F | 2 |
| *P. pinophilum* GH61 | Q42I | 4 |
| *P. pinophilum* GH61 | Q42V | 4 |
| *P. pinophilum* GH61 | S47L | 2 |
| *P. pinophilum* GH61 | A56C | 2 |
| *P. pinophilum* GH61 | A56E | 2 |
| *P. pinophilum* GH61 | G138C | 5 |
| *P. pinophilum* GH61 | T149I | 3 |
| *P. pinophilum* GH61 | V164C | 4 |
| *P. pinophilum* GH61 | V164L | 3 |
| *P. pinophilum* GH61 | I166L | 2 |
| *P. pinophilum* GH61 | T169R | 2 |
| *P. pinophilum* GH61 | S186K | 5 |
| *P. pinophilum* GH61 | S186F | 5 |
| *P. pinophilum* GH61 | S186T | 2 |
| *P. pinophilum* GH61 | S186Y | 4 |
| *P. pinophilum* GH61 | I200V | 2 |
| *P. pinophilum* GH61 | S213E | 2 |
| *P. pinophilum* GH61 | T222R | 5 |
| *P. pinophilum* GH61 | T245P | 3 |

| Wild-Type *T. terrestris* GH61 | Wild-Type Tm (° C.) 56.1 |
|---|---|

| | Mutation | Δ ° C. |
|---|---|---|
| *T. terrestris* GH61 | S42I | 2 |
| *T. terrestris* GH61 | S42V | 2 |
| *T. terrestris* GH61 | Q47L | 2 |
| *T. terrestris* GH61 | S72T | 2 |
| *T. terrestris* GH61 | V139C | 2 |
| *T. terrestris* GH61 | V139G | 2 |
| *T. terrestris* GH61 | V150I | 1 |
| *T. terrestris* GH61 | V165L | 2 |
| *T. terrestris* GH61 | A246P | 3 |

The present invention is further described by the following numbered paragraphs:

[1] A GH61 polypeptide variant, comprising a substitution at one or more positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity and wherein the variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the amino acid sequence of a parent GH61 polypeptide.

[2] The variant of paragraph 1, wherein the parent GH61 polypeptide is selected from the group consisting of: (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410, or (ii) the full-length complement of (i); (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410; and (d) a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, which has cellulolytic enhancing activity.

[3] The variant of paragraph 2, wherein the parent GH61 polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99% or 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[4] The variant of paragraph 2, wherein the parent GH61 polypeptide is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410 or (ii) the full-length complement of (i).

[5] The variant of paragraph 2, wherein the parent GH61 polypeptide is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 408, or 410.

[6] The variant of paragraph 2, wherein the parent GH61 polypeptide comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[7] The variant of paragraph 2, wherein the parent GH61 polypeptide is a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411, wherein the fragment has cellulolytic enhancing activity.

[8] The variant of any of paragraphs 1-7, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 56, 158, 160, 162, 164, 166, 168, 409, or 411.

[9] The variant of any of paragraphs 2-8, wherein the fragment of the variant consists of at least 85% of the amino acid residues, e.g., at least 90% of the amino acid residues or at least 95% of the amino acid residues of the mature polypeptide of the parent GH61 polypeptide.

[10] The variant of any of paragraphs 1-9, wherein the number of substitutions is 1-29, e.g., 1, 2, 3, 4, 5, 6, 7, 8, 9, 10, 11, 12, 13, 14, 15, 16, 17, 18, 19, 20, 21, 22, 23, 24, 25, 26, 27, and 28 substitutions

[11] The variant of any of paragraphs 1-10, which comprises a substitution at a position corresponding to position 26.

[12] The variant of paragraph 11, wherein the substitution is Ile.

[13] The variant of any of paragraphs 1-12, which comprises a substitution at a position corresponding to position 32.

[14] The variant of paragraph 13, wherein the substitution is Glu or Ser.

[15] The variant of any of paragraphs 1-14, which comprises a substitution at a position corresponding to position 34.

[16] The variant of paragraph 15, wherein the substitution is Phe.

[17] The variant of any of paragraphs 1-16, which comprises a substitution at a position corresponding to position 40.

[18] The variant of paragraph 17, wherein the substitution is Ala.

[19] The variant of any of paragraphs 1-18, which comprises a substitution at a position corresponding to position 41.

[20] The variant of paragraph 19, wherein the substitution is Thr.

[21] The variant of any of paragraphs 1-20, which comprises a substitution at a position corresponding to position 42.

[22] The variant of paragraph 21, wherein the substitution is Ile, Glu, or Val.

[23] The variant of any of paragraphs 1-22, which comprises a substitution at a position corresponding to position 47.

[24] The variant of paragraph 23, wherein the substitution is Glu, Leu, or Arg.

[25] The variant of any of paragraphs 1-24, which comprises a substitution at a position corresponding to position 56.

[26] The variant of paragraph 25, wherein the substitution is Cys, Glu, or Thr.

[27] The variant of any of paragraphs 1-26, which comprises a substitution at a position corresponding to position 72.

[28] The variant of paragraph 27, wherein the substitution is Gln or Thr.

[29] The variant of any of paragraphs 1-28, which comprises a substitution at a position corresponding to position 102.

[30] The variant of paragraph 29, wherein the substitution is Lys or Pro.

[31] The variant of any of paragraphs 1-30, which comprises a substitution at a position corresponding to position 123.

[32] The variant of paragraph 31, wherein the substitution is Arg.

[33] The variant of any of paragraphs 1-32, which comprises a substitution at a position corresponding to position 138.

[34] The variant of paragraph 33, wherein the substitution is Cys, Glu, Gly, Lys, Leu, or Met.

[35] The variant of any of paragraphs 1-34, which comprises a substitution at a position corresponding to position 149.

[36] The variant of paragraph 35, wherein the substitution is Ile.

[37] The variant of any of paragraphs 1-36, which comprises a substitution at a position corresponding to position 152.

[38] The variant of paragraph 37, wherein the substitution is Ser.

[39] The variant of any of paragraphs 1-38, which comprises a substitution at a position corresponding to position 163.

[40] The variant of paragraph 39, wherein the substitution is Glu, Phe, or Val.

[41] The variant of any of paragraphs 1-40, which comprises a substitution at a position corresponding to position 164.

[42] The variant of paragraph 41, wherein the substitution is Cys or Leu.

[43] The variant of any of paragraphs 1-42, which comprises a substitution at a position corresponding to position 166.

[44] The variant of paragraph 43, wherein the substitution is Leu.

[45] The variant of any of paragraphs 1-44, which comprises a substitution at a position corresponding to position 169.

[46] The variant of paragraph 45, wherein the substitution is Arg or Cys.

[47] The variant of any of paragraphs 1-46, which comprises a substitution at a position corresponding to position 173.

[48] The variant of paragraph 47, wherein the substitution is Cys.

[49] The variant of any of paragraphs 1-48, which comprises a substitution at a position corresponding to position 186.

[50] The variant of paragraph 49, wherein the substitution is Phe, Lys, Thr, or Tyr.

[51] The variant of any of paragraphs 1-50, which comprises a substitution at a position corresponding to position 200.

[52] The variant of paragraph 51, wherein the substitution is Ile or Val.

[53] The variant of any of paragraphs 1-52, which comprises a substitution at a position corresponding to position 207.

[54] The variant of paragraph 53, wherein the substitution is Pro.

[55] The variant of any of paragraphs 1-54, which comprises a substitution at a position corresponding to position 213.

[56] The variant of paragraph 55, wherein the substitution is Glu.

[57] The variant of any of paragraphs 1-56, which comprises a substitution at a position corresponding to position 219.

[58] The variant of paragraph 57, wherein the substitution is Glu, Met, Gln, or Cys.

[59] The variant of any of paragraphs 1-58, which comprises a substitution at a position corresponding to position 222.

[60] The variant of paragraph 59, wherein the substitution is Arg.

[61] The variant of any of paragraphs 1-60, which comprises a substitution at a position corresponding to position 234.

[62] The variant of paragraph 61, wherein the substitution is Gly or Lys.

[63] The variant of any of paragraphs 1-62, which comprises a substitution at a position corresponding to position 246.

[64] The variant of paragraph 63, wherein the substitution is Pro.

[65] The variant of any of paragraphs 1-64, which comprises a substitution at a position corresponding to position 249.

[66] The variant of paragraph 65, wherein the substitution is Gln, Arg, or Cys.

[67] The variant of any of paragraphs 1-66, which comprises a substitution at a position corresponding to position 250.

[68] The variant of paragraph 67, wherein the substitution is Cys.

[69] The variant of any of paragraphs 1-68, which comprises a substitution at two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[70] The variant of any of paragraphs 1-68, which comprises a substitution at three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[71] The variant of any of paragraphs 1-68, which comprises a substitution at four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[72] The variant of any of paragraphs 1-68, which comprises a substitution at five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[73] The variant of any of paragraphs 1-68, which comprises a substitution at six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[74] The variant of any of paragraphs 1-68, which comprises a substitution at seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[75] The variant of any of paragraphs 1-68, which comprises a substitution at eight positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[76] The variant of any of paragraphs 1-68, which comprises a substitution at nine positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[77] The variant of any of paragraphs 1-68, which comprises a substitution at ten positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[78] The variant of any of paragraphs 1-68, which comprises a substitution at eleven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[79] The variant of any of paragraphs 1-68, which comprises a substitution at twelve positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[80] The variant of any of paragraphs 1-68, which comprises a substitution at thirteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[81] The variant of any of paragraphs 1-68, which comprises a substitution at fourteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[82] The variant of any of paragraphs 1-68, which comprises a substitution at fifteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[83] The variant of any of paragraphs 1-68, which comprises a substitution at sixteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[84] The variant of any of paragraphs 1-68, which comprises a substitution at seventeen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[85] The variant of any of paragraphs 1-68, which comprises a substitution at eighteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[86] The variant of any of paragraphs 1-68, which comprises a substitution at nineteen positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[87] The variant of any of paragraphs 1-68, which comprises a substitution at twenty positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[88] The variant of any of paragraphs 1-68, which comprises a substitution at twenty-one positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[89] The variant of any of paragraphs 1-68, which comprises a substitution at twenty-two positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[90] The variant of any of paragraphs 1-68, which comprises a substitution at twenty-three positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[91] The variant of any of paragraphs 1-68, which comprises a substitution at twenty-four positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[92] The variant of any of paragraphs 1-68, which comprises a substitution at twenty-five positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[93] The variant of any of paragraphs 1-68, which comprises a substitution at twenty-six positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[94] The variant of any of paragraphs 1-68, which comprises a substitution at twenty-seven positions corresponding to any of positions 26, 32, 34, 40, 41, 42, 47, 56, 72, 102, 123, 138, 149, 152, 163, 164, 166, 169, 186, 200, 207, 213, 219, 222, 234, 246, 249, and 250.

[95] The variant of any of paragraphs 1-68, which comprises a substitution at each position corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250.

[96] The variant of any of paragraphs 1-95, which comprises one or more substitutions selected from the group consisting of 5261; G32E, S; Y34F; V40A; N41T; Q42I, E, V; S47E, L, R; S56C, E, T; S72Q, T; T102K, P; A123R; Q138C, E, G, K, L, M; V149I; D152S; T163E, F, V; V164C, L; I166L; S169R, C; S186F, K, T, Y; F200I,V; G207P; S213E; S219E, M, Q, C; K222R; S234G, K; A246P; N249Q, R, C, and A250C.

[97] The variant of any of paragraphs 1-96, which comprises the substitutions S173C+F253C of the mature polypeptide of SEQ ID NO: 36.

[98] The variant of any of paragraphs 1-96, which comprises the substitutions L111V+D152S+M155L+A162W+Q138K+K229W of the mature polypeptide of SEQ ID NO: 30.

[99] The variant of any of paragraphs 1-96, which comprises the substitutions L111V+D152S+M155L+A162W+547E+K229W of the mature polypeptide of SEQ ID NO: 30.

[100] The variant of any of paragraphs 1-96, which comprises the substitutions L111V+D152S+M155L+A162W+S56A+K229W of the mature polypeptide of SEQ ID NO: 30.

[101] The variant of any of paragraphs 1-96, which comprises the substitutions L111V+D152S+M155L+A162W+T102K+K229W of the mature polypeptide of SEQ ID NO: 30.

[102] The variant of any of paragraphs 1-96, which comprises the substitutions L111V+D152S+M155L+A162W+S186T+K229W of the mature polypeptide of SEQ ID NO: 30.

[103] The variant of any of paragraphs 1-96, which comprises the substitutions L111V+D152S+M155L+A162W+K229W+S234G of the mature polypeptide of SEQ ID NO: 30.

[104] The variant of any of paragraphs 1-96, which comprises the substitutions L111V+D152S+M155L+A162W+T102K+E105K+K229W of the mature polypeptide of SEQ ID NO: 30.

[105] The variant of any of paragraphs 1-96, which comprises the substitutions L111V+D152S+M155L+A162W+Q138K+G188F+K229W of the mature polypeptide of SEQ ID NO: 30.

[106] The variant of any of paragraphs 1-96, which comprises the substitutions L111V+D152S+M155L+A162W+Q138K+V149I+G188F+K229W of the mature polypeptide of SEQ ID NO: 30.

[107] The variant of any of paragraphs 1-96, which comprises the substitutions L111V+D152S+M155L+A162W+S169C+G188F+K229W+A250C of the mature polypeptide of SEQ ID NO: 30.

[108] The variant of any of paragraphs 1-96, which comprises the substitutions L111V+D152S+M155L+A162W+S72T+Q138K+V149I+G188F+K229W of the mature polypeptide of SEQ ID NO: 30.

[109] The variant of any of paragraphs 1-96, which comprises the substitutions L111V+D152S+M155L+A162W+Q138K+V149I+G188F+G207P+K229W of the mature polypeptide of SEQ ID NO: 30

[110] The variant of any of paragraphs 1-109, which further comprises a substitution at positions corresponding to positions 111, 152, 155, and 162 of the mature polypeptide of SEQ ID NO: 30, wherein the variant has cellulolytic enhancing activity.

[111] The variant of paragraph 110, wherein the number of additional substitutions is 1-4, e.g., such as 1, 2, 3, or 4 substitutions.

[112] The variant of paragraph 110 or 111, which comprises a substitution at a position corresponding to position 111.

[113] The variant of paragraph 112, wherein the substitution is Val.

[114] The variant of any of paragraphs 110-113, which comprises a substitution at a position corresponding to position 152.

[115] The variant of paragraph 114, wherein the substitution is Ser.

[116] The variant of any of paragraphs 110-115, which comprises a substitution at a position corresponding to position 155.

[117] The variant of paragraph 116, wherein the substitution is Leu.

[118] The variant of any of paragraphs 110-117, which comprises a substitution at a position corresponding to position 162.

[119] The variant of paragraph 118, wherein the substitution is Trp.

[120] The variant of any of paragraphs 110-119, which comprises a substitution at two positions corresponding to any of positions 111, 152, 155, and 162.

[121] The variant of any of paragraphs 110-119, which comprises a substitution at three positions corresponding to any of positions 111, 152, 155, and 162.

[122] The variant of any of paragraphs 110-119, which comprises a substitution at each position corresponding to positions 111, 152, 155, and 162.

[123] The variant of any of paragraphs 110-119, which comprises one or more substitutions selected from the group consisting of L111V, D152S, M155L, and A162W.

[124] The variant of any of paragraphs 1-123, which further comprises a substitution at positions corresponding to positions 96, 98, 200, 202, and 204 of the mature polypeptide of SEQ ID NO: 30, wherein the variant has cellulolytic enhancing activity.

[125] The variant of paragraph 124, wherein the number of additional substitutions is 1-5, e.g., such as 1, 2, 3, 4, or 5 substitutions.

[126] The variant of paragraph 124 or 125, which comprises a substitution at a position corresponding to position 96.

[127] The variant of paragraph 126, wherein the substitution is Val.

[128] The variant of any of paragraphs 124-127, which comprises a substitution at a position corresponding to position 98.

[129] The variant of paragraph 128 wherein the substitution is Leu.

[130] The variant of any of paragraphs 124-129, which comprises a substitution at a position corresponding to position 200.

[131] The variant of paragraph 130, wherein the substitution is Ile.

[132] The variant of any of paragraphs 124-131, which comprises a substitution at a position corresponding to position 202.

[133] The variant of paragraph 132, wherein the substitution is Leu.

[134] The variant of any of paragraphs 124-133, which comprises a substitution at a position corresponding to position 204.

[135] The variant of paragraph 134, wherein the substitution is Val.

[136] The variant of any of paragraphs 124-135, which comprises a substitution at two positions corresponding to any of positions 96, 98, 200, 202, and 204.

[137] The variant of any of paragraphs 124-135, which comprises a substitution at three positions corresponding to any of positions 96, 98, 200, 202, and 204.

[138] The variant of any of paragraphs 124-135, which comprises a substitution at four positions corresponding to any of positions 96, 98, 200, 202, and 204.

[139] The variant of any of paragraphs 124-135, which comprises a substitution at each position corresponding to positions 96, 98, 200, 202, and 204.

[140] The variant of any of paragraphs 124-135, which comprises one or more substitutions selected from the group consisting of I96V, F98L, F200I, I202L, and I204V.

[141] The variant of any of paragraphs 1-140, which further comprises a substitution at positions corresponding to positions 105, 154, 188, 189, 216, and 229 of the mature polypeptide of SEQ ID NO: 30, wherein the variant has cellulolytic enhancing activity.

[142] The variant of paragraph 141, wherein the number of additional substitutions is 1-6, e.g., 1, 2, 3, 4, 5, or 6 substitutions.

[143] The variant of paragraph 141 or 142, which comprises a substitution at a position corresponding to position 105.

[144] The variant of paragraph 143, wherein the substitution is Pro or Lys.

[145] The variant of any of paragraphs 141-144, which comprises a substitution at a position corresponding to position 154.

[146] The variant of paragraph 145, wherein the substitution is Leu.

[147] The variant of any of paragraphs 141-146, which comprises a substitution at a position corresponding to position 188.

[148] The variant of paragraph 147, wherein the substitution is Ala or Trp.

[149] The variant of any of paragraphs 141-148, which comprises a substitution at a position corresponding to position 189.

[150] The variant of paragraph 149, wherein the substitution is Lys.

[151] The variant of any of paragraphs 141-150, which comprises a substitution at a position corresponding to position 216.

[152] The variant of paragraph 151, wherein the substitution is Leu or Tyr.

[153] The variant of any of paragraphs 141-152, which comprises a substitution at a position corresponding to position 229.

[154] The variant of paragraph 153, wherein the substitution is Trp, His, Ile, or Tyr.

[155] The variant of any of paragraphs 141-154, which comprises one or more substitutions selected from the group consisting of E105P,K; E154I, L; G188F, M, A,W; N189H, K; A216L, Y; and A229W, H, I, Y.

[156] The variant of any of paragraphs 1-155, which has an increased thermostability of at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to the parent.

[157] An isolated polynucleotide encoding the variant of any of paragraphs 1-156.

[158] A nucleic acid construct comprising the polynucleotide of paragraph 157.

[159] An expression vector comprising the polynucleotide of paragraph 157.

[160] A recombinant host cell comprising the polynucleotide of paragraph 157.

[161] A method of producing a GH61 polypeptide variant, comprising: cultivating the host cell of paragraph 160 under conditions suitable for expression of the variant.

[162] The method of paragraph 161, further comprising recovering the variant.

[163] A transgenic plant, plant part or plant cell transformed with the polynucleotide of paragraph 157.

[164] A method of producing a variant of any of paragraphs 1-156, comprising: cultivating a transgenic plant or a plant cell comprising a polynucleotide encoding the variant under conditions conducive for production of the variant.

[165] The method of paragraph 164, further comprising recovering the variant.

[166] A method for obtaining a GH61 polypeptide variant, comprising introducing into a parent GH61 polypeptide a substitution at one or more positions corresponding to positions 26, 32, 34, 40, 41, 42, 47, 56, 72, 102, 123, 138, 149, 152, 163, 164, 166, 169, 186, 200, 207, 213, 219, 222, 234, 246, 249, and 250 of the mature polypeptide of SEQ ID NO: 30, wherein the variant has cellulolytic enhancing activity; and recovering the variant.

[167] The method of paragraph 166, further comprising introducing into the parent GH61 polypeptide a substitution at one or more positions corresponding to positions 111, 152, 155, and 162 of the mature polypeptide of SEQ ID NO: 30, wherein the variant has cellulolytic enhancing activity.

[168] The method of paragraph 166 or 167, further comprising introducing into the parent GH61 polypeptide a substitution at one or more positions corresponding to positions 96, 98, 200, 202, and 204 of the mature polypeptide of SEQ ID NO: 30, wherein the variant has cellulolytic enhancing activity.

[169] The method of any of paragraphs 166-168, further comprising introducing into the parent GH61 polypeptide a substitution at one or more positions corresponding to positions 105, 154, 188, 189, 216, and 229 of the mature polypeptide of SEQ ID NO: 30, wherein the variant has cellulolytic enhancing activity.

[170] A process for degrading or converting a cellulosic material, comprising: treating the cellulosic material with an enzyme composition in the presence of the GH61 polypeptide variant having cellulolytic enhancing activity of any of paragraphs 1-156.

[171] The process of paragraph 170, wherein the cellulosic material is pretreated.

[172] The process of paragraph 170 or 171, further comprising recovering the degraded cellulosic material.

[173] The process of any of paragraphs 170-172, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[174] The process of paragraph 173, wherein the cellulase is one or more enzymes selected from the group consisting of an endoglucanase, a cellobiohydrolase, and a beta-glucosidase.

[175] The process of paragraph 173, wherein the hemicellulase is one or more enzymes selected from the group consisting of a xylanase, an acetyxylan esterase, a feruloyl esterase, an arabinofuranosidase, a xylosidase, and a glucuronidase.

[176] The process of any of paragraphs 170-175, wherein the degraded cellulosic material is a sugar.

[177] The process of paragraph 176, wherein the sugar is selected from the group consisting of glucose, xylose, mannose, galactose, and arabinose.

[178] A process for producing a fermentation product, comprising: (a) saccharifying a cellulosic material with an enzyme composition in the presence of the GH61 polypeptide variant having cellulolytic enhancing activity of any of paragraphs 1-156; (b) fermenting the saccharified cellulosic material with one or more fermenting microorganisms to produce the fermentation product; and (c) recovering the fermentation product from the fermentation.

[179] The process of paragraph 178, wherein the cellulosic material is pretreated.

[180] The process of paragraph 178 or 179, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[181] The process of paragraph 180, wherein the cellulase is one or more enzymes selected from the group consisting of an endoglucanase, a cellobiohydrolase, and a beta-glucosidase.

[182] The process of paragraph 180, wherein the hemicellulase is one or more enzymes selected from the group consisting of a xylanase, an acetyxylan esterase, a feruloyl esterase, an arabinofuranosidase, a xylosidase, and a glucuronidase.

[183] The process of any of paragraphs 178-182, wherein steps (a) and (b) are performed simultaneously in a simultaneous saccharification and fermentation.

[184] The process of any of paragraphs 178-183, wherein the fermentation product is an alcohol, an alkane, a cycloalkane, an alkene, an amino acid, a gas, isoprene, a ketone, an organic acid, or polyketide.

[185] A process of fermenting a cellulosic material, comprising: fermenting the cellulosic material with one or more fermenting microorganisms, wherein the cellulosic material is saccharified with an enzyme composition in the presence of the GH61 polypeptide variant having cellulolytic enhancing activity of any of paragraphs 1-156.

[186] The process of paragraph 185, wherein the cellulosic material is pretreated before saccharification.

[187] The process of paragraph 185 or 186, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[188] The process of paragraph 187, wherein the cellulase is one or more enzymes selected from the group consisting of an endoglucanase, a cellobiohydrolase, and a beta-glucosidase.

[189] The process of paragraph 187, wherein the hemicellulase is one or more enzymes selected from the group consisting of a xylanase, an acetyxylan esterase, a feruloyl esterase, an arabinofuranosidase, a xylosidase, and a glucuronidase.

[190] The process of any of paragraphs 185-189, wherein the fermenting of the cellulosic material produces a fermentation product.

[191] The process of paragraph 190, further comprising recovering the fermentation product from the fermentation.

[192] The process of paragraph 190 or 191, wherein the fermentation product is an alcohol, an alkane, a cycloalkane, an alkene, an amino acid, a gas, isoprene, a ketone, an organic acid, or polyketide.

[193] A composition comprising the variant of any of paragraphs 1-156.

[194] A whole broth formulation or cell culture composition, comprising the variant of any of paragraphs 1-156.

[195] A detergent composition, comprising a surfactant and the variant of any of paragraphs 1-156.

[196] The composition of paragraph 195, further comprising one or more enzymes selected from the group consisting of an amylase, arabinase, cutinase, carbohydrase, cellulase, galactanase, laccase, lipase, mannanase, oxidase, pectinase, peroxidase, protease, and xylanase.

[197] The composition of paragraph 195 or 196, which is formulated as a bar, a tablet, a powder, a granule, a paste, or a liquid.

[198] A method for cleaning or washing a hard surface or laundry, the method comprising contacting the hard surface or the laundry with the composition of any of paragraphs 195-197.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A variant of a parent GH61 polypeptide having cellulolytic enhancing activity, comprising a substitution at one or more positions corresponding to positions 138, 219, 26, 32, 34, 40, 41, 42, 47, 56, 72, 102, 123, 149, 152, 163, 164, 166, 169, 186, 200, 207, 213, 222, 234, 246, 249, and 250 of the mature polypeptide of SEQ ID NO: 30, wherein the substitution at position 138 is with Cys, Glu, Gly, Lys, Leu, or Met, the substitution at position 219 is with Glu, Met, Gln, or Cys, the substitution at position 26 is with Ile, the substitution at position 32 is with Glu or Ser, the substitution at position 34 is with Phe, the substitution at position 40 is with Ala, the substitution at position 41 is with Thr, the substitution at position 42 is with Ile, Glu, or Val, the substitution at position 47 is with Glu, Leu, or Arg, the substitution at position 56 is with Cys, Glu, or Thr, the substitution at position 72 is with Gln or Thr, the substitution at position 102 is with Lys or Pro, the substitution at position 123 is with Arg, the substitution at position 149 is with Ile, the substitution at position 152 is with Ser, the substitution at position 163 is with Glu, Phe, or Val, the substitution at position 164 is with Cys or Leu, the substitution at position 166 is with Leu, the substitution at position 169 is with Arg or Cys, the substitution at position 186 is with Phe, Lys, Thr, or Tyr, the substitution at position 200 is with Ile or Val, the substitution at position 207 is with Pro, the substitution at position 213 is with Glu, the substitution at position 222 is with Arg, the substitution at position 234 is with Gly or Lys, the substitution at position 246 is with Pro, the substitution at position 249 is with Gln, Arg, or Cys, and the substitution at position 250 is with Cys, wherein the variant has cellulolytic enhancing activity, wherein the variant has increased thermostability relative to the parent GH61 polypeptide, and wherein the parent GH61 polypeptide is selected from the group consisting of:
 (a) a GH61 polypeptide having at least 98% sequence identity to the mature polypeptide of SEQ ID NO: 30; and
 (b) a GH61 polypeptide encoded by a polynucleotide having at least 98% sequence identity to the mature polypeptide coding sequence of SEQ ID NO: 29; wherein the variant has at least 98% but less than 100% sequence identity to the mature polypeptide of SEQ ID NO: 30.

2. The variant of claim 1, wherein the parent GH61 polypeptide comprises the mature polypeptide of SEQ ID NO: 30.

3. The variant of claim 1, which comprises one or more substitutions selected from the group consisting of S261; G32E,S; Y34F; V40A; N41T; Q42I,E,V; S47E,L,R; S56C, E,T; S72Q,T; S102K,P; A123R; Q138C,E,G,K,L,M; V149I; D152S; T163E,F,V; V164C,L; I166L; S169R,C; S186F,K, T,Y; F200I,V; G207P; S213E; S219E,M,Q,C; K222R; S234G,K; A246P; N249Q,R,C, and A250C.

4. The variant of claim 1, which further comprises a substitution at one or more positions corresponding to positions 111, 152, 155, 162, 96, 98, 200, 202, 204, 105, 154, 188, 189, and 216 of the mature polypeptide of SEQ ID NO: 30, wherein the variant has cellulolytic enhancing activity and wherein the substitution at position 111 is with Val, the substitution at position 152 is with Ser, the substitution at position 155 is with Leu, the substitution at position 162 is with Trp, the substitution at position 96 is with Val, the substitution at position 98 is with Leu, the substitution at position 200 is with Ile, the substitution at position 202 is with Leu, the substitution at position 204 is with Val, the substitution at position 105 is with Pro or Lys, the substitution at position 154 is with Leu, the substitution at position 188 is with Ala or Trp, the substitution at position 189 is with Lys, and the substitution at position 152 is with Leu or Tyr.

5. The variant of claim 4, which comprises one or more substitutions selected from the group consisting of L111V, D152S, M155L, A162W, I96V, F98L, F200I, I202L, I204V, E105P,K; E154L; G188A,W; N189K; and A216L,Y.

6. An isolated polynucleotide encoding the variant of claim 1.

7. A recombinant host cell comprising the polynucleotide of claim 6.

8. A method of producing a GH61 polypeptide variant, comprising: cultivating the recombinant host cell of claim 7 under conditions suitable for expression of the variant.

9. A transgenic plant, plant part or plant cell transformed with the polynucleotide of claim 6.

10. A method of producing the variant of claim 1, comprising: cultivating a transgenic plant or a plant cell comprising a polynucleotide encoding the variant under conditions conducive for production of the variant.

11. A process for degrading or converting a cellulosic material, comprising: treating the cellulosic material with an enzyme composition comprising the GH61 polypeptide variant having cellulolytic enhancing activity of claim 1.

12. A process for producing a fermentation product, comprising: (a) saccharifying a cellulosic material with an enzyme composition comprising the GH61 polypeptide variant having cellulolytic enhancing activity of claim 1; (b) fermenting the saccharified cellulosic material with one or more fermenting microorganisms to produce the fermentation product; and (c) recovering the fermentation product from the fermentation.

13. A process of fermenting a cellulosic material, comprising: fermenting the cellulosic material with one or more fermenting microorganisms, wherein the cellulosic material is saccharified with an enzyme composition comprising the GH61 polypeptide variant having cellulolytic enhancing activity of claim 1.

14. A composition comprising the variant of claim 1.

15. A whole broth formulation or cell culture composition, comprising the variant of claim 1.

16. A detergent composition, comprising a surfactant and the variant of claim 1.

17. The variant of claim 1, wherein the parent GH61 polypeptide has at least 98% sequence identity to the mature polypeptide of SEQ ID NO: 30.

18. The variant of claim 1, wherein the parent GH61 polypeptide has at least 99% sequence identity to the mature polypeptide of SEQ ID NO: 30.

19. The variant of claim 1, wherein the parent GH61 polypeptide consists of the mature polypeptide of SEQ ID NO: 30.

20. The process of claim 11, wherein the cellulosic material is pretreated.

21. The process of claim 11, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

22. The process of claim 11, further comprising recovering the degraded or converted cellulosic material.

23. The process of claim 22, wherein the degraded or converted cellulosic material is a sugar selected from the group consisting of glucose, xylose, mannose, galactose, and arabinose.

24. The process of claim 12, wherein the cellulosic material is pretreated.

25. The process of claim 12, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

26. The process of claim 12, wherein steps (a) and (b) are performed simultaneously in a simultaneous saccharification and fermentation.

27. The process of claim 12, wherein the fermentation product is an alcohol, an alkane, a cycloalkane, an alkene, an amino acid, a gas, isoprene, a ketone, an organic acid, or polyketide.

28. The process of claim 13, wherein the cellulosic material is pretreated.

29. The process of claim 13, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

30. The process of claim 13, wherein the fermenting of the cellulosic material produces a fermentation product.

31. The process of claim 30, further comprising recovering the fermentation product from the fermentation.

32. The process of claim 30, wherein the fermentation product is an alcohol, an alkane, a cycloalkane, an alkene, an amino acid, a gas, isoprene, a ketone, an organic acid, or polyketide.

* * * * *